US011903916B2

(12) United States Patent
Tripp et al.

(10) Patent No.: US 11,903,916 B2
(45) Date of Patent: *Feb. 20, 2024

(54) METHODS OF USING PROBENECID FOR TREATMENT OF CORONAVIRUS INFECTIONS

(71) Applicant: University of Georgia Research Foundation, Inc., Athens, GA (US)

(72) Inventors: Ralph A. Tripp, Watkinsville, GA (US); Jackelyn Murray, Monroe, GA (US); Robert Jeff Hogan, Watkinsville, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 130 days.

This patent is subject to a terminal disclaimer.

(21) Appl. No.: 17/465,932

(22) Filed: Sep. 3, 2021

(65) Prior Publication Data

US 2021/0393564 A1 Dec. 23, 2021

Related U.S. Application Data

(63) Continuation of application No. 16/875,487, filed on May 15, 2020, now Pat. No. 11,116,737.

(60) Provisional application No. 63/023,021, filed on May 11, 2020, provisional application No. 63/008,624, filed on Apr. 10, 2020.

(51) Int. Cl.
| | |
|---|---|
| *A61K 31/195* | (2006.01) |
| *A61K 31/63* | (2006.01) |
| *A61P 31/12* | (2006.01) |
| *A61P 31/14* | (2006.01) |
| *A61K 9/00* | (2006.01) |

(52) U.S. Cl.
CPC ............ *A61K 31/195* (2013.01); *A61P 31/14* (2018.01); *A61K 9/0019* (2013.01); *A61K 9/0053* (2013.01)

(58) Field of Classification Search
CPC ....... A61K 31/63; A61K 31/195; A61P 31/14; A61P 31/12
See application file for complete search history.

(56) References Cited

U.S. PATENT DOCUMENTS

| | | | |
|---|---|---|---|
| 4,831,025 A | 5/1989 | Godtfredsen | |
| 5,972,309 A | 10/1999 | Kallick | |
| 6,180,639 B1 | 1/2001 | Coates | |
| 6,506,785 B2 | 1/2003 | Evans | |
| 6,551,584 B2 | 4/2003 | Bandyopadhyay | |
| 6,664,239 B2 | 12/2003 | Mitchell | |
| 6,740,655 B2 | 5/2004 | Magee | |
| 6,756,369 B2 | 6/2004 | Mitchell | |
| 6,878,728 B1 | 4/2005 | Hale | |
| 6,884,784 B1 | 4/2005 | Mitchell | |
| 7,094,397 B2 | 8/2006 | Stratton | |
| 7,129,241 B2 | 10/2006 | Eggenweiler | |
| 7,135,471 B2 | 11/2006 | Eggenweiler | |
| 7,312,328 B2 | 12/2007 | Eggenweiler | |
| 7,354,941 B2 | 4/2008 | Marfat | |
| 7,547,680 B2 | 6/2009 | Kikuchi | |
| 7,790,723 B2 | 9/2010 | Eggenweiler | |
| 7,795,268 B2 | 9/2010 | Zeng | |
| 7,960,403 B2 | 6/2011 | Chan Chun Kong | |
| 8,124,613 B2 | 2/2012 | Moinet | |
| 8,455,497 B2 | 6/2013 | Hale | |
| 8,557,831 B2 | 10/2013 | Johnson | |
| 8,633,201 B2 | 1/2014 | Aicher | |
| 8,691,991 B2 | 4/2014 | Johns | |
| 8,697,713 B2 | 4/2014 | Jäkel | |
| 8,946,142 B2 | 2/2015 | Yamashita | |
| 8,999,709 B2 | 4/2015 | Fernández Miguel | |
| 8,999,969 B2 | 4/2015 | Mackman | |

(Continued)

FOREIGN PATENT DOCUMENTS

| | | |
|---|---|---|
| AP | 90A | 7/1990 |
| AU | 2009221761 A1 | 9/2009 |

(Continued)

OTHER PUBLICATIONS

Kamakshi et al. ("Pulse Therapy: A decisive treatment modality in dermatological disorders." Indian Journal of Applied Research; vol. 6 | Issue : 8 | Aug. 2016 | ISSN-2249-555X | IF : 3.919 | IC Value : 74.50). (Year: 2016).*
Adelson, et al. "Treatment of urinary infections in pregnancy using single versus 10-day dosing", J Natl Med Assoc., 84(1):73-5 (1992).
Ahmed, et al. "Repositioning of drugs using open-access data portal DTome: A test case with probenecid (Review)", Int J Mol Med., (2016).
Benemid (Probenecid) dosing, indications, interactions, adverse effects, and more, retrieved from https://reference.medscape.com/drug/probenecid-342832, on May 11, 2020.

(Continued)

*Primary Examiner* — Jeffrey S Lundgren
*Assistant Examiner* — Chris E Simmons
(74) *Attorney, Agent, or Firm* — PABST PATENT GROUP LLP

(57) ABSTRACT

Compositions and methods of treating a subject for a coronavirus infection are provided. The methods typically include administering the subject an effective amount of probenecid, a metabolite or analog thereof, or a pharmaceutically acceptable salt thereof. The methods can by therapeutic and/or prophylactic. The amount of probenecid or a pharmaceutically acceptable salt thereof can be effective to, for example, reduce viral replication, reduce one or more symptoms of disease, disorder, or illness associated with virus, or a combination thereof. In preferred embodiments, the virus is a Severe acute respiratory syndrome-related coronavirus such as SARS-CoV-2 or SARS-CoV, a Middle East respiratory syndrome-related coronavirus such as MERS-CoV, or a coronavirus that causes the common cold.

25 Claims, 2 Drawing Sheets

Specification includes a Sequence Listing.

(56) References Cited

U.S. PATENT DOCUMENTS

| | | |
|---|---|---|
| 9,078,929 B2 | 7/2015 | Kuebelbeck |
| 10,065,993 B2 | 9/2018 | Kuebelbeck |
| 10,150,800 B2 | 12/2018 | Roschke |
| 10,160,778 B2 | 12/2018 | Liu |
| 10,273,252 B2 | 4/2019 | Iwase |
| 10,675,227 B2 | 6/2020 | Latta |
| 11,116,737 B1* | 9/2021 | Tripp .......... A61K 31/195 |
| 2001/0041190 A1* | 11/2001 | Ward .......... A61K 9/0075 424/43 |
| 2002/0016293 A1 | 2/2002 | Ratain |
| 2002/0044968 A1 | 4/2002 | Van Lengerich |
| 2002/0111495 A1 | 8/2002 | Magee |
| 2002/0123520 A1 | 9/2002 | Marfat |
| 2002/0150585 A1 | 10/2002 | Marciani |
| 2003/0027845 A1 | 2/2003 | Marfat |
| 2003/0049302 A1 | 3/2003 | Pauletti |
| 2003/0144300 A1 | 7/2003 | Magee |
| 2003/0186989 A1 | 10/2003 | Marfat |
| 2003/0203926 A1 | 10/2003 | Kois |
| 2003/0220330 A1 | 11/2003 | Yoshitaka |
| 2004/0023916 A1 | 2/2004 | Millan |
| 2004/0048903 A1 | 3/2004 | Chambers |
| 2004/0054974 A1 | 3/2004 | Acar |
| 2004/0067954 A1 | 4/2004 | Eggenweiler |
| 2004/0071757 A1 | 4/2004 | Rolf |
| 2004/0171798 A1 | 9/2004 | Magee |
| 2004/0259863 A1 | 12/2004 | Eggenweiler |
| 2004/0265323 A1 | 12/2004 | McCormick |
| 2005/0059686 A1 | 3/2005 | Eggenweiler |
| 2005/0075326 A1 | 4/2005 | Chan Chun Kong |
| 2005/0075407 A1 | 4/2005 | Tamarkin |
| 2005/0112554 A1 | 5/2005 | Zhao |
| 2005/0222160 A1 | 10/2005 | Eggenweiler |
| 2005/0261641 A1 | 11/2005 | Warchol |
| 2006/0009651 A1 | 1/2006 | Chan |
| 2006/0047116 A1 | 3/2006 | Youngman |
| 2006/0052408 A1 | 3/2006 | Peckham |
| 2006/0058284 A1 | 3/2006 | Yang |
| 2006/0122166 A1 | 6/2006 | Duan |
| 2006/0122228 A1 | 6/2006 | Zeldis |
| 2006/0142241 A1 | 6/2006 | Yoo |
| 2006/0229336 A1 | 10/2006 | Kazmierski |
| 2006/0233743 A1 | 10/2006 | Kelly |
| 2006/0240037 A1 | 10/2006 | Fey |
| 2006/0270676 A1 | 11/2006 | Eggenweiler |
| 2006/0286041 A1 | 12/2006 | Goeggel |
| 2007/0044693 A1 | 3/2007 | Smyrniotis |
| 2007/0115822 A1 | 5/2007 | Odijk et al. |
| 2007/0124152 A1 | 5/2007 | Johns |
| 2007/0141096 A1 | 6/2007 | Van Lengerich |
| 2007/0142365 A1 | 6/2007 | Johns |
| 2007/0148703 A1 | 6/2007 | Tamai |
| 2007/0211212 A1 | 9/2007 | Bennwik |
| 2008/0066741 A1 | 3/2008 | LeMahieu |
| 2008/0152640 A1 | 6/2008 | Prehm |
| 2008/0194523 A1 | 8/2008 | Johns |
| 2008/0194554 A1 | 8/2008 | McLean |
| 2008/0214503 A1 | 9/2008 | Johns |
| 2008/0214527 A1 | 9/2008 | Kawasuji |
| 2008/0220441 A1 | 9/2008 | Birnbaum |
| 2008/0234231 A1 | 9/2008 | Johns |
| 2009/0047238 A1 | 2/2009 | Chan Chun Kong |
| 2009/0053172 A1 | 2/2009 | Aquino |
| 2009/0142790 A1 | 6/2009 | Fang |
| 2009/0298948 A1 | 12/2009 | Davis |
| 2010/0016262 A1 | 1/2010 | Mehal |
| 2010/0048538 A1 | 2/2010 | Soares Da Silva |
| 2010/0056548 A1 | 3/2010 | Aicher |
| 2010/0105708 A1 | 4/2010 | Jaekel |
| 2010/0159001 A1 | 6/2010 | Cardinal |
| 2010/0226943 A1 | 9/2010 | Brennan |
| 2010/0285001 A1 | 11/2010 | Land |
| 2010/0297271 A1 | 11/2010 | Mehal |
| 2011/0105434 A1 | 5/2011 | Exley |
| 2011/0105976 A1 | 5/2011 | Berlin |
| 2011/0269141 A1 | 11/2011 | Murayama |
| 2012/0082659 A1 | 4/2012 | Land |
| 2012/0114670 A1 | 5/2012 | Land |
| 2012/0121711 A1 | 5/2012 | Hu |
| 2013/0020969 A1 | 1/2013 | Leivenzon |
| 2013/0046021 A1 | 2/2013 | Rubinstein |
| 2013/0116312 A2 | 5/2013 | Khan |
| 2013/0136770 A1 | 5/2013 | Zeldis |
| 2013/0203969 A1 | 8/2013 | Jaber |
| 2013/0280806 A1 | 10/2013 | Rubin |
| 2013/0289107 A1 | 10/2013 | Brown |
| 2014/0080727 A1 | 3/2014 | Sulem |
| 2014/0121237 A1 | 5/2014 | Tripp |
| 2015/0072961 A1 | 3/2015 | Yu |
| 2015/0079035 A1 | 3/2015 | Stockwell |
| 2015/0272870 A1 | 10/2015 | Lin |
| 2016/0015062 A1 | 1/2016 | Sandau |
| 2016/0258954 A1 | 9/2016 | Lerner |
| 2016/0263200 A1 | 9/2016 | Cunningham |
| 2016/0297748 A1 | 10/2016 | Stockwell |
| 2017/0157038 A1 | 6/2017 | Peyman |
| 2017/0172971 A1 | 6/2017 | Andersson |
| 2017/0312217 A9 | 11/2017 | Lin |
| 2018/0200164 A1 | 7/2018 | Latta |
| 2019/0204136 A1 | 7/2019 | Fitzgerald |
| 2019/0234940 A1 | 8/2019 | Lam |
| 2019/0365798 A1 | 12/2019 | Beal |
| 2019/0374516 A1 | 12/2019 | Dunne |
| 2020/0101025 A1 | 4/2020 | Masiz |
| 2020/0138756 A1 | 5/2020 | Mrsny |
| 2020/0253878 A1 | 8/2020 | Dunne |
| 2020/0397854 A1 | 12/2020 | Berna |

FOREIGN PATENT DOCUMENTS

| | | |
|---|---|---|
| AU | 2012261721 A1 | 9/2014 |
| CA | 1302263 C | 6/1992 |
| CN | 101584735 A | 11/2009 |
| DE | 3812605 A1 | 6/1990 |
| DK | 1252158 T3 | 8/2005 |
| EP | 0082667 A1 | 6/1983 |
| EP | 0594223 B1 | 3/2000 |
| EP | 0526253 B1 | 11/2002 |
| EP | 1104760 B1 | 3/2003 |
| EP | 1229034 B1 | 4/2005 |
| EP | 1194404 B1 | 5/2006 |
| EP | 1624899 B1 | 11/2010 |
| EP | 2046740 B1 | 5/2012 |
| EP | 2317995 B1 | 12/2016 |
| ES | 2006672 A6 | 5/1989 |
| GB | 1072771 A * | 6/1967 |
| IE | 20000303 A1 | 2/2003 |
| IL | 93223 | 11/1990 |
| IN | 5520DELNP2007 A | 8/2007 |
| IN | 9223DELNP20008 A | 3/2009 |
| IN | 505DELNP2009 A | 8/2010 |
| JP | 2006176427 A | 7/2006 |
| JP | 2015151361 A | 8/2015 |
| KR | 1020030007314 A | 1/2003 |
| NZ | 555624 B | 9/2009 |
| NZ | 563759 A | 6/2010 |
| PH | 12003500817 A1 | 9/2003 |
| WO | 1995007919 | 3/1995 |
| WO | 1996034604 | 11/1996 |
| WO | 9640165 | 12/1996 |
| WO | 1998018610 | 5/1998 |
| WO | 1998050033 | 11/1998 |
| WO | 2000021504 | 4/2000 |
| WO | 2000048636 | 8/2000 |
| WO | 2000057187 | 9/2000 |
| WO | 2000072868 | 12/2000 |
| WO | 2001013897 | 3/2001 |
| WO | 0157036 | 8/2001 |
| WO | 2001057025 | 8/2001 |
| WO | 2001057036 | 8/2001 |
| WO | 2002030395 | 4/2002 |
| WO | 2002051814 | 7/2002 |
| WO | 2002060875 | 8/2002 |
| WO | 2002060896 | 8/2002 |

(56) References Cited

FOREIGN PATENT DOCUMENTS

| | | |
|---|---|---|
| WO | 2002060898 | 8/2002 |
| WO | 2003039548 | 5/2003 |
| WO | 2003074562 A2 | 9/2003 |
| WO | 2004062600 A2 | 7/2004 |
| WO | 2004080393 | 9/2004 |
| WO | 2005077050 | 8/2005 |
| WO | 2006050165 | 5/2006 |
| WO | 2006058008 | 6/2006 |
| WO | 2006060919 | 6/2006 |
| WO | 2006067401 | 6/2006 |
| WO | 2006115137 | 11/2006 |
| WO | 2006130174 | 12/2006 |
| WO | 2006136244 | 12/2006 |
| WO | 2007044693 | 4/2007 |
| WO | 2007059905 A2 | 5/2007 |
| WO | 2007065256 A1 | 6/2007 |
| WO | 2007109547 | 9/2007 |
| WO | 2007115822 | 10/2007 |
| WO | 2008006547 | 1/2008 |
| WO | 2008012511 | 1/2008 |
| WO | 2008062905 | 5/2008 |
| WO | 2008088233 | 7/2008 |
| WO | 2008116165 A2 | 9/2008 |
| WO | 2008127291 A2 | 10/2008 |
| WO | 2008133982 A2 | 11/2008 |
| WO | 2008133982 A3 | 5/2009 |
| WO | 2009082818 | 7/2009 |
| WO | 2009082819 | 7/2009 |
| WO | 2009082819 A1 | 7/2009 |
| WO | 2009100532 | 8/2009 |
| WO | 2009082818 A8 | 9/2009 |
| WO | 2009111040 | 9/2009 |
| WO | 2011041311 A2 | 4/2011 |
| WO | 2011041311 A3 | 8/2011 |
| WO | 2011150067 A1 | 12/2011 |
| WO | 2012024367 | 2/2012 |
| WO | 2013028334 | 2/2013 |
| WO | 2013111014 A1 | 8/2013 |
| WO | 2013116312 | 8/2013 |
| WO | 2013142817 | 9/2013 |
| WO | 2014081405 | 5/2014 |
| WO | 2014111957 | 7/2014 |
| WO | 2014168255 A1 | 10/2014 |
| WO | 2016029127 A1 | 2/2016 |
| WO | 2018005445 A1 | 1/2018 |
| WO | 2018013871 A1 | 1/2018 |
| WO | 2019023468 | 1/2019 |
| WO | 2019081573 | 5/2019 |
| WO | 2019097187 | 5/2019 |
| WO | 2019133531 | 7/2019 |
| WO | 2019148132 | 8/2019 |
| WO | 2019161152 | 8/2019 |
| WO | 2019177927 A1 | 9/2019 |
| WO | 2019204136 | 10/2019 |
| WO | 2019204136 A1 | 10/2019 |
| WO | 2020052677 | 3/2020 |
| WO | 2020113028 A1 | 6/2020 |
| WO | 2020127573 A1 | 6/2020 |
| WO | 2020222187 A1 | 11/2020 |
| WO | 2020229761 A1 | 11/2020 |
| WO | 2020247665 | 12/2020 |

OTHER PUBLICATIONS

Biospace.com ("XORTX Launches XRx-101, A New Program to Treat Coronavirus COVID-19 Infection." https://www.biospace.com/article/releases/xortx-launches-xrx-101-a-new-program-to-treat-coronavirus-covid-19-infection/ (Mar. 16, 2020)) (Year: 2020).
Bitter, et al., "Nasal Drug Delivery in Humans", Topical Applications and the Mucosa, 40:20-35 (2011).
Cheng, et al., "Kidney impairment is associated with in-hospital death of COVID-19 patients", <www.medrxiv.org/content/10.1101/2020.02.18.20023242v1.>MedRxiv, 1-21 (2020).

Chiang & Benet, "Dose-dependent kinetics of probenecid in rhesus monkeys-intravenous bolus studies", Pharmacology, 23(6):326-36 (1981).
Coronaviridae Study Group of the International Committee on Taxonomy of Viruses, "The species Severe acute respiratory syndromerelated coronavirus: classifying 2019-nCoV and naming it SARS-CoV-2", Nat. Microbiol., 5:536-544 (2020).
Crone & Lassen, "The mechanism of the increased renal excretion of urate during the administration of probenecid," Acta Pharmacol Toxicol (Copenh)., 11(3):301-6 (1955).
Cunningham, et al. "Clinical pharmacokinetics of probenecid." Clin Pharmacokinet., 6(2):135-51 (1981).
Cutler, et al., "In vitro and in vivo assessment of renal drug transporters in the disposition of mesna and dimesna", J Clin Pharmacol., 52(4):530-42 (2012).
Dayton, et al., "The effect of probenecid, phenylbutazone, and their analogues on the excretion of L-ascorbic acid in rats," J. Med. Chem., 9:941-944 (1966).
Dayton, et al., "The metabolism of probenecid in man," N. Y. Acad. Sci., 179:399-402 (1971).
Djupesland, "Nasal drug delivery devices: characteristics and performance in a clinical perspective—a review", Drug Deliv. and Transl. Res., 3:42-62 (2013).
El-Farrash, et al., "Allopurinol as a potential therapeutic agent for recurrent herpes labialis", J Med Dent Sci., 50(2):147-54 (2003).
Emanuelsson & Paalzow, "Dose-dependent pharmacokinetics of probenecid in the rat", Biopharm Drug Dispos., 9(1):59-70 (1988).
Emanuelsson & Paalzow, "Hepatic and renal clearances of probenecid in the rat," Pharmacology, 38(1):61-8 (1989).
Emanuelsson, et al., "Non-linear elimination and protein binding of probenecid", Eur J Clin Pharmacol., 32(4):395-401 (1987).
EMedicine Health ("Medication and Drugs: Generic name: colchicine and probenecid" (2015) https://web.archive.org/w.
European Search Report dated Apr. 23, 2021, in European Patent Application No. 20202059.0.
Evaluation of Alternative Oseltamivir (Tamiflu) Dosing Strategies, retrieved from https://clinicaltrials.gov/ct2/show/NCT00304434, on Jun. 18, 2020, last updated Sep. 23, 2009.
GenBank Accession No. AY274119.3, 11 pages, accessed Jun. 17, 2020.
GenBank Accession No. JX869059.2, 12 pages, accessed Jun. 17, 2020.
GenBank Accession No. MN908947.3, 11 pages, accessed Jun. 17, 2020.
GenBank Accession No. MN985325.1, 11 pages, accessed Jun. 17, 2020.
Gerk, et al., "Interactions between cimetidine, nitrofurantoin, and probenecid active transport into rat milk", J Pharmacol Exp Ther., 296(1):175-80 (2001).
Ghadiri, et al., "Strategies to Enhance Drug Absorption via Nasal and Pulmonary Routes", Pharmaceutics, 11(3): 113, 20 pages (2019).
Gollapudi, et al, "Probenecid reverses multidrug resistance in multidrug resistance-associated protein-overexpressing HL60/AR and H69/AR cells but not in P-glycoprotein-overexpressing HL60/Tax and P388/ADR cells", Cancer Chemother Pharmacol., 40(2):150-8 (1997).
Guarino, et al., "Mass spectral identification of probenecid metabolites in rat bile," Eur. J. Pharmacol., 8:244-252 (1969).
Guerrini, et al., "Pharmacokinetics of probenecid in sheep", J Vet Pharmacol Ther., 8(2):128-35 (1985).
Gutman, et al. ,"Combination of probenecid-sulphadoxine-pyrimethamine for intermittent preventive treatment in pregnancy", Malar J., 11:39 (2012). doi: 10.1186/1475-2875-11-39.
He, et al., "Analysis of multimerization of the SARS coronavirus nucleocapsid protein", Biochem. and Biophys. res. Comm., 316:476-483 (2004).
Holodniy, et al. "Pharmacokinetics and tolerability of oseltamivir combined with probenecid", Antimicrob Agents Chemother. 52(9):3013-21 (2008).
Howton, "Probenecid with Oseltamivir for Human Influenza A (H5N1) Virus Infection?", N Engl J Med., 354(8):879-80 (2006).
Ibrahim, et al., "Pharmacodynamics of Pulse Dosing versus Standard Dosing: In Vitro Metronidazole Activity against Bacteroides

(56) References Cited

OTHER PUBLICATIONS fragilis and Bacteroides thetaiotaomicron", Antimicrobial Agents and Chemotherapy, 48(11):4195-4199 (2004).
Ilett, et al. "Transfer of probenecid and cephalexin into breast milk", Ann Pharmacother., 40(5):986-9 (2006).
Israili, et al., "Metabolites of probenecid. Chemical, physical, and pharmacological studies," J. Med. Chem., 15(7): 709-713 (1972).
Jorquera, et al., "Verdinexor (KPT-335), a Selective Inhibitor of Nuclear Export, Reduces Respiratory Syncytial Virus replication In Vitro", Journal of Virology, 93(4):e01684-18 (2019).
Kakizaki, et al. "Probenecid: its chromatographic determination, plasma protein binding, and in vivo pharmacokinetics in dogs", J Vet Med Sci., (2006).
Krick, et al. "Dual Oxidase 2 (Duox2) Regulates Pannexin 1-mediated ATP Release in Primary Human Airway Epithelial Cells via Changes in Intracellular pH and Not H2O2 Production", J Biol Chem., 291(12):6423-32 (2016).
Lai, et al., "Treatment of severe acute respiratory syndrome", Eur. J. Clin. Microbiol. Infect. Dis., 24:583-591 (2005).
Laskin, et al. "Effects of probenecid on the pharmacokinetics and elimination of acyclovir in humans." Antimicrob Agents Chemother., 21(5):804-7 (1982).
Lee & Loeffler, "Gout and pregnancy", J Obstet Gynaecol Br Emp., 69:299-304 (1962).
Liu, et al., "Research and Development on Therapeutic Agents and Vaccines for COVID-19 and Related Human Coronavirus Diseases," ACS Cent Sci., 6(3): 315-331, and 18 pages of supplemental information (2020), Published online Mar. 12, 2020. doi: 10.1021/acscentsci.0c00272.
McDermott, et al., "Pharmacokinetics of zidovudine plus probenecid", J Infect Dis., 166(3):687-8 (1992).
Miranda, et al. "Alteration of zidovudine pharmacokinetics by probenecid in patients with AIDS or AIDS-related complex", Clin Pharmacol Ther., 46(5):494-500 (1989).
Momper, et al. "Pharmacokinetics of low-dose cidofovir in kidney transplant recipients with BK virus infection", Transpl Infect Dis., 15(1):34-41 (2013).
Nigam, et al., "The Organic Anion Transporter (OAT) Family: A Systems Biology Perspective", Physiol.Rev., 95(1):83-123 (2015).
Noormohame, et al. "Renal excretion and pharmacokinetics of foscarnet in HIV sero-positive patients: effect of probenecid pretreatment," Br J Clin Pharmacol., 43(1):112-5 (1997).
NR-52281, SARS-Related Coronavirus 2, Isolate USA-WA1/2020 (Viruses), accessed online Apr. 10, 2020.
Perel, et al., "Studies of the renal excretion of probenecid acyl glucuronide in man," Eur. J. Clin. Pharmacol, 3:106-112 (1971).
Pérez-Mazliah, et al. "Allopurinol reduces antigen-specific and polyclonal activation of human T cells", Front Immunol., 3:295 (2012).
Perwitasari, et al., "Targeting Organic Anion Transporter 3 with Probenecid as a Novel Anti-Influenza A Virus Strategy", Antimicrob. Agents Chemother., 57(1):475-83 (2013).
Perwitasari, et al., "Verdinexor, a Novel Selective Inhibitor of Nuclear Export, Reduces Influenza A Virus Replication In Vitro and In Vivo", J. of Virology, 88(17): 10288-10243 (2014).
Pharmacological Study of Oseltamivir in Healthy Volunteers (SEA002), retrieved from https://clinicaltrials.gov/ct2/show/NCT00439530, on Jun. 18, 2020, last updated Jul. 28, 2009.
Pickens, et al., "Verdinexor Targeting of CRM1 is a Promising Therapeutic Approach against RSV and Influenza Viruses", Viruses, 10(48):1-24 (2018).
Pires, et al., "Intranasal Drug Delivery: How, Why and What for", J. Pharm. Pharmaceut. Sci., 12(3):288-311 (2009).
Probenecid (probenecid) dose, indications, adverse effects, interactions retrieved from https://www.pdr.net/drug-summary/Probenecid--probenecid-1984 , on May 11, 2020.
Probenecid CAS#57-66-9, retrieved from https://www.chemsrc.com/en/cas/57-66-9_242920.html, on Apr. 10, 2020.
Probenecid Tablets—FDA Prescribing Information, side effects and uses, retrieved from https://www.drugs.com/pro/probenecid-tablets.html, on Apr. 10, 2020.
Probenecid, Science Direct, retrieved from https://www.sciencedirect.com/topics/pharmacology-toxicology-and-pharmaceutical-science/probenecid , on May 15, 2020.
Qi, et al. "Differential distribution of probenecid as detected by on-tissue mass spectrometry", Cell Tissue Res., 360(2):427-9 (2015).
Ramnitz, et al. "Phenotypic and Genotypic Characterization and Treatment of a Cohort With Familial Tumoral Calcinosis/Hyperostosis-Hyperphosphatemia Syndrome", J Bone Miner Res., 31(10):1845-1854 (2016).
Ratia, et al., "A noncovalent class of papain-like protease/ deubiquitinase inhibitors blocks SARS virus replication", Proc. Natl. Acad. Sci. USA, 105(42):16119-16124 (2008).
Rayner, et al. "Population pharmacokinetics of oseltamivir when coadministered with probenecid", J Clin Pharmacol., 48(8):935-47 (2008).
Rosli, et al., "Repurposing drugs targeting the PX2w7 receptor to limit hyperminflammation and disease during influenza virus infection", British Journal of Pharmacological Society, 176:3834-3844 (2019).
Roy, et al. "Exploration of inclusion complexes of probenecid with α and β-cyclodextrins: Enhancing the utility of the drug", Journal of Molecular Structure, (2017).
Schackis, "Hyperuricaemia and preeclampsia: is there a pathogenic link?" Med Hypotheses, 63(2):239-44 (2004).
Selen, et al. "Pharmacokinetics of probenecid following oral doses to human volunteers", J Pharm Sci., 71(11):1238-42 (1982).
Stocker, et al. "Pharmacokinetic and pharmacodynamic interaction between allopurinol and probenecid in patients with gout", J Rheumatol., 38(5):904-10 (2011).
Takeda, et al. "Characterization of organic anion transport inhibitors using cells stably expressing human organic anion transporters", Eur J Pharmacol., 11;419(2-3):113-20 (2011).
Vossen, et al. "Single-dose pharmacokinetics of cidofovir in continuous venovenous hemofiltration", Antimicrob Agents Chemother. 58(4):1952-5 (2014).
Vree, et al. "Capacity-limited renal glucuronidation of probenecid by humans. A pilot Vmax-finding study", Pharm Weekbl Sci., 14(5):325-31 (1992).
Wang, et al "Renal secretion of the antiviral nucleoside analog AM188 is inhibited by probenecid, p-aminohippuric acid, and cimetidine in the isolated perfused rat kidney", Pharm Res., 21(6):982-8 (2004).
Weber, et al. "Probenecid pharmacokinetics in cystic fibrosis." Dev Pharmacol Ther., 16(1):7-12 (1991).
WHO, "Pneumonia of unknown cause—China" World Health Organization: Online Jan. 5, 2020.
Wolf, et al. "Pharmacokinetics and renal effects of cidofovir with a reduced dose of probenecid in HIV-infected patients with cytomegalovirus retinitis", J Clin Pharmacol., 43(1):43-51 (2003).
Wu, et al. "Pharmacokinetic properties and bioequivalence of two compound formulations of 1500 mg ampicillin (1167 mg)/probenecid (333 mg): a randomized-sequence, single-dose, open-label, two-period crossover study in healthy Chinese male volunteers", Clin Ther., 32(3):597-606 (2010).
Wu, et al., "A new coronavirus associated with human respiratory disease in China," Nature, 579(7798): 265-269, and 19 pages of supplemental information and Erratum (2020), Published online Feb. 3, 2020. doi: 10.1038/s41586-020-2008-3.
Zacchei & Weidner, "GLC determination of probenecid in biological fluids." J Pharm Sci., 62(12):1972-5 (1973).
Zhang, et al. "Simultaneous Determination of Cefalexin, Cefazolin, Flucloxacillin, and Probenecid by Liquid Chromatography-Tandem Mass Spectrometry for Total and Unbound Concentrations in Human Plasma," Ther Drug Monit. 40(6):682-692 (2018).
Ahmed, et al., "Preliminary Identification of Potential Vaccine Targets for the COVID-19 A Coronavirus (SARS-CoV-2) Based on SARS-CoV Immunological Studies", Viruses, 12(3): 254, pp. 1-15 (2020).
Alberta Precision Laboratories, Alberta COVID Variants Surveillance Plan, Jan. 2020 [retrieved on Jul. 14, 2021]. Retrieved from

(56) References Cited

OTHER PUBLICATIONS the internet: <URL: https://www.departmentofmedicine.com/meoc/covid-alberta-variants-surveillance-plan.pdf>.

Box, et al., "Lack of antiviral activity of probenecid in Vero E6 cells and Syrian golden hamsters: a need for better understanding of inter-lab differences in preclinical assays", bioRxiv, (2022).

Murray, et al., "Probenecid Inhibits SARS-CoV-2 Replication In Vivo and In Vitro", bioRxiv, May 2021 [retrieved on Jul. 14, 2021]. Retrieved from the internet: <URL: https://www.biorxiv.org/contenV10.1101/2021.05.21.445119v1>.

Perel, et al., "Identification and renal excretion of probenecid metabolites in man," Life Sciences, 9, 23, 1337-1343 (1970).

Samsami, et al., "COVID-19 Pneumonia in Asymptomatic Trauma Patients; Report of 8 Cases, Archives of Academic Emergency Medicine", 8(1): e46:1-3 (2020).

Shang, et al., "Structural basis of receptor recognition by SARS-CoV-2", Nature, 581(7807):221-224 (2020a).

Shang, et al., "The outbreak of SARS-CoV-2 pneumonia calls for viral vaccines", NPJ Vaccines, 5(18):1-3 (2020b).

International Search Report for corresponding PCT application PCT/US2021/026588 dated Sep. 15, 2021.

\* cited by examiner

SEQUENCE LISTING

```
<160> NUMBER OF SEQ ID NOS: 4

<210> SEQ ID NO 1
<211> LENGTH: 29903
<212> TYPE: DNA
<213> ORGANISM: Severe acute respiratory syndrome coronavirus 2 isolate
      Wuhan-Hu-1

<400> SEQUENCE: 1
attaaaggtt tataccttcc caggtaacaa accaaccaac tttcgatctc ttgtagatct      60
gttctctaaa cgaactttaa aatctgtgtg gctgtcactc ggctgcatgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaagatgga gagccttgtc cctggtttca acgagaaaac     300
acacgtccaa ctcagtttgc ctgttttaca ggttcgcgac gtgctcgtac gtggctttgg     360
agactccgtg gaggaggtct tatcagaggc acgtcaacat cttaaagatg gcacttgtgg     420
cttagtagaa gttgaaaaag gcgttttgcc tcaacttgaa cagccctatg tgttcatcaa     480
acgttcggat gctcgaactg cacctcatgg tcatgttatg gttgagctgg tagcagaact     540
cgaaggcatt cagtacggtc gtagtggtga gacacttggt gtccttgtcc ctcatgtggg     600
cgaaatacca gtggcttacc gcaaggttct tcttcgtaag aacggtaata aaggagctgg     660
```

```
tggccatagt tacggcgccg atctaaagtc atttgactta ggcgacgagc ttggcactga    720
tccttatgaa gattttcaag aaaactggaa cactaaacat agcagtggtg ttacccgtga    780
actcatgcgt gagcttaacg gaggggcata cactcgctat gtcgataaca acttctgtgg    840
ccctgatggc taccctcttg agtgcattaa agaccttcta gcacgtgctg gtaaagcttc    900
atgcactttg tccgaacaac tggactttat tgacactaag aggggtgtat actgctgccg    960
tgaacatgag catgaaattg cttggtacac ggaacgttct gaaaagagct atgaattgca   1020
gacacctttt gaaattaaat tggcaaagaa atttgacacc ttcaatgggg aatgtccaaa   1080
ttttgtattt cccttaaatt ccataatcaa gactattcaa ccaagggttg aaaagaaaaa   1140
gcttgatggc tttatgggta gaattcgatc tgtctatcca gttgcgtcac caaatgaatg   1200
caaccaaatg tgcctttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaatttt attgtccagc   1380
atgtcacaat tcagaagtag gacctgagca tagtcttgcc gaataccata tgaatctgg    1440 cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat cttttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat tgtcacgca   2400 ctcaaaggga ttgtacagaa agtgtgttaa atccagagaa gaaactggcc tactcatgcc   2460
tctaaaagcc ccaaaagaaa ttatcttctt agagggagaa cacttcccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caacaatac    2700 cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
```

```
tgagtttaaa ttggcttcac atatgtattg ttctttctac cctccagatg aggatgaaga    3060
agaaggtgat tgtgaagaag aagagtttga gccatcaact caatatgagt atggtactga    3120
agatgattac caaggtaaac ctttggaatt tggtgccact tctgctgctc ttcaacctga    3180
agaagagcaa gaagaagatt ggttagatga tgatagtcaa caaactgttg gtcaacaaga    3240
cggcagtgag gacaatcaga caactactat tcaaacaatt gttgaggttc aacctcaatt    3300
agagatggaa cttacaccag ttgttcagac tattgaagtg aatagtttta gtggttattt    3360
aaaacttact gacaatgtat acattaaaaa tgcagacatt gtggaagaag ctaaaaaggt    3420
aaaaccaaca gtggttgtta atgcagccaa tgtttacctt aaacatggag gaggtgttgc    3480
aggagcctta aataaggcta ctaacaatgc catgcaagtt gaatctgatg attacatagc    3540
tactaatgga ccacttaaag tgggtggtag ttgtgtttta agcggacaca atcttgctaa    3600
acactgtctt catgttgtcg gcccaaatgt taacaaaggt gaagacattc aacttcttaa    3660
gagtgcttat gaaaattta atcagcacga agttctactt gcaccattat tatcagctgg    3720
tatttttggt gctgaccta tacattcttt aagagtttgt gtagatactg ttcgcacaaa    3780
tgtctactta gctgtctttg ataaaaatct ctatgacaaa cttgtttcaa gcttttggga    3840
aatgaagagt gaaaagcaag ttgaacaaaa gatcgctgag attcctaaag aggaagttaa    3900
gccatttata actgaaagta aaccttcagt tgaacagaga aaacaagatg ataagaaaat    3960
caaagcttgt gttgaagaag ttacaacaac tctggaagaa actaagttcc tcacagaaaa    4020
cttgttactt tatattgaca ttaatggcaa tcttcatcca gattctgcca ctcttgttag    4080
tgacattgac atcactttct aaagaaaga tgctccatat atagtgggtg atgttgttca    4140
agagggtgtt ttaactgctg tggttatacc tactaaaaag gctggtggca ctactgaaat    4200
gctagcgaaa gctttgagaa aagtgccaac agacaattat ataaccactt acccgggtca    4260
gggtttaaat ggttacactg tagaggaggc aaagacagtg cttaaaaagt gtaaaagtgc    4320
cttttacatt ctaccatcta ttatctctaa tgagaagcaa gaaattcttg gaactgtttc    4380
ttggaatttg cgagaaatgc ttgcacatgc agaagaaaca cgcaaattaa tgcctgtctg    4440
tgtggaaact aaagccatag tttcaactat acagcgtaaa tataagggta ttaaaataca    4500
agagggtgtg gttgattatg gtgctagatt ttacttttac accagtaaaa caactgtagc    4560
gtcacttatc aacacactta acgatctaaa tgaaactctt gttacaatgc cacttggcta    4620
tgtaacacat ggcttaaatt tggaagaagc tgctcggtat atgagatctc tcaaagtgcc    4680
agctacagtt tctgtttctt cacctgatgc tgttacagcg tataatggtt atcttacttc    4740
ttcttctaaa acacctgaag aacattttat tgaaaccatc tcacttgctg gttcctataa    4800
agattggtcc tattctggac aatctacaca actaggtata gaatttctta agagaggtga    4860
taaaagtgta tattacacta gtaatcctac cacattccac ctagatggtg aagttatcac    4920
ctttgacaat cttaagacac ttctttcttt gagagaagtg aggactatta aggtgtttac    4980
aacagtagac aacattaacc tccacacgca agttgtggac atgtcaatga catatggaca    5040
acagtttggt ccaacttatt tggatggagc tgatgttact aaaataaaac ctcataattc    5100
acatgaaggt aaaacatttt atgtttacc taatgatgac actctacgtg ttgaggcttt    5160
tgagtactac cacacaactg atcctagttt tctgggtagg tacatgtcag cattaaatca    5220
cactaaaaag tggaaatacc cacaagttaa tggtttaact tctattaaat gggcagataa    5280
caactgttat cttgccactg cattgttaac actccaacaa atagagttga agtttaatcc    5340
acctgctcta caagatgctt attacagagc aagggctggt gaagctgcta actttgtgc    5400
```

```
acttatctta gcctactgta ataagacagt aggtgagtta ggtgatgtta gagaaacaat    5460
gagttacttg tttcaacatg ccaatttaga ttcttgcaaa agagtcttga acgtggtgtg    5520
taaaacttgt ggacaacagc agacaaccct taagggtgta gaagctgtta tgtacatggg    5580
cacactttct tatgaacaat ttaagaaagg tgttcagata ccttgtacgt gtggtaaaca    5640
agctacaaaa tatctagtac aacaggagtc accttttgtt atgatgtcag caccacctgc    5700
tcagtatgaa cttaagcatg gtacatttac ttgtgctagt gagtacactg gtaattacca    5760
gtgtggtcac tataaacata taacttctaa agaaactttg tattgcatag acggtgcttt    5820
acttacaaag tcctcagaat acaaaggtcc tattacggat gttttctaca agaaaacag    5880 ttacacaaca accataaaac cagttactta taaattggat ggtgttgttt gtacagaaat    5940
tgaccctaag ttggacaatt attataagaa agacaattct tatttcacag agcaaccaat    6000
tgatcttgta ccaaaccaac catatccaaa cgcaagcttc gataatttta gtttgtatg    6060 tgataatatc aaatttgctg atgatttaaa ccagttaact ggttataaga aacctgcttc    6120
aagagagctt aaagttacat ttttccctga cttaaatggt gatgtggtgg ctattgatta    6180
taaacactac acaccctctt ttaagaaagg agctaaattg ttacataaac ctattgtttg    6240
gcatgttaac aatgcaacta ataaagccac gtataaacca aatacctggt gtatacgttg    6300
tctttggagc acaaaaccag ttgaaacatc aaattcgttt gatgtactga agtcagagga    6360
cgcgcaggga atggataatc ttgcctgcga agatctaaaa ccagtctctg aagaagtagt    6420
ggaaaatcct accatacaga aagacgttct tgagtgtaat gtgaaaacta ccgaagttgt    6480
aggagacatt atacttaaac cagcaaataa tagtttaaaa attacagaag aggttggcca    6540
cacagatcta atggctgctt atgtagacaa ttcagtctt actattaaga aacctaatga    6600
attatctaga gtattaggtt tgaaaaccct tgctactcat ggtttagctg ctgttaatag    6660
tgtcccttgg gatactatag ctaattatgc taagccttt cttaacaaag ttgttagtac    6720
aactactaac atagttacac ggtgtttaaa ccgtgtttgt actaattata tgccttattt    6780 ctttactttta ttgctacaat tgtgtacttt tactagaagt acaaattcta gaattaaagc    6840
atctatgccg actactatag caaagaatac tgttaagagt gtcggtaaat tttgtctaga    6900
ggcttcattt aattatttga agtcacctaa tttttctaaa ctgataaata ttataatttg    6960
gttttactta ttaagtgttt gcctaggttc tttaatctac tcaaccgctg ctttaggtgt    7020
tttaatgtct aatttaggca tgccttctta ctgtactggt tacagagaag gctatttgaa    7080
ctctactaat gtcactattg caacctactg tactggttct ataccttgta gtgtttgtct    7140
tagtggttta gattctttag acacctatcc ttctttagaa actatacaaa ttaccatttc    7200
atcttttaaa tgggatttaa ctgcttttgg cttagttgca gagtggtttt ggcatatat    7260 tcttttcact aggttttct atgtacttgg attggctgca atcatgcaat gttttttcag    7320 ctatttgca gtacattta ttagtaattc ttggcttatg tggttaataa ttaatcttgt    7380
acaaatggcc ccgatttcag ctatggttag aatgtacatc ttctttgcat cattttatta    7440
tgtatggaaa agttatgtgc atgttgtaga cggttgtaat tcatcaactt gtatgatgtg    7500
ttacaaacgt aatagagcaa caagagtcga atgtacaact attgttaatg gtgttagaag    7560
gtccttttat gtctatgcta atggaggtaa aggcttttgc aaactacaca attggaattg    7620
tgttaattgt gatacattct gtgctggtag tacatttatt agtgatgaag ttgcgagaga    7680
cttgtcacta cagtttaaaa gaccaataaa tcctactgac cagtcttctt acatcgttga    7740
```

```
tagtgttaca gtgaagaatg gttccatcca tctttacttt gataaagctg gtcaaaagac    7800
ttatgaaaga cattctctct ctcattttgt taacttagac aacctgagag ctaataacac    7860
taaaggttca ttgcctatta atgttatagt ttttgatggt aaatcaaaat gtgaagaatc    7920
atctgcaaaa tcagcgtctg tttactacag tcagcttatg tgtcaaccta tactgttact    7980
agatcaggca ttagtgtctg atgttggtga tagtgcggaa gttgcagtta aaatgtttga    8040
tgcttacgtt aatacgtttt catcaacttt taacgtacca atggaaaaac tcaaaacact    8100
agttgcaact gcagaagctg aacttgcaaa gaatgtgtcc ttagacaatg tcttatctac    8160
tttattttca gcagctcggc aagggtttgt tgattcagat gtagaaacta agatgttgt     8220 tgaatgtctt aaattgtcac atcaatctga catagaagtt actggcgata gttgtaataa    8280
ctatatgctc acctataaca aagttgaaaa catgacaccc cgtgaccttg gtgcttgtat    8340
tgactgtagt gcgcgtcata ttaatgcgca ggtagcaaaa agtcacaaca ttgctttgat    8400
atggaacgtt aaagatttca tgtcattgtc tgaacaacta cgaaaacaaa tacgtagtgc    8460
tgctaaaaag aataacttac cttttaagtt gacatgtgca actactagac aagttgttaa    8520
tgttgtaaca acaaagatag cacttaaggg tggtaaaatt gttaataatt ggttgaagca    8580
gttaattaaa gttacacttg tgttcctttt tgttgctgct attttctatt taataacacc    8640
tgttcatgtc atgtctaaac atactgactt tcaagtgaa atcataggat acaaggctat     8700
tgatggtggt gtcactcgtg acatagcatc tacagatact tgttttgcta caaacatgc     8760 tgattttgac acatggttta gccagcgtgg tggtagttat actaatgaca agcttgccc     8820 attgattgct gcagtcataa caagagaagt gggttttgtc gtgcctggtt tgcctggcac    8880
gatattacgc acaactaatg gtgactttt gcatttctta cctagagttt ttagtgcagt    8940
tggtaacatc tgttacacac catcaaaact tatagagtac actgactttg caacatcagc    9000
ttgtgttttg gctgctgaat gtacaatttt taaagatgct tctggtaagc cagtaccata    9060
ttgttatgat accaatgtac tagaaggttc tgttgcttat gaaagtttac gccctgacac    9120
acgttatgtg ctcatggatg gctctattat tcaatttcct aacacctacc ttgaaggttc    9180
tgttagagtg gtaacaactt ttgattctga gtactgtagg cacggcactt gtgaaagatc    9240
agaagctggt gttttgtgtat ctactagtgg tagatgggta cttaacaatg attattacag    9300
atctttacca ggagttttct gtggtgtaga tgctgtaaat ttacttacta atatgtttac    9360
accactaatt caacctattg gtgctttgga catatcagca tctatagtag ctggtggtat    9420
tgtagctatc gtagtaacat gccttgccta ctatttatg aggtttagaa gagcttttgg    9480
tgaatacagt catgtagttg cctttaatac tttactattc cttatgtcat tcactgtact    9540
ctgtttaaca ccagtttact cattcttacc tggtgtttat tctgttattt acttgtactt    9600
gacattttat cttactaatg atgtttcttt tttagcacat attcagtgga tggttatgtt    9660 cacacccttta gtacctttct ggataacaat tgcttatatc atttgtattt ccacaaagca    9720
tttctattgg ttctttagta attacctaaa gagacgtgta gtctttaatg gtgtttcctt    9780
tagtactttt gaagaagctg cgctgtgcac cttttttgtta aataaagaaa tgtatctaaa    9840
gttgcgtagt gatgtgctat tacctcttac gcaatataat agatacttag ctctttataa    9900
taagtacaag tattttagtg gagcaatgga tacaactagc tacagagaag ctgcttgttg    9960
tcatctcgca aaggctctca atgacttcag taactcaggt tctgatgttc tttaccaacc   10020
accacaaacc tctatcacct cagctgtttt gcagagtggt tttagaaaaa tggcattccc   10080
atctggtaaa gttgagggtt gtatggtaca agtaacttgt ggtacaacta cacttaacgg   10140
```

```
tctttggctt gatgacgtag tttactgtcc aagacatgtg atctgcacct ctgaagacat   10200
gcttaaccct aattatgaag atttactcat tcgtaagtct aatcataatt tcttggtaca   10260
ggctggtaat gttcaactca gggttattgg acattctatg caaaattgtg tacttaagct   10320
taaggttgat acagccaatc ctaagacacc taagtataag tttgttcgca ttcaaccagg   10380
acagactttt tcagtgttag cttgttacaa tggttcacca tctggtgttt accaatgtgc   10440
tatgaggccc aatttcacta ttaagggttc attccttaat ggttcatgtg gtagtgttgg   10500
ttttaacata gattatgact gtgtctcttt tgttacatg caccatatgg aattaccaac    10560
tggagttcat gctggcacag acttagaagg taacttttat ggaccttttg ttgacaggca   10620
aacagcacaa gcagctggta cggacacaac tattacagtt aatgttttag cttggttgta   10680
cgctgctgtt ataaatggag acaggtggtt tctcaatcga tttaccacaa ctcttaatga   10740
ctttaacctt gtggctatga agtacaatta tgaacctcta acacaagacc atgttgacat   10800
actaggacct ctttctgctc aaactggaat tgccgtttta gatatgtgtg cttcattaaa   10860
agaattactg caaaatggta tgaatggacg taccatattg ggtagtgctt tattagaaga   10920
tgaatttaca ccttttgatg ttgttagaca atgctcaggt gttactttcc aaagtgcagt   10980
gaaaagaaca atcaagggta cacaccactg gttgttactc acaattttga cttcacttttt   11040 agttttagtc cagagtactc aatggtcttt gttcttttt ttgtatgaaa atgccttttt   11100
accttttgct atgggtatta ttgctatgtc tgcttttgca atgatgtttg tcaaacataa   11160
gcatgcattt ctctgtttgt ttttgttacc ttctcttgcc actgtagctt attttaatat   11220
ggtctatatg cctgctagtt gggtgatgcg tattatgaca tggttggata tggttgatac   11280
tagtttgtct ggttttaagc taaaagactg tgttatgtat gcatcagctg tagtgttact   11340
aatccttatg acagcaagaa ctgtgtatga tgatggtgct aggagagtgt ggacacttat   11400
gaatgtcttg acactcgttt ataaagttta ttatggtaat gctttagatc aagccatttc   11460
catgtgggct cttataatct ctgttacttc taactactca ggtgtagtta caactgtcat   11520 gttttttggcc agaggtattg tttttatgtg tgttgagtat tgccctattt tcttcataac   11580
tggtaataca cttcagtgta taatgctagt ttattgtttc ttaggctatt tttgtacttg   11640
ttactttggc ctcttttgtt tactcaaccg ctactttaga ctgactcttg gtgtttatga   11700
ttacttagtt tctacacagg agtttagata tatgaattca cagggactac tcccacccaa   11760
gaatagcata gatgccttca aactcaacat taaattgttg ggtgttggtg gcaaaccttg   11820
tatcaaagta gccactgtac agtctaaaat gtcagatgta aagtgcacat cagtagtctt   11880
actctcagtt ttgcaacaac tcagagtaga atcatcatct aaattgtggg ctcaatgtgt   11940
ccagttacac aatgacattc tcttagctaa agatactact gaagcctttg aaaaaatggt   12000
ttcactactt tctgttttgc tttccatgca gggtgctgta gacataaaca agctttgtga   12060
agaaatgctg gacaacaggg caaccttaca agctatagcc tcagagttta gttcccttcc   12120
atcatatgca gcttttgcta ctgctcaaga agcttatgag caggctgttg ctaatggtga   12180
ttctgaagtt gttcttaaaa agttgaagaa gtctttgaat gtggctaaat ctgaatttga   12240
ccgtgatgca gccatgcaac gtaagttgga aaagatggct gatcaagcta tgacccaaat   12300
gtataaacag gctagatctg aggacaagag ggcaaaagtt actagtgcta tgcagacaat   12360
gcttttcact atgcttagaa agttggataa tgatgcactc aacaacatta tcaacaatgc   12420
aagagatggt tgtgttccct tgaacataat acctcttaca acagcagcca aactaatggt   12480
```

```
tgtcatacca gactataaca catataaaaa tacgtgtgat ggtacaacat ttacttatgc   12540
atcagcattg tgggaaatcc aacaggttgt agatgcagat agtaaaattg ttcaacttag   12600
tgaaattagt atggacaatt cacctaattt agcatggcct cttattgtaa cagctttaag   12660
ggccaattct gctgtcaaat tacagaataa tgagcttagt cctgttgcac tacgacagat   12720
gtcttgtgct gccggtacta cacaaactgc ttgcactgat gacaatgcgt tagcttacta   12780
caacacaaca aagggaggta ggtttgtact tgcactgtta tccgatttac aggatttgaa   12840
atgggctaga ttccctaaga gtgatggaac tggtactatc tatacagaac tggaaccacc   12900
ttgtaggttt gttacagaca cacctaaagg tcctaaagtg aagtatttat actttattaa   12960
aggattaaac aacctaaata gaggtatggt acttggtagt ttagctgcca cagtacgtct   13020
acaagctggt aatgcaacag aagtgcctgc caattcaact gtattatctt tctgtgcttt   13080
tgctgtagat gctgctaaag cttacaaaga ttatctagct agtgggggac aaccaatcac   13140
taattgtgtt aagatgttgt gtacacacac tggtactggt caggcaataa cagttacacc   13200
ggaagccaat atggatcaag aatcctttgg tggtgcatcg tgttgtctgt actgccgttg   13260
ccacatagat catccaaatc ctaaaggatt ttgtgactta aaaggtaagt atgtacaaat   13320
acctacaact tgtgctaatg accctgtggg ttttacactt aaaaacacag tctgtaccgt   13380
ctgcggtatg tggaaaggtt atggctgtag ttgtgatcaa ctccgcgaac ccatgcttca   13440
gtcagctgat gcacaatcgt ttttaaacgg gtttgcggtg taagtgcagc ccgtcttaca   13500
ccgtgcggca caggcactag tactgatgtc gtatacaggg cttttgacat ctacaatgat   13560
aaagtagctg gttttgctaa attcctaaaa actaattgtt gtcgcttcca agaaaaggac   13620
gaagatgaca atttaattga ttcttacttt gtagttaaga gacacacttt ctctaactac   13680
caacatgaag aaacaattta taatttactt aaggattgtc cagctgttgc taaacatgac   13740
ttctttaagt ttagaataga cggtgacatg gtaccacata tatcacgtca acgtcttact   13800
aaatacacaa tggcagacct cgtctatgct ttaaggcatt ttgatgaagg taattgtgac   13860
acattaaaag aaatacttgt cacatacaat tgttgtgatg atgattattt caataaaaag   13920
gactggtatg attttgtaga aaacccagat atattacgcg tatacgccaa cttaggtgaa   13980
cgtgtacgcc aagctttgtt aaaaacagta caattctgtg atgccatgcg aaatgctggt   14040
attgttggtg tactgacatt agataatcaa gatctcaatg gtaactggta tgatttcggt   14100
gatttcatac aaaccacgcc aggtagtgga gttcctgttg tagattctta ttattcattg   14160
ttaatgccta tattaccctt gaccagggct taactgcag agtcacatgt tgacactgac   14220
ttaacaaagc cttacattaa gtgggatttg ttaaaatatg acttcacgga agagaggtta   14280
aaactctttg accgttattt taaatattgg gatcagacat accacccaaa ttgtgttaac   14340
tgtttggatg acagatgcat tctgcattgt gcaaacttta tgtttttatt ctctacagtg   14400
ttcccaccta caagttttgg accactagtg agaaaaatat tgttgatgg tgttccattt   14460 gtagtttcaa ctggatacca cttcagagag ctaggtgttg tacataatca ggatgtaaac   14520
ttacatagct ctagacttag ttttaaggaa ttacttgtgt atgctgctga ccctgctatg   14580
cacgctgctt ctggtaatct attactagat aaacgcacta cgtgcttttc agtagctgca   14640
cttactaaca atgttgcttt tcaaactgtc aaacccggta attttaacaa agacttctat   14700
gactttgctg tgtctaaggg tttctttaag gaaggaagtt ctgttgaatt aaaacacttc   14760
ttctttgctc aggatggtaa tgctgctatc agcgattatg actactatcg ttataatcta   14820
ccaacaatgt gtgatatcag acaactacta tttgtagttg aagttgttga taagtacttt   14880
```

```
gattgttacg atggtggctg tattaatgct aaccaagtca tcgtcaacaa cctagacaaa   14940
tcagctggtt ttccatttaa taaatggggt aaggctagac tttattatga ttcaatgagt   15000
tatgaggatc aagatgcact tttcgcatat acaaaacgta atgtcatccc tactataact   15060
caaatgaatc ttaagtatgc cattagtgca aagaatagag ctcgcaccgt agctggtgtc   15120
tctatctgta gtactatgac caatagacag tttcatcaaa aattattgaa atcaatagcc   15180
gccactagag gagctactgt agtaattgga acaagcaaat tctatggtgg ttggcacaac   15240
atgttaaaaa ctgtttatag tgatgtagaa acccctcacc ttatgggttg ggattatcct   15300
aaatgtgata gagccatgcc taacatgctt agaattatgg cctcacttgt tcttgctcgc   15360
aaacatacaa cgtgttgtag cttgtcacac cgtttctata gattagctaa tgagtgtgct   15420
caagtattga gtgaaatggt catgtgtggc ggttcactat atgttaaacc aggtggaacc   15480
tcatcaggag atgccacaac tgcttatgct aatagtgttt ttaacatttg tcaagctgtc   15540
acggccaatg ttaatgcact tttatctact gatggtaaca aaattgccga taagtatgtc   15600
cgcaatttac aacacagact ttatgagtgt ctctatagaa atagagatgt tgacacagac   15660
tttgtgaatg agttttacgc atatttgcgt aaacatttct caatgatgat actctctgac   15720
gatgctgttg tgtgtttcaa tagcacttat gcatctcaag gtctagtggc tagcataaag   15780
aactttaagt cagttcttta ttatcaaaac aatgttttta tgtctgaagc aaaatgttgg   15840
actgagactg accttactaa aggacctcat gaattttgct ctcaacatac aatgctagtt   15900
aaacagggtg atgattatgt gtaccttcct tacccagatc catcaagaat cctaggggcc   15960
ggctgttttg tagatgatat cgtaaaaaca gatggtacac ttatgattga acggttcgtg   16020
tctttagcta tagatgctta cccacttact aaacatccta atcaggagta tgctgatgtc   16080
tttcatttgt acttacaata cataagaaag ctacatgatg agttaacagg acacatgtta   16140
gacatgtatt ctgttatgct tactaatgat aacacttcaa ggtattggga acctgagttt   16200
tatgaggcta tgtacacacc gcatacagtc ttacaggctg ttgggcttg tgttctttgc   16260 aattcacaga cttcattaag atgtggtgct tgcatacgta gaccattctt atgttgtaaa   16320
tgctgttacg accatgtcat atcaacatca cataaattag tcttgtctgt taatccgtat   16380
gtttgcaatg ctccaggttg tgatgtcaca gatgtgactc aactttactt aggaggtatg   16440
agctattatt gtaaatcaca taaaccaccc attagttttc cattgtgtgc taatggacaa   16500
gtttttggtt tatataaaaa tacatgtgtt ggtagcgata atgttactga ctttaatgca   16560
attgcaacat gtgactggac aaatgctggt gattacattt tagctaacac ctgtactgaa   16620
agactcaagc tttttgcagc agaaacgctc aaagctactg aggagacatt taaactgtct   16680
tatggtattg ctactgtacg tgaagtgctg tctgacagaa aattacatct ttcatgggaa   16740
gttggtaaac ctagaccacc acttaaccga aattatgtct ttactggtta tcgtgtaact   16800
aaaaacagta agtacaaat aggagagtac acctttgaaa aaggtgacta tggtgatgct   16860
gttgtttacc gaggtacaac aacttacaaa ttaaatgttg gtgattattt tgtgctgaca   16920
tcacatacag taatgccatt aagtgcacct acactagtgc cacaagagca ctatgttaga   16980
attactggct tatacccaac actcaatatc tcagatgagt tttctagcaa tgttgcaaat   17040
tatcaaaagg ttggtatgca aaagtattct acactccagg gaccacctgg tactggtaag   17100
agtcattttg ctattggcct agctctctac taccctttct ctcgcatagt gtatacagct   17160
tgctctcatg ccgctgttga tgcactatgt gagaaggcat taaaatattt gcctatagat   17220
```

```
aaatgtagta gaattatacc tgcacgtgct cgtgtagagt gttttgataa attcaaagtg   17280
aattcaacat tagaacagta tgtcttttgt actgtaaatg cattgcctga gacgacagca   17340
gatatagttg tctttgatga aatttcaatg gccacaaatt atgatttgag tgttgtcaat   17400
gccagattac gtgctaagca ctatgtgtac attggcgacc ctgctcaatt acctgcacca   17460
cgcacattgc taactaaggg cacactagaa ccagaatatt tcaattcagt gtgtagactt   17520
atgaaaacta taggtccaga catgttcctc ggaacttgtc ggcgttgtcc tgctgaaatt   17580
gttgacactg tgagtgcttt ggtttatgat aataagctta aagcacataa agacaaatca   17640
gctcaatgct ttaaaatgtt ttataagggt gttatcacgc atgatgtttc atctgcaatt   17700
aacaggccac aaataggcgt ggtaagagaa ttccttacac gtaaccctgc ttggagaaaa   17760
gctgtcttta tttcacctta taattcacag aatgctgtag cctcaaagat tttgggacta   17820
ccaactcaaa ctgttgattc atcacagggc tcagaatatg actatgtcat attcactcaa   17880
accactgaaa cagctcactc ttgtaatgta aacagattta atgttgctat taccagagca   17940
aaagtaggca tactttgcat aatgtctgat agagaccttt atgacaagtt gcaatttaca   18000
agtcttgaaa ttccacgtag gaatgtggca actttacaag ctgaaaatgt aacaggactc   18060
tttaaagatt gtagtaaggt aatcactggg ttacatccta cacaggcacc tacacacctc   18120
agtgttgaca ctaaattcaa aactgaaggt ttatgtgttg atatacctgg catacctaag   18180
gacatgacct atagaagact catctctatg atgggtttta aaatgaatta tcaagttaat   18240
ggttacccta acatgtttat cacccgcgaa gaagctataa gacatgtacg tgcatggatt   18300
ggcttcgatg tcgaggggtg tcatgctact agagaagctg ttggtaccaa tttacccttta   18360 cagctaggtt tttctacagg tgttaaccta gttgctgtac ctacaggtta tgttgataca   18420
cctaataata cagatttttc cagagttagt gctaaaccac cgcctggaga tcaatttaaa   18480
cacctcatac cacttatgta caaggacttt ccttggaatg tagtgcgtat aaagattgta   18540
caaatgttaa gtgacacact taaaaatctc tctgacagag tcgtatttgt cttatgggca   18600
catggctttg agttgacatc tatgaagtat tttgtgaaaa taggacctga gcgcacctgt   18660
tgtctatgtg atagacgtgc cacatgcttt tccactgctt cagacactta tgcctgttgg   18720
catcattcta ttggatttga ttacgtctat aatccgttta tgattgatgt tcaacaatgg   18780
ggttttacag gtaacctaca aagcaaccat gatctgtatt gtcaagtcca tggtaatgca   18840
catgtagcta gttgtgatgc aatcatgact aggtgtctag ctgtccacga gtgctttgtt   18900
aagcgtgttg actggactat tgaatatcct ataattggtg atgaactgaa gattaatgcg   18960
gcttgtagaa aggttcaaca catggttgtt aaagctgcat tattagcaga caaattccca   19020
gttcttcacg acattggtaa ccctaaagct attaagtgtg tacctcaagc tgatgtagaa   19080
tggaagttct atgatgcaca gccttgtagt gacaaagctt ataaaataga agaattattc   19140
tattcttatg ccacacattc tgacaaattc acagatggtg tatgcctatt ttggaattgc   19200
aatgtcgata gatatcctgc taattccatt gtttgtagat ttgacactag agtgctatct   19260
aaccttaact tgcctggttg tgatggtggc agtttgtatg taaataaaca tgcattccac   19320
acaccagctt ttgataaaag tgcttttgtt aatttaaaac aattaccatt tttctattac   19380
tctgacagtc catgtgagtc tcatggaaaa caagtagtgt cagatataga ttatgtacca   19440
ctaaagtctg ctacgtgtat aacacgttgc aatttaggtg gtgctgtctg tagacatcat   19500
gctaatgagt acagattgta tctcgatgct tataacatga tgatctcagc tggctttagc   19560
ttgtgggttt acaaacaatt tgatacttat aacctctgga acacttttac aagacttcag   19620
```

```
agtttagaaa atgtggcttt taatgttgta aataagggac actttgatgg acaacagggt   19680
gaagtaccag tttctatcat taataacact gtttacacaa aagttgatgg tgttgatgta   19740
gaattgtttg aaaataaaac aacattacct gttaatgtag catttgagct ttgggctaag   19800
cgcaacatta aaccagtacc agaggtgaaa atactcaata atttgggtgt ggacattgct   19860
gctaatactg tgatctggga ctacaaaaga gatgctccag cacatatatc tactattggt   19920
gtttgttcta tgactgacat agccaagaaa ccaactgaaa cgatttgtgc accactcact   19980
gtcttttttg atggtagagt tgatggtcaa gtagacttat ttagaaatgc ccgtaatggt   20040
gttcttatta cagaaggtag tgttaaaggt ttacaaccat ctgtaggtcc caaacaagct   20100
agtcttaatg gagtcacatt aattggagaa gccgtaaaaa cacagttcaa ttattataag   20160
aaagttgatg gtgttgtcca acaattacct gaaacttact ttactcagag tagaaattta   20220
caagaattta aacccaggag tcaaatggaa attgatttct tagaattagc tatggatgaa   20280
ttcattgaac ggtataaatt agaaggctat gccttcgaac atatcgttta tggagatttt   20340
agtcatagtc agttaggtgg tttacatcta ctgattggac tagctaaacg ttttaaggaa   20400 tcacctttg aattagaaga ttttattcct atggacagta cagttaaaaa ctatttcata   20460
acagatgcgc aaacaggttc atctaagtgt gtgtgttctg ttattgattt attacttgat   20520
gattttgttg aaataataaa atcccaagat ttatctgtag tttctaaggt tgtcaaagtg   20580
actattgact atacagaaat ttcatttatg ctttggtgta agatggcca tgtagaaaca   20640 ttttacccaa aattcaaatc tagtcaagcg tggcaaccgg gtgttgctat gcctaatctt   20700
tacaaaatgc aaagaatgct attagaaaag tgtgaccttc aaaattatgg tgatagtgca   20760
acattaccta aaggcataat gatgaatgtc gcaaaatata ctcaactgtg tcaatattta   20820
aacacattaa cattagctgt acctataat atgagagtta tacattttgg tgctggttct   20880
gataaaggag ttgcaccagg tacagctgtt ttaagacagt ggttgcctac gggtacgctg   20940
cttgtcgatt cagatcttaa tgactttgtc tctgatgcag attcaacttt gattggtgat   21000
tgtgcaactg tacatacagc taataaatgg gatctcatta ttagtgatat gtacgacct   21060 aagactaaaa atgttacaaa agaaaatgac tctaaagagg gttttttcac ttacatttgt   21120
gggtttatac aacaaagct agctcttgga ggttccgtgg ctataaagat aacagaacat   21180
tcttggaatg ctgatctttta taagctcatg ggacacttcg catggtggac agcctttgtt   21240
actaatgtga atgcgtcatc atctgaagca tttttaattg gatgtaatta tcttggcaaa   21300
ccacgcgaac aaatagatgg ttatgtcatg catgcaaatt acatattttg gaggaataca   21360
aatccaattc agttgtcttc ctattcttta tttgacatga gtaaatttcc ccttaaatta   21420
aggggtactg ctgttatgtc tttaaaagaa ggtcaaatca atgatatgat ttatctctct   21480
cttagtaaag gtagacttat aattagagaa acaacagag ttgttatttc tagtgatgtt   21540
cttgttaaca actaaacgaa caatgtttgt ttttcttgtt ttattgccac tagtctctag   21600
tcagtgtgtt aatcttacaa ccagaactca attacccct gcatacacta attctttcac   21660
acgtggtgtt tattaccctg acaaagtttt cagatcctca gttttacatt caactcagga   21720
cttgttctta cctttctttt ccaatgttac ttggttccat gctatacatg tctctgggac   21780
caatggtact aagaggtttg ataaccctgt cctaccattt aatgatggtg tttatttgc   21840 ttccactgag aagtctaaca taataagagg ctggattttt ggtactactt tagattcgaa   21900
gacccagtcc ctacttattg ttaataacgc tactaatgtt gttattaaag tctgtgaatt   21960
```

```
tcaattttgt aatgatccat ttttgggtgt ttattaccac aaaaacaaca aaagttggat   22020
ggaaagtgag ttcagagttt attctagtgc gaataattgc acttttgaat atgtctctca   22080
gccttttctt atggaccttg aaggaaaaca gggtaatttc aaaaatctta gggaatttgt   22140
gtttaagaat attgatggtt attttaaaat atattctaag cacacgccta ttaatttagt   22200
gcgtgatctc cctcagggtt tttcggcttt agaaccattg gtagatttgc caataggtat   22260
taacatcact aggtttcaaa ctttacttgc tttacataga agttatttga ctcctggtga   22320
ttcttcttca ggttggacag ctggtgctgc agcttattat gtgggttatc ttcaacctag   22380
gacttttcta ttaaaatata atgaaaatgg aaccattaca gatgctgtag actgtgcact   22440
tgaccctctc tcagaaacaa agtgtacgtt gaaatccttc actgtagaaa aaggaatcta   22500
tcaaacttct aactttagag tccaaccaac agaatctatt gttagatttc ctaatattac   22560
aaacttgtgc ccttttggtg aagttttaa cgccaccaga tttgcatctg tttatgcttg   22620
gaacaggaag agaatcagca actgtgttgc tgattattct gtcctatata attccgcatc   22680
attttccact tttaagtgtt atggagtgtc tcctactaaa ttaaatgatc tctgctttac   22740
taatgtctat gcagattcat ttgtaattag aggtgatgaa gtcagacaaa tcgctccagg   22800
gcaaactgga aagattgctg attataatta taaattacca gatgatttta caggctgcgt   22860
tatagcttgg aattctaaca atcttgattc taaggttggt ggtaattata attacctgta   22920
tagattgttt aggaagtcta atctcaaacc ttttgagaga gatatttcaa ctgaaatcta   22980
tcaggccggt agcacacctt gtaatggtgt tgaaggtttt aattgttact tcccttaca   23040 atcatatggt ttccaaccca ctaatggtgt tggttaccaa ccatacagag tagtagtact   23100
ttcttttgaa cttctacatg caccagcaac tgtttgtgga cctaaaaagt ctactaattt   23160
ggttaaaaac aaatgtgtca atttcaactt caatggttta acaggcacag gtgttcttac   23220
tgagtctaac aaaaagtttc tgcctttcca acaatttggc agagacattg ctgacactac   23280
tgatgctgtc cgtgatccac agacacttga gattcttgac attacaccat gttcttttgg   23340
tggtgtcagt gttataacac caggaacaaa tacttctaac caggttgctg ttctttatca   23400
ggatgttaac tgcacagaag tccctgttgc tattcatgca gatcaactta ctcctacttg   23460
gcgtgtttat tctacaggtt ctaatgtttt tcaaacacgt gcaggctgtt taataggggc   23520
tgaacatgtc aacaactcat atgagtgtga catacccatt ggtgcaggta tatgcgctag   23580
ttatcagact cagactaatt ctcctcggcg ggcacgtagt gtagctagtc aatccatcat   23640
tgcctacact atgtcacttg gtgcagaaaa ttcagttgct tactctaata actctattgc   23700
catacccaca aattttacta ttagtgttac cacagaaatt ctaccagtgt ctatgaccaa   23760
gacatcagta gattgtacaa tgtacatttg tggtgattca actgaatgca gcaatctttt   23820
gttgcaatat ggcagttttt gtacacaatt aaaccgtgct ttaactggaa tagctgttga   23880
acaagacaaa aacacccaag aagtttttgc acaagtcaaa caaatttaca aaacaccacc   23940
aattaaagat tttggtggtt ttaatttttc acaaatatta ccagatccat caaaaccaag   24000
caagaggtca tttattgaag atctactttt caacaaagtg acacttgcag atgctggctt   24060
catcaaacaa tatggtgatt gccttggtga tattgctgct agagacctca tttgtgcaca   24120
aaagtttaac ggccttactg ttttgccacc tttgctcaca gatgaaatga ttgctcaata   24180
cacttctgca ctgttagcgg gtacaatcac ttctggttgg acctttggtg caggtgctgc   24240
attacaaata ccatttgcta tgcaaatggc ttataggttt aatggtattg gagttacaca   24300
gaatgttctc tatgagaacc aaaaattgat tgccaaccaa tttaatagtg ctattggcaa   24360
```

```
aattcaagac tcactttctt ccacagcaag tgcacttgga aaacttcaag atgtggtcaa   24420
ccaaaatgca caagctttaa acacgcttgt taaacaactt agctccaatt ttggtgcaat   24480
ttcaagtgtt ttaaatgata tcctttcacg tcttgacaaa gttgaggctg aagtgcaaat   24540
tgataggttg atcacaggca gacttcaaag tttgcagaca tatgtgactc aacaattaat   24600
tagagctgca gaaatcagag cttctgctaa tcttgctgct actaaaatgt cagagtgtgt   24660
acttggacaa tcaaaagag ttgattttg tggaaagggc tatcatctta tgtccttccc     24720
tcagtcagca cctcatggtg tagtcttctt gcatgtgact tatgtccctg cacaagaaaa   24780
gaacttcaca actgctcctg ccatttgtca tgatggaaaa gcacactttc ctcgtgaagg   24840
tgtctttgtt tcaaatggca cacactggtt tgtaacacaa aggaattttt atgaaccaca   24900
aatcattact acagacaaca catttgtgtc tggtaactgt gatgttgtaa taggaattgt   24960
caacaacaca gtttatgatc ctttgcaacc tgaattagac tcattcaagg aggagttaga   25020
taaatatttt aagaatcata catcaccaga tgttgattta ggtgacatct ctggcattaa   25080
tgcttcagtt gtaaacattc aaaaagaaat tgaccgcctc aatgaggttg ccaagaattt   25140
aaatgaatct ctcatcgatc tccaagaact tggaaagtat gagcagtata taaaatggcc   25200
atggtacatt tggctaggtt ttatagctgg cttgattgcc atagtaatgg tgacaattat   25260
gctttgctgt atgaccagtt gctgtagttg tctcaagggc tgttgttctt gtggatcctg   25320
ctgcaaattt gatgaagacg actctgagcc agtgctcaaa ggagtcaaat tacattacac   25380
ataaacgaac ttatggattt gtttatgaga atcttcacaa ttggaactgt aactttgaag   25440
caaggtgaaa tcaaggatgc tactccttca gattttgttc gcgctactgc aacgataccg   25500
atacaagcct cactccctt cggatggctt attgttggcg ttgcacttct tgctgttttt   25560
cagagcgctt ccaaaatcat aaccctcaaa aagagatggc aactagcact ctccaagggt   25620
gttcactttg tttgcaactt gctgttgttg tttgtaacag tttactcaca cctttttgctc  25680 gttgctgctg gccttgaagc ccctttttctc tatctttatg ctttagtcta cttcttgcag   25740
agtataaact ttgtaagaat aataatgagg ctttggcttt gctggaaatg ccgttccaaa   25800
aacccattac tttatgatgc caactatttt ctttgctggc atactaattg ttacgactat   25860 tgtataccctt acaatagtgt aacttcttca attgtcatta cttcaggtga tggcacaaca   25920
agtcctattt ctgaacatga ctaccagatt ggtggttata ctgaaaaatg gaatctgga    25980 gtaaaagact gtgttgtatt acacagttac ttcacttcag actattacca gctgtactca   26040
actcaattga gtacagacac tggtgttgaa catgttacct tcttcatcta caataaaatt   26100
gttgatgagc ctgaagaaca tgtccaaatt cacacaatcg acggttcatc cggagttgtt   26160
aatccagtaa tggaaccaat ttatgatgaa ccgacgacga ctactagcgt gcctttgtaa   26220
gcacaagctg atgagtacga acttatgtac tcattcgttt cggaagagac aggtacgtta   26280
atagttaata gcgtacttct tttctttgct ttcgtggtat tcttgctagt tacactagcc   26340
atccttactg cgcttcgatt gtgtgcgtac tgctgcaata ttgttaacgt gagtcttgta   26400
aaaccttctt tttacgttta ctctcgtgtt aaaaatctga attcttctag agttcctgat   26460
cttctggtct aaacgaacta atattatat tagttttttct gtttggaact ttaattttag   26520
ccatggcaga ttccaacggt actattaccg ttgaagagct taaaaagctc cttgaacaat   26580
ggaacctagt aataggtttc ctattcctta catggatttg tcttctacaa tttgcctatg   26640
ccaacaggaa taggtttttg tatataatta agttaatttt cctctggctg ttatggccag   26700
```

```
taactttagc ttgttttgtg cttgctgctg tttacagaat aaattggatc accggtggaa    26760
ttgctatcgc aatggcttgt cttgtaggct tgatgtggct cagctacttc attgcttctt    26820
tcagactgtt tgcgcgtacg cgttccatgt ggtcattcaa tccagaaact aacattcttc    26880
tcaacgtgcc actccatggc actattctga ccagaccgct tctagaaagt gaactcgtaa    26940
tcggagctgt gatccttcgt ggacatcttc gtattgctgg acaccatcta ggacgctgtg    27000
acatcaagga cctgcctaaa gaaatactg ttgctacatc acgaacgctt tcttattaca     27060
aattgggagc ttcgcagcgt gtagcaggtg actcaggttt tgctgcatac agtcgctaca    27120
ggattggcaa ctataaatta aacacagacc attccagtag cagtgacaat attgctttgc    27180
ttgtacagta agtgacaaca gatgtttcat ctcgttgact ttcaggttac tatagcagag    27240
atattactaa ttattatgag gacttttaaa gtttccattt ggaatcttga ttacatcata    27300
aacctcataa ttaaaaattt atctaagtca ctaactgaga ataaatattc tcaattagat    27360
gaagagcaac caatggagat tgattaaacg aacatgaaaa ttattctttt cttggcactg    27420
ataacactcg ctacttgtga gctttatcac taccaagagt gtgttagagg tacaacagta    27480
cttttaaaag aaccttgctc ttctggaaca tacgagggca attcaccatt tcatcctcta    27540
gctgataaca aatttgcact gacttgcttt agcactcaat ttgcttttgc ttgtcctgac    27600
ggcgtaaaac acgtctatca gttacgtgcc agatcagttt cacctaaaact gttcatcaga    27660 caagaggaag ttcaagaact ttactctcca attttcttta ttgttgcggc aatagtgttt    27720
ataacacttt gcttcacact caaaagaaag acagaatgat tgaactttca ttaattgact    27780
tctatttgtg ctttttagcc tttctgctat tccttgtttt aattatgctt attatctttt    27840
ggttctcact tgaactgcaa gatcataatg aaacttgtca cgcctaaacg aacatgaaat    27900
ttcttgtttt cttaggaatc atcacaactg tagctgcatt tcaccaagaa tgtagtttac    27960
agtcatgtac tcaacatcaa ccatatgtag ttgatgaccc gtgtcctatt cacttctatt    28020
ctaaatggta tattagagta ggagctagaa aatcagcacc tttaattgaa ttgtgcgtgg    28080
atgaggctgg ttctaaatca cccattcagt acatcgatat cggtaattat acagtttcct    28140
gtttaccttt tacaattaat tgccaggaac ctaaattggg tagtcttgta gtgcgttgtt    28200
cgttctatga agacttttta gagtatcatg acgttcgtgt tgttttagat ttcatctaaa    28260
cgaacaaact aaaatgtctg ataatggacc ccaaaatcag cgaaatgcac ccgcattac     28320 gtttggtgga cccctcagatt caactggcag taaccagaat ggagaacgca gtggggcgcg    28380
atcaaaacaa cgtcggcccc aaggtttacc aataatact gcgtcttggt tcaccgctct     28440
cactcaacat ggcaaggaag accttaaatt ccctcgagga caaggcgttc aattaacac     28500 caatagcagt ccagatgacc aaattggcta ctaccgaaga gctaccagac gaattcgtgg    28560
tggtgacggt aaaatgaaag atctcagtcc aagatggtat ttctactacc taggaactgg    28620
gccagaagct ggacttccct atggtgctaa caaagacggc atcatatggg ttgcaactga    28680
gggagccttg aatacaccaa aagatcacat tggcacccgc aatcctgcta acaatgctgc    28740
aatcgtgcta caacttcctc aaggaacaac attgccaaaa ggcttctacg cagaagggag    28800
cagaggcggc agtcaagcct cttctcgttc ctcatcacgt agtcgcaaca gttcaagaaa    28860
ttcaactcca ggcagcagta ggggaacttc tcctgctaga atggctggca atggcggtga    28920
tgctgctctt gctttgctgc tgcttgacag attgaaccag cttgagagca aaatgtctgg    28980
taaaggccaa caacaacaag gccaaactgt cactaagaaa tctgctgctg aggcttctaa    29040
gaagcctcgg caaaaacgta ctgccactaa agcatacaat gtaacacaag ctttcggcag    29100
```

```
acgtggtcca gaacaaaccc aaggaaattt tggggaccag gaactaatca gacaaggaac    29160
tgattacaaa cattggccgc aaattgcaca atttgccccc agcgcttcag cgttcttcgg    29220
aatgtcgcgc attggcatgg aagtcacacc ttcgggaacg tggttgacct acacaggtgc    29280
catcaaattg gatgacaaag atccaaattt caaagatcaa gtcattttgc tgaataagca    29340
tattgacgca tacaaaacat tcccaccaac agagcctaaa aaggacaaaa agaagaaggc    29400
tgatgaaact caagccttac cgcagagaca agagaaacag caaactgtga ctcttcttcc    29460
tgctgcagat ttggatgatt tctccaaaca attgcaacaa tccatgagca gtgctgactc    29520
aactcaggcc taaactcatg cagaccacac aaggcagatg ggctatataa acgttttcgc    29580
ttttccgttt acgatatata gtctactctt gtgcagaatg aattctcgta actacatagc    29640
acaagtagat gtagttaact ttaatctcac atagcaatct ttaatcagtg tgtaacatta    29700
gggaggactt gaaagagcca ccacattttc accgaggcca cgcggagtac gatcgagtgt    29760
acagtgaaca atgctaggga gagctgccta tatggaagag ccctaatgtg taaaattaat    29820
tttagtagtg ctatccccat gtgattttaa tagcttctta ggagaatgac aaaaaaaaaa    29880
aaaaaaaaaa aaaaaaaaaa aaa                                            29903
```

<210> SEQ ID NO 2
<211> LENGTH: 29882
<212> TYPE: DNA
<213> ORGANISM: Severe acute respiratory syndrome coronavirus 2 isolate 2019-nCoV/USA-WA1/2020

<400> SEQUENCE: 2

```
attaaaggtt tataccttcc caggtaacaa accaaccaac tttcgatctc ttgtagatct      60
gttctctaaa cgaactttaa aatctgtgtg gctgtcactc ggctgcatgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaagatgga gagccttgtc cctggtttca acgagaaaac     300
acacgtccaa ctcagtttgc ctgttttaca ggttcgcgac gtgctcgtac gtggctttgg     360
agactccgtg gaggaggtct tatcagaggc acgtcaacat cttaaagatg gcacttgtgg     420
cttagtagaa gttgaaaaag gcgttttgcc tcaacttgaa cagccctatg tgttcatcaa     480
acgttcggat gctcgaactg cacctcatgg tcatgttatg gttgagctgg tagcagaact     540
cgaaggcatt cagtacggtc gtagtggtga cacttggt gtccttgtcc ctcatgtggg     600
cgaaatacca gtggcttacc gcaaggttct tcttcgtaag aacggtaata aaggagctgg     660
tggccatagt tacggcgccg atctaaagtc atttgactta ggcgacgagc ttggcactga     720
tccttatgaa gattttcaag aaaactggaa cactaaacat agcagtggtg ttacccgtga     780
actcatgcgt gagcttaacg gaggggcata cactcgctat gtcgataaca acttctgtgg     840
ccctgatggc taccctcttg agtgcattaa agaccttcta gcacgtgctg gtaaagcttc     900
atgcactttg tccgaacaac tggactttat tgacactaag aggggtgtat actgctgccg     960
tgaacatgag catgaaattg cttggtacac ggaacgttct gaaaagagct atgaattgca    1020 gacaccttt gaaattaaat tggcaaagaa atttgacacc ttcaatgggg aatgtccaaa    1080
ttttgtattt cccttaaatt ccataatcaa gactattcaa ccaagggttg aaagaaaaa    1140 gcttgatggc tttatgggta gaattcgatc tgtctatcca gttgcgtcac caaatgaatg    1200
caaccaaatg tgcctttcaa ctctcatgaa gtgtgatcat tgtggtgaaa cttcatggca    1260
```

```
gacgggcgat tttgttaaag ccacttgcga attttgtggc actgagaatt tgactaaaga    1320
aggtgccact acttgtggtt acttacccca aaatgctgtt gttaaaattt attgtccagc    1380
atgtcacaat tcagaagtag gacctgagca tagtcttgcc gaataccata atgaatctgg    1440
cttgaaaacc attcttcgta agggtggtcg cactattgcc tttggaggct gtgtgttctc    1500
ttatgttggt tgccataaca agtgtgccta ttgggttcca cgtgctagcg ctaacatagg    1560
ttgtaaccat acaggtgttg ttggagaagg ttccgaaggt cttaatgaca accttcttga    1620
aatactccaa aaagagaaag tcaacatcaa tattgttggt gactttaaac ttaatgaaga    1680
gatcgccatt attttggcat cttttttctgc ttccacaagt gcttttgtgg aaactgtgaa    1740
aggtttggat tataaagcat tcaaacaaat tgttgaatcc tgtggtaatt ttaaagttac    1800
aaaaggaaaa gctaaaaaag gtgcctggaa tattggtgaa cagaaatcaa tactgagtcc    1860
tctttatgca tttgcatcag aggctgctcg tgttgtacga tcaattttct cccgcactct    1920
tgaaactgct caaaattctg tgcgtgtttt acagaaggcc gctataacaa tactagatgg    1980
aatttcacag tattcactga gactcattga tgctatgatg ttcacatctg atttggctac    2040
taacaatcta gttgtaatgg cctacattac aggtggtgtt gttcagttga cttcgcagtg    2100
gctaactaac atctttggca ctgtttatga aaaactcaaa cccgtccttg attggcttga    2160
agagaagttt aaggaaggtg tagagtttct tagagacggt tgggaaattg ttaaattat    2220
ctcaacctgt gcttgtgaaa tgtcggtgg acaaattgtc acctgtgcaa aggaaattaa    2280
ggagagtgtt cagacattct taagcttgt aaataaattt ttggctttgt gtgctgactc    2340
tatcattatt ggtggagcta aacttaaagc cttgaattta ggtgaaacat tgtcacgca    2400
ctcaaaggga ttgtacagaa agtgtgttaa atccagagaa gaaactggcc tactcatgcc    2460
tctaaaagcc ccaaaagaaa ttatcttctt agagggagaa acacttccca cagaagtgtt    2520
aacagaggaa gttgtcttga aaactggtga tttacaacca ttagaacaac ctactagtga    2580
agctgttgaa gctccattgg ttggtacacc agtttgtatt aacgggctta tgttgctcga    2640
aatcaaagac acagaaaagt actgtgccct tgcacctaat atgatggtaa caaacaatac    2700
cttcacactc aaaggcggtg caccaacaaa ggttactttt ggtgatgaca ctgtgataga    2760
agtgcaaggt tacaagagtg tgaatatcac ttttgaactt gatgaaagga ttgataaagt    2820
acttaatgag aagtgctctg cctatacagt tgaactcggt acagaagtaa atgagttcgc    2880
ctgtgttgtg gcagatgctg tcataaaaac tttgcaacca gtatctgaat tacttacacc    2940
actgggcatt gatttagatg agtggagtat ggctacatac tacttatttg atgagtctgg    3000
tgagtttaaa ttggcttcac atatgtattg ttctttctac cctccagatg aggatgaaga    3060
agaaggtgat tgtgaagaag aagagtttga gccatcaact caatatgagt atggtactga    3120
agatgattac caaggtaaac ctttggaatt tggtgccact tctgctgctc ttcaacctga    3180
agaagagcaa gaagaagatt ggttagatga tgatagtcaa caaactgttg gtcaacaaga    3240
cggcagtgag gacaatcaga caactactat tcaaacaatt gttgaggttc aacctcaatt    3300
agagatggaa cttacaccag ttgttcagac tattgaagtg aatagtttta gtggttattt    3360
aaaacttact gacaatgtat acattaaaaa tgcagacatt gtggaagaag ctaaaaaggt    3420
aaaaccaaca gtggttgtta atgcagccaa tgtttacctt aaacatggag gaggtgttgc    3480
aggagcctta aataaggcta ctaacaatgc catgcaagtt gaatctgatg attacatagc    3540
tactaatgga ccacttaaag tgggtggtag ttgtgtttta agcggacaca atcttgctaa    3600
```

-continued

```
acactgtctt catgttgtcg gcccaaatgt taacaaaggt gaagacattc aacttcttaa    3660
gagtgcttat gaaaatttta atcagcacga agttctactt gcaccattat tatcagctgg    3720
tattttggt gctgacccta tacattcttt aagagtttgt gtagatactg ttcgcacaaa    3780
tgtctactta gctgtctttg ataaaaatct ctatgacaaa cttgtttcaa gcttttgga    3840
aatgaagagt gaaaagcaag ttgaacaaaa gatcgctgag attcctaaag aggaagttaa    3900
gccatttata actgaaagta aaccttcagt tgaacagaga aaacaagatg ataagaaaat    3960
caaagcttgt gttgaagaag ttacaacaac tctggaagaa actaagttcc tcacagaaaa    4020
cttgttactt tatattgaca ttaatggcaa tcttcatcca gattctgcca ctcttgttag    4080
tgacattgac atcactttct taaagaaaga tgctccatat atagtgggtg atgttgttca    4140
agagggtgtt ttaactgctg tggttatacc tactaaaaag gctggtggca ctactgaaat    4200
gctagcgaaa gctttgagaa aagtgccaac agacaattat ataaccactt acccgggtca    4260
gggtttaaat ggttacactg tagaggaggc aaagacagtg cttaaaaagt gtaaaagtgc    4320
cttttacatt ctaccatcta ttatctctaa tgagaagcaa gaaattcttg gaactgtttc    4380
ttggaatttg cgagaaatgc ttgcacatgc agaagaaaca cgcaaattaa tgcctgtctg    4440
tgtggaaact aaagccatag tttcaactat acagcgtaaa tataagggta ttaaaataca    4500
agagggtgtg gttgattatg gtgctagatt ttacttttac accagtaaaa caactgtagc    4560
gtcacttatc aacacactta acgatctaaa tgaaactctt gttacaatgc cacttggcta    4620
tgtaacacat ggcttaaatt tggaagaagc tgctcggtat atgagatctc tcaaagtgcc    4680
agctacagtt tctgtttctt cacctgatgc tgttacagcg tataatggtt atcttacttc    4740
ttcttctaaa acacctgaag aacattttat tgaaaccatc tcacttgctg gttcctataa    4800
agattggtcc tattctggac aatctacaca actaggtata gaatttctta agagaggtga    4860
taaaagtgta tattacacta gtaatcctac cacattccac ctagatggtg aagttatcac    4920
ctttgacaat cttaagacac ttctttcttt gagagaagtg aggactatta aggtgtttac    4980
aacagtagac aacattaacc tccacacgca agttgtggac atgtcaatga catatggaca    5040
acagtttggt ccaacttatt tggatggagc tgatgttact aaaataaaac ctcataattc    5100
acatgaaggt aaaacatttt atgttttacc taatgatgac actctacgtg ttgaggcttt    5160
tgagtactac cacacaactg atccagtttt tctgggtagg tacatgtcag cattaaatca    5220
cactaaaaag tggaaatacc cacaagttaa tggtttaact tctattaaat gggcagataa    5280
caactgttat cttgccactg cattgttaac actccaacaa atagagttga gtttaatcc    5340
acctgctcta caagatgctt attacagagc aagggctggt gaagctgcta acttttgtgc    5400
acttatctta gcctactgta ataagacagt aggtgagtta ggtgatgtta gagaaacaat    5460
gagttacttg tttcaacatg ccaatttaga ttcttgcaaa agagtcttga cgtggtgtg    5520
taaaacttgt ggacaacagc agacaaccct taagggtgta gaagctgtta tgtacatggg    5580
cacactttct tatgaacaat ttaagaaagg tgttcagata ccttgtacgt gtggtaaaca    5640
agctacaaaa tatctagtac aacaggagtc acctttgtt atgatgtcag caccacctgc    5700
tcagtatgaa cttaagcatg gtacatttac ttgtgctagt gagtacactg gtaattacca    5760
gtgtggtcac tataaacata taacttctaa agaaactttg tattgcatag acggtgcttt    5820
acttacaaag tcctcagaat acaaggtcc tattacggat gttttctaca agaaaacag    5880
ttacacaaca accataaaac cagttactta taaattggat ggtgttgttt gtacagaaat    5940
tgaccctaag ttgacaatt attataagaa agacaattct tatttcacag agcaaccaat    6000
```

```
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca atacctggt gtatacgttg    6300 tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780 ctttactta ttgctacaat tgtgtacttt tactagaagt acaaattcta gaattaaagc    6840
atctatgccg actactatag caaagaatac tgttaagagt gtcggtaaat tttgtctaga   6900
ggcttcattt aattatttga agtcacctaa ttttctaaa ctgataaata ttataatttg    6960
gttttactaa ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattcttag acacctatcc ttctttagaa actatacaaa ttaccatttc    7200
atcttttaaa tgggatttaa ctgcttttgg cttagttgca gagtggtttt tggcatatat   7260
tcttttcact aggttttct atgtacttgg attggctgca atcatgcaat tgttttcag    7320 ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agtatgtgc atgttgtaga cggttgtaat tcatcaactt gtatgatgtg    7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcatttgt taacttagac aacctgagag ctaataacac    7860
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aatgtttga    8040 tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta agatgttgt    8220 tgaatgtctc aaattgtcac atcaatctga catagaagtt actggcgata gttgtaataa   8280
ctatatgctc acctataaca aagttgaaaa catgacaccc cgtgaccttg gtgcttgtat   8340
```

```
tgactgtagt gcgcgtcata ttaatgcgca ggtagcaaaa agtcacaaca ttgctttgat    8400
atggaacgtt aaagatttca tgtcattgtc tgaacaacta cgaaaacaaa tacgtagtgc    8460
tgctaaaaag aataacttac cttttaagtt gacatgtgca actactagac aagttgttaa    8520
tgttgtaaca acaaagatag cacttaaggg tggtaaaatt gttaataatt ggttgaagca    8580
gttaattaaa gttacacttg tgttccttttt tgttgctgct attttctatt taataacacc    8640
tgttcatgtc atgtctaaac atactgactt ttcaagtgaa atcataggat acaaggctat    8700
tgatggtggt gtcactcgtg acatagcatc tacagatact tgttttgcta acaaacatgc    8760
tgattttgac acatggttta gtcagcgtgg tggtagttat actaatgaca aagcttgccc    8820
attgattgct gcagtcataa caagagaagt gggttttgtc gtgcctggtt tgcctggcac    8880
gatattacgc acaactaatg tgactttttt gcatttctta cctagagttt ttagtgcagt    8940
tggtaacatc tgttacacac catcaaaact tatagagtac actgactttg caacatcagc    9000
ttgtgttttg gctgctgaat gtacaatttt taaagatgct tctggtaagc cagtaccata    9060
ttgttatgat accaatgtac tagaaggttc tgttgcttat gaaagtttac gccctgacac    9120
acgttatgtg ctcatggatg gctctattat tcaatttcct aacacctacc ttgaaggttc    9180
tgttagagtg gtaacaactt tgattctga gtactgtagg cacggcactt gtgaaagatc    9240
agaagctggt gtttgtgtat ctactagtgg tagatgggta cttaacaatg attattacag    9300
atctttacca ggagttttct gtggtgtaga tgctgtaaat ttacttacta atatgtttac    9360
accactaatt caacctattg gtgctttgga catatcagca tctatagtag ctggtggtat    9420
tgtagctatc gtagtaacat gccttgccta ctattttatg aggttagaa gagcttttgg    9480 tgaatacagt catgtagttg cctttaatac tttactattc cttatgtcat tcactgtact    9540
ctgtttaaca ccagtttact cattcttacc tggtgtttat tctgttattt acttgtactt    9600 gacatttat cttactaatg atgtttcttt tttagcacat attcagtgga tggttatgtt    9660
cacaccttta gtacctttct ggataacaat tgcttatatc atttgtattt ccacaaagca    9720
tttctattgg ttcttagta attacctaaa gagacgtgta gtctttaatg gtgtttcctt    9780 tagtacttttt gaagaagctg cgctgtgcac cttttttgtta aataaagaaa tgtatctaaa    9840
gttgcgtagt gatgtgctat tacctcttac gcaatataat agatacttag ctcttttataa    9900 taagtacaag tattttagtg gagcaatgga tacaactagc tacagagaag ctgcttgttg    9960
tcatctcgca aaggctctca atgacttcag taactcaggt tctgatgttc tttaccaacc    10020
accacaaacc tctatcacct cagctgtttt gcagagtggt tttagaaaaa tggcattccc    10080
atctggtaaa gttgagggtt gtatggtaca agtaacttgt ggtacaacta cacttaacgg    10140 tcttggtt gatgacgtag tttactgtcc aagacatgtg atctgcacct ctgaagacat    10200 gcttaacct aattatgaag atttactcat tcgtaagtct aatcataatt tcttggtaca    10260
ggctggtaat gttcaactca gggttattgg acattctatg caaaattgtg tacttaagct    10320
taaggttgat acagccaatc ctaagacacc taagtataag tttgttcgca ttcaaccagg    10380
acagactttt tcagtgttag cttgttacaa tggttcacca tctggtgttt accaatgtgc    10440
tatgaggccc aatttcacta ttaagggttc attccttaat ggtcatgtg gtagtgttgg    10500 ttttaacata gattatgact gtgtctcttt tgttacatg caccatatgg aattaccaac    10560
tggagttcat gctggcacag acttagaagg taacttttat ggaccttttg ttgacaggca    10620
aacagcacaa gcagctggta cggacacaac tattacagtt aatgttttag cttggttgta    10680
cgctgctgtt ataaatggag acaggtggtt tctcaatcga tttaccacaa ctcttaatga    10740
```

```
ctttaaccttt gtggctatga agtacaatta tgaacctcta acacaagacc atgttgacat    10800
actaggacct ctttctgctc aaactggaat tgccgtttta gatatgtgtg cttcattaaa    10860
agaattactg caaaatggta tgaatggacg taccatattg ggtagtgctt tattagaaga    10920
tgaatttaca ccttttgatg ttgttagaca atgctcaggt gttactttcc aaagtgcagt    10980
gaaaagaaca atcaagggta cacaccactg gttgttactc acaattttga cttcactttt    11040
agttttagtc cagagtactc aatggtcttt gttctttttt ttgtatgaaa atgcettttt    11100 accttttgct atgggtatta ttgctatgtc tgcttttgca atgatgtttg tcaaacataa    11160
gcatgcattt ctctgtttgt ttttgttacc ttctcttgcc actgtagctt attttaatat    11220
ggtctatatg cctgctagtt gggtgatgcg tattatgaca tggttggata tggttgatac    11280
tagtttgtct ggttttaagc taaaagactg tgttatgtat gcatcagctg tagtgttact    11340
aatccttatg acagcaagaa ctgtgtatga tgatggtgct aggagagtgt ggacacttat    11400
gaatgtcttg acactcgttt ataaagttta ttatggtaat gctttagatc aagccatttc    11460
catgtgggct cttataatct ctgttacttc taactactca ggtgtagtta caactgtcat    11520 gttttttggcc agaggtattg ttttatgtg tgttgagtat tgccctattt tcttcataac    11580
tggtaataca cttcagtgta taatgctagt ttattgtttc ttaggctatt tttgtacttg    11640
ttactttggc ctcttttgtt tactcaaccg ctactttaga ctgactcttg gtgtttatga    11700
ttacttagtt tctacacagg agtttagata tatgaattca cagggactac tcccacccaa    11760
gaatagcata gatgccttca aactcaacat taaattgttg ggtgttggtg caaaccttg    11820 tatcaaagta gccactgtac agtctaaaat gtcagatgta aagtgcacat cagtagtctt    11880
actctcagtt ttgcaacaac tcagagtaga atcatcatct aaattgtggg ctcaatgtgt    11940
ccagttacac aatgacattc tcttagctaa agatactact gaagcctttg aaaaaatggt    12000
ttcactactt tctgttttgc tttccatgca gggtgctgta gacataaaca agctttgtga    12060
agaaatgctg gacaacaggg caaccttaca agctatagcc tcagagttta gttcccttcc    12120
atcatatgca gcttttgcta ctgctcaaga agcttatgag caggctgttg ctaatggtga    12180
ttctgaagtt gttcttaaaa agttgaagaa gtctttgaat gtggctaaat ctgaatttga    12240
ccgtgatgca gccatgcaac gtaagttgga aaagatggct gatcaagcta tgacccaaat    12300
gtataaacag ctagatctg aggacaagag ggcaaaagtt actagtgcta tgcagacaat    12360
gcttttcact atgctagaa agttggataa tgatgcactc aacaacatta tcaacaatgc    12420
aagagatggt tgtgttccct tgaacataat acctcttaca acagcagcca aactaatggt    12480
tgtcatacca gactataaca catataaaaa tacgtgtgat ggtacaacat ttacttatgc    12540
atcagcattg tgggaaatcc aacaggttgt agatgcagat agtaaaattg ttcaacttag    12600
tgaaattagt atggacaatt cacctaattt agcatggcct cttattgtaa cagctttaag    12660
ggccaattct gctgtcaaat tacagaataa tgagcttagt cctgttgcac tacgacagat    12720
gtcttgtgct gccggtacta cacaaactgc ttgcactgat gacaatgcgt tagcttacta    12780
caacacaaca aagggaggta ggtttgtact tgcactgtta tccgatttac aggatttgaa    12840
atgggctaga ttccctaaga gtgatggaac tggtactatc tatacagaac tggaaccacc    12900
ttgtaggttt gttacagaca cacctaaagg tcctaaagtg aagtatttat actttattaa    12960
aggattaaac aacctaaata gaggtatggt acttggtagt ttagctgcca cagtacgtct    13020
acaagctggt aatgcaacag aagtgcctgc caattcaact gtattatctt tctgtgcttt    13080
```

-continued

```
tgctgtagat gctgctaaag cttacaaaga ttatctagct agtggggac aaccaatcac    13140 taattgtgtt aagatgttgt gtacacacac tggtactggt caggcaataa cagttacacc    13200
ggaagccaat atggatcaag aatcctttgg tggtgcatcg tgttgtctgt actgccgttg    13260
ccacatagat catccaaatc ctaaaggatt ttgtgactta aaaggtaagt atgtacaaat    13320
acctacaact tgtgctaatg accctgtggg ttttacactt aaaaacacag tctgtaccgt    13380
ctgcggtatg tggaaaggtt atggctgtag ttgtgatcaa ctccgcgaac ccatgcttca    13440
gtcagctgat gcacaatcgt ttttaaacgg gtttgcggtg taagtgcagc ccgtcttaca    13500
ccgtgcggca caggcactag tactgatgtc gtatacaggg cttttgacat ctacaatgat    13560
aaagtagctg gttttgctaa attcctaaaa actaattgtt gtcgcttcca agaaaaggac    13620
gaagatgaca atttaattga ttcttacttt gtagttaaga dacacacttt ctctaactac    13680
caacatgaag aaacaattta aatttactt aaggattgtc cagctgttgc taaacatgac    13740
ttctttaagt ttagaataga cggtgacatg gtaccacata tatcacgtca acgtcttact    13800
aaatacacaa tggcagacct cgtctatgct ttaaggcatt ttgatgaagg taattgtgac    13860
acattaaaag aaatacttgt cacatacaat tgttgtgatg atgattattt caataaaaag    13920
gactggtatg atttttgtaga aaacccagat atattacgcg tatacgccaa cttaggtgaa    13980
cgtgtacgcc aagctttgtt aaaaacagta caattctgtg atgccatgcg aaatgctggt    14040
attgttggtg tactgacatt agataatcaa gatctcaatg gtaactggta tgatttcggt    14100
gatttcatac aaaccacgcc aggtagtgga gttcctgttg tagattctta ttattcattg    14160
ttaatgccta tattaaccctt gaccagggct ttaactgcag agtcacatgt tgacactgac    14220
ttaacaaagc cttacattaa gtgggattta ttaaaatatg acttcacgga agagaggtta    14280
aaactctttg accgttattt taaatattgg gatcagacat accacccaaa ttgtgttaac    14340
tgtttggatg acagatgcat tctgcattgt gcaaacttta tgttttatt ctctacagtg    14400 ttcccaccta caagttttgg accactagtg agaaaaatat ttgttgatgg tgttccattt    14460
gtagtttcaa ctggatacca cttcagagag ctaggtgttg tacataatca ggatgtaaac    14520
ttacatagct ctagacttag ttttaaggaa ttacttgtgt atgctgctga ccctgctatg    14580
cacgctgctt ctggtaatct attactagat aaacgcacta cgtgcttttc agtagctgca    14640
cttactaaca atgttgcttt tcaaactgtc aaacccggta attttaacaa agactttcat    14700
gactttgctg tgtctaaggg tttctttaag gaaggaagtt ctgttgaatt aaaacacttc    14760
ttctttgctc aggatggtaa tgctgctatc agcgattatg actactatcg ttataatcta    14820
ccaacaatgt gtgatatcag acaactacta tttgtagttg aagttgttga taagtacttt    14880
gattgttacg atggtggctg tattaatgct aaccaagtca tcgtcaacaa cctagacaaa    14940
tcagctggtt ttccatttaa taaatggggt aaggctagac tttattatga ttcaatgagt    15000
tatgaggatc aagatgcact tttcgcatat acaaaacgta atgtcatccc tactataact    15060
caaatgaatc ttaagtatgc cattagtgca aagaatagag ctcgcaccgt agctggtgtc    15120
tctatctgta gtactatgac caatagacag tttcatcaaa aattattgaa atcaatagcc    15180
gccactagag gagctactgt agtaattgga acaagcaaat tctatggtgg ttggcacaac    15240
atgttaaaaa ctgtttatag tgatgtagaa aaccctcacc ttatgggttg ggattatcct    15300
aaatgtgata gagccatgcc taacatgctt agaattatgg cctcacttgt tcttgctcgc    15360
aaacatacaa cgtgttgtag cttgtcacac cgtttctata tattagctaa tgagtgtgct    15420
caagtattga gtgaaatggt catgtgtggc ggttcactat atgttaaacc aggtggaacc    15480
```

```
tcatcaggag atgccacaac tgcttatgct aatagtgttt ttaacatttg tcaagctgtc    15540
acggccaatg ttaatgcact tttatctact gatggtaaca aaattgccga taagtatgtc    15600
cgcaatttac aacacagact ttatgagtgt ctctatagaa atagagatgt tgacacagac    15660
tttgtgaatg agttttacgc atatttgcgt aaacatttct caatgatgat actctctgac    15720
gatgctgttg tgtgtttcaa tagcacttat gcatctcaag gtctagtggc tagcataaag    15780
aactttaagt cagttctttta ttatcaaaac aatgttttta tgtctgaagc aaaatgttgg    15840
actgagactg accttactaa aggacctcat gaattttgct ctcaacatac aatgctagtt    15900
aaacagggtg atgattatgt gtaccttcct tacccagatc catcaagaat cctaggggcc    15960
ggctgttttg tagatgatat cgtaaaaaca gatggtacac ttatgattga acggttcgtg    16020
tctttagcta tagatgctta cccacttact aaacatccta atcaggagta tgctgatgtc    16080
tttcatttgt acttacaata cataagaaag ctacatgatg agttaacagg acacatgtta    16140
gacatgtatt ctgttatgct tactaatgat aacacttcaa ggtattggga acctgagttt    16200
tatgaggcta tgtacacacc gcatacagtc ttacaggctg ttggggcttg tgttctttgc    16260
aattcacaga cttcattaag atgtggtgct tgcatacgta gaccattctt atgttgtaaa    16320
tgctgttacg accatgtcat atcaacatca cataaattag tcttgtctgt taatccgtat    16380
gtttgcaatg ctccaggttg tgatgtcaca gatgtgactc aacttactt aggaggtatg    16440
agctattatt gtaaatcaca taaccacccc attagttttc cattgtgtgc taatggacaa    16500
gttttggtt tatataaaaa tacatgtgtt ggtagcgata atgttactga ctttaatgca    16560
attgcaacat gtgactggac aaatgctggt gattacattt tagctaacac ctgtactgaa    16620
agactcaagc ttttttgcagc agaaacgctc aaagctactg aggagacatt taaactgtct    16680
tatggtattg ctactgtacg tgaagtgctg tctgacagag aattacatct ttcatgggaa    16740
gttggtaaac ctagaccacc acttaaccga aattatgtct ttactggtta tcgtgtaact    16800
aaaaacagta agtacaaat aggagagtac acctttgaaa aaggtgacta tggtgatgct    16860
gttgtttacc gaggtacaac aacttacaaa ttaaatgttg gtgattattt tgtgctgaca    16920
tcacatacag taatgccatt aagtgcacct acactagtgc cacaagagca ctatgttaga    16980
attactggct tatacccaac actcaatatc tcagatgagt tttctagcaa tgttgcaaat    17040
tatcaaaagg ttggtatgca aaagtattct acactccagg gaccacctgg tactggtaag    17100
agtcattttg ctattggcct agctctctac taccttctg ctcgcatagt gtatacagct    17160
tgctctcatg ccgctgttga tgcactatgt gagaaggcat taaaatattt gcctatagat    17220
aaatgtagta gaattatacc tgcacgtgct cgtgtagagt gttttgataa attcaaagtg    17280
aattcaacat tagaacagta tgtctttgt actgtaaatg cattgcctga tacgacagca    17340
gatatagttg tctttgatga aatttcaatg gccacaaatt atgatttgag tgttgtcaat    17400
gccagattac gtgctaagca ctatgtgtac attggcgacc ctgctcaatt acctgcacca    17460
cgcacattgc taactaaggg cacactagaa ccagaatatt tcaattcagt gtgtagactt    17520
atgaaaacta taggtccaga catgttcctc ggaacttgtc ggcgttgtcc tgctgaaatt    17580
gttgacactg tgagtgcttt ggtttatgat aataagctta aagcacataa agacaaatca    17640
gctcaatgct ttaaaatgtt ttataagggt gttatcacgc atgatgtttc atctgcaatt    17700
aacaggccac aaataggcgt ggtaagagaa ttccttacac gtaaccctgc ttggagaaaa    17760
gctgtcttta tttcacccta taattcacag aatgctgtag cctcaaagat tttgggacta    17820
```

```
ccaactcaaa ctgttgattc atcacagggc tcagaatatg actatgtcat attcactcaa    17880
accactgaaa cagctcactc ttgtaatgta aacagattta atgttgctat taccagagca    17940
aaagtaggca tactttgcat aatgtctgat agagaccttt atgacaagtt gcaatttaca    18000
agtcttgaaa ttccacgtag gaatgtggca actttacaag ctgaaaatgt aacaggactt    18060
tttaaagatt gtagtaaggt aatcactggg ttacatccta cacaggcacc tacacacctc    18120
agtgttgaca ctaaattcaa aactgaaggt ttatgtgttg ataccctgg catacctaag     18180 gacatgacct atagaagact catctctatg atgggtttta aaatgaatta tcaagttaat    18240
ggttacccta acatgtttat cacccgcgaa gaagctataa gacatgtacg tgcatggatt    18300
ggcttcgatg tcgaggggtg tcatgctact agagaagctg ttggtaccaa tttacccttta   18360 cagctaggtt tttctacagg tgttaaccta gttgctgtac ctacaggtta tgttgataca    18420
cctaataata cagattttc cagagttagt gctaaaccac cgcctggaga tcaatttaaa     18480
cacctcatac cacttatgta caaaggactt ccttggaatg tagtgcgtat aaagattgta    18540
caaatgttaa gtgacacact taaaaatctc tctgacagag tcgtatttgt cttatgggca    18600
catggctttg agttgacatc tatgaagtat tttgtgaaaa taggacctga gcgcacctgt    18660
tgtctatgtg atagacgtgc cacatgcttt tccactgctt cagacactta tgcctgttgg    18720
catcattcta ttggatttga ttacgtctat aatccgttta tgattgatgt tcaacaatgg    18780
ggttttacag gtaacctaca aagcaaccat gatctgtatt gtcaagtcca tggtaatgca    18840
catgtagcta gttgtgatgc aatcatgact aggtgtctag ctgtccacga gtgctttgtt    18900
aagcgtgttg actggactat tgaatatcct ataattggtg atgaactgaa gattaatgcg    18960
gcttgtagaa aggttcaaca catggttgtt aaagctgcat tattagcaga caaattccca    19020
gttcttcacg acattggtaa ccctaaagct attaagtgtg tacctcaagc tgatgtagaa    19080
tggaagttct atgatgcaca gccttgtagt gacaaagctt ataaaataga agaattattc    19140
tattcttatg ccacacattc tgacaaattc acagatggtg tatgcctatt ttggaattgc    19200
aatgtcgata gatatcctgc taattccatt gtttgtagat ttgacactag agtgctatct    19260
aaccttaact gcctggttg tgatggtggc agttttgtatg taaataaaca tgcattccac    19320
acaccagctt ttgataaaag tgcttttgtt aatttaaaac aattaccatt tttctattac    19380
tctgacagtc catgtgagtc tcatggaaaa caagtagtgt cagatataga ttatgtacca    19440
ctaaagtctg ctacgtgtat aacacgttgc aatttaggtg gtgctgtctg tagacatcat    19500
gctaatgagt acagattgta tctcgatgct tataacatga tgatctcagc tggctttagc    19560
ttgtgggttt acaaacaatt tgatacttat aacctctgga acactttac aagacttcag    19620 agtttagaaa atgtggcttt taatgttgta aataagggac actttgatgg acaacagggt   19680
gaagtaccag tttctatcat taataacact gtttacacaa aagttgatgg tgttgatgta    19740 gaattgttg aaaataaaac aacattacct gttaatgtag catttgagct ttgggctaag    19800
cgcaacatta aaccagtacc agaggtgaaa atactcaata atttgggtgt ggacattgct    19860
gctaatactg tgatctggga ctacaaaaga gatgctccag cacatatatc tactattggt    19920
gtttgttcta tgactgacat agccaagaaa ccaactgaaa cgatttgtgc accactcact    19980
gtcttttttg atggtagagt tgatggtcaa gtagacttat ttagaaatgc ccgtaatggt    20040
gttcttatta cagaaggtag tgttaaaggt ttacaaccat ctgtaggtcc caaacaagct    20100
agtcttaatg gagtcacatt aattggagaa gccgtaaaaa cacagttcaa ttattataag    20160
aaagttgatg gtgttgtcca acaattacct gaaacttact ttactcagag tagaaattta    20220
```

```
caagaattta aacccaggag tcaaatggaa attgatttct tagaattagc tatggatgaa   20280
ttcattgaac ggtataaatt agaaggctat gccttcgaac atatcgttta tggagatttt   20340
agtcatagtc agttaggtgg tttacatcta ctgattggac tagctaaacg ttttaaggaa   20400
tcaccttttg aattagaaga ttttattcct atggacagta cagttaaaaa ctatttcata   20460
acagatgcgc aaacaggttc atctaagtgt gtgtgttctg ttattgattt attacttgat   20520
gattttgttg aaataataaa atcccaagat ttatctgtag tttctaaggt tgtcaaagtg   20580
actattgact atacagaaat ttcatttatg ctttggtgta agatggcca tgtagaaaca    20640 tttacccaa aattacaatc tagtcaagcg tggcaaccgg gtgttgctat gcctaatctt    20700
tacaaaatgc aaagaatgct attagaaaag tgtgaccttc aaaattatgg tgatagtgca   20760
acattaccta aaggcataat gatgaatgtc gcaaaatata ctcaactgtg tcaatattta   20820
aacacattaa cattagctgt accctataat atgagagtta tacattttgg tgctggttct   20880
gataaaggag ttgcaccagg tacagctgtt ttaagacagt ggttgcctac gggtacgctg   20940
cttgtcgatt cagatcttaa tgactttgtc tctgatgcag attcaacttt gattggtgat   21000
tgtgcaactg tacatacagc taataaatgg gatctcatta ttagtgatat gtacgaccct   21060
aagactaaaa atgttacaaa agaaaatgac tctaagagg gttttttcac ttacatttgt    21120
gggtttatac aacaaaagct agctcttgga ggttccgtgg ctataaagat aacagaacat   21180
tcttggaatg ctgatctta taagctcatg ggacacttcg catggtggac agcctttgtt    21240
actaatgtga atgcgtcatc atctgaagca tttttaattg gatgtaatta tcttggcaaa   21300
ccacgcgaac aaatagatgg ttatgtcatg catgcaaatt acatattttg gaggaataca   21360
aatccaattc agttgtcttc ctattcttta tttgacatga gtaaatttcc ccttaaatta   21420 agggggtactg ctgttatgtc tttaaaagaa ggtcaaatca atgatatgat tttatctctt   21480
cttagtaaag gtagacttat aattagagaa acaacagag ttgttatttc tagtgatgtt    21540
cttgttaaca actaaacgaa caatgtttgt ttttcttgtt ttattgccac tagtctctag   21600
tcagtgtgtt aatcttacaa ccagaactca attaccccct gcatacacta attctttcac   21660
acgtggtgtt tattaccctg acaaagtttt cagatcctca gttttacatt caactcagga   21720
cttgttctta cctttctttt ccaatgttac ttggttccat gctatacatg tctctgggac   21780
caatggtact aagaggtttg ataaccctgt cctaccattt aatgatggtg tttatttgc    21840 ttccactgag aagtctaaca taataagagg ctggattttt ggtactactt tagattcgaa   21900
gacccagtcc ctacttattg ttaataacgc tactaatgtt gttattaaag tctgtgaatt   21960
tcaattttgt aatgatccat ttttgggtgt ttattaccac aaaaacaaca aaagttggat   22020
ggaaagtgag ttcagagttt attctagtgc gaataattgc acttttgaat atgtctctca   22080
gccttttctt atggaccttg aaggaaaaca gggtaatttc aaaaatctta gggaatttgt   22140
gtttaagaat attgatggtt attttaaaat atattctaag cacacgccta ttaatttagt   22200
gcgtgatctc cctcagggtt tttcggcttt agaaccattg gtagatttgc caataggtat   22260
taacatcact aggtttcaaa ctttacttgc tttacataga agttatttga ctcctggtga   22320
ttcttcttca ggttggacag ctggtgctgc agcttattat gtgggttatc ttcaacctag   22380
gacttttcta ttaaaatata tgaaaatggg aaccattaca gatgctgtag actgtgcact   22440
tgacccctct tcagaaacaa agtgtacgtt gaaatccttc actgtagaaa aggaatcta    22500 tcaaacttct aactttagag tccaaccaac agaatctatt gttagatttc ctaatattac   22560
```

```
aaacttgtgc cctttttggtg aagttttttaa cgccaccaga tttgcatctg tttatgcttg    22620
gaacaggaag agaatcagca actgtgttgc tgattattct gtcctatata attccgcatc    22680
attttccact tttaagtgtt atggagtgtc tcctactaaa ttaaatgatc tctgctttac    22740
taatgtctat gcagattcat ttgtaattag aggtgatgaa gtcagacaaa tcgctccagg    22800
gcaaactgga aagattgctg attataatta taaattacca gatgattta  caggctgcgt    22860 tatagcttgg aattctaaca atcttgattc taaggttggt ggtaattata attacctgta    22920
tagattgttt aggaagtcta atctcaaacc ttttgagaga gatatttcaa ctgaaatcta    22980
tcaggccgga agcacacctt gtaatggtgt tgaaggtttt aattgttact ttccttaca     23040 atcatatggt ttccaaccca ctaatggtgt tggttaccaa ccatacagag tagtagtact    23100
ttcttttgaa cttctacatg caccagcaac tgtttgtgga cctaaaaagt ctactaattt    23160
ggttaaaaac aaatgtgtca atttcaactt caatggttta acaggcacag gtgttcttac    23220
tgagtctaac aaaaagtttc tgcctttcca acaatttggc agagacattg ctgacactac    23280
tgatgctgtc cgtgatccac agacacttga gattcttgac attacaccat gttcttttgg    23340
tggtgtcagt gttataacac caggaacaaa tacttctaac caggttgctg ttctttatca    23400
ggatgttaac tgcacagaag tccctgttgc tattcatgca gatcaactta ctcctacttg    23460
gcgtgtttat tctacaggtt ctaatgtttt tcaaacacgt gcaggctgtt aatagggc     23520 tgaacatgtc aacaactcat atgagtgtga catacccatt ggtgcaggta tatgcgctag    23580
ttatcagact cagactaatt ctcctcggcg ggcacgtagt gtagctagtc aatccatcat    23640
tgcctacact atgtcacttg gtgcagaaaa ttcagttgct tactctaata actctattgc    23700
catacccaca aattttacta ttagtgttac cacagaaatt ctaccagtgt ctatgaccaa    23760
gacatcagta gattgtacaa tgtacatttg tggtgattca actgaatgca gcaatctttt    23820
gttgcaatat ggcagttttt gtacacaatt aaaccgtgct ttaactggaa tagctgttga    23880
acaagacaaa aacaccccaag aagtttttgc acaagtcaaa caaatttaca aaacaccacc    23940
aattaaagat tttggtggtt ttaatttttc acaaatatta ccagatccat caaaaccaag    24000
caagaggtca tttattgaag atctactttt caacaaagtg acacttgcag atgctggctt    24060
catcaaacaa tatggtgatt gccttggtga tattgctgct agagacctca tttgtgcaca    24120
aaagtttaac ggccttactg ttttgccacc tttgctcaca gatgaaatga ttgctcaata    24180
cacttctgca ctgttagcgg gtacaatcac ttctggttgg acctttggtg caggtgctgc    24240
attacaaata ccatttgcta tgcaaatggc ttataggttt aatggtattg gagttacaca    24300
gaatgttctc tatgagaacc aaaaaattgat tgccaaccaa tttaatagtg ctattggcaa    24360
aattcaagac tcactttctt ccacagcaag tgcacttgga aaacttcaag atgtggtcaa    24420
ccaaaatgca caagctttaa acacgcttgt taaacaactt agctccaatt ttggtgcaat    24480
ttcaagtgtt ttaaatgata tcctttcacg tcttgacaaa gttgaggctg aagtgcaaat    24540
tgataggttg atcacaggca gacttcaaag tttgcagaca tatgtgactc aacaattaat    24600
tagagctgca gaaatcagag cttctgctaa tcttgctgct actaaaatgt cagagtgtgt    24660
acttggacaa tcaaaagag ttgattttg tggaaagggc tatcatctta tgtccttccc     24720
tcagtcagca cctcatggtg tagtcttctt gcatgtgact tatgtccctg cacaagaaaa    24780
gaacttcaca actgctcctg ccatttgtca tgatggaaaa gcacactttc ctcgtgaagg    24840
tgtctttgtt tcaaatggca cacactggtt tgtaacacaa aggaatttttt atgaaccaca    24900 aatcattact acagacaaca catttgtgtc tggtaactgt gatgttgtaa taggaattgt    24960
```

```
caacaacaca gtttatgatc ctttgcaacc tgaattagac tcattcaagg aggagttaga   25020
taaatatttt aagaatcata catcaccaga tgttgattta ggtgacatct ctggcattaa   25080
tgcttcagtt gtaaacattc aaaaagaaat tgaccgcctc aatgaggttg ccaagaattt   25140
aaatgaatct ctcatcgatc tccaagaact tggaaagtat gagcagtata taaaatggcc   25200
atggtacatt tggctaggtt ttatagctgg cttgattgcc atagtaatgg tgacaattat   25260
gctttgctgt atgaccagtt gctgtagttg tctcaagggc tgttgttctt gtggatcctg   25320
ctgcaaattt gatgaagacg actctgagcc agtgctcaaa ggagtcaaat tacattacac   25380
ataaacgaac ttatggattt gtttatgaga atcttcacaa ttggaactgt aactttgaag   25440
caaggtgaaa tcaaggatgc tactccttca gattttgttc gcgctactgc aacgataccg   25500
atacaagcct cactcccttt cggatggctt attgttggcg ttgcacttct tgctgttttt   25560
cagagcgctt ccaaaatcat aaccctcaaa aagagatggc aactagcact ctccaagggt   25620
gttcactttg tttgcaactt gctgttgttg tttgtaacag tttactcaca ccttttgctc   25680
gttgctgctg gccttgaagc ccctttctc tatctttatg ctttagtcta cttcttgcag   25740
agtataaact ttgtaagaat aataatgagg ctttggcttt gctggaaatg ccgttccaaa   25800
aacccattac tttatgatgc caactatttt ctttgctggc atactaattg ttacgactat   25860
tgtatacctt acaatagtgt aacttcttca attgtcatta cttcaggtga tggcacaaca   25920
agtcctattt ctgaacatga ctaccagatt ggtggttata ctgaaaaatg gaatctgga   25980 gtaaaagact gtgttgtatt acacagttac ttcacttcag actattacca gctgtactca   26040
actcaattga gtacagacac tggtgttgaa catgttacct tcttcatcta caataaaatt   26100
gttgatgagc ctgaagaaca tgtccaaatt cacacaatcg acggttcatc cggagttgtt   26160
aatccagtaa tggaaccaat ttatgatgaa ccgacgacga ctactagcgt gcctttgtaa   26220
gcacaagctg atgagtacga acttatgtac tcattcgttt cggaagagac aggtacgtta   26280
atagttaata gcgtacttct ttttcttgct ttcgtggtat tcttgctagt tacactagcc   26340
atccttactg cgcttcgatt gtgtgcgtac tgctgcaata ttgttaacgt gagtcttgta   26400
aaaccttctt tttacgttta ctctcgtgtt aaaaatctga attcttctag agttcctgat   26460
cttctggtct aaacgaacta aatattatat tagttttct gtttggaact ttaatttag   26520 ccatggcaga ttccaacggt actattaccg ttgaagagct taaaaagctc cttgaacaat   26580
ggaacctagt aataggtttc ctattcctta catggatttg tcttctacaa tttgcctatg   26640
ccaacaggaa taggttttg tatataatta agttaatttt cctctggctg ttatggccag   26700
taactttagc ttgttttgtg cttgctgctg tttacagaat aaattggatc accggtggaa   26760
ttgctatcgc aatggcttgt cttgtaggct tgatgtggct cagctacttc attgcttctt   26820
tcagactgtt tgcgcgtacg cgttccatgt ggtcattcaa tccagaaact aacattcttc   26880
tcaacgtgcc actccatggc actattctga ccagaccgct tctagaaagt gaactcgtaa   26940
tcggagctgt gatccttcgt ggacatcttc gtattgctgg acaccatcta ggacgctgtg   27000
acatcaagga cctgcctaaa gaaatcactg ttgctacatc acgaacgctt tcttattaca   27060
aattgggagc ttcgcagcgt gtagcaggtg actcaggttt gctgcatac agtcgctaca   27120 ggattggcaa ctataaatta aacacagacc attccagtag cagtgacaat attgctttgc   27180
ttgtacagta agtgacaaca gatgtttcat ctcgttgact ttcaggttac tatagcagag   27240
atattactaa ttattatgag gacttttaaa gtttccattg gaatcttga ttacatcata   27300
```

-continued

| | | | | | |
|---|---|---|---|---|---|
| aacctcataa | ttaaaaattt | atctaagtca | ctaactgaga | ataaatattc | tcaattagat | 27360 |
| gaagagcaac | caatggagat | tgattaaacg | aacatgaaaa | ttattctttt | cttggcactg | 27420 |
| ataacactcg | ctacttgtga | gctttatcac | taccaagagt | gtgttagagg | tacaacagta | 27480 |
| cttttaaaag | aaccttgctc | ttctggaaca | tacgagggca | attcaccatt | tcatcctcta | 27540 |
| gctgataaca | aatttgcact | gacttgcttt | agcactcaat | ttgcttttgc | ttgtcctgac | 27600 |
| ggcgtaaaac | acgtctatca | gttacgtgcc | agatcagttt | cacctaaact | gttcatcaga | 27660 |
| caagaggaag | ttcaagaact | ttactctcca | atttttctta | ttgttgcggc | aatagtgttt | 27720 |
| ataacacttt | gcttcacact | caaaagaaag | acagaatgat | tgaactttca | ttaattgact | 27780 |
| tctatttgtg | cttttagcc | tttctgctat | tccttgtttt | aattatgctt | attatctttt | 27840 |
| ggttctcact | tgaactgcaa | gatcataatg | aaacttgtca | cgcctaaacg | aacatgaaat | 27900 |
| ttcttgtttt | cttaggaatc | atcacaactg | tagctgcatt | tcaccaagaa | tgtagtttac | 27960 |
| agtcatgtac | tcaacatcaa | ccatatgtag | ttgatgaccc | gtgtcctatt | cacttctatt | 28020 |
| ctaaatggta | tattagagta | ggagctagaa | aatcagcacc | tttaattgaa | ttgtgcgtgg | 28080 |
| atgaggctgg | ttctaaatca | cccattcagt | acatcgatat | cggtaattat | acagtttcct | 28140 |
| gttcacctt  | tacaattaat | tgccaggaac | ctaaattggg | tagtcttgta | gtgcgttgtt | 28200 |
| cgttctatga | agactttta  | gagtatcatg | acgttcgtgt | tgtttagat  | ttcatctaaa | 28260 |
| cgaacaaact | aaaatgtctg | ataatggacc | ccaaaatcag | cgaaatgcac | ccgcattac  | 28320 |
| gtttggtgga | ccctcagatt | caactggcag | taaccagaat | ggagaacgca | gtggggcgcg | 28380 |
| atcaaaacaa | cgtcggcccc | aaggtttacc | caataatact | gcgtcttggt | tcaccgctct | 28440 |
| cactcaacat | ggcaaggaag | accttaaatt | ccctcgagga | caaggcgttc | caattaacac | 28500 |
| caatagcagt | ccagatgacc | aaattggcta | ctaccgaaga | gctaccagac | gaattcgtgg | 28560 |
| tggtgacggt | aaaatgaaag | atctcagtcc | aagatggtat | ttctactacc | taggaactgg | 28620 |
| gccagaagct | ggacttccct | atggtgctaa | caaagacggc | atcatatggg | ttgcaactga | 28680 |
| gggagccttg | aatacaccaa | aagatcacat | tggcacccgc | aatcctgcta | caatgctgc  | 28740 |
| aatcgtgcta | caacttcctc | aaggaacaac | attgccaaaa | ggcttctacg | cagaagggag | 28800 |
| cagaggcggc | agtcaagcct | cttctcgttc | ctcatcacgt | agtcgcaaca | gttcaagaaa | 28860 |
| ttcaactcca | ggcagcagta | ggggaacttc | tcctgctaga | atggctggca | atggcggtga | 28920 |
| tgctgctctt | gctttgctgc | tgcttgacag | attgaaccag | cttgagagca | aaatgtctgg | 28980 |
| taaaggccaa | caacaacaag | gccaaactgt | cactaagaaa | tctgctgctg | aggcttctaa | 29040 |
| gaagcctcgg | caaaaacgta | ctgccactaa | agcatacaat | gtaacacaag | ctttcggcag | 29100 |
| acgtggtcca | gaacaaaccc | aaggaaattt | tggggaccag | gaactaatca | gacaaggaac | 29160 |
| tgattacaaa | cattggccgc | aaattgcaca | atttgccccc | agcgcttcag | cgttcttcgg | 29220 |
| aatgtcgcgc | attggcatgg | aagtcacacc | ttcgggaacg | tggttgacct | acacaggtgc | 29280 |
| catcaaattg | gatgacaaag | atccaaattt | caaagatcaa | gtcattttgc | tgaataagca | 29340 |
| tattgacgca | tacaaaacat | tcccaccaac | agagcctaaa | aaggacaaaa | agaagaaggc | 29400 |
| tgatgaaact | caagccttac | cgcagagaca | gaagaaacag | caaactgtga | ctcttcttcc | 29460 |
| tgctgcagat | ttggatgatt | tctccaaaca | attgcaacaa | tccatgagca | gtgctgactc | 29520 |
| aactcaggcc | taaactcatg | cagaccacac | aaggcagatg | ggctatataa | acgttttcgc | 29580 |
| ttttccgttt | acgatatata | gtctactctt | gtgcagaatg | aattctcgta | actacatagc | 29640 |
| acaagtagat | gtagttaact | ttaatctcac | atagcaatct | ttaatcagtg | tgtaacatta | 29700 |

```
gggaggactt gaaagagcca ccacattttc accgaggcca cgcggagtac gatcgagtgt    29760
acagtgaaca atgctaggga gagctgccta tatggaagag ccctaatgtg taaaattaat    29820
tttagtagtg ctatccccat gtgattttaa tagcttctta ggagaatgac aaaaaaaaaa    29880
aa                                                                   29882
```

<210> SEQ ID NO 3
<211> LENGTH: 29751
<212> TYPE: DNA
<213> ORGANISM: Severe acute respiratory syndrome-related coronavirus
      isolate Tor2

<400> SEQUENCE: 3

```
atattaggtt tttacctacc caggaaaagc caaccaacct cgatctcttg tagatctgtt      60
ctctaaacga actttaaaat ctgtgtagct gtcgctcggc tgcatgccta gtgcacctac     120
gcagtataaa caataataaa ttttactgtc gttgacaaga aacgagtaac tcgtccctct     180
tctgcagact gcttacggtt tcgtccgtgt tgcagtcgat catcagcata cctaggtttc     240
gtccgggtgt gaccgaaagg taagatggag agccttgttc ttggtgtcaa cgagaaaaca     300
cacgtccaac tcagtttgcc tgtccttcag gttagaacg tgctagtgcg tggcttcggg      360
gactctgtgg aagaggccct atcggaggca cgtgaacacc tcaaaaatgg cacttgtggt     420
ctagtagagc tggaaaaagg cgtactgccc cagcttgaac agccctatgt gttcattaaa     480
cgttctgatg ccttaagcac caatcacggc cacaaggtcg ttgagctggt tgcagaaatg     540
gacggcattc agtacggtcg tagcggtata acactgggag tactcgtgcc acatgtgggc     600
gaaaccccaa ttgcataccg caatgttctt cttcgtaaga acggtaataa gggagccggt     660
ggtcatagct atggcatcga tctaaagtct tatgacttag gtgacgagct tggcactgat     720
cccattgaag attatgaaca aaactggaac actaagcatg gcagtggtgc actccgtgaa     780
ctcactcgtg agctcaatgg aggtgcagtc actcgctatg tcgacaacaa tttctgtggc     840
ccagatgggt accctcttga ttgcatcaaa gattttctcg cacgcgcggg caagtcaatg     900
tgcactcttt ccgaacaact tgattacatc gagtcgaaga gaggtgtcta ctgctgccgt     960
gaccatgagc atgaaattgc ctggttcact gagcgctctg ataagagcta cgagcaccag    1020
acacccttcg aaattaagag tgccaagaaa tttgacactt tcaaagggga atgcccaaag    1080
tttgtgtttc ctcttaactc aaaagtcaaa gtcattcaac cacgtgttga aagaaaaag    1140 actgagggtt tcatggggcg tatacgctct gtgtaccctg ttgcatctcc acaggagtgt    1200
aacaatatgc acttgtctac cttgatgaaa tgtaatcatt gcgatgaagt tcatggcag    1260 acgtgcgact ttctgaaagc cacttgtgaa cattgtggca ctgaaaattt agttattgaa    1320
ggacctacta catgtgggta cctacctact aatgctgtag tgaaaatgcc atgtcctgcc    1380
tgtcaagacc cagagattgg acctgagcat agtgttgcag attatcacaa ccactcaaac    1440
attgaaactc gactccgcaa gggaggtagg actagatgtt ttggaggctg tgtgtttgcc    1500
tatgttggct gctataataa gcgtgcctac tgggttcctc gtgctagtgc tgatattggc    1560
tcaggccata ctggcattac tggtgacaat gtggagacct tgaatgagga tctccttgag    1620
atactgagtc gtgaacgtgt taacattaac attgttggcg attttcattt gaatgaagag    1680
gttgccatca ttttggcatc tttctctgct tctacaagtg cctttattga cactataaag    1740
agtcttgatt acaagtcttt caaaaccatt gttgagtcct gcggtaacta taagttacc    1800 aagggaaagc ccgtaaaagg tgcttggaac attggacaac agagatcagt tttaacacca    1860
```

```
ctgtgtggtt ttccctcaca ggctgctggt gttatcagat caattttgc gcgcacactt      1920 gatgcagcaa accactcaat tcctgatttg caaagagcag ctgtcaccat acttgatggt      1980
atttctgaac agtcattacg tcttgtcgac gccatggttt atacttcaga cctgctcacc      2040
aacagtgtca ttattatggc atatgtaact ggtggtcttg tacaacagac ttctcagtgg      2100
ttgtctaatc ttttgggcac tactgttgaa aaactcaggc ctatctttga atggattgag      2160
gcgaaactta gtgcaggagt tgaatttctc aaggatgctt gggagattct caaatttctc      2220
attacaggtg ttttttgacat cgtcaagggt caaatacagg ttgcttcaga taacatcaag      2280
gattgtgtaa aatgcttcat tgatgttgtt aacaaggcac tcgaaatgtg cattgatcaa      2340
gtcactatcg ctggcgcaaa gttgcgatca ctcaacttag gtgaagtctt catcgctcaa      2400
agcaagggac tttaccgtca gtgtatacgt ggcaaggagc agctgcaact actcatgcct      2460
cttaaggcac caaaagaagt aacctttctt gaaggtgatt cacatgacac agtacttacc      2520
tctgaggagg ttgttctcaa gaacggtgaa ctcgaagcac tcgagacgcc cgttgatagc      2580
ttcacaaatg gagctatcgt tggcacacca gtctgtgtaa atggcctcat gctcttagag      2640
attaaggaca aagaacaata ctgcgcattg tctcctggtt tactggctac aaacaatgtc      2700
tttcgcttaa aaggggggtgc accaattaaa ggtgtaacct ttggagaaga tactgtttgg      2760
gaagttcaag gttacaagaa tgtgagaatc acatttgagc ttgatgaacg tgttgacaaa      2820
gtgcttaatg aaaagtgctc tgtctacact gttgaatccg gtaccgaagt tactgagttt      2880
gcatgtgttg tagcagaggc tgttgtgaag actttacaac cagtttctga tctccttacc      2940
aacatgggta ttgatcttga tgagtggagt gtagctacat tctacttatt tgatgatgct      3000
ggtgaagaaa acttttcatc acgtatgtat tgttcctttt accctccaga tgaggaagaa      3060
gaggacgatg cagagtgtga ggaagaagaa attgatgaaa cctgtgaaca tgagtacggt      3120
acagaggatg attatcaagg tctccctctg gaatttggtg cctcagctga aacagttcga      3180
gttgaggaag aagaagagga agactggctg gatgatacta ctgagcaatc agagattgag      3240
ccagaaccag aacctacacc tgaagaacca gttaatcagt ttactggtta tttaaaactt      3300
actgacaatg ttgccattaa atgtgttgac atcgttaagg aggcacaaag tgctaatcct      3360
atggtgattg taaatgctgc taacatacac ctgaaacatg gtggtggtgt agcaggtgca      3420
ctcaacaagg caaccaatgg tgccatgcaa aaggagagtg atgattacat taagctaaat      3480
ggccctctta cagtaggagg gtcttgtttg ctttctggac ataatcttgc taagaagtgt      3540
ctgcatgttg ttggacctaa cctaaatgca ggtgaggaca tccagcttct taaggcagca      3600
tatgaaaatt tcaattcaca ggacatctta cttgcaccat tgttgtcagc aggcatattt      3660
ggtgctaaac cacttcagtc tttacaagtg tgcgtgcaga cggttcgtac acaggtttat      3720
attgcagtca atgacaaagc tctttatgag caggttgtca tggattatct tgataacctg      3780
aagcctagag tggaagcacc taaacaagag agccaccaa acacagaaga ttccaaaact      3840
gaggagaaat ctgtcgtaca gaagcctgtc gatgtgaagc aaaaattaa ggcctgcatt      3900 gatgaggtta ccacaacact ggaagaaact aagtttctta ccaataagtt actcttgttt      3960
gctgatatca atggtaagct ttaccatgat tctcagaaca tgcttagagg tgaagatatg      4020
tctttccttg agaaggatgc accttacatg gtaggtgatg ttatcactag tggtgatatc      4080
acttgtgttg taatacccctc caaaaaggct ggtggcacta ctgagatgct ctcaagagct      4140
ttgaagaaag tgccagttga tgagtatata accacgtacc ctggacaagg atgtgctggt      4200
```

-continued

```
tatacacttg aggaagctaa gactgctctt aagaaatgca aatctgcatt ttatgtacta    4260
ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagccccgt cgagtttcat cttgacggtg aggttctttc acttgacaaa    4860
ctaaagagtc tcttatccct gcgggaggtt aagactataa aagtgttcac aactgtggac    4920
aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgtg gtgaagcttt cgagtactac    5100
catactcttg atgagagttt tcttggtagg tacatgtctg ctttaaacca cacaagaaa    5160 tggaaatttc ctcaagttgg tggtttaact tcaattaaat gggctgataa caattgttat    5220
ttgtctagtg ttttattagc acttcaacag cttgaagtca aattcaatgc accagcactt    5280
caagaggctt attatagagc ccgtgctggt gatgctgcta cttttgtgc actcatactc    5340 gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttcttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gtttttctaca aggaaacatc ttacactaca    5820
accatcaagc ctgtgtcgta taaactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatt tgcttgtga aagtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacacaag agttaggtca tgaggatctt    6480
atggctgctt atgtggaaaa cacaagcatt accattaaga aacctaatga gctttcacta    6540
gccttaggtt taaaaacaat tgccactcat ggtattgctg caattaatag tgttccttgg    6600
```

```
agtaaaattt tggcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
acaactattg ctaaaaatag tgttaagagt gttgctaaat tatgtttgga tgccggcatt    6840
aattatgtga agtcacccaa attttctaaa ttgttcacaa tcgctatgtg gctattgttg    6900
ttaagtattt gcttaggttc tctaatctgt gtaactgctg cttttggtgt actcttatct    6960
aattttggtg ctccttctta ttgtaatggc gttagagaat tgtatcttaa ttcgtctaac    7020
gttactacta tggatttctg tgaaggttct tttccttgca gcatttgttt aagtggatta    7080
gactcccttg attcttatcc agctcttgaa accattcagg tgacgatttc atcgtacaag    7140
ctagacttga caattttagg tctggccgct gagtgggttt tggcatatat gttgttcaca    7200
aaattctttt atttattagg tctttcagct ataatgcagg tgttctttgg ctattttgct    7260
agtcatttca tcagcaattc ttggctcatg tggtttatca ttagtattgt acaaatggca    7320 cccgttctg caatggttag gatgtacatc ttctttgctt ctttctacta catatggaag    7380
agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg gcgcgcttca cctctacttt gacaaggctg gtcaaaagac ctatgagaga    7740
catccgctct cccattttgt caatttagac aatttgagag ctaacaacac taaaggttca    7800
ctgcctatta atgtcatagt ttttgatggc aagtccaaat gcgacgagtc tgcttctaag    7860
tctgcttctg tgtactacag tcagctgatg tgccaaccta ttctgttgct tgaccaagct    7920
cttgtatcag acgttggaga tagtactgaa gtttccgtta agatgtttga tgcttatgtc    7980
gacacctttt cagcaacttt tagtgttcct atggaaaaac ttaaggcact tgttgctaca    8040
gctcacagcg agttagcaaa gggtgtagct ttagatggtg tcctttctac attcgtgtca    8100
gctgcccgac aagtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca agtagcaaaa agtcacaatg tttcactcat ctggaatgta    8340
aaagactaca tgtctttatc tgaacagctg cgtaaacaaa ttcgtagtgc tgccaagaag    8400
aacaacatac cttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtcatacaca   8580 ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta aagagagat tggtttcata gtgcctggct taccgggtac tgtgctgaga    8820
gcaatcaatg gtgacttctt gcatttccta cctcgtgttt ttagtgctgt tggcaacatt    8880
tgctacacac cttccaaact cattgagtat agtgattttg ctacctctgc ttgcgttctt    8940
```

-continued

```
gctgctgagt gtacaatttt taaggatgct atgggcaaac ctgtgccata ttgttatgac      9000
actaatttgc tagagggttc tatttcttat agtgagcttc gtccagacac tcgttatgtg      9060
cttatggatg gttccatcat acagtttcct aacacttacc tggagggttc tgttagagta      9120
gtaacaactt ttgatgctga gtactgtaga catggtacat gcgaaaggtc agaagtaggt      9180
atttgcctat ctaccagtgg tagatgggtt cttaataatg agcattacag agctctatca      9240
ggagttttct gtggtgttga tgcgatgaat ctcatagcta acatctttac tcctcttgtg      9300
caacctgtgg gtgcttttaga tgtgtctgct tcagtagtgg ctggtggtat tattgccata      9360
ttggtgactt gtgctgccta ctactttatg aaattcagac gtgttttggg tgagtacaac      9420
catgttgttg ctgctaatgc acttttgttt ttgatgtctt tcactatact ctgtctggta      9480
ccagcttaca gctttctgcc gggagtctac tcagtctttt acttgtactt gacattctat      9540
ttcaccaatg atgtttcatt cttggctcac cttcaatggt ttgccatgtt ttctcctatt      9600
gtgccttttt ggataacagc aatctatgta ttctgtattt ctctgaagca ctgccattgg      9660
ttctttaaca actatcttag gaaaagagtc atgtttaatg gagttacatt tagtaccttc      9720
gaggaggctg ctttgtgtac cttttttgctc aacaaggaaa tgtacctaaa attgcgtagc      9780
gagacactgt tgccacttac acagtataac aggtatcttg ctctatataa caagtacaag      9840
tatttcagtg gagccttaga tactaccagc tatcgtgaag cagcttgctg ccacttagca      9900
aaggctctaa atgactttag caactcaggt gctgatgttc tctaccaacc accacagaca      9960
tcaatcactt ctgctgttct gcagagtggt tttaggaaaa tggcattccc gtcaggcaaa     10020
gttgaagggt gcatggtaca agtaacctgt ggaactacaa ctcttaatgg attgtggttg     10080
gatgacacag tatactgtcc aagacatgtc atttgcacag cagaagacat gcttaatcct     10140
aactatgaag atctgctcat tcgcaaatcc aaccatagct tcttgttca ggctggcaat     10200 gttcaacttc gtgttattgg ccattctatg caaaattgtc tgcttaggct taaagttgat     10260
acttctaacc ctaagacacc caagtataaa tttgtccgta tccaacctgg tcaaacattt     10320
tcagttctag catgctacaa tggttcacca tctggtgttt atcagtgtgc catgagacct     10380
aatcatacca ttaaaggttc tttccttaat ggatcatgtg gtagtgttgg ttttaacatt     10440
gattatgatt gcgtgtcttt ctgctatatg catcatatgg agcttccaac aggagtacac     10500
gctggtactg acttagaagg taaattctat ggtccatttg ttgacagaca aactgcacag     10560
gctgcaggta cagacacaac cataacatta atgtttttgg catggctgta tgctgctgtt     10620
atcaatggtg ataggtggtt tcttaataga ttcaccacta ctttgaatga ctttaacctt     10680
gtggcaatga agtacaacta tgaaccttttg acacaagatc atgttgacat attgggacct     10740 cttttctgctc aaacaggaat tgccgtctta gatatgtgtg ctgcttttgaa agagctgctg     10800 cagaatggta tgaatggtcg tactatcctt ggtagcacta ttttagaaga tgagtttaca     10860
ccatttgatg ttgttagaca atgctctggt gttaccttcc aaggtaagtt caagaaaatt     10920
gttaagggca ctcatcattg gatgctttta actttcttga catcactatt gattcttgtt     10980
caaagtacac agtggtcact gtttttcttt gtttacgaga atgcttttt gccatttact     11040 cttggtatta tggcaattgc tgcatgtgct atgctgcttg ttaagcataa gcacgcattc     11100
ttgtgcttgt ttctgttacc ttctcttgca acagttgctt actttaatat ggtctacatg     11160
cctgctagct gggtgatgcg tatcatgaca tggcttgaat tggctgacac tagcttgtct     11220
ggttataggc ttaaggattg tgttatgtat gcttcagctt tagttttgct tattctcatg     11280
acagctcgca ctgtttatga tgatgctgct agacgtgttt ggacactgat gaatgtcatt     11340
```

-continued

```
acacttgttt acaaagtcta ctatggtaat gctttagatc aagctatttc catgtgggcc   11400
ttagttattt ctgtaacctc taactattct ggtgtcgtta cgactatcat gtttttagct   11460
agagctatag tgtttgtgtg tgttgagtat tacccattgt tatttattac tggcaacacc   11520
ttacagtgta tcatgcttgt ttattgtttc ttaggctatt gttgctgctg ctactttggc   11580
cttttctgtt tactcaaccg ttacttcagg cttactcttg gtgtttatga ctacttggtc   11640
tctacacaag aatttaggta tatgaactcc caggggcttt tgcctcctaa gagtagtatt   11700
gatgctttca agcttaacat taagttgttg ggtattggag gtaaaccatg tatcaaggtt   11760
gctactgtac agtctaaaat gtctgacgta aagtgcacat ctgtggtact gctctcggtt   11820
cttcaacaac ttagagtaga gtcatcttct aaattgtggg cacaatgtgt acaactccac   11880
aatgatattc ttcttgcaaa agacacaact gaagctttcg agaagatggt ttctcttttg   11940
tctgttttgc tatccatgca gggtgctgta gacattaata ggttgtgcga ggaaatgctc   12000
gataaccgtg ctactcttca ggctattgct tcagaattta gttctttacc atcatatgcc   12060
gcttatgcca ctgcccagga ggcctatgag caggctgtag ctaatggtga ttctgaagtc   12120
gttctcaaaa agtaaagaa atcttttgaat gtggctaaat ctgagtttga ccgtgatgct   12180
gccatgcaac gcaagttgga aaagatggca gatcaggcta tgacccaaat gtacaaacag   12240
gcaagatctg aggacaagag ggcaaaagta actagtgcta tgcaaacaat gctcttcact   12300
atgcttagga agcttgataa tgatgcactt aacaacatta tcaacaatgc gcgtgatggt   12360
tgtgttccac tcaacatcat accattgact acagcagcca aactcatggt tgttgtccct   12420
gattatggta cctacaagaa cacttgtgat ggtaacacct ttacatatgc atctgcactc   12480
tgggaaatcc agcaagttgt tgatgcggat agcaagattg ttcaacttag tgaaattaac   12540
atggacaatt caccaaattt ggcttggcct cttattgtta cagctctaag agccaactca   12600
gctgttaaac tacagaataa tgaactgagt ccagtagcac tacgacagat gtcctgtgcg   12660
gctggtacca cacaaacagc ttgtactgat gacaatgcac ttgcctacta taacaattcg   12720
aagggaggta ggtttgtgct ggcattacta tcagaccacc aagatctcaa atggctagga   12780
ttccctaaga gtgatggtac aggtacaatt tacacagaac tggaaccacc ttgtaggttt   12840
gttacagaca caccaaaagg gcctaaagtg aaatacttgt acttcatcaa aggcttaaac   12900
aacctaaata gaggtatggt gctgggcagt ttagctgcta cagtacgtct tcaggctgga   12960
aatgctacag aagtacctgc caattcaact gtgctttcct tctgtgcttt tgcagtagac   13020
cctgctaaag catataagga ttacctagca agtggaggac aaccaatcac caactgtgtg   13080
aagatgttgt gtacacacac tggtacagga caggcaatta ctgtaacacc agaagctaac   13140
atggaccaag agtcctttgg tggtgcttca tgttgtctgt attgtagatg ccacattgac   13200
catccaaatc ctaaaggatt ctgtgacttg aaaggtaagt acgtccaaat acctaccact   13260
tgtgctaatg acccagtggg ttttacactt agaaacacag tctgtaccgt ctgcggaatg   13320
tggaaaggtt atggctgtag ttgtgaccaa ctccgcgaac ccttgatgca gtctgcggat   13380
gcatcaacgt ttttaaacgg gtttgcggtg taagtgcagc ccgtcttaca ccgtgcggca   13440
caggcactag tactgatgtc gtctacaggg cttttgtatt ttacaacgaa aaagttgctg   13500
gttttgcaaa gttcctaaaa actaattgct gtcgcttcca ggagaaggat gaggaaggca   13560
atttattaga ctcttacttt gtagttaaga ggcatactat gtctaactac caacatgaag   13620
agactatttg taacttggtt aaagattgtc cagcggttgc tgtccatgac ttttccaagt   13680
```

```
ttagagtaga tggtgacatg gtaccacata tatcacgtca gcgtctaact aaatacacaa   13740
tggctgattt agtctatgct ctacgtcatt ttgatgaggg taattgtgat acattaaaag   13800
aaatactcgt cacatacaat tgctgtgatg atgattattt caataagaag gattggtatg   13860
acttcgtaga gaatcctgac atcttacgcg tatatgctaa cttaggtgag cgtgtacgcc   13920
aatcattatt aaagactgta caattctgcg atgctatgcg tgatgcaggc attgtaggcg   13980
tactgacatt agataatcag gatcttaatg ggaactggta cgatttcggt gatttcgtac   14040
aagtagcacc aggctgcgga gttcctattg tggattcata ttactcattg ctgatgccca   14100
tcctcacttt gactagggca ttggctgctg agtcccatat ggatgctgat ctcgcaaaac   14160
cacttattaa gtgggatttg ctgaaatatg attttacgga agagagactt tgtctcttcg   14220
accgttattt aaatattgg gaccagacat accatcccaa ttgtattaac tgtttggatg   14280
ataggtgtat ccttcattgt gcaaacttta atgtgttatt ttctactgtg tttccaccta   14340
caagttttgg accactagta agaaaaatat ttgtagatgg tgttcctttt gttgtttcaa   14400
ctggatacca ttttcgtgag ttaggagtcg tacataatca ggatgtaaac ttacatagct   14460
cgcgtctcag ttttcaaggaa cttttagtgt atgctgctga tccagctatg catgcagctt   14520
ctggcaattt attgctagat aaacgcacta catgcttttc agtagctgca ctaacaaaca   14580
atgttgcttt tcaaactgtc aaacccggta attttaataa agacttttat gactttgctg   14640
tgtctaaagg ttttctttaag gaaggaagtt ctgttgaact aaaacacttc ttctttgctc   14700
aggatggcaa cgctgctatc agtgattatg actattatcg ttataatctg ccaacaatgt   14760
gtgatatcag acaactccta ttcgtagttg aagttgttga taaatacttt gattgttacg   14820
atggtggctg tattaatgcc aaccaagtaa tcgttaacaa tctggataaa tcagctggtt   14880
tcccatttaa taaatggggt aaggctagac tttattatga ctcaatgagt tatgaggatc   14940
aagatgcact tttcgcgtat actaagcgta atgtcatccc tactataact caaatgaatc   15000
ttaagtatgc cattagtgca aagaatagag ctcgcaccgt agctggtgtc tctatctgta   15060
gtactatgac aaatagacag tttcatcaga aattattgaa gtcaatagcc gccactagag   15120
gagctactgt ggtaattgga acaagcaagt tttacggtgg ctggcataat atgttaaaaa   15180
ctgtttacag tgatgtagaa actccacacc ttatgggttg ggattatcca aaatgtgaca   15240
gagccatgcc taacatgctt aggataatgg cctctcttgt tcttgctcgc aaacataaca   15300
cttgctgtaa cttatcacac cgtttctaca ggttagctaa cgagtgtgcg caagtattaa   15360
gtgagatggt catgtgtggc ggctcactat atgttaaacc aggtggaaca tcatccggtg   15420
atgctacaac tgcttatgct aatagtgtct ttaacatttg tcaagctgtt acagccaatg   15480
taaatgcact tctttcaact gatggtaata agatagctga caagtatgtc cgcaatctac   15540
aacacaggct ctatgagtgt ctctatagaa atagggatgt tgatcatgaa ttcgtggatg   15600
agttttacgc ttacctgcgt aaacatttct ccatgatgat tctttctgat gatgccgttg   15660
tgtgctataa cagtaactat gcggctcaag gtttagtagc tagcattaag aactttaagg   15720 cagttctta ttatcaaaat aatgtgttca tgtctgaggc aaaatgttgg actgagactg   15780
accttactaa aggaccctcac gaattttgct cacagcatac aatgctagtt aaacaaggag   15840
atgattacgt gtacctgcct tacccagatc catcaagaat attaggcgca ggctgttttg   15900
tcgatgatat tgtcaaaaca gatggtacac ttatgattga aaggttcgtg tcactggcta   15960
ttgatgctta cccacttaca aaacatccta atcaggagta tgctgatgtc tttcacttgt   16020
atttacaata cattagaaag ttacatgatg agcttactgg ccacatgttg gacatgtatt   16080
```

```
ccgtaatgct aactaatgat aacacctcac ggtactggga acctgagttt tatgaggcta    16140
tgtacacacc acatacagtc ttgcaggctg taggtgcttg tgtattgtgc aattcacaga    16200
cttcacttcg ttgcggtgcc tgtattagga gaccattcct atgttgcaag tgctgctatg    16260
accatgtcat ttcaacatca cacaaattag tgttgtctgt taatccctat gtttgcaatg    16320
ccccaggttg tgatgtcact gatgtgacac aactgtatct aggaggtatg agctattatt    16380
gcaagtcaca taagcctccc attagttttc cattatgtgc taatggtcag ggttttggtt    16440
tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ccactgtacg cgaagtactc tctgacagag aattgcatct ttcatgggag gttggaaaac    16680
ctagaccacc attgaacaga aactatgtct ttactggtta ccgtgtaact aaaaatagta    16740
aagtacagat tggagagtac acctttgaaa aaggtgacta tggtgatgct gttgtgtaca    16800
gaggtactac gacatacaag ttgaatgttg gtgattactt tgtgttgaca tctcacactg    16860
taatgccact tagtgcacct actctagtgc cacaagagca ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcatttg     17040 ccatcggact tgctctctat tacccatctg ctcgcatagt gtatacggca tgctctcatg    17100
cagctgttga tgccctatgt gaaaaggcat taaatatttt gcccatagat aaatgtagta    17160
gaatcatacc tgcgcgtgcg cgcgtagagt gttttgataa attcaaagtg aattcaacac    17220
tagaacagta tgtttctgc actgtaaatg cattgccaga acaactgct gacattgtag       17280 tctttgatga aatctctatg ctactaatt atgacttgag tgttgtcaat gctagacttc      17340
gtgcaaaaca ctacgtctat attggcgatc ctgctcaatt accagcccc cgcacattgc      17400 tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
tcaaaatgtt ctacaaaggt gttattacac atgatgtttc atctgcaatc aacagacctc    17640
aaataggcgt tgtaagagaa tttcttacac gcaatcctgc ttggagaaaa gctgtttta    17700 tctcacctta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaatgt aactggactt tttaaggact     18000
gtagtaagat cattactggt cttcatccta caccggcacc tacacacctc agcgttgata    18060
taaagttcaa gactgaagga ttatgtgttg acataccagg cataccaaag gacatgacct    18120
accgtagact catctctatg atgggtttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc cagctaggat    18300
tttctacagg tgttaactta gtagctgtac cgactggtta tgttgacact gaaaataaca    18360
cagaattcac cagagttaat gcaaaacctc caccaggtga ccagtttaaa catcttatac    18420
```

```
cactcatgta taaaggcttg ccctggaatg tagtgcgtat taagatagta caaatgctca    18480
gtgatacact gaaaggattg tcagacagag tcgtgttcgt cctttgggcg catggctttg    18540
agcttacatc aatgaagtac tttgtcaaga ttggacctga agaacgtgt tgtctgtgtg    18600 acaaacgtgc aacttgcttt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaataccct attataggag atgaactgag ggttaattct gcttgcagaa    18900
aagtacaaca catggttgtg aagtctgcat tgcttgctga taagtttcca gttcttcatg    18960
acattggaaa tccaaaggct atcaagtgtg tgcctcaggc tgaagtagaa tggaagttct    19020
acgatgctca gccatgtagt gacaaagctt acaaaataga ggaactcttc tattcttatg    19080
ctacacatca cgataaattc actgatggtg tttgtttgtt ttggaattgt aacgttgatc    19140
gttacccagc caatgcaatt gtgtgtaggt ttgacacaag agtcttgtca aacttgaact    19200
taccaggctg tgatggtggt agtttgtatg tgaataagca tgcattccac actccagctt    19260
tcgataaaag tgcatttact aatttaaagc aattgccttt cttttactat tctgatagtc    19320
cttgtgagtc tcatggcaaa caagtagtgt cggatattga ttatgttcca ctcaaatctg    19380
ctacgtgtat tacacgatgc aatttaggtg gtgctgtttg cagacaccat gcaaatgagt    19440
accgacagta cttggatgca tataatatga tgatttctgc tggatttagc ctatggattt    19500
acaaacaatt tgatacttat aacctgtgga atacatttac caggttacag agtttagaaa    19560
atgtggctta taatgttgtt aataaaggac actttgatgg acacgccggc gaagcacctg    19620
tttccatcat taataatgct gtttacacaa aggtagatgg tattgatgtg gagatctttg    19680
aaaataagac aacacttcct gttaatgttg catttgagct ttgggctaag cgtaacatta    19740
aaccagtgcc agagattaag atactcaata atttgggtgt tgatatcgct gctaatactg    19800
taatctggga ctacaaaaga gaagccccag cacatgtatc tacaataggt gtctgcacaa    19860
tgactgacat tgccaagaaa cctactgaga gtgcttgttc ttcacttact gtcttgtttg    19920
atggtagagt ggaaggacag gtagaccttt ttagaaacgc ccgtaatggt gttttaataa    19980
cagaaggttc agtcaaaggt ctaacacctt caaagggacc agcacaagct agcgtcaatg    20040
gagtcacatt aattggagaa tcagtaaaaa cacagtttaa ctactttaag aaagtagacg    20100
gcattattca acagttgcct gaaacctact ttactcagag cagagactta gaggatttta    20160
agcccagatc acaaatggaa actgactttc tcgagctcgc tatggatgaa ttcatacagc    20220
gatataagct cgagggctat gccttcgaac acatcgttta tggagatttc agtcatggac    20280
aacttggcgg tcttcattta atgataggct tagccaagcg ctcacaagat tcaccactta    20340
aattagagga tttatccct atggacagca cagtgaaaaa ttacttcata acagatgcgc    20400
aaacaggttc atcaaaatgt gtgtgttctg tgattgatct tttacttgat gactttgtcg    20460
agataataaa gtcacaagat ttgtcagtga tttcaaaagt ggtcaaggtt acaattgact    20520
atgctgaaat ttcattcatg ctttggtgta aggatggaca tgttgaaacc ttctacccaa    20580
aactacaagc aagtcaagcg tggcaaccag gtgttgcgat gcctaacttg tacaagatgc    20640
aaagaatgct tcttgaaaag tgtgaccttc agaattatgg tgaaaatgct gttataccaa    20700
aaggaataat gatgaatgtc gcaaagtata ctcaactgtg tcaatactta aatacactta    20760
ctttagctgt accctacaac atgagagtta ttcactttgg tgctggctct gataaaggag    20820
```

```
ttgcaccagg tacagctgtg ctcagacaat ggttgccaac tggcacacta cttgtcgatt    20880
cagatcttaa tgacttcgtc tccgacgcag attctacttt aattggagac tgtgcaacag    20940
tacatacggc taataaatgg gaccttatta ttagcgatat gtatgaccct aggaccaaac    21000
atgtgacaaa agagaatgac tctaaagaag ggttttcac ttatctgtgt ggatttataa     21060
agcaaaaact agccctgggt ggttctatag ctgtaaagat aacagagcat tcttggaatg    21120 ctgacccttta caagcttatg ggccatttct catggtggac agcttttgtt acaaatgtaa   21180
atgcatcatc atcggaagca tttttaattg gggctaacta tcttggcaag ccgaaggaac    21240
aaattgatgg ctataccatg catgctaact acatttctg gaggaacaca aatcctatcc     21300
agttgtcttc ctattcactc tttgacatga gcaaatttcc tcttaaatta agggaactg     21360 ctgtaatgtc tcttaaggag aatcaaatca atgatatgat ttattctctt ctggaaaaag    21420
gtaggcttat cattagagaa acaacagag ttgtggtttc aagtgatatt cttgttaaca     21480
actaaacgaa catgtttatt ttcttattat ttcttactct cactagtggt agtgaccttg    21540
accggtgcac cacttttgat gatgttcaag ctcctaatta cactcaacat acttcatcta    21600
tgaggggggt tactatcct gatgaaattt ttagatcaga cactctttat ttaactcagg     21660 attatttct tccattttat tctaatgtta cagggtttca tactattaat catacgtttg     21720
gcaaccctgt cataccttt aaggatggta tttattttgc tgccacagag aaatcaaatg     21780
ttgtccgtgg ttgggttttt ggttctacca tgaacaacaa gtcacagtcg gtgattatta    21840
ttaacaattc tactaatgtt gttatacgag catgtaactt tgaattgtgt gacaaccctt    21900
tctttgctgt ttctaaaccc atgggtacac agacacatac tatgatattc gataatgcat    21960
ttaattgcac tttcgagtac atatctgatg ccttttcgct tgatgtttca gaaaagtcag    22020
gtaattttaa acacttacga gagtttgtgt ttaaaaataa agatgggttt ctctatgttt    22080
ataagggcta tcaacctata gatgtagttc gtgatctacc ttctggtttt aacactttga    22140
aacctatttt taagttgcct cttggtatta acattacaaa ttttagagcc attcttacag    22200
ccttttcacc tgctcaagac atttgggca cgtcagctgc agcctatttt gttggctatt     22260
taaagccaac tacattatg ctcaagtatg atgaaaatgg tacaatcaca gatgctgttg     22320
attgttctca aaatccactt gctgaactca aatgctctgt taagagcttt gagattgaca    22380
aaggaattta ccagacctct aatttcaggg ttgttccctc aggagatgtt gtgagattcc    22440
ctaatattac aaacttgtgt ccttttggag aggtttttaa tgctactaaa ttcccttctg    22500
tctatgcatg ggagagaaaa aaaatttcta ttgtgttgc tgattactct gtgctctaca    22560
actcaacatt tttttcaacc tttaagtgct atggcgtttc tgccactaag ttgaatgatc    22620
tttgcttctc caatgtctat gcagattctt tgtagtcaa gggagatgat gtaagacaaa    22680
tagcgccagg acaaactggt gttattgctg attataatta taaattgcca gatgatttca    22740
tgggttgtgt ccttgcttgg aatactagga acattgatgc tacttcaact ggtaattata    22800
attataaata taggtatctt agacatggca agcttaggcc ctttgagaga gacatatcta    22860
atgtgccttt ctcccctgat ggcaaacctt gcaccccacc tgctcttaat tgttattggc    22920
cattaaatga ttatggtttt tacaccacta ctggcattgg ctaccaacct tacagagttg    22980
tagtactttc ttttgaactt ttaaatgcac cggccacggt tgtggacca aaattatcca    23040 ctgacccttat taagaaccag tgtgtcaatt ttaatttaa tggactcact ggtactggtg    23100
tgttaactcc ttcttcaaag agatttcaac catttcaaca atttggccgt gatgtttctg    23160
```

```
atttcactga ttccgttcga gatcctaaaa catctgaaat attagacatt tcaccttgcg    23220
cttttggggg tgtaagtgta attacacctg gaacaaatgc ttcatctgaa gttgctgttc    23280
tatatcaaga tgttaactgc actgatgttt ctacagcaat tcatgcagat caactcacac    23340
cagcttggcg catatattct actggaaaca atgtattcca gactcaagca ggctgtctta    23400
taggagctga gcatgtcgac acttcttatg agtgcgacat tcctattgga gctggcattt    23460
gtgctagtta ccatacagtt tctttattac gtagtactag ccaaaaatct attgtggctt    23520
atactatgtc tttaggtgct gatagttcaa ttgcttactc taataacacc attgctatac    23580
ctactaactt ttcaattagc attactacag aagtaatgcc tgtttctatg gctaaaacct    23640
ccgtagattg taatatgtac atctgcggag attctactga atgtgctaat ttgcttctcc    23700
aatatggtag cttttgcaca caactaaatc gtgcactctc aggtattgct gctgaacagg    23760
atcgcaacac acgtgaagtg ttcgctcaag tcaaacaaat gtacaaaacc ccaactttga    23820
aatattttgg tggttttaat ttttcacaaa tattacctga ccctctaaag ccaactaaga    23880 ggtctttat tgaggacttg ctctttaata aggtgacact cgctgatgct ggcttcatga    23940
agcaatatgg cgaatgccta ggtgatatta tgctagaga tctcatttgt gcgcagaagt    24000
tcaatggact tacagtgttg ccacctctgc tcactgatga tatgattgct gcctacactg    24060
ctgctctagt tagtggtact gccactgctg gatggacatt tggtgctggc gctgctcttc    24120
aaataccttt tgctatgcaa atggcatata ggttcaatgg cattggagtt acccaaaatg    24180
ttctctatga gaaccaaaaa caaatcgcca accaatttaa caaggcgatt agtcaaattc    24240
aagaatcact acaacaaca tcaactgcat gggcaagct gcaagacgtt gttaaccaga    24300
atgctcaagc attaaacaca cttgttaaac aacttagctc taattttggt gcaatttcaa    24360
gtgtgctaaa tgatatcctt tcgcgacttg ataaagtcga ggcggaggta caaattgaca    24420
ggttaattac aggcagactt caaagccttc aaacctatgt aacacaacaa ctaatcaggg    24480
ctgctgaaat cagggcttct gctaatcttg ctgctactaa aatgtctgag tgtgttcttg    24540
gacaatcaaa aagagttgac ttttgtggaa agggctacca ccttatgtcc ttcccacaag    24600
cagccccgca tggtgttgtc ttcctacatg tcacgtatgt gccatcccag gagaggaact    24660
tcaccacagc gccagcaatt tgtcatgaag gcaaagcata cttccctcgt gaaggtgttt    24720
ttgtgtttaa tggcacttct ggtttatta cacagaggaa cttctttttct ccacaaataa    24780 ttactacaga caatacattt gtctcaggaa attgtgatgt cgttattggc atcattaaca    24840
acacagttta tgatcctctg caacctgagc ttgactcatt caaagaagag ctggacaagt    24900
acttcaaaaa tcatacatca ccagatgttg atcttggcga catttcaggc attaacgctt    24960
ctgtcgtcaa cattcaaaaa gaaattgacc gcctcaatga ggtcgctaaa aatttaaatg    25020
aatcactcat tgaccttcaa gaattgggaa aatatgagca atatattaaa tggccttggt    25080
atgtttggct cggcttcatt gctggactaa ttgccatcgt catggttaca atcttgcttt    25140
gttgcatgac tagttgttgc agttgcctca agggtgcatg ctcttgtggt tcttgctgca    25200
agtttgatga ggatgactct gagccagttc tcaagggtgt caaattacat tacacataaa    25260
cgaacttatg gatttgttta tgagattttt tactcttaga tcaattactg cacagccagt    25320
aaaaattgac aatgcttctc ctgcaagtac tgttcatgct acagcaacga taccgctaca    25380
agcctcactc cctttcggat ggcttgttat tggcgttgca tttcttgctg tttttcagag    25440
cgctaccaaa ataattgcgc tcaataaaag atggcagcta gccctttata agggcttcca    25500
gttcatttgc aatttactgc tgctatttgt taccatctat tcacatcttt tgcttgtcgc    25560
```

```
tgcaggtatg gaggcgcaat ttttgtacct ctatgccttg atatattttc tacaatgcat    25620
caacgcatgt agaattatta tgagatgttg gctttgttgg aagtgcaaat ccaagaaccc    25680
attactttat gatgccaact actttgtttg ctggcacaca cataactatg actactgtat    25740
accatataac agtgtcacag atacaattgt cgttactgaa ggtgacggca tttcaacacc    25800
aaaactcaaa gaagactacc aaattggtgg ttattctgag gataggcact caggtgttaa    25860
agactatgtc gttgtacatg gctatttcac cgaagtttac taccagcttg agtctacaca    25920
aattactaca gacactggta ttgaaaatgc tacattcttc atctttaaca agcttgttaa    25980
agacccaccg aatgtgcaaa tacacacaat cgacggctct tcaggagttg ctaatccagc    26040
aatggatcca atttatgatg agccgacgac gactactagc gtgcctttgt aagcacaaga    26100
aagtgagtac gaacttatgt actcattcgt ttcggaagaa acaggtacgt taatagttaa    26160
tagcgtactt ctttttcttg ctttcgtggt attcttgcta gtcacactag ccatccttac    26220
tgcgcttcga ttgtgtgcgt actgctgcaa tattgttaac gtgagtttag taaaaccaac    26280
ggtttacgtc tactcgcgtg ttaaaaatct gaactcttct gaaggagttc ctgatcttct    26340
ggtctaaacg aactaactat tattattatt ctgtttggaa ctttaacatt gcttatcatg    26400
gcagacaacg gtactattac cgttgaggag cttaaacaac tcctgaaaca atggaaccta    26460
gtaataggtt tcctattcct agcctggatt atgttactac aatttgccta ttctaatcgg    26520
aacaggtttt tgtacataat aaagcttgtt ttcctctggc tcttgtggcc agtaacactt    26580
gcttgttttg tgcttgctgc tgtctacaga attaattggg tgactggcgg gattgcgatt    26640
gcaatggctt gtattgtagg cttgatgtgg cttagctact tcgttgcttc cttcaggctg    26700
tttgctcgta cccgctcaat gtggtcattc aacccagaaa caaacattct tctcaatgtg    26760
cctctccggg ggacaattgt gaccagaccg ctcatggaaa gtgaacttgt cattggtgct    26820
gtgatcattc gtggtcactt gcgaatggcc ggacactccc tagggcgctg tgacattaag    26880
gacctgccaa aagagatcac tgtggctaca tcacgaacgc tttcttatta caaattagga    26940
gcgtcgcagc gtgtaggcac tgattcaggt tttgctgcat acaaccgcta ccgtattgga    27000
aactataaat taaatacaga ccacgccggt agcaacgaca atattgcttt gctagtacag    27060
taagtgacaa cagatgtttc atcttgttga cttccaggtt acaatagcag agatattgat    27120
tatcattatg aggactttca ggattgctat ttggaatctt gacgttataa taagttcaat    27180
agtgagacaa ttatttaagc ctctaactaa gaagaattat tcggagttag atgatgaaga    27240
acctatggag ttagattatc cataaaacga acatgaaaat tattctcttc ctgacattga    27300
ttgtatttac atcttgcgag ctatatcact atcaggagtg tgttagaggt acgactgtac    27360
tactaaaaga accttgccca tcaggaacat acgagggcaa ttcaccattt caccctcttg    27420
ctgacaataa atttgcacta acttgcacta gcacacactt tgcttttgct tgtgctgacg    27480
gtactcgaca tacctatcag ctgcgtgcaa gatcagtttc accaaaactt ttcatcagac    27540
aagaggaggt tcaacaagag ctctactcgc cactttttct cattgttgct gctctagtat    27600
ttttaatact ttgcttcacc attaagagaa agacagaatg aatgagctca ctttaattga    27660
cttctatttg tgcttttag cctttctgct attccttgtt ttaataatgc ttattatatt    27720
ttggttttca ctcgaaatcc aggatctaga agaaccttgt accaaagtct aaacgaacat    27780
gaaacttctc attgttttga cttgtatttc tctatgcagt tgcatatgca ctgtagtaca    27840
gcgctgtgca tctaataaac ctcatgtgct tgaagatcct tgtaaggtac aacactaggg    27900
```

```
gtaatactta tagcactgct tggctttgtg ctctaggaaa ggttttacct tttcatagat    27960
ggcacactat ggttcaaaca tgcacaccta atgttactat caactgtcaa gatccagctg    28020
gtggtgcgct tatagctagg tgttggtacc ttcatgaagg tcaccaaact gctgcattta    28080
gagacgtact tgttgtttta aataaacgaa caaattaaaa tgtctgataa tggaccccaa    28140
tcaaaccaac gtagtgcccc ccgcattaca tttggtggac ccacagattc aactgacaat    28200
aaccagaatg gaggacgcaa tgggcaagg ccaaaacagc gccgacccca aggtttaccc    28260
aataatactg cgtcttggtt cacagctctc actcagcatg gcaaggagga acttagattc    28320
cctcgaggcc agggcgttcc aatcaacacc aatagtggtc cagatgacca aattggctac    28380
taccgaagag ctacccgacg agttcgtggt ggtgacggca aaatgaaaga gctcagcccc    28440
agatggtact tctattacct aggaactggc ccagaagctt cacttcccta cggcgctaac    28500
aaagaaggca tcgtatgggt tgcaactgag ggagccttga atacacccaa agaccacatt    28560
ggcacccgca atcctaataa caatgctgcc accgtgctac aacttcctca aggaacaaca    28620
ttgccaaaag gcttctacgc agagggaagc agaggcggca gtcaagcctc ttctcgctcc    28680
tcatcacgta gtcgcggtaa ttcaagaaat tcaactcctg gcagcagtag gggaaattct    28740
cctgctcgaa tggctagcgg aggtggtgaa actgccctcg cgctattgct gctagacaga    28800
ttgaaccagc ttgagagcaa agtttctggt aaaggccaac aacaacaagg ccaaactgtc    28860
actaagaaat ctgctgctga ggcatctaaa aagcctcgcc aaaaacgtac tgccacaaaa    28920
cagtacaacg tcactcaagc atttgggaga cgtggtccag aacaaaccca aggaaatttc    28980
ggggaccaag acctaatcag acaaggaact gattacaaac attggccgca aattgcacaa    29040
tttgctccaa gtgcctctgc attctttgga atgtcacgca ttggcatgga agtcacacct    29100
tcgggaacat ggctgactta tcatggagcc attaaattgg atgacaaaga tccacaattc    29160
aaagacaacg tcatactgct gaacaagcac attgacgcat acaaaacatt cccaccaaca    29220
gagcctaaaa aggacaaaaa gaaaaagact gatgaagctc agcctttgcc gcagagacaa    29280
aagaagcagc ccactgtgac tcttcttcct gcggctgaca tggatgattt ctccagacaa    29340
cttcaaaatt ccatgagtgg agcttctgct gattcaactc aggcataaac actcatgatg    29400
accacacaag gcagatgggc tatgtaaacg ttttcgcaat tccgtttacg atacatagtc    29460
tactcttgtg cagaatgaat tctcgtaact aaacagcaca gtaggttta gttaacttta    29520 atctcacata gcaatcttta atcaatgtgt aacattaggg aggacttgaa agagccacca    29580
cattttcatc gaggccacgc ggagtacgat cgagggtaca gtgaataatg ctagggagag    29640
ctgcctatat ggaagagccc taatgtgtaa aattaatttt agtagtgcta tccccatgtg    29700
attttaatag cttcttagga gaatgacaaa aaaaaaaaaa aaaaaaaaa a    29751
```

<210> SEQ ID NO 4
<211> LENGTH: 30119
<212> TYPE: DNA
<213> ORGANISM: Human betacoronavirus 2c EMC/2012

<400> SEQUENCE: 4

```
gatttaagtg aatagcttgg ctatctcact tccctcgtt ctcttgcaga actttgattt    60
taacgaactt aaataaaagc cctgttgttt agcgtatcgt tgcacttgtc tggtgggatt    120
gtggcattaa tttgcctgct catctaggca gtggacatat gctcaacact gggtataatt    180
ctaattgaat actattttc agttagacg tcgtgtctct tgtacgtctc ggtcacaata    240
cacggtttcg tccggtgcgt ggcaattcgg ggcacatcat gtctttcgtg gctggtgtga    300
```

```
ccgcgcaagg tgcgcgcggt acgtatcgag cagcgctcaa ctctgaaaaa catcaagacc    360
atgtgtctct aactgtgcca ctctgtggtt caggaaacct ggttgaaaaa ctttcaccat    420
ggttcatgga tggcgaaaat gcctatgaag tggtgaaggc catgttactt aaaaaggagc    480
cacttctcta tgtgcccatc cggctggctg acacactag acacctccca ggtcctcgtg    540
tgtacctggt tgagaggctc attgcttgtg aaaatccatt catggttaac caattggctt    600
atagctctag tgcaaatggc agcctggttg gcacaacttt gcagggcaag cctattggta    660
tgttcttccc ttatgacatc gaacttgtca caggaaagca aaatattctc ctgcgcaagt    720
atggccgtgg tggttatcac tacacccat tccactatga gcgagacaac acctcttgcc    780
ctgagtggat ggacgatttt gaggcggatc ctaaaggcaa atatgcccag aatctgctta    840
agaagttgat tggcggtgat gtcactccag ttgaccaata catgtgtggc gttgatggaa    900
aacccattag tgcctacgca ttttaatgg ccaaggatgg aataaccaaa ctggctgatg    960
ttgaagcgga cgtcgcagca cgtgctgatg acgaaggctt catcacatta aagaacaatc   1020
tatatagatt ggtttggcat gttgagcgta aagacgttcc atatcctaag caatctattt   1080
ttactattaa tagtgtggtc caaaaggatg tgttgaaaaa cactcctcct cactattta    1140 ctcttggatg caaaatttta acgctcaccc cacgcaacaa gtggagtggc gtttctgact   1200
tgtccctcaa acaaaaactc ctttacacct tctatggtaa ggagtcactt gagaacccaa   1260
cctacattta ccactccgca ttcattgagt gtggaagttg tggtaatgat tcctggctta   1320
cagggaatgc tatccaaggg tttgcctgtg atgtggggc atcatataca gctaatgatg   1380
tcgaagtcca atcatctggc atgattaagc caaatgctct tctttgtgct acttgcccct   1440
ttgctaaggg tgatagctgt tcttctaatt gcaaacattc agttgctcag ttggttagtt   1500 accttttctga acgctgtaat gttattgctg attctaagtc cttcacactt atctttggtg   1560
gcgtagctta cgcctacttt ggatgtgagg aaggtactat gtactttgtg cctagagcta   1620
agtctgttgt ctcaaggatt ggagactcca tctttacagg ctgtactggc tcttggaaca   1680
aggtcactca aattgctaac atgttcttgg aacagactca gcattccctt aactttgtgg   1740
gagagttcgt tgtcaacgat gttgtcctcg caattctctc tggaaccaca actaatgttg   1800
acaaaatacg ccagcttctc aaaggtgtca cccttgacaa gttgcgtgat tatttagctg   1860
actatgacgt agcagtcact gccggcccat tcatggaata tgctattaat gttggtggta   1920
caggattaca gtatgccgcc attactgcac cttatgtagt tctcactggc ttaggtgagt   1980
cctttaagaa agttgcaacc ataccgtata aggtttgcaa ctctgttaag gatactctgg   2040
cttattatgc tcacagcgtg ttgtacagag ttttccctta tgacatggat tctggtgtgt   2100
catcctttag tgaactactt tttgattgcg ttgatctttc agtagcttct acctatttt    2160 tagtccgcat cttgcaagat aagactggcg actttatgtc tacaattatt acttcctgcc   2220
aaactgctgt tagtaagctt ctagatacat gttttgaagc tacagaagca acatttaact   2280
tcttgttaga tttggcagga ttgttcagaa tctttctccg caatgcctat gtgtacactt   2340
cacaagggtt tgtggtggtc aatggcaaag ttttctacac tgtcaaacaa gtgttagact   2400
tgcttaataa gggtatgcaa cttttgcata caaaggtctc ctgggctggt tctaaaatca   2460
ttgctgttat ctacagcggc agggagtctc taatattccc atcgggaacc tattactgtg   2520
tcaccactaa ggctaagtcc gttcaacaag atcttgacgt tattttgcct ggtgagtttt   2580
ccaagaagca gttaggactg ctccaaccta ctgacaattc tacaactgtt agtgttactg   2640
```

-continued

| | |
|---|---|
| tatccagtaa catggttgaa actgttgtgg gtcaacttga gcaaactaat atgcatagtc | 2700 |
| ctgatgttat agtaggtgac tatgtcatta ttagtgaaaa attgtttgtg cgtagtaagg | 2760 |
| aagaagacgg atttgccttc taccctgctt gcactaatgg tcatgctgta ccgactctct | 2820 |
| ttagacttaa gggaggtgca cctgtaaaaa aagtagcctt tggcggtgat caagtacatg | 2880 |
| aggttgctgc tgtaagaagt gttactgtcg agtacaacat tcatgctgta ttagacacac | 2940 |
| tacttgcttc ttctagtctt agaacctttg ttgtagataa gtcttttgtca attgaggagt | 3000 |
| ttgctgacgt agtaaaggaa caagtctcag acttgcttgt taaattactg cgtggaatgc | 3060 |
| cgattccaga ttttgattta gacgatttta ttgacgcacc atgctattgc tttaacgctg | 3120 |
| agggtgatgc atcctggtct tctactatga tcttctctct tcaccccgtc gagtgtgacg | 3180 |
| aggagtgttc tgaagtagag gcttcagatt tagaagaagg tgaatcagag tgcatttctg | 3240 |
| agacttcaac tgaacaagtt gacgtttctc atgagacttc tgacgacgag tgggctgctg | 3300 |
| cagttgatga agcgttccct ctcgatgaag cagaagatgt tactgaatct gtgcaagaag | 3360 |
| aagcacaacc agtagaagta cctgttgaag atattgcgca ggttgtcata gctgacacct | 3420 |
| tacaggaaac tcctgttgtg cctgatactg ttgaagtccc accgcaagtg gtgaaacttc | 3480 |
| cgtctgcacc tcagactatc cagcccgagg taaaagaagt tgcacctgtc tatgaggctg | 3540 |
| ataccgaaca gacacagaat gttactgtta aacctaagag gttacgcaaa aagcgtaatg | 3600 |
| ttgacccttt gtccaatttt gaacataagg ttattacaga gtgcgttacc atagttttag | 3660 |
| gtgacgcaat tcaagtagcc aagtgctatg gggagtctgt gttagttaat gctgctaaca | 3720 |
| cacatcttaa gcatggcggt ggtatcgctg gtgctattaa tgcggcttca aaaggggctg | 3780 |
| tccaaaaaga gtcagatgag tatattctgg ctaaagggcc gttacaagta ggagattcag | 3840 |
| ttctcttgca aggccattct ctagctaaga atatcctgca tgtcgtaggc ccagatgccc | 3900 |
| gcgctaaaca ggatgtttct ctccttagta agtgctataa ggctatgaat gcatatcctc | 3960 |
| ttgtagtcac tcctcttgtt tcagcaggca tatttggtgt aaaaccagct gtgtcttttg | 4020 |
| attatcttat tagggaggct aagactagag ttttagtcgt cgttaattcc caagatgtct | 4080 |
| ataagagtct taccatagtt gacattccac agagtttgac ttttttcatat gatgggttac | 4140 |
| gtggcgcaat acgtaaagct aaagattatg gttttactgt ttttgtgtgc acagacaact | 4200 |
| ctgctaacac taaagttctt aggaacaagg gtgttgatta tactaagaag tttcttacag | 4260 |
| ttgacggtgt gcaatattat tgctacacgt ctaaggacac tttagatgat atcttacaac | 4320 |
| aggctaataa gtctgttggt attatatcta tgccttttgg atatgtgtct catggtttag | 4380 |
| acttaatgca agcagggagt gtcgtgcgta gagttaacgt gcccacgtg tgtctcctag | 4440 |
| ctaataaaga gcaagaagct attttgatgt ctgaagacgt taagttaaac ccttcagaag | 4500 |
| atttttataaa gcacgtccgc actaatggtg gttacaattc ttggcattta gtcgagggtg | 4560 |
| aactattggt gcaagactta cgcttaaata agctcctgca ttggtctgat caaaccatat | 4620 |
| gctacaagga tagtgtgttt tatgttgtaa agaatagtac agcttttcca tttgaaacac | 4680 |
| tttcagcatg tcgtgcgtat ttggattcac gcacgacaca gcagttaaca atcgaagtct | 4740 |
| tagtgactgt cgatggtgta aatttttgaa cagtcgttct aaataataag aacacttata | 4800 |
| gatcacagct tggatgcgtt ttctttaatg gtgctgatat ttctgacacc attcctgatg | 4860 |
| agaaacagaa tggtcacagt ttatatctag cagacaattt gactgctgat gaaacaaagg | 4920 |
| cgcttaaaga gttatatggc cccgttgatc ctacttcctt acacagattc tattcactta | 4980 |
| aggctgcagt ccatgggtgg aagatggttg tgtgtgataa ggtacgttct ctcaaattga | 5040 |

```
gtgataataa ttgttatctt aatgcagtta ttatgacact tgatttattg aaggacatta    5100
aatttgttat acctgctcta cagcatgcat ttatgaaaca taagggcggt gattcaactg    5160
acttcatagc cctcattatg gcttatggca attgcacatt tggtgctcca gatgatgcct    5220
ctcggttact tcataccgtg cttgcaaagg ctgagttatg ctgttctgca cgcatggttt    5280
ggagagagtg gtgcaatgtc tgtggcataa aagatgttgt tctacaaggc ttaaaagctt    5340
gttgttacgt gggtgtgcaa actgttgaag atctgcgtgc tcgcatgaca tatgtatgcc    5400
agtgtggtgg tgaacgtcat cggcaattag tcgaacacac cacccctgg ttgctgctct    5460 caggcacacc aaatgaaaaa ttggtgacaa cctccacggc gcctgatttt gtagcattta    5520
atgtctttca gggcattgaa acggctgttg gccattatgt tcatgctcgc ctgaagggtg    5580
gtcttatttt aaagtttgac tctggcaccg ttagcaagac ttcagactgg aagtgcaagg    5640
tgacagatgt acttttcccc ggccaaaaat acagtagcga ttgtaatgtc gtacggtatt    5700
ctttggacgg taatttcaga acagaggttg atcccgacct atctgctttc tatgttaagg    5760
atggtaaata ctttacaagt gaaccacccg taacatattc accagctaca atttagctg    5820 gtagtgtcta cactaatagc tgccttgtat cgtctgatgg acaacctggc ggtgatgcta    5880
ttagtttgag ttttaataac cttttagggt ttgattctag taaaccagtc actaagaaat    5940
acacttactc cttcttgcct aaagaagacg gcgatgtgtt gttggctgag tttgacactt    6000
atgaccctat ttataagaat ggtgccatgt ataaaggcaa accaattctt tgggtcaata    6060
aagcatctta tgatactaat cttaataagt tcaatagagc tagtttgcgt caaattttg    6120 acgtagcccc cattgaactc gaaaataaat tcacacctt gagtgtggag tctacaccag    6180
ttgaacctcc aactgtagat gtggtagcac ttcaacagga aatgacaatt gtcaaatgta    6240
agggtttaaa taaccctttc gtgaaggaca atgtcagttt cgttgctgat gattcaggta    6300
ctcccgttgt tgagtatctg tctaaagaag acctacatac attgtatgta gaccctaagt    6360
atcaagtcat tgtcttaaaa gacaatgtac tttcttctat gcttagattg cacaccgttg    6420
agtcaggtga tattaacgtt gttgcagctt ccggatcttt gacacgtaaa gtgaagttac    6480
tatttagggc ttcatttat ttcaaagaat ttgctacccg cactttcact gctaccactg    6540
ctgtaggtag ttgtataaag agtgtagtgc ggcatctagg tgttactaaa ggcatattga    6600
caggctgttt tagttttgcc aagatgttat ttatgcttcc actagcttac tttagtgatt    6660
caaaactcgg caccacagag gttaaagtga gtgctttgaa aacagccggc gttgtgacag    6720
gtaatgttgt aaaacagtgt tgcactgctg ctgttgattt aagtatggat aagttgcgcc    6780
gtgtggattg gaaatcaacc ctacggttgt tacttatgtt atgcacaact atggtattgt    6840
tgtcttctgt gtatcacttg tatgtcttca atcaggtctt atcaagtgat gttatgtttg    6900
aagatgccca aggtttgaaa aagttctaca agaagttag agcttaccta ggaatctctt    6960
ctgcttgtga cggtcttgct tcagcttata gggcgaattc cttttgatgta cctacattct    7020 gcgcaaaccg ttctgcaatg tgtaattggt gcttgattag ccaagattcc ataactcact    7080
acccagctct taagatggtt caaacacatc ttagccacta tgttcttaac atagattggt    7140 tgtggttgc atttgagact ggtttggcat acatgctcta tacctcggcc ttcaactggt    7200
tgttgttggc aggtacattg cattattct ttgcacagac ttccatattt gtagactggc    7260
ggtcatacaa ttatgctgtg tctagtgcct tctggttatt cacccacatt ccaatggcgg    7320
gtttggtacg aatgtataat ttgttagcat gccttggct tttacgcaag ttttatcagc    7380
```

-continued

| | |
|---|---|
| atgtaatcaa tggttgcaaa gatacggcat gcttgctctg ctataagagg aaccgactta | 7440 |
| ctagagttga agcttctacc gttgtctgtg gtggaaaacg tacgttttat atcacagcaa | 7500 |
| atggcggtat ttcattctgt cgtaggcata attggaattg tgtggattgt gacactgcag | 7560 |
| gtgtggggaa taccttcatc tgtgaagaag tcgcaaatga cctcactacc gccctacgca | 7620 |
| ggcctattaa cgctacggat agatcacatt attatgtgga ttccgttaca gttaaagaga | 7680 |
| ctgttgttca gtttaattat cgtagagacg gtcaaccatt ctacgagcgg tttcccctct | 7740 |
| gcgcttttac aaatctagat aagttgaagt tcaaagaggt ctgtaaaact actactggta | 7800 |
| tacctgaata caactttatc atctacgact catcagatcg tggccaggaa agtttagcta | 7860 |
| ggtctgcatg tgtttattat tctcaagtct tgtgtaaatc aattcttttg gttgactcaa | 7920 |
| gtttggttac ttctgttggt gattctagtg aaatcgccac taaaatgttt gattcctttg | 7980 |
| ttaatagttt cgtctcgctg tataatgtca cacgcgataa gttggaaaaa cttatctcta | 8040 |
| ctgctcgtga tggcgtaagg cgaggcgata acttccatag tgtcttaaca acattcattg | 8100 |
| acgcagcacg aggccccgca ggtgtggagt ctgatgttga gaccaatgaa attgttgact | 8160 |
| ctgtgcagta tgctcataaa catgacatac aaattactaa tgagagctac aataattatg | 8220 |
| taccctcata tgttaaacct gatagtgtgt ctaccagcga tttaggtagt ctcattgatt | 8280 |
| gtaatgcggc ttcagttaac caaattgtct tgcgtaattc taatggtgct tgcatttgga | 8340 |
| acgctgctgc atatatgaaa ctctcggatg cacttaaacg acagattcgc attgcatgcc | 8400 |
| gtaagtgtaa tttagctttc cggttaacca cctcaaagct acgcgctaat gataatatct | 8460 |
| tatcagttag attcactgct aacaaaattg ttggtggtgc tcctacatgg tttaatgcgt | 8520 |
| tgcgtgactt tacgttaaag ggttatgttc ttgctaccat tattgtgttt ctgtgtgctg | 8580 |
| tactgatgta tttgtgttta cctacatttt ctatggcacc tgttgaattt tatgaagacc | 8640 |
| gcatcttgga ctttaaagtt cttgataatg gtatcattag ggatgtaaat cctgatgata | 8700 |
| agtgctttgc taataagcac cggtccttca cacaatggta tcatgagcat gttggtggtg | 8760 |
| tctatgacaa ctctatcaca tgcccattga cagttgcagt aattgctgga gttgctggtg | 8820 |
| ctcgcattcc agacgtacct actacattgg cttgggtgaa caatcagata attttctttg | 8880 |
| tttctcgagt ctttgctaat acaggcagtg tttgctacac tcctatagat gagatacccc | 8940 |
| ataagagttt ctctgatagt ggttgcattc ttccatctga gtgcactatg tttagggatg | 9000 |
| cagagggccg tatgacacca tactgccatg atcctactgt tttgcctggg cttttgcgt | 9060 |
| acagtcagat gaggcctcat gttcgttacg acttgtatga tggtaacatg tttattaaat | 9120 |
| ttcctgaagt agtatttgaa agtacactta ggattactag aactctgtca actcagtact | 9180 |
| gccggttcgg tagttgtgag tatgcacaag agggtgtttg tattaccaca aatggctcgt | 9240 |
| gggccatttt taatgaccac catcttaata gacctggtgt ctattgtggc tctgatttta | 9300 |
| ttgacattgt caggcggtta gcagtatcac tgttccagcc tattacttat ttccaattga | 9360 |
| ctacctcatt ggtcttgggt ataggtttgt gtgcgttcct gactttgctc ttctattata | 9420 |
| ttaataagt aaaacgtgct tttgcagatt acacccagtg tgctgtaatt gctgttgttg | 9480 |
| ctgctgttct taatagcttg tgcatctgct tgttaccctc tataccattg tgtatagtac | 9540 |
| cttacactgc attgtactat tatgctacat tctatttac taatgagcct gcatttatta | 9600 |
| tgcatgtttc ttggtacatt atgttcgggc ctatcgttcc catatggatg acctgcgtct | 9660 |
| atacagttgc aatgtgcttt agacacttct tctgggtttt agcttatttt agtaagaaac | 9720 |
| atgtagaagt ttttactgat ggtaagctta attgtagttt ccaggacgct gcctctaata | 9780 |

```
tctttgttat taacaaggac acttatgcag ctcttagaaa ctctttaact aatgatgcct    9840
attcacgatt tttggggttg tttaacaagt ataagtactt ctctggtgct atggaaacag    9900
ccgcttatcg tgaagctgca gcatgtcatc ttgctaaagc cttacaaaca tacagcgaga    9960
ctggtagtga tcttctttac caaccaccca actgtagcat aacctctggc gtgttgcaaa   10020
gcggtttggt gaaaatgtca catcccagtg gagatgttga ggcttgtatg gttcaggtta   10080
cctgcggtag catgactctt aatggtcttt ggcttgacaa cacagtctgg tgcccacgac   10140
acgtaatgtg cccggctgac cagttgtctg atcctaatta tgatgccttg ttgatttcta   10200
tgactaatca tagtttcagt gtgcaaaaac acattggcgc tccagcaaac ttgcgtgttg   10260
ttggtcatgc catgcaaggc actcttttga agttgactgt cgatgttgct aaccctagca   10320
ctccagccta cacttttaca acagtgaaac ctggcgcagc atttagtgtg ttagcatgct   10380
ataatggtcg tccgactggt acattcactg ttgtaatgcg ccctaactac acaattaagg   10440
gttcctttct gtgtggttct tgtggtagtg ttggttacac caaggagggt agtgtgatca   10500
atttctgtta catgcatcaa atggaacttg ctaatggtac ataccggt tcagcatttg   10560
atggtactat gtatggtgcc tttatggata acaagtgca ccaagttcag ttaacagaca   10620
aatactgcag tgttaatgta gtagcttggc tttacgcagc aatacttaat ggttgcgctt   10680
ggtttgtaaa acctaatcgc actagtgttg tttctttaa tgaatgggct cttgccaacc   10740
aattcactga atttgttggc actcaatccg ttgacatgtt agctgtcaaa acaggcgttg   10800
ctattgaaca gctgctttat gcgatccaac aactgtatac tgggttccag ggaaagcaaa   10860
tccttggcag taccatgttg gaagatgaat tcacacctga ggatgttaat atgcagatta   10920
tgggtgtggt tatgcagagt ggtgtgagaa aagttacata tggtactgcg cattggttgt   10980
ttgcgaccct tgtctcaacc tatgtgataa tcttacaagc cactaaattt actttgtgga   11040
actacttgtt tgagactatt cccacacagt tgttcccact cttatttgtg actatggcct   11100
tcgttatgtt gttggttaaa cacaaacaca cctttttgac acttttcttg ttgcctgtgg   11160
ctatttgttt gacttatgca aacatagtct acgagcccac tactcccatt tcgtcagcgc   11220
tgattgcagt tgcaaattgg cttgccccca ctaatgctta tatgcgcact acacatactg   11280
atattggtgt ctacattagt atgtcacttg tattagtcat tgtagtgaag agattgtaca   11340
acccatcact ttctaacttt gcgttagcat tgtgcagtgg tgtaatgtgg ttgtacactt   11400
atagcattgg agaagcctca agccccattg cctatctggt ttttgtcact acactcacta   11460
gtgattatac gattacagtc tttgttactg tcaaccttgc aaaagtttgc acttatgcca   11520
tctttgctta ctcaccacag cttacacttg tgtttccgga agtgaagatg atactttttat   11580
tatacacatg tttaggtttc atgtgtactt gctattttgg tgtcttctct cttttgaacc   11640
ttaagcttag agcacctatg ggtgtctatg actttaaggt ctcaacacaa gagttcagat   11700
tcatgactgc taacaatcta actgcaccta gaaattcttg ggaggctatg gctctgaact   11760
ttaagttaat aggtattggc ggtacacctt gtataaaggt tgctgctatg cagtctaaac   11820
ttacagatct taaatgcaca tctgtggttc tcctctctgt gctccaacag ttacacttag   11880
aggctaatag taggcctgg gctttctgtg ttaaatgcca taatgatata ttggcagcaa   11940
cagacccag tgaggctttc gagaaattcg taagtctctt tgctactttta atgacttttt   12000
ctggtaatgt agatcttgat gcgttagcta gtgatatttt tgcactcct agcgtacttc   12060
aagctactct ttctgagttt tcacacttag ctaccttgc tgagttggaa ctgcgcagga   12120
```

-continued

```
aagcctatca ggaagctatg gactctggtg acacctcacc acaagttctt aaggctttgc    12180
agaaggctgt taatatagct aaaaacgcct atgagaagga taaggcagtg gcccgtaagt    12240
tagaacgtat ggctgatcag gctatgactt ctatgtataa gcaagcacgt gctgaagaca    12300
agaaagcaaa aattgtcagt gctatgcaaa ctatgttgtt tggtatgatt aagaagctcg    12360
acaacgatgt tcttaatggt atcatttcta acgctaggaa tggttgtata cctcttagtg    12420
tcatcccact gtgtgcttca aataaacttc gcgttgtaat tcctgacttc accgtctgga    12480
atcaggtagt cacatatccc tcgcttaact acgctggggc tttgtgggac attacagtta    12540
taaacaatgt ggacaatgaa attgttaagt cttcagatgt tgtagacagc aatgaaaatt    12600
taacatggcc acttgtttta gaatgcacta gggcatccac ttctgccgtt aagttgcaaa    12660
ataatgagat caaaccttca ggtctaaaaa ccatggttgt gtctgcgggt caagagcaaa    12720
ctaactgtaa tactagttcc ttagcttatt acgaacctgt gcagggtcgt aaaatgctga    12780
tggctcttct ttctgataat gcctatctca aatgggcgcg tgttgaaggt aaggacggat    12840
ttgtcagtgt agagctacaa cctccttgca aattcttgat tgcgggacca aaaggacctg    12900
aaatccgata tctctatttt gttaaaaatc ttaacaacct tcatcgcggg caagtgttag    12960
ggcacattgc tgcgactgtt agattgcaag ctggttctaa caccgagttt gcctctaatt    13020
cctcggtgtt gtcacttgtt aacttcaccg ttgatcctca aaaagcttat ctcgatttcg    13080
tcaatgcggg aggtgcccca ttgacaaatt gtgttaagat gcttactcct aaaactggta    13140
caggtatagc tatatctgtt aaaccagaga gtacagctga tcaagagact tatggtggag    13200
cttcagtgtg tctctattgc cgtgcgcata tagaacatcc tgatgtctct ggtgtttgta    13260
aatataaggg taagtttgtc caaatccctg ctcagtgtgt ccgtgaccct gtgggatttt    13320
gtttgtcaaa taccccctgt aatgtctgtc aatattggat tggatatggg tgcaattgtg    13380
actcgcttag gcaagcagca ctgccccaat ctaaagattc caattttttta aacgagtccg    13440
gggttctatt gtaaatgccc gaatagaacc ctgttcaagt ggtttgtcca ctgatgtcgt    13500
ctttagggca tttgacatct gcaactataa ggctaaggtt gctggtattg aaaatactaa    13560
caagactaat acttgtaggt ttgtagaatt agatgaccaa gggcatcatt tagactccta    13620
ttttgtcgtt aagaggcata ctatggagaa ttatgaacta gagaagcact gttacgactt    13680
gttacgtgac tgtgatgctg tagctcccca tgatttcttc atctttgatg tagacaaagt    13740
taaaacacct catattgtac gtcagcgttt aactgagtac actatgatgg atcttgtata    13800
tgccctgagg cactttgatc aaaatagcga agtgcttaag gctatcttag tgaagtatgg    13860
ttgctgtgat gttacctact tgaaaataa actctggttt gattttgttg aaaatcccag    13920
tgttattggt gtttatcata acttggaga acgtgtacgc caagctatct taaacactgt    13980
taaattttgt gaccacatgg tcaaggctgg tttagtcggt gtgctcacac tagacaacca    14040
ggaccttaat ggcaagtggt atgattttgg tgacttcgta atcactcaac ctggttcagg    14100
agtagctata gttgatagct actattctta tttgatgcct gtgctctcaa tgaccgattg    14160
tctggccgct gagacacata gggattgtga ttttaataaa ccactcattg agtggccact    14220
tactgagtat gattttactg attataaggt acaactcttt gagaagtact ttaaatattg    14280
ggatcagacg tatcacgcaa attgcgttaa ttgtactgat gaccgttgtg tgttacattg    14340
tgctaatttc aatgtattgt ttgctatgac catgcctaag acttgtttcg gacccatagt    14400
ccgaaagatc tttgttgatg gcgtgccatt tgtagtatct tgtggttatc actacaaaga    14460
attaggttta gtcatgaata tggatgttag tctccataga cataggctct ctcttaagga    14520
```

```
gttgatgatg tatgccgctg atccagccat gcacattgcc tcctctaacg cttttcttga   14580
tttgaggaca tcatgtttta gtgtcgctgc acttacaact ggtttgactt ttcaaactgt   14640
gcggcctggc aatttaacc aagacttcta tgatttcgtg gtatctaaag gtttctttaa    14700
ggagggctct tcagtgacgc tcaaacattt tttctttgct caagatggta atgctgctat   14760
tacagattat aattactatt cttataatct gcctactatg tgtgacatca aacaaatgtt   14820
gttctgcatg gaagttgtaa acaagtactt cgaaatctat gacggtggtt gtcttaatgc   14880
ttctgaagtg gttgttaata atttagacaa gagtgctggc catcctttta ataagtttgg   14940
caaagctcgt gtctattatg agagcatgtc ttaccaggag caagatgaac tttttgccat   15000
gacaaagcgt aacgtcattc ctaccatgac tcaaatgaat ctaaatatg ctattagtgc     15060 taagaataga gctcgcactg ttgcaggcgt gtccatactt agcacaatga ctaatcgcca   15120
gtaccatcag aaaatgctta agtccatggc tgcaactcgt ggagcgactt gcgtcattgg   15180
tactacaaag ttctacggtg gctgggattt catgcttaaa acattgtaca agatgttga    15240 taatccgcat cttatgggtt gggattaccc taagtgtgat agagctatgc taatatgtg    15300 tagaatcttc gcttcactca tattagctcg taaacatggc acttgttgta ctacaaggga   15360
cagattttat cgcttggcaa atgagtgtgc tcaggtgcta agcgaatatg ttctatgtgg   15420
tggtggttac tacgtcaaac ctggaggtac cagtagcgga gatgccacca ctgcatatgc   15480
caatagtgtc tttaacattt tgcaggcgac aactgctaat gtcagtgcac ttatgggtgc   15540
taatggcaac aagattgttg acaaagaagt taaagacatg cagtttgatt tgtatgtcaa   15600
tgtttacagg agcactagcc cagaccccaa atttgttgat aaatactatg ctttctttaa   15660
taagcacttt tctatgatga tactgtctga tgacggtgtc gtttgctata atagtgatta   15720
tgcagctaag ggttacattg ctggaataca gaattttaag gaaacgctgt attatcagaa   15780
caatgtcttt atgtctgaag ctaaatgctg ggtggaaacc gatctgaaga aagggccaca   15840
tgaattctgt tcacagcata cgcttatat taaggatggc gacgatggtt acttccttcc    15900
ttatccagac ccttcaagaa ttttgtctgc cggttgcttt gtagatgata tcgttaagac   15960
tgacggtaca ctcatggtag agcggttgt gtctttggct atagatgctt accctctcac    16020
aaagcatgaa gatatagaat accagaatgt attctgggtc tacttacagt atatagaaaa   16080
actgtataaa gaccttacag gacacatgct tgacagttat tctgtcatgc tatgtggtga   16140
taattctgct aagttttggg aagaggcatt ctatagagat ctctatagtt cgcctaccac   16200
tttgcaggct gtcggttcat gcgttgtatg ccattcacag acttccctac gctgtgggac   16260
atgcatccgt agaccatttc tctgctgtaa atgctgctat gatcatgtta tagcaactcc   16320
acataagatg gttttgtctg tttctccta cgtttgtaat gccctggtt gtggcgtttc    16380 agacgttact aagctatatt taggtggtat gagctacttt tgtgtagatc atagacctgt   16440
gtgtagtttt ccactttgcg ctaatggtct tgtattcggc ttatacaaga atatgtgcac   16500
aggtagtcct tctatagttg aatttaatag gttggctacc tgtgactgga ctgaaagtgg   16560
tgattcacac cttgccaata ctacaacaga accactcaaa cttttttgctg ctgagacttt   16620 acgtgccact gaagaggcgt ctaagcagtc ttatgctatt gccaccatca agaaaattgt   16680
tggtgagcgc caactattac ttgtgtggga ggctggcaag tccaaaccac cactcaatcg   16740
taattatgtt tttactggtt atcatataac caaaaatagt aaagtgcagc tcggtgagta   16800
cattttcgag cgcattgatt atagtgatgc tgtatcctac aagtctagta caacgtataa   16860
```

-continued

```
actgactgta ggtgacatct tcgtacttac ctctcactct gtggctacct tgacggcgcc    16920
cacaattgtg aatcaagaga ggtatgttaa aattactggg ttgtacccaa ccattacggt    16980
acctgaagag ttcgcaagtc atgttgccaa cttccaaaaa tcaggttata gtaaatatgt    17040
cactgttcag ggaccacctg gcactggcaa aagtcatttt gctataggdt tagcgattta    17100
ctaccctaca gcacgtgttg tttatacagc atgttcacac gcagctgttg atgctttgtg    17160
tgaaaaagct tttaaatatt tgaacattgc taaatgttcc cgtatcattc ctgcaaaggc    17220
acgtgttgag tgctatgaca ggtttaaagt taatgagaca aattctcaat atttgtttag    17280
tactattaat gctctaccag aaacttctgc cgatattctg gtggttgatg aggttagtat    17340
gtgcactaat tatgatcttt caattattaa tgcacgtatt aaagctaagc acattgtcta    17400
tgtaggagat ccagcacagt tgccagctcc taggactttg ttgactagag cacattgga    17460
accagaaaat ttcaatagtg tcactagatt gatgtgtaac ttaggtcctg acatattttt    17520
aagtatgtgc tacaggtgtc ctaaggaaat agtaagcact gtgagcgctc ttgtctacaa    17580
taataaattg ttagccaaga aggagctttc aggccagtgc tttaaaatac tctataaggg    17640
caatgtgacg catgatgcta gctctgccat taatagacca caactcacat tgtgaagaa    17700
ttttattact gccaatccgg catggagtaa ggcagtcttt atttcgcctt acaattcaca    17760
gaatgctgtg tctcgttcaa tgctgggtct taccactcag actgttgatt cctcacaggg    17820
ttcagaatac cagtacgtta tcttctgtca acagcagat acggcacatg ctaacaacat    17880
taacagattt aatgttgcaa tcactcgtgc ccaaaaaggt attctttgtg ttatgacatc    17940
tcaggcactc tttgagtcct tagagtttac tgaattgtct tttactaatt acaagctcca    18000
gtctcagatt gtaactggcc ttttttaaaga ttgctctaga gaaacttctg gcctctcacc    18060
tgcttatgca ccaacatatg ttagtgttga tgacaagtat aagacgagtg atgagctttg    18120
cgtgaatctt aatttacccg caaatgtccc atactctcgt gttatttcca ggatgggctt    18180
taaactcgat gcaacagttc ctggatatcc taagctttt attactcgtg aagaggctgt    18240
aaggcaagtt cgaagctgga taggcttcga tgttgagggt gctcatgctt cccgtaatgc    18300
atgtggcacc aatgtgcctc tacaattagg atttttcaact ggtgtgaact tgttgttca    18360
gccagttggt gttgtagaca ctgagtgggg taacatgtta acgggcattg ctgcacgtcc    18420
tccaccaggt gaacagtta agcacctcgt gcctcttatg cataagggg ctgcgtggcc    18480
tattgttaga cgacgtatag tgcaaatgtt gtcagacact ttagacaaat tgtctgatta    18540
ctgtacgttt gttttgttggg ctcatggctt tgaattaacg tctgcatcat acttttgcaa    18600
gataggtaag gaacagaagt gttgcatgtg caatagacgc gctgcagcgt actcttcacc    18660
tctgcaatct tatgcctgct ggactcattc ctgcggttat gattatgtct acaacccttt    18720
ctttgtcgat gttcaacagt ggggttatgt aggcaatctt gctactaatc acgatcgtta    18780
ttgctctgtc catcaaggag ctcatgtggc ttctaatgat gcaataatga ctcgttgttt    18840
agctattcat tcttgttttt tagaacgtgt ggattgggat atagagtatc cttatatctc    18900
acatgaaaag aaattgaatt cctgttgtag aatcgttgag cgcaacgtcg tacgtgctgc    18960
tcttcttgcc ggtcatttg acaaagtcta tgatattggc aatcctaaag gaattcctat    19020
tgttgatgac cctgtggttg attggcatta ttttgatgca cagcccttga ccaggaaggt    19080
acaacagctt ttctatacag aggacatggc ctcaagattt gctgatgggc tctgcttatt    19140
ttggaactgt aatgtaccaa aatatcctaa taatgcaatt gtatgcaggt ttgacacacg    19200
tgtgcattct gagttcaatt tgccaggttg tgatggcggt agtttgtatg ttaacaagca    19260
```

```
cgcttttcat acaccagcat atgatgtgag tgcattccgt gatctgaaac ctttaccatt    19320
cttttattat tctactacac catgtgaagt gcatggtaat ggtagtatga tagaggatat    19380
tgattatgta cccctaaaat ctgcagtctg tattacagct tgtaatttag ggggcgctgt    19440
ttgtaggaag catgctacag agtacagaga gtatatggaa gcatataatc ttgtctctgc    19500
atcaggtttc cgcctttggt gttataagac ctttgatatt tataatctct ggtctacttt    19560
tacaaaagtt caaggtttgg aaaacattgc ttttaatgtt gttaaacaag gccattttat    19620
tggtgttgag ggtgaactac ctgtagctgt agtcaatgat aagatcttca ccaagagtgg    19680
cgttaatgac atttgtatgt ttgagaataa aaccactttg cctactaata tagcttttga    19740
actctatgct aagcgtgctg tacgctcgca tcccgatttc aaattgctac acaatttaca    19800
agcagacatt tgctacaagt tcgtcctttg ggattatgaa cgtagcaata tttatggtac    19860
tgctactatt ggtgtatgta agtacactga tattgatgtt aattcagctt tgaatatatg    19920
ttttgacata cgcgataatt gttcattgga gaagttcatg tctactccca atgccatctt    19980
tatttctgat agaaaaatca agaaatacccc ttgtatggta ggtcctgatt atgcttactt    20040
caatggtgct atcatccgtg atagtgatgt tgttaaacaa ccagtgaagt tctacttgta    20100
taagaaagtc aataatgagt ttattgatcc tactgagtgt atttacactc agagtcgctc    20160
ttgtagtgac ttcctacccc tttctgacat ggagaaagac tttctatctt ttgatagtga    20220
tgttttcatt aagaagtatg gcttggaaaa ctatgctttt gagcacgtag tctatggaga    20280
cttctctcat actacgttag gcggtcttca cttgcttatt ggtttataca agaagcaaca    20340
ggaaggtcat attattatgg aagaaatgct aaaaggtagc tcaactattc ataactatttt   20400 tattactgag actaacacag cggcttttaa ggcggtgtgt tctgttatag atttaaagct    20460
tgacgacttt gttatgattt taaagagtca agaccttggc gtagtatcca aggttgtcaa    20520
ggttcctatt gacttaacaa tgattgagtt tatgttatgg tgtaaggatg acaggttca    20580 aaccttctac cctcgactcc aggcttctgc agattggaaa cctggtcatg caatgccatc    20640
cctctttaaa gttcaaaatg taaaccttga acgttgtgag cttgctaatt acaagcaatc    20700
tattcctatg cctcgcggtg tgcacatgaa catcgctaaa tatatgcaat tgtgccagta    20760
tttaaatact tgcacattag ccgtgcctgc caatatgcgt gttatacatt ttggcgctgg    20820
ttctgataaa ggtatcgctc ctggtaacctc agttttacga cagtggcttc ctacagatgc    20880
cattattata gataatgatt taaatgagtt cgtgtcagat gctgacataa ctttatttgg    20940
agattgtgta actgtacgtg tcggccaaca agtggatctt gttatttccg acatgtatga    21000
tcctactact aagaatgtaa caggtagtaa tgagtcaaag gctttattct ttacttacct    21060
gtgtaacctc attaataata atcttgctct tggtgggtct gttgctatta aaataacaga    21120
acactcttgg agcgttgaac tttatgaact tatgggaaaa tttgcttggt ggactgtttt    21180
ctgcaccaat gcaaatgcat cctcatctga aggattcctc ttaggtatta attacttggg    21240
tactattaaa gaaaatatag atggtggtgc tatgcacgcc aactatatat tttggagaaa    21300
ttccactcct atgaatctga gtacttactc actttttgat ttatccaagt tcaattaaa    21360 attaaaagga acaccagttc ttcaattaaa ggagagtcaa attaacgaac tcgtaatatc    21420
tctcctgtcg cagggtaagt tacttatccg tgacaatgat acactcagtg tttctactga    21480
tgttcttgtt aacacctaca gaaagttacg ttgatgtagg gccagattct gttaagtctg    21540
cttgtattga ggttgatata caacagactt tctttgataa aacttggcct aggccaattg    21600
```

```
atgtttctaa ggctgacggt attatatacc ctcaaggccg tacatattct aacataacta   21660
tcacttatca aggtcttttt ccctatcagg gagaccatgg tgatatgtat gtttactctg   21720
caggacatgc tacaggcaca actccacaaa agttgtttgt agctaactat tctcaggacg   21780
tcaaacagtt tgctaatggg tttgtcgtcc gtataggagc agctgccaat tccactggca   21840
ctgttattat tagcccatct accagcgcta ctatacgaaa aatttacccT gcttttatgc   21900
tgggttcttc agttggtaat ttctcagatg gtaaaatggg ccgcttcttc aatcatactc   21960
tagttctttt gcccgatgga tgtggcactt tacttagagc ttttttattgt attctagagc   22020 ctcgctctgg aaatcattgt cctgctggca attcctatac ttcttttgcc acttatcaca   22080
ctcctgcaac agattgttct gatggcaatt acaatcgtaa tgccagtctg aactcttta   22140 aggagtattt taatttacgt aactgcaccT ttatgtacac ttataacatt accgaagatg   22200
agattttaga gtggtttggc attacacaaa ctgctcaagg tgttcacctc ttctcatctc   22260
ggtatgttga tttgtacggc ggcaatatgt ttcaatttgc caccttgcct gtttatgata   22320
ctattaagta ttattctatc attcctcaca gtattcgttc tatccaaagt gatagaaaag   22380
cttgggctgc cttctacgta tataaacttc aaccgttaac tttcctgttg gattttTctg   22440
ttgatggtta tatacgcaga gctatagact gtgggttTaa tgatttgtca caactccact   22500
gctcatatga atccttcgat gttgaatctg gagtttattc agtttcgtct ttcgaagcaa   22560
aaccttctgg ctcagttgtg gaacaggctg aaggtgttga atgtgatttt tcacctcttc   22620
tgtctggcac acctcctcag gtttataatt tcaagcgttt ggttttTacc aattgcaatt   22680
ataatcttac caaattgctt tcactttttt ctgtgaatga ttTtacttgt agtcaaatat   22740
ctccagcagc aattgctagc aactgttatt cttcactgat tttggattac ttttcatacc   22800
cacttagtat gaaatccgat ctcagtgtta gttctgctgg tccaatatcc cagtttaatt   22860
ataaacagtc ctTttctaat cccacatgtt tgattttagc gactgttcct cataacctta   22920
ctactattac taagcctctt aagtacagct atattaacaa gtgctctcgt cttctttctg   22980
atgatcgtac tgaagtacct cagttagtga acgctaatca atactcaccc tgtgtatcca   23040
ttgtcccatc cactgtgtgg gaagacggtg attattatag gaaacaacta tctccacttg   23100
aaggtggtgg ctggcttgtt gctagtggct caactgttgc catgactgag caattacaga   23160
tgggctttgg tattacagtt caatatggta cagacaccaa tagtgtttgc cccaagcttg   23220
aatttgctaa tgacacaaaa attgcctctc aattaggcaa ttgcgtggaa tattccctct   23280
atggtgtttc gggccgtggt gttttttcaga attgcacagc tgtaggtgtt cgacagcagc   23340
gctttgttta tgatgcgtac cagaatttag ttggctatta ttctgatgat ggcaactact   23400
actgtttgcg tgcttgtgtt agtgttcctg tttctgtcat ctatgataaa gaaactaaaa   23460
cccacgctac tctatttggt agtgttgcat gtgaacacat ttcttctacc atgtctcaat   23520
actcccgttc tacgcgatca atgcttaaac ggcgagattc tacatatggc ccccttcaga   23580
cacctgttgg ttgtgtccta ggacttgtta attcctcttt gttcgtagag gactgcaagt   23640
tgcctcttgg tcaatctctc tgtgctcttc ctgacacacc tagtactctc acacctcgca   23700
gtgtgcgctc tgttccaggt gaaatgcgct tggcatccat tgcttttaat catcctattc   23760
aggttgatca acttaatagt agttatttta aattaagtat acccactaat ttttcctttg   23820
gtgtgactca ggagtacatt cagacaacca ttcagaaagt tactgttgat tgtaaacagt   23880
acgtttgcaa tggtttccag aagtgtgagc aattactgcg cgagtatggc cagttttgtt   23940
ccaaaataaa ccaggctctc catggtgcca atttacgcca ggatgattct gtacgtaatt   24000
```

```
tgtttgcgag cgtgaaaagc tctcaatcat ctcctatcat accaggtttt ggaggtgact    24060
ttaatttgac acttctagaa cctgtttcta tatctactgg cagtcgtagt gcacgtagtg    24120
ctattgagga tttgctattt gacaaagtca ctatagctga tcctggttat atgcaaggtt    24180
acgatgattg catgcagcaa ggtccagcat cagctcgtga tcttatttgt gctcaatatg    24240
tggctggtta caaagtatta cctcctctta tggatgttaa tatggaagcc gcgtatactt    24300
catctttgct tggcagcata gcaggtgttg gctggactgc tggcttatcc tcctttgctg    24360
ctattccatt tgcacagagt atcttttata ggttaaacgg tgttggcatt actcaacagg    24420
ttctttcaga gaaccaaaag cttattgcca ataagtttaa tcaggctctg ggagctatgc    24480
aaacaggctt cactacaact aatgaagctt ttcagaaggt tcaggatgct gtgaacaaca    24540
atgcacaggc tctatccaaa ttagctagcg agctatctaa tacttttggt gctatttccg    24600
cctctattgg agacatcata caacgtcttg atgttctcga acaggacgcc caaatagaca    24660
gacttattaa tggccgtttg acaacactaa atgctttgt tgcacagcag cttgttcgtt    24720
ccgaatcagc tgctctttcc gctcaattgg ctaaagataa agtcaatgag tgtgtcaagg    24780
cacaatccaa gcgttctgga ttttgcggtc aaggcacaca tatagtgtcc tttgttgtaa    24840
atgcccctaa tggcctttac ttcatgcatg ttggttatta ccctagcaac cacattgagg    24900
ttgtttctgc ttatggtctt tgcgatgcag ctaaccctac taattgtata gcccctgtta    24960
atggctactt tattaaaact aataacacta ggattgttga tgagtggtca tatactggct    25020
cgtccttcta tgcacctgag cccattacct cccttaatac taagtatgtt gcaccacagg    25080
tgacatacca aaacatttct actaacctcc ctcctcctct tctcggcaat ccaccggga    25140 ttgacttcca agatgagttg gatgagtttt caaaaatgt tagcaccagt atacctaatt    25200
ttggttccct aacacagatt aatactacat tactcgatct tacctacgag atgttgtctc    25260
ttcaacaagt tgttaaagcc cttaatgagt cttacataga ccttaaagag cttggcaatt    25320
atacttatta caacaaatgg ccgtggtaca tttggcttgg tttcattgct gggcttgttg    25380
ccttagctct atgcgtcttc ttcatactgt gctgcactgg ttgtggcaca aactgtatgg    25440
gaaaacttaa gtgtaatcgt tgttgtgata gatacgagga atacgacctc gagccgcata    25500
aggttcatgt tcactaatta acgaactatt aatgagagtt caaagaccac ccactctctt    25560
gttagtgttt tcactctctc ttttggtcac tgcatcctca aaacctctct atgtacctga    25620
gcattgtcag aattattctg gttgcatgct tagggcttgt attaaaactg cccaagctga    25680
tacagctggt ctttatacaa attttcgaat tgacgtccca tctgcagaat caactggtac    25740
tcaatcagtt tctgtcgatc ttgagtcaac ttcaactcat gatggtccta ccgaacatgt    25800
tactagtgtg aatcttttg acgttggtta ctcagttaat taacgaactc tatggattac    25860
gtgtctctgc ttaatcaaat ttggcagaag taccttaact caccgtatac tacttgtttg    25920
tacatcccta aacccacagc taagtataca cctttagttg gcacttcatt gcaccctgtg    25980
ctgtggaact gtcagctatc ctttgctggt tatactgaat ctgctgttaa ttctacaaaa    26040
gctttggcca acaggacgc agctcagcga atcgcttggt tgctacataa ggatggagga    26100
atccctgatg gatgttccct ctacctccgg cactcaagtt tattcgcgca aagcgaggaa    26160
gaggagccat tctccaacta agaaactgcg ctacgttaag cgtagatttt ctcttctgcg    26220
ccatgaagac cttagtgtta ttgtccaacc aacacactat gtcagggtta cattttcaga    26280
ccccaacatg tggtatctac gttcgggtca tcatttacac tcagttcaca attggcttaa    26340
```

```
accttatggc ggccaacctg tttctgagta ccatattact ctagctttgc taaatctcac    26400
tgatgaagat ttagctagag attttttcacc cattgcgctc tttttgcgca atgtcagatt   26460
tgagctacat gagttcgcct tgctgcgcaa aactcttgtt cttaatgcat cagagatcta    26520
ctgtgctaac atacatagat ttaagcctgt gtatagagtt aacacggcaa tccctactat    26580
taaggattgg cttctcgttc agggattttc cctttaccat agtggcctcc ctttacatat    26640
gtcaatctct aaattgcatg cactggatga tgttactcgc aattacatca ttacaatgcc    26700
atgctttaga acttaccctc aacaaatgtt tgttactcct ttggccgtag atgttgtctc    26760
catacggtct tccaatcagg gtaataaaca aattgttcat tcttatccca ttttacatca    26820
tccaggattt taacgaacta tggctttctc ggcgtcttta tttaaacccg tccagctagt    26880
cccagtttct cctgcatttc atcgcattga gtcactgac tctattgttt tcacatacat     26940
tcctgctagc ggctatgtag ctgctttagc tgtcaatgtg tgtctcattc ccctattatt    27000
actgctacgt caagatactt gtcgtcgcag cattatcaga actatggttc tctatttcct    27060
tgttctgtat aacttttat tagccattgt actagtcaat ggtgtacatt atccaactgg     27120
aagttgcctg atagccttct tagttatcct cataatactt tggtttgtag atagaattcg    27180
tttctgtctc atgctgaatt cctacattcc actgtttgac atgcgttccc actttattcg    27240
tgttagtaca gtttcttctc atggtatggt ccctgtaata cacaccaaac cattatttat    27300
tagaaacttc gatcagcgtt gcagctgttc tcgttgtttt tatttgcact cttccactta    27360
tatagagtgc acttatatta gccgttttag taagattagc ctagtttctg taactgactt    27420
ctccttaaac ggcaatgttt ccactgtttt cgtgcctgca acgcgcgatt cagttcctct    27480
tcacataatc gccccgagct cgcttatcgt ttaagcagct ctgcgctact atgggtcccg    27540
tgtagaggct aatccattag tctctctttg gacatatgga aaacgaacta tgttaccctt    27600
tgtccaagaa cgaatagggt tgttcatagt aaacttttc attttttaccg tagtatgtgc    27660
tataacactc ttggtgtgta tggctttcct tacggctact agattatgtg tgcaatgtat    27720
gacaggcttc aataccctgt tagttcagcc cgcattatac ttgtataata ctggacgttc    27780
agtctatgta aaattccagg atagtaaacc ccctctacca cctgacgagt gggtttaacg    27840
aactccttca taatgtctaa tatgacgcaa ctcactgagg cgcagattat tgccattatt    27900
aaagactgga actttgcatg gtccctgatc tttctcttaa ttactatcgt actacagtat    27960
ggatacccat cccgtagtat gactgtctat gtctttaaaa tgtttgtttt atggctccta    28020
tggccatctt ccatggcgct atcaatattt agcgccgttt atccaattga tctagcttcc    28080
cagataatct ctggcattgt agcagctgtt tcagctatga tgtggatttc ctactttgtg    28140
cagagtatcc ggctgtttat gagaactgga tcatggtggt cattcaatcc tgagactaat    28200
tgccttttga acgttccatt tggtggtaca actgtcgtac gtccactcgt agaggactct    28260
accagtgtaa ctgctgttgt aaccaatggc cacctcaaaa tggctggcat gcatttcggt    28320
gcttgtgact acgacagact tcctaatgaa gtcaccgtgg ccaaacccaa tgtgctgatt    28380
gctttaaaaa tggtgaagcg gcaaagctac ggaactaatt ccggcgttgc catttaccat    28440
agatataagg caggtaatta caggagtccg cctattacgg cggatattga acttgcattg    28500
cttcgagctt aggctcttta gtaagagtat cttaattgat tttaacgaat ctcaatttca    28560
ttgttatggc atcccctgct gcacctcgtg ctgtttcctt tgccgataac aatgatataa    28620
caaatacaaa cctatctcga ggtagaggac gtaatccaaa accacgagct gcaccaaata    28680
acactgtctc ttggtacact gggcttaccc aacacgggaa agtccctctt acctttccac    28740
```

```
ctgggcaggg tgtacctctt aatgccaatt ctacccctgc gcaaaatgct gggtattggc    28800
ggagacagga cagaaaaatt aataccggga atggaattaa gcaactggct cccaggtggt    28860
acttctacta cactggaact ggacccgaag cagcactccc attccgggct gttaaggatg    28920
gcatcgtttg ggtccatgaa gatggcgcca ctgatgctcc ttcaactttt gggacgcgga    28980
accctaacaa tgattcagct attgttacac aattcgcgcc cggtactaag cttcctaaaa    29040
acttccacat tgaggggact ggaggcaata gtcaatcatc ttcaagagcc tctagcttaa    29100
gcagaaactc ttccagatct agttcacaag gttcaagatc aggaaactct acccgcggca    29160
cttctccagg tccatctgga atcggagcag taggaggtga tctactttac cttgatcttc    29220
tgaacagact acaagccctt gagtctggca aagtaaagca atcgcagcca aaagtaatca    29280
ctaagaaaga tgctgctgct gctaaaaata agatgcgcca caagcgcact tccaccaaaa    29340
gtttcaacat ggtgcaagct tttggtcttc gcggaccagg agacctccag ggaaactttg    29400
gtgatcttca attgaataaa ctcggcactg aggacccacg ttggcccaa attgctgagc     29460 ttgctcctac agccagtgct tttatgggta tgtcgcaatt taaacttacc catcagaaca    29520
atgatgatca tggcaaccct gtgtacttcc ttcggtacag tggagccatt aaacttgacc    29580
caaagaatcc caactacaat aagtggttgg agcttcttga gcaaaatatt gatgcctaca    29640
aaaccttccc taagaaggaa aagaaacaaa aggcaccaaa agaagaatca acagaccaaa    29700
tgtctgaacc tccaaaggag cagcgtgtgc aaggtagcat cactcagcgc actcgcaccc    29760
gtccaagtgt tcagcctggt ccaatgattg atgttaacac tgattagtgt cactcaaagt    29820
aacaagatcg cggcaatcgt ttgtgtttgg caacccatc tcaccatcgc ttgtccactc     29880
ttgcacagaa tggaatcatg ttgtaattac agtgcaataa ggtaattata acccatttaa    29940
ttgatagcta tgctttatta aagtgtgtag ctgtagagag aatgttaaag actgtcacct    30000
ctgcttgatt gcaagtgaac agtgccccc gggaagagct ctacagtgtg aaatgtaaat      30060
aaaaaatagc tattattcaa ttagattagg ctaattagat gatttgcaaa aaaaaaaa      30119
```

METHODS OF USING PROBENECID FOR TREATMENT OF CORONAVIRUS INFECTIONS

CROSS REFERENCE TO RELATED APPLICATIONS

This application is a continuation of U.S. application Ser. No. 16/875,487, filed May 15, 2020, which claims benefit of U.S. Provisional Application No. 63/008,624, filed Apr. 10, 2020, and U.S. Provisional Application No. 63/023,021, filed May 11, 2020, each of which is specifically incorporated by reference herein in its entirety.

REFERENCE TO SEQUENCE LISTING

The Sequence Listing submitted as a text file named "UGA_2020_148_03.txt," created on May 14, 2020, and having a size of 156,589 bytes is hereby incorporated by reference pursuant to 37 C.F.R. § 1.52(e)(5).

FIELD OF THE INVENTION

The field of the invention generally related to compositions and methods for the treatment of coronavirus-related illnesses.

BACKGROUND OF THE INVENTION

A seventh human coronavirus was recently identified in Wuhan, China (Coronaviridae Study Group of the International Committee on Taxonomy of Viruses, *Nat Microbiol* 2020. DOI: 10.1038/s41564-020-0695-z, WHO "Pneumonia of unknown cause—China;" World Health Organization: Online, 2020). Initially described as COVID-19 after its discovery in December 2019, this virus has now been classified as a betacoronavirus within the same species as the Severe acute respiratory syndrome coronavirus (SARS-CoV), which was responsible for a pandemic in 2002-2003 (Coronaviridae Study Group of the International Committee on Taxonomy of Viruses, *Nat Microbiol* 2020. DOI: 10.1038/s41564-020-0695-z, Ratia, et al., *Proc Natl Acad Sci USA* 2008, 105 (42), 16119-24. DOI: 10.1073/pnas.0805240105). Hence, COVID-19 has now been classified as SARS-CoV-2. Although SARS-CoV-2 does not appear to be as lethal as SARS-CoV, it has rapidly spread worldwide according to a World Health Organization situation report. The rapid spread of SARS-CoV-2 and its ability to cause death particular in older individuals, or individuals with underlying conditions, has created an urgency for the need of antiviral therapeutics and vaccines for use against the virus ("CDC People at Risk for Serious Illness from COVID-19," CDC website).

Thus, it is an object of the invention to provide compositions and methods of treating infections caused by coronaviruses, particularly coronaviruses that cause severe acute respiratory syndrome, including, but limited to SARS-CoV-2.

SUMMARY OF THE INVENTION

Compositions and methods of treating a subject for a coronavirus infection are provided. The methods typically include administering the subject an effective amount of probenecid, a metabolite or analog thereof, or a pharmaceutically acceptable salt thereof. The amount of probenecid, metabolite or analog thereof, or a pharmaceutically acceptable salt thereof can be effective to, for example, reduce viral replication, reduce one or more symptoms of a disease, disorder, or illness associated with virus, or a combination thereof. Symptoms include, but are not limited to, fever, congestion in the nasal sinuses and/or lungs, runny or stuffy nose, cough, sneezing, sore throat, body aches, fatigue, shortness of breath, chest tightness, wheezing when exhaling, chills, muscle aches, headache, diarrhea, tiredness, nausea, vomiting, and combinations thereof. The subject can be, for example, a mammal or a bird. In preferred embodiments, the subject is a human.

The subject can be symptomatic or asymptomatic. In some embodiments, the subject has been, or will be, exposed to the virus. In some embodiments, treatment begins 1, 2, 3, 4, 5, or more hours, days, or weeks prior to or after exposure to the virus. In some embodiments, the subject has not been exposed to the virus. In some embodiments, the subject anticipates being exposed to the virus. Thus, preventative and prophylactic methods are also provided.

The virus can be a Severe acute respiratory syndrome-related coronavirus, a Bat Hp-betacoronavirus Zhejiang2013, a *Rousettus* bat coronavirus GCCDC1, a *Rousettus* bat coronavirus HKU9, *Eidolon* bat coronavirus C704, a *Pipistrellus* bat coronavirus HKU5, a *Tylonycteris* bar coronovirus HKU4, a Middle East respiratory syndrome-related coronavirus, a Hedgehog coronavirus, a murine coronavirus, a Human coronavirus HKU1, a China *Rattus* coronavirus HKU24, a Betacoronavirus 1, a Myodes coronavirus 2JL14, a Human coronavirus NL63, a Human coronavirus 229E, or a Human coronavirus OC43.

In preferred embodiments, the virus is a Severe acute respiratory syndrome-related coronavirus, such as SARS-CoV-2, SARS-CoV, SARSr-CoV RaTG13, SARS-CoV PC4-227, or SARSr-CoV BtKY72.

In some embodiments, the virus is a SARS-CoV-2 having a genome encoded by a nucleic acid sequence having at least 85%, 86%, 87%, 88%, 89%, 90%, 91%, 92%, 93%, 94%, 95%, 96%, 97%, 98%, 99%, or 100% sequence identity SEQ ID NO:1 or 2.

In some embodiments, the Severe acute respiratory syndrome-related coronavirus is SARS-CoV, for example, a SAR-CoV having a genome encoded by a nucleic acid sequence having at least 85%, 86%, 87%, 88%, 89%, 90%, 91%, 92%, 93%, 94%, 95%, 96%, 97%, 98%, 99%, or 100% sequence identity SEQ ID NO:3.

In some embodiments, the virus is a Middle East respiratory syndrome-related coronavirus, for example, a MERS-CoV having a genome encoded by a nucleic acid sequence having at least 85%, 86%, 87%, 88%, 89%, 90%, 91%, 92%, 93%, 94%, 95%, 96%, 97%, 98%, 99%, or 100% sequence identity SEQ ID NO:4.

In some embodiments, the subject has a disease or disorder associated with the virus. For example, in embodiments, a subject exposed or infected with SARS-CoV-2 has COVID-19.

The probenecid, metabolite or analog thereof, or pharmaceutically acceptable salt thereof is typically administered in a pharmaceutical composition including a pharmaceutically acceptable carrier and/or excipient. Thus, pharmaceutical compositions are also provided. Dosage forms are also provided and include, but not limited to 500 mg tablets of probenecid, a metabolite or analog thereof, or pharmaceutically acceptable salt thereof. In some embodiments, the subject is administered a 10 mg-1,000 mg or, 50 mg-500 mg dose of probenecid, metabolite or analog thereof, or pharmaceutically acceptable salt thereof 1, 2, 3, 4, or 5 times per day. In some embodiments, the dosage regimen is a pulse dosage regimen that include 1, 2, 3, or more large bolus doses in close proximity (e.g., minutes or hours apart). In some embodiments, the bolus doses are followed by a drug administration holiday, optionally until the drug level in the subject's serum drops to zero or near zero.

The probenecid, a metabolite or analog thereof, or a pharmaceutically acceptable salt thereof can be administered systemically or locally. Exemplary routes of administration include, but are not limited to, oral, parenteral, topical or mucosal. In some embodiments, the composition is administered to lungs (e.g., pulmonary administration) by oral inhalation or intranasal administration. In some embodiments, the composition is administered intranasally to the nasal mucosa.

DETAILED DESCRIPTION OF THE INVENTION

I. Definitions

Figure 1:
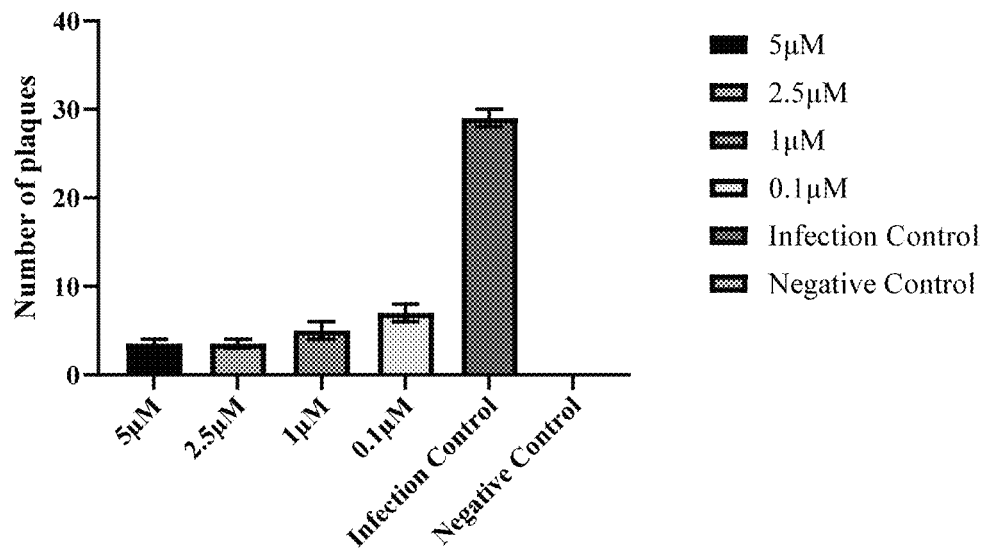
FIG. 1 is a bar graph showing (left-to-right) the effect of probenecid (5 µM, 2.5 µM, 1 µM, or 0.1 µM) compared to controls (DMSO (infected), DMSO (only)) on viral replication using a plaque reduction assay.

As used herein, the terms "individual", "host", "subject", and "patient" are used interchangeably herein, and refer animals, particularly birds and mammals, including, but not limited to, primates such as humans, bats, rodents, such as mice and rats, and other laboratory animals.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being administered.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other forms the values may range in value either above or below the stated value in a range of approx. +/−5%; in other forms the values may range in value either above or below the stated value in a range of approx. +/−2%; in other forms the values may range in value either above or below the stated value in a range of approx. +/−1%. The preceding ranges are intended to be made clear by context, and no further limitation is implied.

II. Compositions

A. Probenecid, Metabolites, Analogs, and Pharmaceutically Acceptable Salts Thereof The disclosed methods include administering a subject in need thereof an effective amount of probenecid, a metabolite or analog thereof, or a pharmaceutically acceptable salt thereof, including, but not limited to a sodium salt thereof.

Probenecid (4-[(dipropylamino) sulfonyl] benzoic acid (CAS No. 57-66-9)) has the structure:

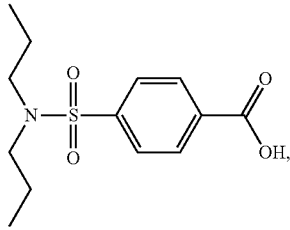 [SMILES: CCCN(CCC)S(=O)(=O)c1ccc(C(=O)O)cc1]

and has been sold under the brand names BENEMID and PROBALAN.

Probenecid is a highly lipid soluble benzoic acid derivative with an excellent safety profile that was developed in the 1950's to decrease the renal tubular excretion of penicillin. Probenecid, USP is a white or nearly white, fine, crystalline powder. Probenecid is soluble in dilute alkali, in alcohol, in chloroform, and in acetone; it is practically insoluble in water and in dilute acids. It has a half life of 6-12 hours. See also Drugbank Accession Number DB01032 (APRD00167).

Metabolites and analogs of probenecid are known, see, for example, Guarino, et al., "Mass spectral identification of probenecid metabolites in rat bile," *Eur. J. Pharmacol.*, 8, 244-252 (1969), Perel, et al., "Identification and renal excretion of probenecid metabolites in man," *Life Sciences*, 9, 23, 1337-1343 (1970), Perel, et al., "Studies of the renal excretion of probenecid acyl glucuronide in man," *Eur. J. Clin. Pharmacol*, 3, 106-112 (1971), Dayton and Perel, "The metabolism of probenecid in man,". *N. Y. Acad. Sci.*, 179, 399-402 (1971), Dayton, et al., "The effect of probenecid, phenylbutazone and their analogues on the excretion of L-ascorbic acid in rats," *J. Med. Chem.* 9, 941-944 (1966), and Israili, et al., "Metabolites of probenecid. Chemical, physical, and pharmacological studies," *J. Med. Chem.*, 15, 7, 709-713 (1972), each of which is specifically incorporated by reference in its entirety.

In some embodiments, the metabolite is a glucuronide derivative of probenecid such as acyl glucuronide or a β-ether glucuronide.

Exemplary probenecid metabolites and analogs include, but are not limited to,
dl-p-(N-Propy-N-2-hydroxypropylsulfamoyl)benzoic Acid,
Propylaminopropyl Acetate,
Piopylaminopropan-3-ol,
p-(N-Propyl-N-3-hydroxypropylsulfamoyl)benzoic Acid,
Propylaminopropionitrile,
p-(N-Propyl-N-3-propionitrilosulfamoyl)benzoic Acid,
p-(N-Propyl-N-2-carboxyethylsulfamoyl)benzoic Acid,
p-(N-Propylsulfamoyl)benzoic Acid,
p-(N,N-Pentamethylenesulfamoyl)benzoic Acid (Piperidyl Analog),
p-(N-Propyl-N-2-propenylsulfamoyl)benzoic Acid, and
p-(N-Propyl-N-2-oxopropylsulfamoyl)benzoic Acid.

Typically the metabolite or analog can on its own, or upon further metabolism thereof by a subject, treat a coronavirus when administered in an effective amount as discussed herein. For example, in some embodiments, the metabolite or analog can on its own, or upon further metabolism thereof by a subject, reduce viral replication.

B. Formulations

Probenecid, metabolites and analogs thereof, and pharmaceutically acceptable salts thereof can be formulated in a pharmaceutical composition. Pharmaceutical compositions can be for administration by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes of administration or using bioerodible inserts and can be formulated in dosage forms appropriate for each route of administration.

The compositions can be administered systemically.

The compositions can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, desintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et. al., (Media, PA: Williams and Wilkins, 1995) which provides information on carriers, materials, equipment and process for preparing tablets and capsules and delayed release dosage forms of tablets, capsules, and granules.

The compound can be administered to a subject with or without the aid of a delivery vehicle. Appropriate delivery vehicles for the compounds are known in the art and can be selected to suit the particular active agent. For example, in some embodiments, the active agent(s) is incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

1. Oral Immediate Release Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

2. Extended Release Dosage Forms

The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

3. Delayed Release Dosage Forms

Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUDRAGIT®. S (soluble at pH 7.0 and above, as a result of a higher degree of esterification), and EUDRAGIT®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Methods of Manufacturing

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, PA: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

4. Formulations for Mucosal and Pulmonary Administration

The probenecid, metabolites and analogs thereof, and pharmaceutical compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In some embodiments, the compound is formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption.

Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, CA).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter, and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

Compositions and methods of preparing inhalation-type pharmaceutical compositions including probenecid are described in U.S. Published Application No. 2015/0272870.

Thus, formulations and methods of administering the disclosed compositions to the nasal mucosa and/or the lungs by intranasal delivery, and to the lung by oral inhalation are provided. With respect to intranasal delivery, the formulation and delivery device can be selected and prepared to drive absorption through the nasal mucosa or the lungs. The nasal mucosa is—compared to other mucous membranes—easily accessible and provides a practical entrance portal for small and large molecules (Bitter, et al., "Nasal Drug Delivery in Humans," in Surber, et al., (eds): *Topical Applications and the Mucosa. Curr Probl Dermatol*. Basel, Karger, 2011, vol 40, pp 20-35, Pires, et al., *J Pharm Pharmaceut Sci.*, 12(3) 288-311, 2009, and Djupesland, *Drug Deliv. and Transl. Res.*, 3:42-62 (2013) DOI 10.1007/s13346-012-0108-9). Intranasal administration offers a rapid onset of therapeutic effects, reduced first-pass effect, reduced gastrointestinal degradation and lung toxicity, noninvasiveness, essentially painless application, and easy and ready use by patients—particularly suited for children—or by physicians in emergency settings. Flu Mist®, for example, is an exemplary effective nasal influenza vaccine spray.

Numerous delivery devices are available for intranasal administration. Devices vary in accuracy of delivery, dose reproducibility, cost and ease of use. Metered-dose systems provide dose accuracy and reproducibility. Differences also exist in force of delivery, spray patterns and emitted droplet size. The latter being important for drug deposition within the nasal cavity. Parameters can be can be modulated to enhance deposition while limiting the fraction of small particles able to bypass the nose and enter the lungs, or reduce deposition while increasing the fraction of small particles able to bypass the nose and enter the lungs.

The following aspects of nasal anatomy can influence drug delivery. During exhalation the soft palate closes automatically, separating the nasal and oral cavities. Thus, it becomes possible to use smaller particles in a nasal spray and still avoid lung deposition. Additionally, during closure of the soft palate there is a communication pathway between the two nostrils, located behind the walls separating the two passages. Under these circumstances, it is possible for airflow to enter via one nostril and leave by the other. This bidirectional delivery concept combines the two anatomical facts into one fully functional device. The device is inserted into one nostril by a sealing nozzle, and the patient blows into the mouthpiece. The combination of closed soft palate and sealed nozzle creates an airflow which enters one nostril, turns 180° through the communication pathway and exits through the other nostril (bidirectional flow). Since delivery occurs during exhalation, small particles cannot enter the lungs.

Particle size, flow rate and direction can be tuned for efficient delivery to the nasal mucosa. By adding an exit resistor to give additional control of the input pressure, it is possible to improve distribution to the sinuses and the middle ear. Manipulation of the flow pattern enables delivery to the olfactory region, thereby possibly achieving direct 'nose-to-brain' delivery. The 180-degree turn behind the septum will trap particles still airborne, allowing targeted delivery of cargo to the adenoid.

Strategies for enhancing drug absorption via nasal and pulmonary routes are also know in the art and can be utilized in the disclosed formulations and methods of delivery. Such strategies include, for example, use of absorption enhancers such as surfactants, cyclodextrins, protease inhibitors, and tight junction modulators, as well as application of carriers such as liposomes and nanoparticles. See, e.g., Ghadiri, et al., *Pharmaceutics*, 11(3): 113 (2019), which is specifically incorporated by reference herein in its entirety.

5. Formulations for Parenteral Administration

Probenecid, metabolites and analogs thereof, and pharmaceutical compositions thereof can be administered in an aqueous solution, by parenteral injection or infusion. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLYSORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

III. Methods of Treatment

Methods of treating a viral infection in subject in need thereof are provided. In some embodiments, the virus can be one that causes a respiratory disease or illness. Thus, methods of treating a respiratory disease or illness, particularly in subject infected with a virus are also provided.

The methods can include administering to a subject an effective amount of probenecid, a metabolite or analog thereof, or a pharmaceutically acceptable salt thereof to reduce viral replication, infection, or a combination thereof.

In some embodiments, the subject has been, or will be, exposed to the virus. In some embodiments, the subject has been exposed to the virus or is experiencing an active viral infection.

The compositions can also be administered prophylactically to, for example, reduce or prevent the effects of future exposure to virus and the infection that may associated therewith. Thus, in some embodiments, the subject has not been exposed to the virus and/or is not yet experiencing an active viral infection. In some embodiments, the subject is a healthy subject.

In some embodiments, the subject will be exposed to the virus. In some embodiments, treatment begins 1, 2, 3, 4, 5, or more hours, days, or weeks prior to or after exposure to the virus.

In some embodiments, the probenecid, a metabolite or analog thereof, or a pharmaceutically acceptable salt thereof is administered in an effective amount to reduce or prevent one or more symptoms of a viral infection. Symptoms include those of an acute respiratory illness, for example, fever, congestion in the nasal sinuses and/or lungs, runny or stuffy nose, cough, sneezing, sore throat, body aches, fatigue, shortness of breath, chest tightness, and wheezing when exhaling. Exemplary viruses and particular symptoms associated with infection thereby are discussed in more detail below. Most typically, the virus is a coronavirus.

In some embodiments, the subject does not have gout, need prolonged penicillin (or other antibiotic) serum levels, pelvic inflammatory disease, or gonorrhea.

In some embodiments, the subject has an influenza infection. See, e.g., Perwitasari, et al., *Antimicrob Agents Chemother*, 57(1):475-83 (2013). doi: 10.1128/AAC.01532-12.)). For example, in some embodiments, the subject has an influenza (e.g., influenza A, influenza B, influenza C, and/or influenza D) infection and an infection from another virus, such as a coronavirus. In some embodiments, the subject does not have an influenza viral infection.

A. Exemplary Dosages and Regimens

Probenecid, metabolites and analogs thereof and pharmaceutically acceptable salt thereof can be administered to a subject in a pharmaceutical composition, such as those discussed above, and can be administered by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes, as discussed in more detail above.

The precise dosage will vary according to a variety of factors such as subject-dependent variables (e.g., age, immune system health, clinical symptoms, route of delivery, etc.).

For treating gout, probenecid has been administered at 250 mg Per os/oral (PO) twice daily for 1 week; increasing to 500 mg PO twice daily to 2 g/day maximum with dosage increases of 500 mg.

For treating prolong penicillin serum levels, probenecid has been administered at 500 mg PO four times daily.

For pelvic inflammatory disease probenecid has been administered at 1 g PO with 2 g cefoxitin intramuscular (IM) as single dose.

For gonorrhea, probenecid has been administered at 1 g PO with 2 g cefoxitin IM as single dose.

A typically pediatric (e.g., age: 2 to 14 years and weight less than 50 kg) administration as an adjuvant to antibiotic therapy is Initial: 25 mg/kg (or 0.7 g/m2) orally once; Maintenance: 40 mg/kg (or 1.2 g/m2) per day orally administered in 4 equally divided doses 4 times a day.

Thus, in general, by way of example only, dosage forms useful in the disclosed methods may include doses in the range of 0.1 mg to 3,000 mg; 25 mg to 2,000 mg; 25 mg to 1,000 mg; 50 mg to 1,000 mg; 100 mg to 1,000 mg; or 250 mg to 1,000 mg, with doses of 10 mg, 25 mg, 45 mg, 50 mg, 100 mg, 150 mg, 200 mg, 250 mg, 300 mg, 350 mg, 400 mg, 450 mg, 500 mg, 550 mg, 600 mg, 750 mg, and 1,000 mg being exemplary doses, which can be administered, for example, 1, 2, 3, 4, or 5 times daily, weekly, bi-week, etc., for 1, 2, 3, 4, or more weeks, and for example until symptoms improve or disappear. In some embodiments, a single treatment can be repeated 1, 2, 3, 4, 5, 6, 7, or more days, weeks, or months apart.

In some embodiments, the treatment regimen is similar to those describe above for, e.g., gout, prolonging penicillin serum levels, pelvic inflammatory disease, gonorrhea, etc.

In a particular embodiments, the probenecid or a metabolite or analog thereof or pharmaceutically acceptable salt thereof is administered as 250 mg twice per day.

As introduced above, recitation of ranges of values herein including the dosage ranges above and elsewhere herein, are merely intended to serve as a shorthand method of referring individually to each separate value falling within the range and each separate value is incorporated into the specification as if it were individually recited herein.

Dosing regimens may be, for example, intermittent dosing or continuous (e.g., constant infusion). The dosing regimens can include administrations of the same or different doses. Thus, the dosing regimen can include dose escalation, dose reduction, or a combination thereof.

In some embodiments, the composition is administered in a pulsed dosage regimen. Pulse dosing refers to dosing approach that produces escalating drug levels early in the dosing interval followed by a prolonged dose-free period. For example, in some embodiments, drug administration is frontloaded by means of, for example, 1, 2, 3, 4, or 5 sequential bolus administrations, after which drug levels are allowed to diminish until the next dose. In some embodiments, the serum drug level is allowed to diminish to about 0.

This type of drug delivery technology could offer therapeutic advantages such as reduced dose frequency and greater patient compliance. In comparison to intermittent dosing, pulse dosing front loads the drug, allowing an extended dose-free period during which drug concentration falls close to zero. However, unlike a single, large bolus dose (e.g., given once daily), short bursts of drug are separated by short dose-free periods, allowing the serum concentration to fluctuate (Ibrahim, et al., *Antimicrobial Agents and Chemotherapy*, 48(11):4195-4199 (2004)). In particular embodiments, pulse dosing is carried out by oral administration or intravenous administration. For example, in some embodiments, the therapy includes discontinuous/intermittent intravenous infusion of very high doses of probenecid, a metabolite or analog thereof, or a pharmaceutically acceptable salt thereof over a short period.

In some embodiments, a large bolus dose of probenecid, a metabolite or analog thereof, or pharmaceutically acceptable salt thereof is between about 1,000 mg and 5,000 mg inclusive, or any subrange or specific dosage there between.

The maximum recommended dosage for probenecid is 2 grams/day PO for adults, adolescents, and children of more than 50 kg, and 40 mg/kg/day (1.2 grams/m2/day) PO (not to exceed 2 grams/day PO) for adolescents and children of 50 kg or less. Thus, in some embodiments, administration does not exceed 5 g, 4 g, 3 g, or 2 g per day. In some embodiments, administration does not exceed 40 mg/kg/day. See also "probenecid—Drug Summary", the Prescribers' Digital Reference.

In some embodiments, a tablet for oral administration contains e.g., 500 mg of probenecid and optionally, one or more of the following inactive ingredients: microcrystalline cellulose, sodium lauryl sulfate, sodium starch glycolate, starch (corn), povidone, colloidal silicon dioxide, magnesium stearate, polyvinyl alcohol, titanium dioxide, polyethylene glycol, talc, D&C Yellow #10 Aluminum Lake, FD&C Yellow #6 Aluminum Lake, and FD&C Blue #2 Aluminum Lake.

B. Combination Therapies

In some embodiments, probenecid, a metabolite or analog thereof, or a pharmaceutically acceptable salt thereof is administered in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of probenecid, a metabolite or analog thereof, or a pharmaceutically acceptable salt thereof. In some embodiments, the second active agent is an antiviral (i.e., a second antiviral), a fever reducer, an antinflammatory, an analgesic, or a combination thereof. In a particular embodiment, the antiviral is oseltamivir phosphate (TAMIFLU®). Tamiflu is a prescription medicine used to treat the flu (influenza) in people 2 weeks of age and older who have had flu symptoms. Probenecid or metabolites or analogs or pharmaceutical salts thereof may enhance the efficacy of antivirals like oseltamivir phosphate as it helps retain excretion of the drug during treatment.

C. Exemplary Viruses and Symptoms

Exemplary viruses and symptoms of illness stemming from infection by the viruses that are treatable by the disclosed methods are also provided. The virus is typically a coronavirus. The current classification of coronaviruses recognizes 39 species in 27 subgenera, five genera and two subfamilies that belong to the family Coronaviridae, suborder Cornidovirineae, order Nidovirales and realm Riboviria (Coronaviridae Study Group of the International Committee on Taxonomy of Viruses, *Nat Microbiol* 2020. DOI: 10.1038/s41564-020-0695-z). They are enveloped viruses with a positive-sense single-stranded RNA genome and a nucleocapsid of helical symmetry. The genome size of coronaviruses ranges from approximately 26 to 32 kilobases, one of the largest among RNA viruses.

Coronaviruses cause diseases in mammals and birds.

In preferred embodiments, the subject is a human. In humans, coronaviruses can cause respiratory tract infections that can range from mild to lethal. Mild illnesses include some cases of the common cold, while more lethal varieties can cause SARS, MERS, and COVID-19 (i.e., caused by SARS-CoV-2).

The subject may have one or more symptoms characteristic of SARS, MERS, or COVID-19.

SARS (i.e., SAR-CoV) usually begins with flu-like signs and symptoms such as fever, chills, muscle aches, headache and occasionally diarrhea. After about a week, signs and symptoms include fever of 100.5 F (38 C) or higher, dry cough, and shortness of breath.

Reported illnesses from COVID-19 (i.e., caused by SARS-CoV-2) have ranged from mild symptoms to severe illness and death for confirmed cases. The most common symptoms are fever, tiredness, dry cough, and shortness of breath. Runny nose, vomiting and diarrhea have also been reported. These symptoms may appear 2-14 days after exposure.

Most people confirmed to have MERS-CoV infection have had severe respiratory illness with symptoms of fever, cough, and/or shortness of breath. Some people also had diarrhea and nausea/vomiting. For many people with MERS, more severe complications followed, such as pneumonia and kidney failure. Some infected people had mild symptoms (such as cold-like symptoms) or no symptoms at all.

In some embodiments, the subject has an underlying condition such as asthma, heart disease, diabetes, cancer, chronic lung disease, chronic heart disease, chronic kidney disease, or a combination thereof.

In other embodiments, the subject is a non-human mammal or a bird. Symptoms caused by coronavirus infection in non-human species vary: in chickens, they cause an upper respiratory tract disease, while in cows and pigs they cause diarrhea.

Coronavirus species and representative viruses thereof include [representative virus (of species)]: SARSr-CoV BtKY72 (Severe acute respiratory syndrome-related coronavirus), SARS-CoV-2 (Severe acute respiratory syndrome-related coronavirus), SARSr-CoV RaTG13 (Severe acute respiratory syndrome-related coronavirus), SARS-CoV PC4-227 (Severe acute respiratory syndrome-related coronavirus), SARS-CoV (Severe acute respiratory syndrome-related coronavirus), Bat-Hp-BetaCovC (Bat Hp-betacoronavirus Zhejiang2013), Ro-BatCoV GCCDC1 (*Rousettus* bat coronavirus GCCDCJ), Ro-BatCoV HKU9 (*Rousettus* bat coronavirus HKU9), Ei-BatCoV C704 (*Eidolon* bat coronavirus C704), Pi-BatCoV HKU5 (*Pipistrellus* bat coronavirus HKU5), Ty-BatCoV HKU4 (*Tylonycteris* bar coronovirus HKU4), MERS-CoV (Middle East respiratory syndrome-related coronavirus), EriCoV (Hedgehog coronavirus), MHV (murine coronavirus), HCoV HKU1 (Human coronavirus HKU1), ChRCoV HKU24 (China *Rattus* coronavirus HKU24), ChRCovC HKU24 (Betacoronavirus 1), MrufCoV 2JL14 (Myodes coronavirus 2JL14), HCoV NL63 (Human coronavirus NL63), HCoV 229E (Human coronavirus 229E), and HCoV OC43 (Human coronavirus OC43). See, e.g., Coronaviridae Study Group of the International Committee on Taxonomy of Viruses, *Nat Microbiol* 2020. DOI: 10.1038/s41564-020-0695-z), which is specifically incorporated by reference in its entirety. In some embodiments, the coronavirus is a common cold coronavirus such as 229E, NL63, OC43, and HKU1.

In particularly preferred embodiments, the virus is a Severe acute respiratory syndrome-related virus, such as, SARSr-CoV BtKY72, SARS-CoV-2, SARSr-CoV RaTG13, SARS-CoV PC4-227, or SARS-CoV, preferably one that infects humans such as SARS-CoV or SARS-CoV-2.

In some embodiments, the virus is a Middle East respiratory syndrome-related virus such as MERS-CoV.

Various strains of the foregoing viruses are known and include the representative genomic sequences provided as, for example, SEQ ID NOS:1-4, the accession numbers provided herein, and those sequences and accession numbers provided in, e.g., Coronaviridae Study Group of the International Committee on Taxonomy of Viruses, *Nat Microbiol* 2020. DOI: 10.1038/s41564-020-0695-z). These, however, are non-limiting examples, and the disclosed compositions and methods can also be used to treat other strains of coronavirus, particularly SARS and MERS coronaviruses. In some embodiments, the (DNA sequence) of the viral genome has a sequence at least 80%, preferably at 85%, more preferably at least 86%, 87%, 88%, 89%, 90%, 91%, 92%, 93%, 94%, 95%, 96%, 97%, 98%, 99%, or 100% sequence identity to one or more of SEQ ID NOS:1, 2, 3, or 4, or another viral accession number provided herein, or a sequence or accession number provided in Coronaviridae Study Group of the International Committee on Taxonomy of Viruses, *Nat Microbiol* 2020. DOI: 10.1038/s41564-020-0695-z, all of which are specifically incorporated by reference herein in their entireties. It will be appreciated that the sequences are provided as DNA sequences, but the viral genome itself will typically have the corresponding RNA sequences. Thus, the corresponding RNA sequences are also expressly provided herein.

GenBank Accession No. MN908947.3, which is specifically incorporated by reference herein in its entirety, provides the following (DNA) genomic sequence for SARS-CoV-2 (Severe acute respiratory syndrome coronavirus 2 isolate Wuhan-Hu-1, complete genome):

```
                                                    (SEQ ID NO: 1)
   1 attaaaggtt tataccttcc caggtaacaa accaaccaac tttcgatctc ttgtagatct 61 gttctctaaa cgaactttaa aatctgtgtg gctgtcactc ggctgcatgc ttagtgcact 121 cacgcagtat aattaataac taattactgt cgttgacagg acacgagtaa ctcgtctatc 181 ttctgcaggc tgcttacggt ttcgtccgtg ttgcagccga tcatcagcac atctaggttt 241 cgtccgggtg tgaccgaaag gtaagatgga gagccttgtc cctggtttca acgagaaaac 301 acacgtccaa ctcagtttgc ctgttttaca ggttcgcgac gtgctcgtac gtggctttgg 361 agactccgtg gaggaggtct tatcagaggc acgtcaacat cttaaagatg gcacttgtgg 421 cttagtagaa gttgaaaaag gcgttttgcc tcaacttgaa cagccctatg tgttcatcaa 481 acgttcggat gctcgaactg cacctcatgg tcatgttatg gttgagctgg tagcagaact 541 cgaaggcatt cagtacggtc gtagtggtga gacacttggt gtccttgtcc ctcatgtggg 601 cgaaatacca gtggcttacc gcaaggttct tcttcgtaag aacggtaata aaggagctgg 661 tggccatagt tacggcgccg atctaaagtc atttgactta ggcgacgagc ttggcactga 721 tccttatgaa gattttcaag aaaactggaa cactaaacat agcagtggtg ttacccgtga 781 actcatgcgt gagcttaacg gaggggcata cactcgctat gtcgataaca acttctgtgg 841 ccctgatggc taccctcttg agtgcattaa agaccttcta gcacgtgctg gtaaagcttc 901 atgcactttg tccgaacaac tggactttat tgacactaag aggggtgtat actgctgccg 961 tgaacatgag catgaaattg cttggtacac ggaacgttct gaaaagagct atgaattgca 1021 gacacctttt gaaattaaat tggcaaagaa atttgacacc ttcaatgggg aatgtccaaa 1081 ttttgtattt cccttaaatt ccataatcaa gactattcaa ccaagggttg aaaagaaaaa 1141 gcttgatggc tttatgggta gaattcgatc tgtctatcca gttgcgtcac caaatgaatg 1201 caaccaaatg tgcctttcaa ctctcatgaa gtgtgatcat tgtggtgaaa cttcatggca 1261 gacgggcgat ttgttaaag ccacttgcga attttgtggc actgagaatt tgactaaaga 1321 aggtgccact acttgtggtt acttacccca aaatgctgtt gttaaaattt attgtccagc 1381 atgtcacaat tcagaagtag gacctgagca tagtcttgcc gaataccata atgaatctgg 1441 cttgaaaacc attcttcgta agggtggtcg cactattgcc tttggaggct gtgtgttctc 1501 ttatgttggt tgccataaca agtgtgccta ttgggttcca cgtgctagcg ctaacatagg 1561 ttgtaaccat acaggtgttg ttggagaagg ttccgaaggt cttaatgaca accttcttga 1621 aatactccaa aaagagaaag tcaacatcaa tattgttggt gactttaaac ttaatgaaga 1681 gatcgccatt attttggcat ctttttctgc ttccacaagt gcttttgtgg aaactgtgaa 1741 aggtttggat tataaagcat tcaaacaaat tgttgaatcc tgtggtaatt ttaaagttac 1801 aaaaggaaaa gctaaaaaag gtgcctggaa tattggtgaa cagaaatcaa tactgagtcc 1861 tctttatgca tttgcatcag aggctgctcg tgttgtacga tcaattttct cccgcactct
```

-continued

```
1921  tgaaactgct caaaattctg tgcgtgtttt acagaaggcc gctataacaa tactagatgg 1981  aatttcacag tattcactga gactcattga tgctatgatg ttcacatctg atttggctac 2041  taacaatcta gttgtaatgg cctacattac aggtggtgtt gttcagttga cttcgcagtg 2101  gctaactaac atctttggca ctgtttatga aaaactcaaa cccgtccttg attggcttga 2161  agagaagttt aaggaaggtg tagagtttct tagagacggt tgggaaattg ttaaatttat 2221  ctcaacctgt gcttgtgaaa ttgtcggtgg acaaattgtc acctgtgcaa aggaaattaa 2281  ggagagtgtt cagacattct ttaagcttgt aaataaattt ttggctttgt gtgctgactc 2341  tatcattatt ggtggagcta aacttaaagc cttgaattta ggtgaaacat ttgtcacgca 2401  ctcaaaggga ttgtacagaa agtgtgttaa atccagagaa gaaactggcc tactcatgcc 2461  tctaaaagcc ccaaaagaaa ttatcttctt agagggagaa acacttccca cagaagtgtt 2521  aacagaggaa gttgtcttga aaactggtga tttacaacca ttagaacaac ctactagtga 2581  agctgttgaa gctccattgg ttggtacacc agtttgtatt aacgggctta tgttgctcga 2641  aatcaaagac acagaaaagt actgtgccct tgcacctaat atgatggtaa caaacaatac 2701  cttcacactc aaaggcggtg caccaacaaa ggttactttt ggtgatgaca ctgtgataga 2761  agtgcaaggt tacaagatgt gaatatcac ttttgaactt gatgaaagga ttgataaagt 2821  acttaatgag aagtgctctg cctatacagt tgaactcggt acagaagtaa atgagttcgc 2881  ctgtgttgtg gcagatgctg tcataaaaac tttgcaacca gtatctgaat tacttacacc 2941  actgggcatt gatttagatg agtggagtat ggctacatac tacttatttg atgagtctgg 3001  tgagtttaaa ttggcttcac atatgtattg ttctttctac cctccagatg aggatgaaga 3061  agaaggtgat tgtgaagaag aagagtttga gccatcaact caatatgagt atggtactga 3121  agatgattac caaggtaaac ctttggaatt tggtgccact tctgctgctc ttcaacctga 3181  agaagagcaa gaagaagatt ggttagatga tgatagtcaa caaactgttg gtcaacaaga 3241  cggcagtgag gacaatcaga caactactat tcaaacaatt gttgaggttc aacctcaatt 3301  agagatggaa cttacaccag ttgttcagac tattgaagtg aatagtttta gtggttattt 3361  aaaacttact gacaatgtat acattaaaaa tgcagacatt gtggaagaag ctaaaaaggt 3421  aaaaccaaca gtggttgtta atgcagccaa tgtttacctt aaacatggag gaggtgttgc 3481  aggagcctta aataaggcta ctaacaatgc catgcaagtt gaatctgatg attacatagc 3541  tactaatgga ccacttaaag tgggtggtag ttgtgtttta agcggacaca atcttgctaa 3601  acactgtctt catgttgtcg gcccaaatgt taacaaaggt gaagacattc aacttcttaa 3661  gagtgcttat gaaaatttta atcagcacga agttctactt gcaccattat tatcagctgg 3721  tattttggt gctgacccta tacattcttt aagagtttgt gtagatactg ttcgcacaaa 3781  tgtctactta gctgtctttg ataaaaatct ctatgacaaa cttgtttcaa gcttttggga 3841  aatgaagagt gaaaagcaag ttgaacaaaa gatcgctgag attcctaaag aggaagttaa 3901  gccatttata actgaaagta aaccttcagt tgaacagaga aaacaagatg ataagaaaat 3961  caaagcttgt gttgaagaag ttacaacaac tctggaagaa actaagttcc tcacagaaaa 4021  cttgttactt tatattgaca ttaatgcaa tcttcatcca gattctgcca ctcttgttag 4081  tgacattgac atcactttct aaagaaaga tgctccatat atagtgggtg atgttgttca 4141  agagggtgtt ttaactgctg tggttatacc tactaaaaag gctggtgca ctactgaaat 4201  gctagcgaaa gctttgagaa agtgccaac agacaattat ataaccactt acccgggtca 4261  gggtttaaat ggttacactg tagaggaggc aaagacagtg cttaaaaagt gtaaaagtgc 4321  cttttacatt ctaccatcta ttatctctaa tgagaagcaa gaaattcttg gaactgtttc
```

-continued

```
4381   ttggaatttg cgagaaatgc ttgcacatgc agaagaaaca cgcaaattaa tgcctgtctg 4441   tgtggaaact aaagccatag tttcaactat acagcgtaaa tataagggta ttaaaataca 4501   agagggtgtg gttgattatg gtgctagatt ttacttttac accagtaaaa caactgtagc 4561   gtcacttatc aacacactta acgatctaaa tgaaactctt gttacaatgc cacttggcta 4621   tgtaacacat ggcttaaatt tggaagaagc tgctcggtat atgagatctc tcaaagtgcc 4681   agctacagtt tctgtttctt cacctgatgc tgttacagcg tataatggtt atcttacttc 4741   ttcttctaaa acacctgaag aacatttat tgaaccatc tcacttgctg gttcctataa 4801   agattggtcc tattctggac aatctacaca actaggtata gaatttctta agagaggtga 4861   taaaagtgta tattacacta gtaatcctac cacattccac ctagatggtg aagttatcac 4921   ctttgacaat cttaagacac ttctttcttt gagagaagtg aggactatta aggtgtttac 4981   aacagtagac aacattaacc tccacacgca agttgtggac atgtcaatga catatggaca 5041   acagtttggt ccaacttatt tggatggagc tgatgttact aaaataaaac ctcataattc 5101   acatgaaggt aaaacatttt atgttttacc taatgatgac actctacgtg ttgaggcttt 5161   tgagtactac cacacaactg atcctagttt tctgggtagg tacatgtcag cattaaatca 5221   cactaaaaag tggaaatacc cacaagttaa tggtttaact tctattaaat gggcagataa 5281   caactgttat cttgccactg cattgttaac actccaacaa atagagttga agtttaatcc 5341   acctgctcta caagatgctt attacagagc aagggctggt gaagctgcta acttttgtgc 5401   acttatctta gcctactgta ataagacagt aggtgagtta ggtgatgtta gagaaacaat 5461   gagttacttg tttcaacatg ccaatttaga ttcttgcaaa agagtcttga acgtggtgtg 5521   taaaacttgt ggacaacagc agacaaccct taagggtgta gaagctgtta tgtacatggg 5581   cacactttct tatgaacaat ttaagaaagg tgttcagata ccttgtacgt gtggtaaaca 5641   agctacaaaa tatctagtac aacaggagtc acctttgtt atgatgtcag caccacctgc 5701   tcagtatgaa cttaagcatg gtacatttac ttgtgctagt gagtacactg gtaattacca 5761   gtgtggtcac tataaacata taacttctaa agaaactttg tattgcatag acggtgcttt 5821   acttacaaag tcctcagaat acaaaggtcc tattcggat gttttctaca agaaaacag 5881   ttacacaaca accataaaac cagttactta taaattggat ggtgttgttt gtacagaaat 5941   tgaccctaag ttggacaatt attataagaa agacaattct tatttcacag agcaaccaat 6001   tgatcttgta ccaaaccaac catatccaaa cgcaagcttc gataattta gtttgtatg 6061   tgataatatc aaatttgctg atgatttaaa ccagttaact ggttataaga aacctgcttc 6121   aagagagctt aaagttacat ttttccctga cttaaatggt gatgtggtgg ctattgatta 6181   taaacactac acaccctctt ttaagaaagg agctaaattg ttacataaac ctattgtttg 6241   gcatgttaac aatgcaacta ataaagccac gtataaacca aatacctggt gtatacgttg 6301   tctttggagc acaaaaccag ttgaaacatc aaattcgttt gatgtactga agtcagagga 6361   cgcgcaggga atggataatc ttgcctgcga agatctaaaa ccagtctctg aagaagtagt 6421   ggaaaatcct accatacaga aagacgttct tgagtgtaat gtgaaaacta ccgaagttgt 6481   aggagacatt atacttaaac cagcaaataa tagtttaaaa attacagaag aggttggcca 6541   cacagatcta atggctgctt atgtagacaa ttctagtctt actattaaga acctaatga 6601   attatctaga gtattaggtt tgaaaaccct tgctactcat ggtttagctg ctgttaatag 6661   tgtcccttgg gatactatag ctaattatgc taagcctttt cttaacaaag ttgttagtac 6721   aactactaac atagttacac ggtgtttaaa ccgtgtttgt actaattata tgccttattt
```

-continued

```
6781  ctttacttta ttgctacaat tgtgtacttt tactagaagt acaaattcta gaattaaagc
6841  atctatgccg actactatag caaagaatac tgttaagagt gtcggtaaat tttgtctaga
6901  ggcttcattt aattatttga agtcacctaa tttttctaaa ctgataaata ttataatttg
6961  gttttactta ttaagtgttt gcctaggttc tttaatctac tcaaccgctg ctttaggtgt
7021  tttaatgtct aatttaggca tgccttctta ctgtactggt tacagagaag gctatttgaa
7081  ctctactaat gtcactattg caacctactg tactggttct ataccttgta gtgtttgtct
7141  tagtggttta gattctttag acacctatcc ttctttagaa actatacaaa ttaccatttc
7201  atctttaaa tgggatttaa ctgcttttgg cttagttgca gagtggtttt tggcatatat
7261  tctttcact aggttttct atgtacttgg attggctgca atcatgcaat tgttttcag
7321  ctattttgca gtacatttta ttagtaattc ttggcttatg tggttaataa ttaatcttgt
7381  acaaatggcc ccgatttcag ctatggttag aatgtacatc ttctttgcat cattttatta
7441  tgtatggaaa agttatgtgc atgttgtaga cggttgtaat tcatcaactt gtatgatgtg
7501  ttacaaacgt aatagagcaa caagagtcga atgtacaact attgttaatg gtgttagaag
7561  gtccttttat gtctatgcta atggaggtaa aggcttttgc aaactacaca attggaattg
7621  tgttaattgt gatacattct gtgctggtag tacatttatt agtgatgaag ttgcgagaga
7681  cttgtcacta cagtttaaaa gaccaataaa tcctactgac cagtcttctt acatcgttga
7741  tagtgttaca gtgaagaatg gttccatcca tctttacttt gataaagctg gtcaaaagac
7801  ttatgaaaga cattctctct ctcattttgt taacttagac aacctgagag ctaataacac
7861  taaaggttca ttgcctatta atgttatagt ttttgatggt aaatcaaaat gtgaagaatc
7921  atctgcaaaa tcagcgtctg tttactacag tcagcttatg tgtcaaccta tactgttact
7981  agatcaggca ttagtgtctg atgttggtga tagtgcggaa gttgcagtta aaatgtttga
8041  tgcttacgtt aatacgtttt catcaacttt taacgtacca atggaaaaac tcaaaacact
8101  agttgcaact gcagaagctg aacttgcaaa gaatgtgtcc ttagacaatg tcttatctac
8161  ttttatttca gcagctcggc aagggtttgt tgattcagat gtagaaacta agatgttgt
8221  tgaatgtctt aaattgtcac atcaatctga catagaagtt actggcgata gttgtaataa
8281  ctatatgctc acctataaca aagttgaaaa catgacaccc cgtgaccttg gtgcttgtat
8341  tgactgtagt gcgcgtcata ttaatgcgca ggtagcaaaa agtcacaaca ttgctttgat
8401  atggaacgtt aaagatttca tgtcattgtc tgaacaacta cgaaaacaaa tacgtagtgc
8461  tgctaaaaag aataacttac cttttaagtt gacatgtgca actactagac aagttgttaa
8521  tgttgtaaca acaaagatag cacttaaggg tggtaaaatt gttaataatt ggttgaagca
8581  gttaattaaa gttacacttg tgttccttttt tgttgctgct attttctatt taataacacc
8641  tgttcatgtc atgtctaaac atactgactt ttcaagtgaa atcataggat acaaggctat
8701  tgatggtggt gtcactcgtg acatagcatc tacagatact tgttttgcta caaacatgc
8761  tgattttgac acatggttta gccagcgtgg tggtagttat actaatgaca agcttgccc
8821  attgattgct gcagtcataa caagagaagt gggttttgtc gtgcctggtt gcctggcac
8881  gatattacgc acaactaatg gtgacttttt gcatttctta cctagagttt ttagtgcagt
8941  tggtaacatc tgttacacac catcaaaact tatagagtac actgactttg caacatcagc
9001  ttgtgttttg gctgctgaat gtacaatttt taaagatgct tctggtaagc cagtaccata
9061  ttgttatgat accaatgtac tagaaggttc tgttgcttat gaaagtttac gccctgacac
9121  acgttatgtg ctcatggatg gctctattat tcaatttcct aacacctacc ttgaaggttc
9181  tgttagagtg gtaacaactt ttgattctga gtactgtagg cacggcactt gtgaaagatc
```

```
9241   agaagctggt gtttgtgtat ctactagtgg tagatgggta cttaacaatg attattacag
9301   atctttacca ggagttttct gtggtgtaga tgctgtaaat ttacttacta atatgtttac
9361   accactaatt caacctattg gtgctttgga catatcagca tctatagtag ctggtggtat
9421   tgtagctatc gtagtaacat gccttgccta ctattttatg aggtttagaa gagcttttgg
9481   tgaatacagt catgtagttg cctttaatac tttactattc cttatgtcat tcactgtact
9541   ctgtttaaca ccagtttact cattcttacc tggtgtttat tctgttattt acttgtactt
9601   gacattttat cttactaatg atgtttcttt tttagcacat attcagtgga tggttatgtt
9661   cacaccttta gtacctttct ggataacaat tgcttatatc atttgtattt ccacaaagca
9721   tttctattgg ttctttagta attacctaaa gagacgtgta gtctttaatg gtgtttcctt
9781   tagtactttt gaagaagctg cgctgtgcac cttttgtta aataaagaaa tgtatctaaa
9841   gttgcgtagt gatgtgctat tacctcttac gcaatataat agatacttag ctctttataa
9901   taagtacaag tattttagtg gagcaatgga tacaactagc tacagagaag ctgcttgttg
9961   tcatctcgca aaggctctca atgacttcag taactcaggt tctgatgttc tttaccaacc
10021  accacaaacc tctatcacct cagctgtttt gcagagtggt tttagaaaaa tggcattccc
10081  atctggtaaa gttgagggtt gtatggtaca agtaacttgt ggtacaacta cacttaacgg
10141  tctttggctt gatgacgtag tttactgtcc aagacatgtg atctgcacct ctgaagacat
10201  gcttaaccct aattatgaag atttactcat tcgtaagtct aatcataatt tcttggtaca
10261  ggctggtaat gttcaactca gggttattgg acattctatg caaaattgtg tacttaagct
10321  taaggttgat acagccaatc ctaagacacc taagtataag tttgttcgca ttcaaccagg
10381  acagactttt tcagtgttag cttgttacaa tggttcacca tctggtgttt accaatgtgc
10441  tatgaggccc aatttcacta ttaagggttc attccttaat ggttcatgtg gtagtgttgg
10501  ttttaacata gattatgact gtgtctcttt tgttacatg caccatatgg aattaccaac
10561  tggagttcat gctggcacag acttagaagg taactttat ggaccttttg ttgacaggca
10621  aacagcacaa gcagctggta cggacacaac tattacagtt aatgttttag cttggttgta
10681  cgctgctgtt ataaatggag acaggtggtt tctcaatcga tttaccacaa ctcttaatga
10741  ctttaacctt gtggctatga agtacaatta tgaacctcta acacaagacc atgttgacat
10801  actaggacct cttttctgctc aaactggaat tgccgtttta gatatgtgtg cttcattaaa
10861  agaattactg caaaatggta tgaatggacg taccatattg ggtagtgctt tattagaaga
10921  tgaatttaca ccttttgatg ttgttagaca atgctcaggt gttacttcc aaagtgcagt
10981  gaaaagaaca atcaagggta cacaccactg gttgttactc acaattttga cttcactttt
11041  agttttagtc cagagtactc aatggtcttt gttcttttt tgtatgaaa atgccttttt
11101  accttttgct atgggtatta ttgctatgtc tgcttttgca atgatgtttg tcaaacataa
11161  gcatgcattt ctctgtttgt ttttgttacc ttctcttgcc actgtagctt attttaatat
11221  ggtctatatg cctgctagtt gggtgatgcg tattatgaca tggttggata tggttgatac
11281  tagtttgtct ggttttaagc taaaagactg tgttatgtat gcatcagctg tagtgttact
11341  aatccttatg acagcaagaa ctgtgtatga tgatggtgct aggagagtgt ggacacttat
11401  gaatgtcttg acactcgttt ataaagttta ttatggtaat gctttagatc aagccatttc
11461  catgtgggct cttataatct ctgttacttc taactactca ggtgtagtta caactgtcat
11521  gttttggcc agaggtattg tttttatgtg tgttgagtat tgccctattt tcttcataac
11581  tggtaataca cttcagtgta taatgctagt ttattgtttc ttaggctatt tttgtacttg
```

```
11641  ttactttggc ctcttttgtt tactcaaccg ctactttaga ctgactcttg gtgtttatga
11701  ttacttagtt tctacacagg agtttagata tatgaattca cagggactac tcccacccaa
11761  gaatagcata gatgccttca aactcaacat taaattgttg ggtgttggtg gcaaaccttg
11821  tatcaaagta gccactgtac agtctaaaat gtcagatgta aagtgcacat cagtagtctt
11881  actctcagtt ttgcaacaac tcagagtaga atcatcatct aaattgtggg ctcaatgtgt
11941  ccagttacac aatgacattc tcttagctaa agatactact gaagcctttg aaaaaatggt
12001  ttcactactt tctgttttgc tttccatgca gggtgctgta gacataaaca agctttgtga
12061  agaaatgctg acaacaggg caaccttaca agctatagcc tcagagttta gttcccttcc
12121  atcatatgca gcttttgcta ctgctcaaga agcttatgag caggctgttg ctaatggtga
12181  ttctgaagtt gttcttaaaa agttgaagaa gtctttgaat gtggctaaat ctgaatttga
12241  ccgtgatgca gccatgcaac gtaagttgga aaagatggct gatcaagcta tgacccaaat
12301  gtataaacag gctagatctg aggacaagag ggcaaaagtt actagtgcta tgcagacaat
12361  gcttttcact atgctagaa agttggataa tgatgcactc aacaacatta tcaacaatgc
12421  aagagatggt tgtgttccct tgaacataat acctcttaca acagcagcca aactaatggt
12481  tgtcatacca gactataaca catataaaaa tacgtgtgat ggtacaacat ttacttatgc
12541  atcagcattg tgggaaatcc aacaggttgt agatgcagat agtaaaattg ttcaacttag
12601  tgaaattagt atggacaatt cacctaattt agcatggcct cttattgtaa cagctttaag
12661  ggccaattct gctgtcaaat tacagaataa tgagcttagt cctgttgcac tacgacagat
12721  gtcttgtgct gccggtacta cacaaactgc ttgcactgat gacaatgcgt tagcttacta
12781  caacacaaca aagggaggta ggtttgtact tgcactgtta tccgatttac aggatttgaa
12841  atgggctaga ttccctaaga gtgatgaac tggtactatc tatacagaac tggaaccacc
12901  ttgtaggttt gttacagaca cacctaaagg tcctaaagtg aagtatttat actttattaa
12961  aggattaaac aacctaaata gaggtatggg acttggtagt ttagctgcca cagtacgtct
13021  acaagctggt aatgcaacag aagtgcctgc caattcaact gtattatctt tctgtgcttt
13081  tgctgtagat gctgctaaag cttacaaaga ttatctagct agtgggggac aaccaatcac
13141  taattgtgtt aagatgttgt gtacacacac tggtactggt caggcaataa cagttacacc
13201  ggaagccaat atggatcaag aatccttggg tggtgcatcg tgttgtctgt actgccgttg
13261  ccacatagat catccaaatc ctaaaggatt ttgtgactta aaaggtaagt atgtacaaat
13321  acctacaact tgtgctaatg accctgtggg ttttacactt aaaaacacag tctgtaccgt
13381  ctgcggtatg tggaaaggtt atggctgtag ttgtgatcaa ctccgcgaac ccatgcttca
13441  gtcagctgat gcacaatcgt ttttaaacgg gtttgcggtg taagtgcagc ccgtcttaca
13501  ccgtgcggca caggcactag tactgatgtc gtatacaggg cttttgacat ctacaatgat
13561  aaagtagctg ttttgctaa attcctaaaa actaattgtt gtcgcttcca agaaaaggac
13621  gaagatgaca atttaattga ttcttacttt gtagttaaga gacacacttt ctctaactac
13681  caacatgaag aaacaattta atttacttt aaggattgtc cagctgttgc taaacatgac
13741  ttctttaagt ttagaataga cggtgacatg gtaccacata tatcacgtca acgtcttact
13801  aaatacacaa tggcagacct cgtctatgct ttaaggcatt ttgatgaagg taattgtgac
13861  acattaaaag aaatacttgt cacatacaat tgttgtgatg atgattattt caataaaaag
13921  gactggtatg attttgtaga aaacccagat atattacgcg tatacgccaa cttaggtgaa
13981  cgtgtacgcc aagctttgtt aaaaacagta caattctgtg atgccatgcg aaatgctggt
14041  attgttggtg tactgacatt agataatcaa gatctcaatg gtaactggta tgatttcggt
```

```
14101  gatttcatac aaaccacgcc aggtagtgga gttcctgttg tagattctta ttattcattg 14161  ttaatgccta tattaacctt gaccagggct ttaactgcag agtcacatgt tgacactgac 14221  ttaacaaagc cttacattaa gtgggatttg ttaaaatatg acttcacgga agagaggtta 14281  aaactctttg accgttattt taaatattgg gatcagacat accacccaaa ttgtgttaac 14341  tgtttggatg acagatgcat tctgcattgt gcaaacttta atgttttatt ctctacagtg 14401  ttcccaccta caagttttgg accactagtg agaaaaatat ttgttgatgg tgttccattt 14461  gtagtttcaa ctggatacca cttcagagag ctaggtgttg tacataatca ggatgtaaac 14521  ttacatagct ctagacttag ttttaaggaa ttacttgtgt atgctgctga ccctgctatg 14581  cacgctgctt ctggtaatct attactagat aaacgcacta cgtgcttttc agtagctgca 14641  cttactaaca atgttgcttt tcaaactgtc aaacccggta attttaacaa agacttctat 14701  gactttgctg tgtctaaggg tttcttttaag gaaggaagtt ctgttgaatt aaaaacacttc 14761  ttctttgctc aggatggtaa tgctgctatc agcgattatg actactatcg ttataatcta 14821  ccaacaatgt gtgatatcag acaactacta tttgtagttg aagttgttga taagtactttt 14881  gattgttacg atggtggctg tattaatgct aaccaagtca tcgtcaacaa cctagacaaa 14941  tcagctggtt ttccatttaa taaatggggt aaggctagac tttattatga ttcaatgagt 15001  tatgaggatc aagatgcact tttcgcatat acaaaacgta atgtcatccc tactataact 15061  caaatgaatc ttaagtatgc cattagtgca aagaatagag ctcgcaccgt agctggtgtc 15121  tctatctgta gtactatgac caatagacag tttcatcaaa aattattgaa atcaatagcc 15181  gccactagag gagctactgt agtaattgga acaagcaaat tctatggtgg ttggcacaac 15241  atgttaaaaa ctgtttatag tgatgtagaa aaccctcacc ttatgggttg ggattatcct 15301  aaatgtgata gagccatgcc taacatgctt agaattatgg cctcacttgt tcttgctcgc 15361  aaacatacaa cgtgttgtag cttgtcacac cgtttctata gattagctaa tgagtgtgct 15421  caagtattga gtgaaatggt catgtgtggc ggttcactat atgttaaacc aggtggaacc 15481  tcatcaggag atgccacaac tgcttatgct aatagtgttt ttaacatttg tcaagctgtc 15541  acggccaatg ttaatgcact tttatctact gatggtaaca aaattgccga taagtatgtc 15601  cgcaatttac aacacagact ttatgagtgt ctctatagaa atagagatgt tgacacagac 15661  tttgtgaatg agttttacgc atatttgcgt aaacatttct caatgatgat actctctgac 15721  gatgctgttg tgtgtttcaa tagcacttat gcatctcaag gtctagtggc tagcataaag 15781  aactttaagt cagttcttta ttatcaaaac aatgttttta tgtctgaagc aaaatgttgg 15841  actgagactg accttactaa aggacctcat gaattttgct ctcaacatac aatgctagtt 15901  aaacagggtg atgattatgt gtaccttcct tacccagatc catcaagaat cctaggggcc 15961  ggctgttttg tagatgatat cgtaaaaaca gatggtacac ttatgattga cggttcgtg 16021  tctttagcta tagatgctta cccacttact aaacatccta atcaggagta tgctgatgtc 16081  tttcatttgt acttacaata cataagaaag ctacatgatg agttaacagg acacatgtta 16141  gacatgtatt ctgttatgct tactaatgat aacacttcaa ggtattggga acctgagttt 16201  tatgaggcta tgtacacacc gcatacagtc ttacaggctg ttgggggcttg tgttctttgc 16261  aattcacaga cttcattaag atgtggtgct tgcatacgta gaccattctt atgttgtaaa 16321  tgctgttacg accatgtcat atcaacatca cataaattag tcttgtctgt taatccgtat 16381  gtttgcaatg ctccaggttg tgatgtcaca gatgtgactc aacttttactt aggaggtatg 16441  agctattatt gtaaatcaca taaaccaccc attagttttc cattgtgtgc taatggacaa
```

-continued

```
16501  gttttggtt tatataaaaa tacatgtgtt ggtagcgata atgttactga ctttaatgca
16561  attgcaacat gtgactggac aaatgctggt gattacattt tagctaacac ctgtactgaa
16621  agactcaagc tttttgcagc agaaacgctc aaagctactg aggagacatt taaactgtct
16681  tatggtattg ctactgtacg tgaagtgctg tctgcagag aattacatct ttcatgggaa
16741  gttggtaaac ctagaccacc acttaaccga aattatgtct ttactggtta tcgtgtaact
16801  aaaaacagta aagtacaaat aggagagtac acctttgaaa aggtgactga tggtgatgct
16861  gttgtttacc gaggtacaac aacttacaaa ttaaatgttg gtgattattt tgtgctgaca
16921  tcacatacag taatgccatt aagtgcacct acactagtgc cacaagagca ctatgttaga
16981  attactggct tatacccaac actcaatatc tcagatgagt tttctagcaa tgttgcaaat
17041  tatcaaaagg ttggtatgca aaagtattct acactccagg accacctgg tactggtaag
17101  agtcattttg ctattggcct agctctctac tacccttctg ctcgcatagt gtatacagct
17161  tgctctcatg ccgctgttga tgcactatgt gagaaggcat taaaatattt gcctatagat
17221  aaatgtagta gaattatacc tgcacgtgct cgtgtagagt gttttgataa attcaaagtg
17281  aattcaacat tagaacagta tgtcttttgt actgtaaatg cattgcctga cacgacagca
17341  gatatagttg tctttgatga aatttcaatg ccacaaatt atgatttgag tgttgtcaat
17401  gccagattac gtgctaagca ctatgtgtac attggcgacc ctgctcaatt acctgcacca
17461  cgcacattgc taactaaggg cacactagaa ccagaatatt tcaattcagt gtgtagactt
17521  atgaaaacta taggtccaga catgttcctc ggaacttgtc ggcgttgtcc tgctgaaatt
17581  gttgacactg tgagtgcttt ggtttatgat aataagctta aagcacataa agacaaatca
17641  gctcaatgct ttaaaatgtt ttataagggt gttatcacgc atgatgtttc atctgcaatt
17701  aacaggccac aaataggcgt ggtaagagaa ttccttacac gtaaccctgc ttggagaaaa
17761  gctgtcttta tttcaccttg taattcacag aatgctgtag cctcaaagat tttgggacta
17821  ccaactcaaa ctgttgattc atcacagggc tcagaatatg actatgtcat attcactcaa
17881  accactgaaa cagctcactc ttgtaatgta aacagattta atgttgctat taccagagca
17941  aaagtaggca actttgcat aatgtctgat agagaccttt atgacaagtt gcaatttaca
18001  agtcttgaaa ttccacgtag gaatgtggca actttacaag ctgaaaatgt aacaggactc
18061  tttaaagatt gtagtaaggt aatcactggg ttacatccta cacaggcacc tacacacctc
18121  agtgttgaca ctaaattcaa aactgaaggt ttatgtgttg acatacctgg catacctaag
18181  gacatgacct atagaagact catctctatg atgggtttta aaatgaatta tcaagttaat
18241  ggttacccta acatgtttat caccccgcgaa gaagctataa gacatgtacg tgcatggatt
18301  ggcttcgatg tcgagggtgtg tcatgctact agagaagctg ttggtaccaa tttaccttta
18361  cagctaggtt tttctacagg tgttaaccta gttgctgtac ctacaggtta tgttgataca
18421  cctaataata cagatttttc cagagttagt gctaaaccac cgcctggaga tcaatttaaa
18481  cacctcatac cacttatgta caaaggactt ccttggaatg tagtgcgtat aaagattgta
18541  caaatgttaa gtgacacact taaaaatctc tctgcagag tcgtatttgt cttatgggca
18601  catggctttg agttgacatc tatgaagtat tttgtgaaaa taggacctga gcgcacctgt
18661  tgtctatgtg atagacgtgc cacatgcttt tccactgctt cagacactta tgcctgttgg
18721  catcattcta ttggatttga ttacgtctat aatccgttta tgattgatgt tcaacaatgg
18781  ggttttacag gtaacctaca aagcaaccat gatctgtatt gtcaagtcca tggtaatgca
18841  catgtagcta gttgtgatgc aatcatgact aggtgtctag ctgtccacga gtgctttgtt
18901  aagcgtgttg actggactat tgaatatcct ataattggtg atgaactgaa gattaatgcg
```

-continued

```
18961  gcttgtagaa aggttcaaca catggttgtt aaagctgcat tattagcaga caaattccca
19021  gttcttcacg acattggtaa ccctaaagct attaagtgtg tacctcaagc tgatgtagaa
19081  tggaagttct atgatgcaca gccttgtagt gacaaagctt ataaaataga agaattattc
19141  tattcttatg ccacacattc tgacaaattc acagatggtg tatgcctatt tggaattgc
19201  aatgtcgata gatatcctgc taattccatt gtttgtagat ttgacactag agtgctatct
19261  aaccttaact tgcctggttg tgatggtggc agtttgtatg taaataaaca tgcattccac
19321  acaccagctt ttgataaaag tgcttttgtt aatttaaaac aattaccatt tttctattac
19381  tctgacagtc catgtgagtc tcatggaaaa caagtagtgt cagatataga ttatgtacca
19441  ctaaagtctg ctacgtgtat aacacgttgc aatttaggtg gtgctgtctg tagacatcat
19501  gctaatgagt acagattgta tctcgatgct tataacatga tgatctcagc tggctttagc
19561  ttgtgggttt acaaacaatt tgatacttat aacctctgga acacttttac aagacttcag
19621  agtttagaaa atgtggcttt taatgttgta aataagggac actttgatgg acaacagggt
19681  gaagtaccag tttctatcat taataacact gtttacacaa agttgatgg tgttgatgta
19741  gaattgtttg aaaataaaac aacattacct gttaatgtag catttgagct ttgggctaag
19801  cgcaacatta aaccagtacc agaggtgaaa atactcaata atttgggtgt ggacattgct
19861  gctaatactg tgatctggga ctacaaaaga gatgctccag cacatatatc tactattggt
19921  gtttgttcta tgactgacat agccaagaaa ccaactgaaa cgatttgtgc accactcact
19981  gtcttttttg atggtagagt tgatggtcaa gtagacttat ttagaaatgc ccgtaatggt
20041  gttcttatta cagaaggtag tgttaaaggt ttacaaccat ctgtaggtcc caaacaagct
20101  agtcttaatg gagtcacatt aattggagaa gccgtaaaaa cacagttcaa ttattataag
20161  aaagttgatg gtgttgtcca acaattaccc gaaacttact ttactcagag tagaaattta
20221  caagaattta aacccaggag tcaaatggaa attgatttct tagaattagc tatggatgaa
20281  ttcattgaac ggtataaatt agaaggctat gccttcgaac atatcgttta tggagatttt
20341  agtcatagtc agttaggtgg tttacatcta ctgattggac tagctaaacg ttttaaggaa
20401  tcacctttg aattagaaga ttttattcct atggacagta cagttaaaaa ctatttcata
20461  acagatgcgc aaacaggttc atctaagtgt gtgtgttctg ttattgattt attacttgat
20521  gattttgttg aaataataaa atcccaagat ttatctgtag tttctaaggt tgtcaaagtg
20581  actattgact atacagaaat ttcatttatg ctttggtgta agatggcca tgtagaaaca
20641  ttttacccaa aattacaatc tagtcaagcg tggcaaccgg gtgttgctat gcctaatctt
20701  tacaaaatgc aaagaatgct attagaaaag tgtgaccttc aaaattatgg tgatagtgca
20761  acattaccta aaggcataat gatgaatgtc gcaaaatata ctcaactgtg tcaatattta
20821  aacacattaa cattagctgt accctataat atgagagtta tacattttgg tgctggttct
20881  gataaaggag ttgcaccagg tacagctgtt ttaagacagt ggttgcctac gggtacgctg
20941  cttgtcgatt cagatcttaa tgactttgtc tctgatgcag attcaacttt gattggtgat
21001  tgtgcaactg tacatacagc taataaatgg gatctcatta ttagtgatat gtacgaccct
21061  aagactaaaa atgttacaaa agaaaatgac tctaagagag gttttttcac ttacatttgt
21121  gggttatac aacaaaagct agctcttgga ggttccgtgg ctataaagat aacagaacat
21181  tcttggaatg ctgatctta aagctcatg ggacacttcg catggtggac agcctttgtt
21241  actaatgtga atgcgtcatc atctgaagca ttttttaattg gatgtaatta tcttggcaaa
21301  ccacgcgaac aaatagatgg ttatgtcatg catgcaaatt acatattttg gaggaataca
```

```
21361  aatccaattc agttgtcttc ctattcttta tttgacatga gtaaatttcc ccttaaatta
21421  aggggtactg ctgttatgtc tttaaaagaa ggtcaaatca atgatatgat tttatctctt
21481  cttagtaaag gtagacttat aattagagaa aacaacagag ttgttatttc tagtgatgtt
21541  cttgttaaca actaaacgaa caatgtttgt ttttcttgtt ttattgccac tagtctctag
21601  tcagtgtgtt aatcttacaa ccagaactca attaccccct gcatacacta attctttcac
21661  acgtggtgtt tattaccctg acaaagtttt cagatcctca gttttacatt caactcagga
21721  cttgttctta cctttctttt ccaatgttac ttggttccat gctatacatg tctctgggac
21781  caatggtact aagaggtttg ataaccctgt cctaccattt aatgatggtg tttatttttgc
21841  ttccactgag aagtctaaca taataagagg ctggattttt ggtactactt tagattcgaa
21901  gacccagtcc ctacttattg ttaataacgc tactaatgtt gttattaaag tctgtgaatt
21961  tcaattttgt aatgatccat ttttgggtgt ttattaccac aaaaacaaca aaagttggat
22021  ggaaagtgag ttcagagttt attctagtgc gaataattgc acttttgaat atgtctctca
22081  gccttttctt atggaccttg aaggaaaaca gggtaaattc aaaaatctta gggaatttgt
22141  gtttaagaat attgatggtt attttaaaat atattctaag cacacgccta ttaatttagt
22201  gcgtgatctc cctcagggtt tttcggcttt agaaccattg gtagatttgc caataggtat
22261  taacatcact aggtttcaaa ctttacttgc tttacataga agttatttga ctcctggtga
22321  ttcttcttca ggttggacag ctggtgctgc agcttattat gtgggttatc ttcaacctag
22381  gacttttcta ttaaaatata atgaaaatgg aaccattaca gatgctgtag actgtgcact
22441  tgaccctctc tcagaaacaa agtgtacgtt gaaatccttc actgtagaaa aggaatccta
22501  tcaaacttct aactttagag tccaaccaac agaatctatt gttagatttc taatattac
22561  aaacttgtgc ccttttggtg aagttttta cgccaccaga tttgcatctg tttatgcttg
22621  gaacaggaag agaatcagca actgtgttgc tgattattct gtcctatata attccgcatc
22681  attttccact tttaagtgtt atggagtgtc tcctactaaa ttaaatgatc tctgctttac
22741  taatgtctat gcagattcat ttgtaattag aggtgatgaa gtcagacaaa tcgctccagg
22801  gcaaactgga aagattgctg attataatta taaattacca gatgatttta caggctgcgt
22861  tatagcttgg aattctaaca atcttgattc taaggttggt ggtaattata attacctgta
22921  tagattgttt aggaagtcta atctcaaacc ttttgagaga gatatttcaa ctgaaatcta
22981  tcaggccggt agcacacctt gtaatggtgt tgaaggtttt aattgttact tccctttaca
23041  atcatatggt ttccaaccca ctaatggtgt tggttaccaa ccatacagag tagtagtact
23101  ttcttttgaa cttctacatg caccagcaac tgtttgtgga cctaaaaagt ctactaattt
23161  ggttaaaaac aaatgtgtca atttcaactt caatggttta acaggcacag gtgttcttac
23221  tgagtctaac aaaaagtttc tgcctttcca acaatttggc agagacattg ctgacactac
23281  tgatgctgtc cgtgatccac agacacttga gattcttgac attacaccat gttcttttgg
23341  tggtgtcagt gttataacac caggaacaaa tacttctaac caggttgctg ttctttatca
23401  ggatgttaac tgcacagaag tccctgttgc tattcatgca gatcaactta ctcctacttg
23461  gcgtgtttat tctacaggtt ctaatgtttt tcaaacacgt gcaggctgtt taataggggc
23521  tgaacatgtc aacaactcat atgagtgtga catacccatt ggtgcaggta tatgcgctag
23581  ttatcagact cagactaatt ctcctcggcg ggcacgtagt gtagctagtc aatccatcat
23641  tgcctacact atgtcacttg gtgcagaaaa ttcagttgct tactctaata actctattgc
23701  catacccaca aatttttacta ttagtgttac cacagaaatt ctaccagtgt ctatgaccaa
23761  gacatcagta gattgtacaa tgtacatttg tggtgattca actgaatgca gcaatctttt
```

```
23821  gttgcaatat ggcagttttt gtacacaatt aaaccgtgct ttaactggaa tagctgttga
23881  acaagacaaa acacccaag aagttttgc acaagtcaaa caaatttaca aacaccacc
23941  aattaaagat tttggtggtt ttaattttc acaaatatta ccagatccat caaaaccaag
24001  caagaggtca tttattgaag atctactttt caacaaagtg acacttgcag atgctggctt
24061  catcaaacaa tatggtgatt gccttggtga tattgctgct agagacctca tttgtgcaca
24121  aaagtttaac ggccttactg ttttgccacc tttgctcaca gatgaaatga ttgctcaata
24181  cacttctgca ctgttagcgg gtacaatcac ttctggttgg accttggtg caggtgctgc
24241  attacaaata ccatttgcta tgcaaatggc ttataggttt aatggtattg agttacaca
24301  gaatgttctc tatgagaacc aaaaattgat tgccaaccaa tttaatagtg ctattggcaa
24361  aattcaagac tcactttctt ccacagcaag tgcacttgga aaacttcaag atgtggtcaa
24421  ccaaaatgca caagctttaa acacgcttgt taaacaactt agctccaatt ttggtgcaat
24481  ttcaagtgtt ttaaatgata tcctttcacg tcttgacaaa gttgaggctg aagtgcaaat
24541  tgataggttg atcacaggca gacttcaaag tttgcagaca tatgtgactc aacaattaat
24601  tagagctgca gaaatcagag cttctgctaa tcttgctgct actaaaatgc cagagtgtgt
24661  acttggacaa tcaaaagag ttgatttttg tggaaagggc tatcatctta tgtccttccc
24721  tcagtcagca cctcatggtg tagtcttctt gcatgtgact tatgtccctg cacaagaaaa
24781  gaacttcaca actgctcctg ccatttgtca tgatggaaaa gcacactttc ctcgtgaagg
24841  tgtctttgtt tcaaatggca cacactggtt tgtaacacaa aggaatttt atgaaccaca
24901  aatcattact acagacaaca catttgtgtc tggtaactgt gatgttgtaa taggaattgt
24961  caacaacaca gtttatgatc cttgcaacc tgaattagac tcattcaagg aggagttaga
25021  taaatattt aagaatcata catcaccaga tgttgattta ggtgacatct ctggcattaa
25081  tgcttcagtt gtaaacattc aaaagaaat tgaccgcctc aatgaggttg ccaagaattt
25141  aaatgaatct ctcatcgatc tccaagaact tggaaagtat gagcagtata taaaatggcc
25201  atggtacatt tggctaggtt ttatagctgg cttgattgcc atagtaatgg tgacaattat
25261  gctttgctgt atgaccagtt gctgtagttg tctcaagggc tgttgttctt gtggatcctg
25321  ctgcaaattt gatgaagacg actctgagcc agtgctcaaa ggagtcaaat tacattacac
25381  ataaacgaac ttatggattt gtttatgaga tcttcacaa ttggaactgt aactttgaag
25441  caaggtgaaa tcaaggatgc tactccttca gattttgttc gcgctactgc aacgataccg
25501  atacaagcct cactcccttt cggatggctt attgttggcg ttgcacttct tgctgttttt
25561  cagagcgctt ccaaaatcat aaccctcaaa aagagatggc aactagcact ctccaaggt
25621  gttcactttg tttgcaactt gctgttgttg tttgtaacag tttactcaca ccttttgctc
25681  gttgctgctg gccttgaagc cccttttctc tatctttatg ctttagtcta cttcttgcag
25741  agtataaact tgtaagaat aataatgagg ctttggcttt gctggaaatg ccgttccaaa
25801  aacccattac tttatgatgc caactatttt ctttgctggc atactaattg ttacgactat
25861  tgtatacctt acaatagtgt aacttcttca attgtcatta cttcaggtga tggcacaaca
25921  agtcctattt ctgaacatga ctaccagatt ggtggttata ctgaaaaatg gaatctgga
25981  gtaaaagact gtgttgtatt acacagttac ttcacttcag actattacca gctgtactca
26041  actcaattga gtacagacac tggtgttgaa catgttacct tcttcatcta caataaaatt
26101  gttgatgagc ctgaagaaca tgtccaaatt cacacaatcg acggttcatc cggagttgtt
26161  aatccagtaa tggaaccaat ttatgatgaa ccgacgacga ctactagcgt gcctttgtaa
```

-continued

```
26221  gcacaagctg atgagtacga acttatgtac tcattcgttt cggaagagac aggtacgtta
26281  atagttaata gcgtacttct ttttcttgct ttcgtggtat tcttgctagt tacactagcc
26341  atccttactg cgcttcgatt gtgtgcgtac tgctgcaata ttgttaacgt gagtcttgta
26401  aaaccttctt tttacgttta ctctcgtgtt aaaaatctga attcttctag agttcctgat
26461  cttctggtct aaacgaacta atatattatat tagttttct gtttggaact ttaattttag
26521  ccatggcaga ttccaacggt actattaccg ttgaagagct aaaaagctc cttgaacaat
26581  ggaacctagt aataggtttc ctattcctta catggatttg tcttctacaa tttgcctatg
26641  ccaacaggaa taggtttttg tatataatta agttaatttt cctctggctg ttatggccag
26701  taactttagc ttgttttgtg cttgctgctg tttacagaat aaattggatc accggtggaa
26761  ttgctatcgc aatggcttgt cttgtaggct tgatgtggct cagctacttc attgcttctt
26821  tcagactgtt tgcgcgtacg cgttccatgt ggtcattcaa tccagaaact aacattcttc
26881  tcaacgtgcc actccatggc actattctga ccagaccgct tctagaaagt gaactcgtaa
26941  tcggagctgt gatccttcgt ggacatcttc gtattgctgg acaccatcta ggacgctgtg
27001  acatcaagga cctgcctaaa gaaatcactg ttgctacatc acgaacgctt tcttattaca
27061  aattgggagc ttcgcagcgt gtagcaggtg actcaggttt tgctgcatac agtcgctaca
27121  ggattggcaa ctataaatta aacacagacc attccagtag cagtgacaat attgctttgc
27181  ttgtacagta agtgacaaca gatgtttcat ctcgttgact ttcaggttac tatagcagag
27241  atattactaa ttattatgag gacttttaaa gttccatttt ggaatcttga ttacatcata
27301  aacctcataa ttaaaaattt atctaagtca ctaactgaga ataaatattc tcaattagat
27361  gaagagcaac caatggagat tgattaaacg aacatgaaaa ttattctttt cttggcactg
27421  ataacactcg ctacttgtga gctttatcac taccaagagt gtgttagagg tacaacagta
27481  cttttaaaag aaccttgctc ttctggaaca tacgagggca attcaccatt tcatcctcta
27541  gctgataaca aatttgcact gacttgcttt agcactcaat tgcttttgc ttgtcctgac
27601  ggcgtaaaac acgtctatca gttacgtgcc agatcagttt cacctaaaact gttcatcaga
27661  caagaggaag ttcaagaact ttactctcca attttttctta ttgttgcggc aatagtgttt
27721  ataacacttt gcttcacact caaaagaaag acagaatgat tgaactttca ttaattgact
27781  tctatttgtg cttttttagcc tttctgctat tccttgtttt aattatgctt attatcttt
27841  ggttctcact tgaactgcaa gatcataatg aaacttgtca cgcctaaacg aacatgaaat
27901  ttcttgtttt cttaggaatc atcacaactg tagctgcatt tcaccaagaa tgtagtttac
27961  agtcatgtac tcaacatcaa ccatatgtag ttgatgaccc gtgtcctatt cacttctatt
28021  ctaaatggta tattagagta ggagctagaa aatcagcacc tttaattgaa ttgtgcgtgg
28081  atgaggctgg ttctaaatca cccattcagt acatcgatat cggtaattat acagtttcct
28141  gtttaccttt tacaattaat tgccaggaac ctaaattggg tagtcttgta gtgcgttgtt
28201  cgttctatga agacttttta gagtatcatg acgttcgtgt tgttttagat ttcatctaaa
28261  cgaacaaact aaaatgtctg ataatggacc ccaaaatcag cgaaatgcac cccgcattac
28321  gtttggtgga ccctcagatt caactggcag taaccagaat ggagaacgca gtggggcgcg
28381  atcaaaacaa cgtcggcccc aaggtttacc caataatact gcgtcttggt tcaccgctct
28441  cactcaacat ggcaaggaag accttaaatt ccctcgagga caaggcgttc aattaacac
28501  caatagcagt ccagatgacc aaattggcta ctaccgaaga gctaccagac gaattcgtgg
28561  tggtgacggt aaaatgaaag atctcagtcc aagatggtat ttctactacc taggaactgg
28621  gccagaagct ggacttccct atggtgctaa caaagacggc atcatatggg ttgcaactga
```

-continued

```
28681  gggagccttg aatacaccaa aagatcacat tggcacccgc aatcctgcta acaatgctgc
28741  aatcgtgcta caacttcctc aaggaacaac attgccaaaa ggcttctacg cagaagggag
28801  cagaggcggc agtcaagcct cttctcgttc ctcatcacgt agtcgcaaca gttcaagaaa
28861  ttcaactcca ggcagcagta ggggaacttc tcctgctaga atggctggca atggcggtga
28921  tgctgctctt gctttgctgc tgcttgacag attgaaccag cttgagagca aaatgtctgg
28981  taaaggccaa caacaacaag gccaaactgt cactaagaaa tctgctgctg aggcttctaa
29041  gaagcctcgg caaaaacgta ctgccactaa agcatacaat gtaacacaag ctttcggcag
29101  acgtggtcca gaacaaaccc aaggaaattt tggggaccag gaactaatca gacaaggaac
29161  tgattacaaa cattggccgc aaattgcaca atttgccccc agcgcttcag cgttcttcgg
29221  aatgtcgcgc attggcatgg aagtcacacc ttcgggaacg tggttgacct acacaggtgc
29281  catcaaattg gatgacaaag atccaaattt caaagatcaa gtcattttgc tgaataagca
29341  tattgacgca tacaaaacat tcccaccaac agagcctaaa aaggacaaaa agaagaaggc
29401  tgatgaaact caagccttac cgcagagaca gaagaaacag caaactgtga ctcttcttcc
29461  tgctgcagat ttggatgatt tctccaaaca attgcaacaa tccatgagca gtgctgactc
29521  aactcaggcc taaactcatg cagaccacac aaggcagatg ggctatataa acgttttcgc
29581  ttttccgttt acgatatata gtctactctt gtgcagaatg aattctcgta actacatagc
29641  acaagtagat gtagttaact ttaatctcac atagcaatct ttaatcagtg tgtaacatta
29701  gggaggactt gaaagagcca ccacattttc accgaggcca cgcggagtac gatcgagtgt
29761  acagtgaaca atgctaggga gagctgccta tatggaagag ccctaatgtg taaaattaat
29821  tttagtagtg ctatccccat gtgattttaa tagcttctta ggagaatgac aaaaaaaaaa
29881  aaaaaaaaaa aaaaaaaaaa aaa.
```

GenBank Accession No. MN985325.1, which is specifically incorporated by reference herein in its entirety, provides the following (DNA) genomic sequence for SARS-CoV-2 (Severe acute respiratory syndrome coronavirus 2 isolate 2019-nCoV/USA-WA1/2020, complete genome):

```
                                                            (SEQ ID NO: 2)
   1  attaaaggtt tataccttcc caggtaacaa accaaccaac tttcgatctc ttgtagatct
  61  gttctctaaa cgaactttaa aatctgtgtg gctgtcactc ggctgcatgc ttagtgcact
 121  cacgcagtat aattaataac taattactgt cgttgacagg acacgagtaa ctcgtctatc
 181  ttctgcaggc tgcttacggt ttcgtccgtg ttgcagccga tcatcagcac atctaggttt
 241  cgtccgggtg tgaccgaaag gtaagatgga gagccttgtc cctggtttca acgagaaaac
 301  acacgtccaa ctcagtttgc ctgttttaca ggttcgcgac gtgctcgtac gtggctttgg
 361  agactccgtg gaggaggtct tatcagaggc acgtcaacat cttaaagatg gcacttgtgg
 421  cttagtagaa gttgaaaaag gcgttttgcc tcaacttgaa cagccctatg tgttcatcaa
 481  acgttcggat gctcgaactg cacctcatgg tcatgttatg gttgagctgg tagcagaact
 541  cgaaggcatt cagtacggtc gtagtggtga cacttggt gtccttgtcc ctcatgtggg
 601  cgaaatacca gtggcttacc gcaaggttct tcttcgtaag aacggtaata aaggagctgg
 661  tggccatagt tacggcgccg atctaaagtc atttgactta ggcgacgagc ttggcactga
 721  tccttatgaa gattttcaag aaaactggaa cactaaacat agcagtggtg ttacccgtga
 781  actcatgcgt gagcttaacg gaggggcata cactcgctat gtcgataaca acttctgtgg
```

-continued

```
 841   ccctgatggc taccctcttg agtgcattaa agaccttcta gcacgtgctg gtaaagcttc
 901   atgcactttg tccgaacaac tggactttat tgacactaag aggggtgtat actgctgccg
 961   tgaacatgag catgaaattg cttggtacac ggaacgttct gaaaagagct atgaattgca
1021   gacaccttt gaaattaaat tggcaaagaa atttgacacc ttcaatgggg aatgtccaaa
1081   ttttgtattt cccttaaatt ccataatcaa gactattcaa ccaagggttg aaaagaaaaa
1141   gcttgatggc tttatgggta gaattcgatc tgtctatcca gttgcgtcac caaatgaatg
1201   caaccaaatg tgcctttcaa ctctcatgaa gtgtgatcat tgtggtgaaa cttcatggca
1261   gacgggcgat tttgttaaag ccacttgcga attttgtggc actgagaatt gactaaaga
1321   aggtgccact acttgtggtt acttacccca aaatgctgtt gttaaatttt attgtccagc
1381   atgtcacaat tcagaagtag gacctgagca tagtcttgcc gaataccata atgaatctgg
1441   cttgaaaacc attcttcgta agggtggtcg cactattgcc tttggaggct gtgtgttctc
1501   ttatgttggt tgccataaca agtgtgccta ttgggttcca cgtgctagcg ctaacatagg
1561   ttgtaaccat acaggtgttg ttggagaagg ttccgaaggt cttaatgaca accttcttga
1621   aatactccaa aaagagaaag tcaacatcaa tattgttggt gactttaaac ttaatgaaga
1681   gatcgccatt attttggcat cttttctgc ttccacaagt gcttttgtgg aaactgtgaa
1741   aggtttggat tataaagcat tcaaacaaat tgttgaatcc tgtggtaatt ttaaagttac
1801   aaaaggaaaa gctaaaaaag gtgcctggaa tattggtgaa cagaaatcaa tactgagtcc
1861   tctttatgca tttgcatcag aggctgctcg tgttgtacga tcaattttct cccgcactct
1921   tgaaactgct caaaattctg tgcgtgtttt acagaaggcc gctataacaa tactagatgg
1981   aatttcacag tattcactga gactcattga tgctatgatg ttcacatctg atttggctac
2041   taacaatcta gttgtaatgg cctacattac aggtggtgtt gttcagttga cttcgcagtg
2101   gctaactaac atctttggca ctgtttatga aaaactcaaa cccgtccttg attggcttga
2161   agagaagttt aaggaaggtg tagagtttct tagagacggt tgggaaattg ttaaatttat
2221   ctcaacctgt gcttgtgaaa ttgtcggtgg acaaattgtc acctgtgcaa aggaaattaa
2281   ggagagtgtt cagacattct ttaagcttgt aaataaattt ttggctttgt gtgctgactc
2341   tatcattatt ggtggagcta aacttaaagc cttgaattta ggtgaaacat tgtcacgca
2401   ctcaagggga ttgtacagaa agtgtgttaa atccagagaa gaaactggcc tactcatgcc
2461   tctaaaagcc ccaaaagaaa ttatcttctt agagggagaa acacttccca cagaagtgtt
2521   aacagaggaa gttgtcttga aactggtga tttacaacca ttagaacaac ctactagtga
2581   agctgttgaa gctccattgg ttggtacacc agtttgtatt aacgggctta tgttgctcga
2641   aatcaaagac acagaaaagt actgtgccct tgcacctaat atgatggtaa caaacaatac
2701   cttcacactc aaaggcggtg caccaacaaa ggttacttt ggtgatgaca ctgtgataga
2761   agtgcaaggt tacaagagtg tgaatatcac ttttgaactt gatgaaagga ttgataaagt
2821   acttaatgag aagtgctctg cctatacagt tgaactcggt acagaagtaa atgagttcgc
2881   ctgtgttgtg gcagatgctg tcataaaaac tttgcaacca gtatctgaat tacttacacc
2941   actgggcatt gatttagatg agtggagtat ggctacatac tactatttg atgagtctgg
3001   tgagtttaa ttggcttcac atatgtattg ttcttctac cctccagatg aggatgaaga
3061   agaaggtgat tgtgaagaag aagagtttga gccatcaact caatatgagt atggtactga
3121   agatgattac caaggtaaac ctttggaatt tggtgccact tctgctgctc ttcaacctga
3181   agaagagcaa gaagaagatt ggttagatga tgatagtcaa caaactgttg gtcaacaaga
3241   cggcagtgag gacaatcaga caactactat tcaaacaatt gttgaggttc aacctcaatt
```

-continued

```
3301  agagatggaa cttacaccag ttgttcagac tattgaagtg aatagtttta gtggttattt
3361  aaaacttact gacaatgtat acattaaaaa tgcagacatt gtggaagaag ctaaaaaggt
3421  aaaaccaaca gtggttgtta atgcagccaa tgtttacctt aaacatggag gaggtgttgc
3481  aggagcctta aataaggcta ctaacaatgc catgcaagtt gaatctgatg attacatagc
3541  tactaatgga ccacttaaag tgggtggtag ttgtgtttta agcggacaca atcttgctaa
3601  acactgtctt catgttgtcg gcccaaatgt taacaaaggt gaagacattc aacttcttaa
3661  gagtgcttat gaaaattta atcagcacga agttctactt gcaccattat tatcagctgg
3721  tattttttggt gctgacccta tacattcttt aagagtttgt gtagatactg ttcgcacaaa
3781  tgtctactta gctgtctttg ataaaaatct ctatgacaaa cttgtttcaa gcttttttgga
3841  aatgaagagt gaaaagcaag ttgaacaaaa gatcgctgag attcctaaag aggaagttaa
3901  gccatttata actgaaagta aaccttcagt tgaacagaga aaacaagatg ataagaaaat
3961  caaagcttgt gttgaagaag ttacaacaac tctggaagaa actaagttcc tcacagaaaa
4021  cttgttactt tatattgaca ttaatggcaa tcttcatcca gattctgcca ctcttgttag
4081  tgacattgac atcactttct taaagaaaga tgctccatat atagtgggtg atgttgttca
4141  agagggtgtt ttaactgctg tggttatacc tactaaaaag ctggtggca ctactgaaat
4201  gctagcgaaa gctttgagaa aagtgccaac agacaattat ataaccactt cccgggtca
4261  gggtttaaat ggttacactg tagaggaggc aaagacagtg cttaaaaagt gtaaaagtgc
4321  cttttacatt ctaccatcta ttatctctaa tgagaagcaa gaaattcttg gaactgtttc
4381  ttggaatttg cgagaaatgc ttgcacatgc agaagaaaca cgcaaattaa tgcctgtctg
4441  tgtggaaact aaagccatag tttcaactat acagcgtaaa tataagggta ttaaaataca
4501  agagggtgtg gttgattatg gtgctagatt ttacttttac accagtaaaa caactgtagc
4561  gtcacttatc aacacactta acgatctaaa tgaaactctt gttacaatgc cacttggcta
4621  tgtaacacat ggcttaaatt tggaagaagc tgctcggtat atgagatctc tcaaagtgcc
4681  agctacagtt tctgttttct cacctgatgc tgttacagcg tataatggtt atcttacttc
4741  ttcttctaaa acacctgaag aacatttat tgaaaccatc tcacttgctg gttcctataa
4801  agattggtcc tattctggac aatctacaca actaggtata gaatttctta agagaggtga
4861  taaaagtgta tattacacta gtaatcctac cacattccac ctagatggtg aagttatcac
4921  ctttgacaat cttaagacac ttctttcttt gagagaagtg aggactatta aggtgtttac
4981  aacagtagac aacattaacc tccacacgca agttgtggac atgtcaatga catatggaca
5041  acagtttggt ccaacttatt tggatggagc tgatgttact aaaataaaac ctcataattc
5101  acatgaaggt aaaacatttt atgttttacc taatgatgac actctacgtg ttgaggcttt
5161  tgagtactac cacacaactg atcctagttt tctgggtagg tacatgtcag cattaaatca
5221  cactaaaaag tggaaatacc cacaagttaa tggtttaact tctattaaat gggcagataa
5281  caactgttat cttgccactg cattgttaac actccaacaa atagagttga agtttaatcc
5341  acctgctcta caagatgctt attacagagc aagggctggt gaagctgcta cttttgtgc
5401  acttatctta gcctactgta ataagacagt aggtgagtta ggtgatgtta gagaaacaat
5461  gagttacttg tttcaacatg ccaattttaga ttcttgcaaa agagtcttga acgtggtgtg
5521  taaaacttgt ggacaacagc agacaaccct taagggtgta gaagctgtta tgtacatggg
5581  cacactttct tatgaacaat taagaaagg tgttcagata ccttgtacgt gtggtaaaca
5641  agctacaaaa tatctagtac aacaggagtc accttttgtt atgatgtcag caccacctgc
```

-continued

```
5701   tcagtatgaa cttaagcatg gtacatttac ttgtgctagt gagtacactg gtaattacca
5761   gtgtggtcac tataaacata aacttctaa agaaactttg tattgcatag acggtgcttt
5821   acttacaaag tcctcagaat acaaaggtcc tattacggat gttttctaca aagaaaacag
5881   ttacacaaca accataaaac cagttactta taaattggat ggtgttgttt gtacagaaat
5941   tgaccctaag ttggacaatt attataagaa agacaattct tatttcacag agcaaccaat
6001   tgatcttgta ccaaaccaac catatccaaa cgcaagcttc gataatttta agtttgtatg
6061   tgataatatc aaatttgctg atgatttaaa ccagttaact ggttataaga aacctgcttc
6121   aagagagctt aaagttacat ttttccctga cttaaatggt gatgtggtgg ctattgatta
6181   taaacactac acaccctctt ttaagaaagg agctaaattg ttacataaac ctattgtttg
6241   gcatgttaac aatgcaacta ataaagccac gtataaacca atacctggt gtatacgttg
6301   tctttggagc acaaaaccag ttgaaacatc aaattcgttt gatgtactga agtcagagga
6361   cgcgcaggga atggataatc ttgcctgcga agatctaaaa ccagtctctg aagaagtagt
6421   ggaaaatcct accatacaga aagacgttct tgagtgtaat gtgaaaacta ccgaagttgt
6481   aggagacatt atacttaaac cagcaaataa tagtttaaaa attacagaag aggttggcca
6541   cacagatcta atggctgctt atgtagacaa ttctagtctt actattaaga aacctaatga
6601   attatctaga gtattaggtt tgaaaaccct tgctactcat ggtttagctg ctgttaatag
6661   tgtcccttgg gatactatag ctaattatgc taagcctttt cttaacaaag ttgttagtac
6721   aactactaac atagttacac ggtgtttaaa ccgtgtttgt actaattata tgccttattt
6781   ctttacttta ttgctacaat tgtgtacttt tactagaagt acaaattcta gaattaaagc
6841   atctatgccg actactatag caaagaatac tgttaagagt gtcggtaaat tttgtctaga
6901   ggcttcattt aattatttga agtcacctaa tttttctaaa ctgataaata ttataaatttg
6961   gttttactaa ttaagtgttt gcctaggttc tttaatctac tcaaccgctg ctttaggtgt
7021   tttaatgtct aatttaggca tgccttctta ctgtactggt tacagagaag gctatttgaa
7081   ctctactaat gtcactattg caacctactg tactggttct ataccttgta gtgtttgtct
7141   tagtggttta gattcttag acacctatcc ttctttagaa actatacaaa ttaccatttc
7201   atcttttaaa tgggatttaa ctgcttttgg cttagttgca gagtggtttt tggcatatat
7261   tcttttcact aggttttctc atgtacttgg attggctgca atcatgcaat tgttttttcag
7321   ctattttgca gtacatttta ttagtaattc ttggcttatg tggttaataa ttaatcttgt
7381   acaaatggcc ccgatttcag ctatggttag aatgtacatc ttctttgcat cattttatta
7441   tgtatggaaa agttatgtgc atgttgtaga cggttgtaat tcatcaactt gtatgatgtg
7501   ttacaaacgt aatagagcaa caagagtcga atgtacaact attgttaatg gtgttagaag
7561   gtcctttat gtctatgcta atggaggtaa aggcttttgc aaactacaca attggaattg
7621   tgttaattgt gatacattct gtgctggtag tacatttatt agtgatgaag ttgcgagaga
7681   cttgtcacta cagtttaaaa gaccaataaa tcctactgac cagtcttctt acatcgttga
7741   tagtgttaca gtgaagaatg gttccatcca tctttacttt gataaagctg gtcaaaagac
7801   ttatgaaaga cattctctct ctcattttgt taacttagac aacctgagag ctaataacac
7861   taaaggttca ttgcctatta atgttatagt ttttgatggt aaatcaaaat gtgaagaatc
7921   atctgcaaaa tcagcgtctg tttactacag tcagcttatg tgtcaaccta tactgttact
7981   agatcaggca ttagtgtctg atgttggtga tagtgcggaa gttgcagtta aaatgtttga
8041   tgcttacgtt aatacgtttt catcaacttt taacgtacca atggaaaac tcaaaacact
8101   agttgcaact gcagaagctg aacttgcaaa gaatgtgtcc ttagacaatg tcttatctac
```

```
8161   ttttatttca gcagctcggc aagggtttgt tgattcagat gtagaaacta agatgttgt
8221   tgaatgtctt aaattgtcac atcaatctga catagaagtt actggcgata gttgtaataa
8281   ctatatgctc acctataaca aagttgaaaa catgacaccc cgtgaccttg gtgcttgtat
8341   tgactgtagt gcgcgtcata ttaatgcgca ggtagcaaaa agtcacaaca ttgctttgat
8401   atggaacgtt aaagatttca tgtcattgtc tgaacaacta cgaaaacaaa tacgtagtgc
8461   tgctaaaaag aataacttac cttttaagtt gacatgtgca actactgagc aagttgttaa
8521   tgttgtaaca acaaagatag cacttaaggg tggtaaaatt gttaataatt ggttgaagca
8581   gttaattaaa gttacacttg tgttccttt tgttgctgct attttctatt taataacacc
8641   tgttcatgtc atgtctaaac atactgactt ttcaagtgaa atcataggat acaaggctat
8701   tgatggtggt gtcactcgtg acatagcatc tacagatact tgttttgcta caaacatgc
8761   tgattttgac acatggttta gtcagcgtgg tggtagttat actaatgaca aagcttgccc
8821   attgattgct gcagtcataa caagagaagt gggttttgtc gtgcctggtt tgcctggcac
8881   gatattacgc acaactaatg gtgactttt gcatttctta cctagagttt ttagtgcagt
8941   tggtaacatc tgttacacac catcaaaact tatagagtac actgactttg caacatcagc
9001   ttgtgttttg gctgctgaat gtacaatttt taaagatgct tctggtaagc cagtaccata
9061   ttgttatgat accaatgtac tagaaggttc tgttgcttat gaaagtttac gccctgacac
9121   acgttatgtg ctcatggatg gctctattat tcaatttcct aacacctacc ttgaaggttc
9181   tgttagagtg gtaacaactt ttgattctga gtactgtagg cacggcactt gtgaaagatc
9241   agaagctggt gtttgtgtat ctactagtgg tagatgggta cttaacaatg attattacag
9301   atctttacca ggagttttct gtggtgtaga tgctgtaaat ttacttacta atatgtttac
9361   accactaatt caacctattg gtgctttgga catatcagca tctatagtag ctggtggtat
9421   tgtagctatc gtagtaacat gccttgccta ctattttatg aggtttagaa gagcttttgg
9481   tgaatacagt catgtagttg cctttaatac tttactattc cttatgtcat tcactgtact
9541   ctgtttaaca ccagtttact cattcttacc tggtgtttat tctgttattt acttgtactt
9601   gacatttat cttactaatg atgtttcttt tttagcacat attcagtgga tggttatgtt
9661   cacaccttta gtaccttct ggataacaat tgcttatatc atttgtattt ccacaaagca
9721   tttctattgg ttctttagta attacctaaa gagacgtgta gtctttaatg gtgtttcctt
9781   tagtactttt gaagaagctg cgctgtgcac cttttttgtta aataaagaaa tgtatctaaa
9841   gttgcgtagt gatgtgctat tacctcttac gcaatataat agatacttag ctctttataa
9901   taagtacaag tattttagtg gagcaatgga tacaactagc tacagagaag ctgcttgttg
9961   tcatctcgca aaggctctca atgacttcag taactcaggt tctgatgttc tttaccaacc
10021  accacaaacc tctatcacct cagctgtttt gcagagtggt tttagaaaaa tggcattccc
10081  atctggtaaa gttgaggggt gtatggtaca agtaacttgt ggtacaacta cacttaacgg
10141  tctttggctt gatgacgtag tttactgtcc aagacatgtg atctgcacct ctgaagacat
10201  gcttaaccct aattatgaag atttactcat tcgtaagtct aatcataatt tcttggtaca
10261  ggctggtaat gttcaactca gggttattgg acattctatg caaaattgtg tacttaagct
10321  taaggttgat acagccaatc ctaagacacc taagtataag tttgttcgca ttcaaccagg
10381  acagactttt tcagtgttag cttgttacaa tggttcacca tctggtgttt accaatgtgc
10441  tatgaggccc aatttcacta ttaagggttc attccttaat ggttcatgtg gtagtgttgg
10501  ttttaacata gattatgact gtgtctcttt tgttacatg caccatatgg aattaccaac
```

-continued

```
10561  tggagttcat gctggcacag acttagaagg taacttttat ggaccttttg ttgacaggca
10621  aacagcacaa gcagctggta cggacacaac tattacagtt aatgttttag cttggttgta
10681  cgctgctgtt ataaatggag acaggtggtt tctcaatcga tttaccacaa ctcttaatga
10741  ctttaacctt gtggctatga agtacaatta tgaacctcta acacaagacc atgttgacat
10801  actaggacct ctttctgctc aaactggaat tgccgtttta gatatgtgtg cttcattaaa
10861  agaattactg caaaatggta tgaatggacg taccatattg ggtagtgctt tattagaaga
10921  tgaatttaca ccttttgatg ttgttagaca atgctcaggt gttactttcc aaagtgcagt
10981  gaaaagaaca atcaagggta cacaccactg gttgttactc acaattttga cttcactttt
11041  agttttagtc cagagtactc aatggtcttt gttctttttt ttgtatgaaa atgccttttt
11101  accttttgct atgggtatta ttgctatgtc tgcttttgca atgatgtttg tcaaacataa
11161  gcatgcattt ctctgtttgt ttttgttacc ttctcttgcc actgtagctt attttaatat
11221  ggtctatatg cctgctagtt gggtgatgcg tattatgaca tggttggata tggttgatac
11281  tagtttgtct ggttttaagc taaaagactg tgttatgtat gcatcagctg tagtgttact
11341  aatccttatg acagcaagaa ctgtgtatga tgatggtgct aggagagtgt ggacacttat
11401  gaatgtcttg acactcgttt ataaagttta ttatgttaat gctttagatc aagccatttc
11461  catgtgggct cttataatct ctgttacttc taactactca ggtgtagtta caactgtcat
11521  gttttggcc agaggtattg tttttatgtg tgttgagtat tgccctattt cttcataac
11581  tggtaataca cttcagtgta taatgctagt ttattgtttc ttaggctatt tttgtacttg
11641  ttactttggc ctctttttgtt tactcaaccg ctactttaga ctgactcttg gtgtttatga
11701  ttacttagtt tctacacagg agtttagata tatgaattca cagggactac tcccacccaa
11761  gaatagcata gatgccttca aactcaacat taaattgttg ggtgttggtg gcaaaccttg
11821  tatcaaagta gccactgtac agtctaaaat gtcagatgta aagtgcacat cagtagtctt
11881  actctcagtt ttgcaacaac tcagagtaga atcatcatct aaattgtggg ctcaatgtgt
11941  ccagttacac aatgacattc tcttagctaa agatactact gaagcctttg aaaaaatggt
12001  ttcactactt tctgtttttgc tttccatgca gggtgctgta gacataaaca agctttgtga
12061  agaaatgctg gacaacaggg caaccttaca agctatagcc tcagagttta gttcccttcc
12121  atcatatgca gcttttgcta ctgctcaaga agcttatgag caggctgttg ctaatggtga
12181  ttctgaagtt gttcttaaaa agttgaagaa gtctttgaat gtggctaaat ctgaatttga
12241  ccgtgatgca gccatgcaac gtaagttgga aaagatggct gatcaagcta tgacccaaat
12301  gtataaacag gctagatctg aggacaagag ggcaaaagtt actagtgcta tgcagacaat
12361  gcttttcact atgcttagaa agttggataa tgatgcactc aacaacatta tcaacaatgc
12421  aagagatggt tgtgttccct tgaacataat acctcttaca acagcagcca aactaatggt
12481  tgtcatacca gactataaca catataaaaa tacgtgtgat ggtacaacat ttacttatgc
12541  atcagcattg tgggaaatcc aacaggttgt agatgcagat agtaaaattg ttcaacttag
12601  tgaaattagt atggacaatt cacctaattt agcatggcct cttattgtaa cagctttaag
12661  ggccaattct gctgtcaaat tacagaataa tgagcttagt cctgttcac tacgacagat
12721  gtcttgtgct gccggtacta cacaaactgc ttgcactgat gacaatgcgt tagcttacta
12781  caacacaaca aagggaggta ggtttgtact tgcactgtta tccgattac aggatttgaa
12841  atgggctaga ttccctaaga gtgatggaac tggtactatc tatacagaac tggaaccacc
12901  ttgtaggttt gttacagaca cacctaaagg tcctaaagtg aagtatttat actttattaa
12961  aggattaaac aacctaaata gaggtatggt acttggtagt ttagctgcca cagtacgtct
```

-continued

```
13021  acaagctggt aatgcaacag aagtgcctgc caattcaact gtattatctt tctgtgcttt
13081  tgctgtagat gctgctaaag cttacaaaga ttatctagct agtgggggac aaccaatcac
13141  taattgtgtt aagatgttgt gtacacacac tggtactggt caggcaataa cagttacacc
13201  ggaagccaat atggatcaag aatcctttgg tggtgcatcg tgttgtctgt actgccgttg
13261  ccacatagat catccaaatc ctaaaggatt tgtgacttaa aaggtaagt atgtacaaat
13321  acctcaaact tgtgctaatg accctgtggg ttttacactt aaaaacacag tctgtaccgt
13381  ctgcggtatg tggaaaggtt atggctgtag ttgtgatcaa ctccgcgaac ccatgcttca
13441  gtcagctgat gcacaatcgt ttttaaacgg gtttgcgtg taagtgcagc ccgtcttaca
13501  ccgtgcggca caggcactag tactgatgtc gtatacaggg cttttgacat ctacaatgat
13561  aaagtagctg gttttgctaa attcctaaaa actaattgtt gtcgcttcca agaaaaggac
13621  gaagatgaca atttaattga ttcttacttt gtagttaaga gacacacttt ctctaactac
13681  caacatgaag aaacaattta aatttacttt aaggattgtc cagctgttgc taaacatgac
13741  ttctttaagt ttagaataga cggtgacatg gtaccacata tatcacgtca acgtcttact
13801  aaatacacaa tggcagacct cgtctatgct ttaaggcatt ttgatgaagg taattgtgac
13861  acattaaaag aaatacttgt cacatacaat tgttgtgatg atgattattt caataaaaag
13921  gactggtatg attttgtaga aaacccagat atattacgcg tatacgccaa cttaggtgaa
13981  cgtgtacgcc aagctttgtt aaaaacagta caattctgtg atgccatgcg aaatgctggt
14041  attgttggtg tactgacatt agataatcaa gatctcaatg gtaactggta tgatttcggt
14101  gatttcatac aaaccacgcc aggtagtgga gttcctgttg tagattctta ttattcattg
14161  ttaatgccta tattaacctt gaccagggct ttaactgcag agtcacatgt tgacactgac
14221  ttaacaaagc cttacattaa gtgggatttg ttaaaatatg acttcacgga agagaggtta
14281  aaactctttg accgttattt taaatattgg gatcagacat accacccaaa ttgtgttaac
14341  tgtttggatg acagatgcat tctgcattgt gcaaacttta atgttttatt ctctacagtg
14401  ttcccaccta caagttttgg accactagtg agaaaaatat tgttgatgg tgttccattt
14461  gtagtttcaa ctggatacca cttcagagag ctaggtgttg tacataatca ggatgtaaac
14521  ttacatagct ctagacttag ttttaaggaa ttacttgtgt atgctgctga ccctgctatg
14581  cacgctgctt ctggtaatct attactagat aaacgcacta cgtgcttttc agtagctgca
14641  cttactaaca atgttgcttt tcaaactgtc aaacccggta attttaacaa agacttctat
14701  gactttgctg tgtctaaggg tttctttaag gaaggaagtt ctgttgaatt aaaacacttc
14761  ttctttgctc aggatggtaa tgctgctatc agcgattatg actactatcg ttataatcta
14821  ccaacaatgt gtgatatcag acaactacta tttgtagttg aagttgttga taagtacttt
14881  gattgttacg atggtggctg tattaatgct aaccaagtca tcgtcaacaa cctagacaaa
14941  tcagctggtt ttccatttaa taaatgggt aaggctagac tttattatga ttcaatgagt
15001  tatgaggatc aagatgcact tttcgcatat acaaaacgta atgtcatccc tactataact
15061  caaatgaatc ttaagtatgc cattagtgca aagaatagag ctcgcaccgt agctggtgtc
15121  tctatctgta gtactatgac caatagacag tttcatcaaa aattattgaa atcaatagcc
15181  gccactagag gagctactgt agtaattgga acaagcaaat ctatggtgg ttggcacaac
15241  atgttaaaaa ctgtttatag tgatgtagaa aaccctcacc ttatgggttg ggattatcct
15301  aaatgtgata gagccatgcc taacatgctt agaattatgg cctcacttgt tcttgctcgc
15361  aaacatacaa cgtgttgtag cttgtcacac cgtttctata gattagctaa tgagtgtgct
```

```
15421  caagtattga gtgaaatggt catgtgtggc ggttcactat atgttaaacc aggtggaacc
15481  tcatcaggag atgccacaac tgcttatgct aatagtgttt ttaacatttg tcaagctgtc
15541  acggccaatg ttaatgcact tttatctact gatggtaaca aaattgccga taagtatgtc
15601  cgcaatttac aacacagact ttatgagtgt ctctatagaa atagagatgt tgacacagac
15661  tttgtgaatg agttttacgc atatttgcgt aaacatttct caatgatgat actctctgac
15721  gatgctgttg tgtgtttcaa tagcacttat gcatctcaag gtctagtggc tagcataaag
15781  aactttaagt cagttcttta ttatcaaaac aatgttttta tgtctgaagc aaaatgttgg
15841  actgagactg accttactaa aggacctcat gaattttgct ctcaacatac aatgctagtt
15901  aaacagggtg atgattatgt gtaccttcct tacccagatc catcaagaat cctagggggcc
15961  ggctgttttg tagatgatat cgtaaaaaca gatggtacac ttatgattga acggttcgtg
16021  tctttagcta tagatgctta cccacttact aaacatccta atcaggagta tgctgatgtc
16081  tttcatttgt acttacaata cataagaaag ctacatgatg agttaacagg acacatgtta
16141  gacatgtatt ctgttatgct tactaatgat aacacttcaa ggtattggga acctgagttt
16201  tatgaggcta tgtacacacc gcatacagtc ttacaggctg ttggggcttg tgttctttgc
16261  aattcacaga cttcattaag atgtggtgct tgcatacgta gaccattctt atgttgtaaa
16321  tgctgttacg accatgtcat atcaacatca cataaattag tcttgtctgt taatccgtat
16381  gtttgcaatg ctccaggttg tgatgtcaca gatgtgactc aactttactt aggaggtatg
16441  agctattatt gtaaatcaca taaaccaccc attagttttc cattgtgtgc taatggacaa
16501  gttttttggtt tatataaaaa tacatgtgtt ggtagcgata atgttactga ctttaatgca
16561  attgcaacat gtgactggac aaatgctggt gattacattt tagctaacac ctgtactgaa
16621  agactcaagc tttttgcagc agaaacgctc aaagctactg aggagacatt taaactgtct
16681  tatggtattg ctactgtacg tgaagtgctg tctgacagag aattacatct ttcatgggaa
16741  gttggtaaac ctagaccacc acttaaccga aattatgtct ttactggtta tcgtgtaact
16801  aaaaacagta agtacaaat aggagagtac acctttgaaa aaggtgacta tggtgatgct
16861  gttgtttacc gaggtacaac aacttacaaa ttaaatgttg gtgattattt tgtgctgaca
16921  tcacatacag taatgccatt aagtgcacct acactagtgc cacaagagca ctatgttaga
16981  attactggct tataccccaac actcaatatc tcagatgagt tttctagcaa tgttgcaaat
17041  tatcaaaagg ttggtatgca aaagtattct acactccagg gaccacctgg tactggtaag
17101  agtcattttg ctattggcct agctctctac taccccttctg ctcgcatagt gtatacagct
17161  tgctctcatg ccgctgttga tgcactatgt gagaaggcat taaaatattt gcctatagat
17221  aaatgtagta gaattatacc tgcacgtgct cgtgtagagt gttttgataa attcaaagtg
17281  aattcaacat tagaacagta tgtcttttgt actgtaaatg cattgcctga tgacgacagca
17341  gatatagttg tctttgatga aatttcaatg gccacaaatt atgatttgag tgttgtcaat
17401  gccagattac gtgctaagca ctatgtgtac attggcgacc ctgctcaatt acctgcacca
17461  cgcacattgc taactaaggg cacactagaa ccagaatatt tcaattcagt gtgtagactt
17521  atgaaaacta taggtccaga catgttcctc ggaacttgtc ggcgttgtcc tgctgaaatt
17581  gttgacactg tgagtgcttt ggtttatgat aataagctta agcacataa agacaaatca
17641  gctcaatgct ttaaaatgtt ttataagggt gttatcacgc atgatgtttc atctgcaatt
17701  aacaggccac aaataggcgt ggtaagagaa ttccttacac gtaaccctgc ttggagaaaa
17761  gctgtcttta tttcacctta taattcacag aatgctgtag cctcaaagat tttgggacta
17821  ccaactcaaa ctgttgattc atcacagggc tcagaatatg actatgtcat attcactcaa
```

-continued

```
17881  accactgaaa cagctcactc ttgtaatgta aacagattta atgttgctat taccagagca
17941  aaagtaggca tactttgcat aatgtctgat agagaccttt atgacaagtt gcaatttaca
18001  agtcttgaaa ttccacgtag gaatgtggca actttacaag ctgaaaatgt aacaggactt
18061  tttaaagatt gtagtaaggt aatcactggg ttacatccta cacaggcacc tacacacctc
18121  agtgttgaca ctaaattcaa aactgaaggt ttatgtgttg acatacctgg catacctaag
18181  gacatgacct atagaagact catctctatg atgggtttta aaatgaatta tcaagttaat
18241  ggttacccta acatgtttat cacccgcgaa gaagctataa gacatgtacg tgcatggatt
18301  ggcttcgatg tcgagggggtg tcatgctact agagaagctg ttggtaccaa tttaccttta
18361  cagctaggtt tttctacagg tgttaaccta gttgctgtac ctacaggtta tgttgataca
18421  cctaataata cagatttttc cagagttagt gctaaaccac cgcctggaga tcaatttaaa
18481  cacctcatac cacttatgta caaaggactt ccttggaatg tagtgcgtat aaagattgta
18541  caaatgttaa gtgacacact taaaaatctc tctgacagag tcgtatttgt cttatgggca
18601  catggctttg agttgacatc tatgaagtat tttgtgaaaa taggacctga gcgcacctgt
18661  tgtctatgtg atagacgtgc cacatgcttt tccactgctt cagacactta tgcctgttgg
18721  catcattcta ttggatttga ttacgtctat aatccgttta tgattgatgt tcaacaatgg
18781  ggttttacag gtaacctaca aagcaaccat gatctgtatt gtcaagtcca tggtaatgca
18841  catgtagcta gttgtgatgc aatcatgact aggtgtctag ctgtccacga gtgctttgtt
18901  aagcgtgttg actggactat tgaatatcct ataattggtg atgaactgaa gattaatgcg
18961  gcttgtagaa aggttcaaca catggttgtt aaagctgcat tattagcaga caaattccca
19021  gttcttcacg acattggtaa ccctaaagct attaagtgtg tacctcaagc tgatgtagaa
19081  tggaagttct atgatgcaca gccttgtagt gacaaagctt ataaaataga agaattattc
19141  tattcttatg ccacacattc tgacaaattc acagatggtg tatgcctatt ttggaattgc
19201  aatgtcgata gatatcctgc taattccatt gtttgtagat ttgacactag agtgctatct
19261  aaccttaact tgcctggttg tgatggtggc agtttgtatg taaataaaca tgcattccac
19321  acaccagctt ttgataaaag tgcttttgtt aatttaaaac aattaccatt tttctattac
19381  tctgacagtc catgtgagtc tcatggaaaa caagtagtgt cagatataga ttatgtacca
19441  ctaaagtctg ctacgtgtat aacacgttgc aatttaggtg gtgctgtctg tagacatcat
19501  gctaatgagt acagattgta tctcgatgct tataacatga tgatctcagc tggctttagc
19561  ttgtgggttt acaaacaatt tgatacttat aacctctgga acactttttac aagacttcag
19621  agtttagaaa atgtggcttt taatgttgta aataagggac actttgatgg acaacagggt
19681  gaagtaccag tttctatcat taataacact gtttacacaa agttgatgg tgttgatgta
19741  gaattgtttg aaaataaaac aacattacct gttaatgtag catttgagct ttgggctaag
19801  cgcaacatta aaccagtacc agaggtgaaa atactcaata atttgggtgt ggacattgct
19861  gctaatactg tgatctggga ctacaaaaga gatgctccag cacatatatc tactattggt
19921  gtttgttcta tgactgacat agccaagaaa ccaactgaaa cgatttgtgc accactcact
19981  gtctttttg atggtagagt tgatggtcaa gtagacttat ttagaaatgc ccgtaatggt
20041  gttcttatta cagaaggtag tgttaaaggt ttacaaccat ctgtaggtcc caaacaagct
20101  agtcttaatg gagtcacatt aattggagaa gccgtaaaaa cacagttcaa ttattataag
20161  aaagttgatg gtgttgtcca acaattacct gaaacttact ttactcagag tagaaattta
20221  caagaattta aacccaggag tcaaatggaa attgatttct tagaattagc tatggatgaa
```

-continued

```
20281  ttcattgaac ggtataaatt agaaggctat gccttcgaac atatcgttta tggagatttt
20341  agtcatagtc agttaggtgg tttacatcta ctgattggac tagctaaacg ttttaaggaa
20401  tcaccttttg aattagaaga ttttattcct atggacagta cagttaaaaa ctatttcata
20461  acagatgcgc aaacaggttc atctaagtgt gtgtgttctg ttattgattt attacttgat
20521  gattttgttg aaataataaa atcccaagat ttatctgtag tttctaaggt tgtcaaagtg
20581  actattgact atacagaaat ttcatttatg ctttggtgta agatggcca tgtagaaaca
20641  ttttacccaa aattacaatc tagtcaagcg tggcaaccgg tgttgctat gcctaatctt
20701  tacaaaatgc aaagaatgct attagaaaag tgtgaccttc aaaattatgg tgatagtgca
20761  acattaccta aaggcataat gatgaatgtc gcaaaatata ctcaactgtg tcaatattta
20821  aacacattaa cattagctgt accctataat atgagagtta tacattttgg tgctggttct
20881  gataaaggag ttgcaccagg tacagctgtt ttaagacagt ggttgcctac gggtacgctg
20941  cttgtcgatt cagatcttaa tgactttgtc tctgatgcag attcaacttt gattggtgat
21001  tgtgcaactg tacatacagc taataaatgg gatctcatta ttagtgatat gtacgaccct
21061  aagactaaaa atgttacaaa agaaaatgac tctaaagagg gttttttcac ttacatttgt
21121  gggtttatac aacaaaagct agctcttgga ggttccgtgg ctataaagat aacagaacat
21181  tcttggaatg ctgatcttta taagctcatg ggacacttcg catggtggac agcctttgtt
21241  actaatgtga atgcgtcatc atctgaagca ttttttaattg gatgtaatta tcttggcaaa
21301  ccacgcgaac aaatagatgg ttatgtcatg catgcaaatt acatattttg gaggaataca
21361  aatccaattc agttgtcttc ctattcttta tttgacatga gtaaatttcc ccttaaatta
21421  aggggtactg ctgttatgtc tttaaaagaa ggtcaaatca atgatatgat tttatctctt
21481  cttagtaaag gtagacttat aattagagaa acaacagag ttgttattc tagtgatgtt
21541  cttgttaaca actaaacgaa caatgtttgt ttttcttgtt ttattgccac tagtctctag
21601  tcagtgtgtt aatcttacaa ccagaactca attccccct gcatacacta attctttcac
21661  acgtggtgtt tattaccctg acaaagtttt cagatcctca gttttacatt caactcagga
21721  cttgttctta ccttctttt ccaatgttac ttggttccat gctatacatg tctctgggac
21781  caatggtact aagaggtttg ataaccctgt cctaccattt aatgatggtg tttattttgc
21841  ttccactgag aagtctaaca taataagagg ctggatttt ggtactactt tagattcgaa
21901  gacccagtcc ctacttattg ttaataacgc tactaatgtt gttattaaag tctgtgaatt
21961  tcaattttgt aatgatccat ttttgggtgt ttattaccac aaaaacaaca aaagttggat
22021  ggaaagtgag ttcagagttt attctagtgc gaataattgc acttttgaat atgtctctca
22081  gccttttctt atggaccttg aaggaaaaca gggtaatttc aaaaatctta gggaatttgt
22141  gtttaagaat attgatggtt atttaaaat atattctaag cacacgccta ttaatttagt
22201  gcgtgatctc cctcagggtt tttcggcttt agaaccattg gtagatttgc caataggtat
22261  taacatcact aggtttcaaa ctttacttgc tttacataga agttattga ctcctggtga
22321  ttcttcttca ggttggacag ctggtgctgc agcttattat gtgggttatc ttcaacctag
22381  gacttttcta ttaaaatata atgaaaatgg aaccattaca gatgctgtag actgtgcact
22441  tgacccctctc tcagaaacaa agtgtacgtt gaaatccttc actgtagaaa aaggaatcta
22501  tcaaacttct aacttagag tccaaccaac agaatctatt gttagatttc ctaatattac
22561  aaacttgtgc ccttttggtg aagtttttaa cgccaccaga tttgcatctg tttatgcttg
22621  gaacaggaag agaatcagca actgtgttgc tgattattct gtcctatata attccgcatc
22681  attttccact tttaagtgtt atggagtgtc tcctactaaa ttaaatgatc tctgctttac
```

-continued

```
22741   taatgtctat gcagattcat ttgtaattag aggtgatgaa gtcagacaaa tcgctccagg
22801   gcaaactgga aagattgctg attataatta taaattacca gatgatttta caggctgcgt
22861   tatagcttgg aattctaaca atcttgattc taaggttggt ggtaattata attacctgta
22921   tagattgttt aggaagtcta atctcaaacc ttttgagaga gatatttcaa ctgaaatcta
22981   tcaggccggt agcacacctt gtaatggtgt tgaaggtttt aattgttact tcctttaca
23041   atcatatggt ttccaaccca ctaatggtgt tggttaccaa ccatacagag tagtagtact
23101   ttcttttgaa cttctacatg caccagcaac tgtttgtgga cctaaaagt ctactaattt
23161   ggttaaaaac aaatgtgtca atttcaactt caatggttta acaggcacag gtgttcttac
23221   tgagtctaac aaaaagtttc tgcctttcca acaatttggc agagacattg ctgacactac
23281   tgatgctgtc cgtgatccac agacacttga gattcttgac attacaccat gttcttttgg
23341   tggtgtcagt gttataacac caggaacaaa tacttctaac caggttgctg ttctttatca
23401   ggatgttaac tgcacagaag tccctgttgc tattcatgca gatcaactta ctcctacttg
23461   gcgtgtttat tctacaggtt ctaatgtttt tcaaacacgt gcaggctgtt aataggggc
23521   tgaacatgtc aacaactcat atgagtgtga catacccatt ggtgcaggta tatgcgctag
23581   ttatcagact cagactaatt ctcctcggcg ggcacgtagt gtagctagtc aatccatcat
23641   tgcctacact atgtcacttg gtgcagaaaa ttcagttgct tactctaata actctattgc
23701   catacccaca aatttactta ttagtgttac cacagaaatt ctaccagtgt ctatgaccaa
23761   gacatcagta gattgtacaa tgtacatttg tggtgattca actgaatgca gcaatctttt
23821   gttgcaatat ggcagttttt gtacacaatt aaaccgtgct ttaactggaa tagctgttga
23881   acaagacaaa aacacccaag aagttttttgc acaagtcaaa caaatttaca aaacaccacc
23941   aattaaagat tttggtggtt ttaattttct acaaatatta ccagatccat caaaaccaag
24001   caagaggtca tttattgaag atctactttt caacaaagtg acacttgcag atgctggctt
24061   catcaaacaa tatggtgatt gccttggtga tattgctgct agagacctca tttgtgcaca
24121   aaagtttaac ggccttactg ttttgccacc tttgctcaca gatgaaatga ttgctcaata
24181   cacttctgca ctgttagcgg gtacaatcac ttctggttgg accttttggtg caggtgctgc
24241   attacaaata ccatttgcta tgcaaatggc ttataggttt aatggtattg gagttacaca
24301   gaatgttctc tatgagaacc aaaaattgat tgccaaccaa tttaatagtg ctattggcaa
24361   aattcaagac tcactttctt ccacagcaag tgcacttgga aaacttcaag atgtggtcaa
24421   ccaaaatgca caagctttaa acacgcttgt taaacaactt agctccaatt ttggtgcaat
24481   ttcaagtgtt ttaaatgata tcctttcacg tcttgacaaa gttgaggctg aagtgcaaat
24541   tgataggttg atcacaggca gacttcaaag tttgcagaca tatgtgactc aacaattaat
24601   tagagctgca gaaatcagag cttctgctaa tcttgctgct actaaaatgt cagagtgtgt
24661   acttggacaa tcaaaaagag ttgattttttg tggaaagggc tatcatctta tgtccttccc
24721   tcagtcagca cctcatggtg tagtcttctt gcatgtgact tatgtccctg cacaagaaaa
24781   gaacttcaca actgctcctg ccatttgtca tgatggaaaa gcacactttc tcgtgaagg
24841   tgtctttgtt tcaaatggca cacactggtt tgtaacacaa aggaattttt atgaaccaca
24901   aatcattact acagacaaca catttgtgtc tggtaactgt gatgttgtaa taggaattgt
24961   caacaacaca gtttatgatc ctttgcaacc tgaattagac tcattcaagg aggagttaga
25021   taaatatttt aagaatcata catcaccaga tgttgattta ggtgacatct ctggcattaa
25081   tgcttcagtt gtaaacattc aaaaagaaat tgaccgcctc aatgaggttg ccaagaattt
```

```
25141  aaatgaatct ctcatcgatc tccaagaact tggaaagtat gagcagtata taaaatggcc
25201  atggtacatt tggctaggtt ttatagctgg cttgattgcc atagtaatgg tgacaattat
25261  gctttgctgt atgaccagtt gctgtagttg tctcaagggc tgttgttctt gtggatcctg
25321  ctgcaaattt gatgaagacg actctgagcc agtgctcaaa ggagtcaaat tacattacac
25381  ataaacgaac ttatggattt gtttatgaga atcttcacaa ttggaactgt aactttgaag
25441  caaggtgaaa tcaaggatgc tactccttca gattttgttc gcgctactgc aacgataccg
25501  atacaagcct cactcccttt cggatggctt attgttggcg ttgcacttct tgctgttttt
25561  cagagcgctt ccaaaatcat aaccctcaaa aagagatggc aactagcact ctccaagggt
25621  gttcactttg tttgcaactt gctgttgttg tttgtaacag tttactcaca ccttttgctc
25681  gttgctgctg gccttgaagc cccttttctc tatctttatg ctttagtcta cttcttgcag
25741  agtataaact tgtaagaat aataatgagg ctttggcttt gctggaaatg ccgttccaaa
25801  aacccattac tttatgatgc caactatttt ctttgctggc atactaattg ttacgactat
25861  tgtataccttt acaatagtgt aacttcttca attgtcatta cttcaggtga tggcacaaca
25921  agtcctattt ctgaacatga ctaccagatt ggtggttata ctgaaaaatg ggaatctgga
25981  gtaaaagact gtgttgtatt acacagttac ttcacttcag actattacca gctgtactca
26041  actcaattga gtacagacac tggtgttgaa catgttacct tcttcatcta caataaaatt
26101  gttgatgagc ctgaagaaca tgtccaaatt cacacaatcg acggttcatc cggagttgtt
26161  aatccagtaa tggaaccaat ttatgatgaa ccgacgacga ctactagcgt gcctttgtaa
26221  gcacaagctg atgagtacga acttatgtac tcattcgttt cggaagagac aggtacgtta
26281  atagttaata gcgtacttct ttttcttgct ttcgtggtat tcttgctagt tacactagcc
26341  atccttactg cgcttcgatt gtgtgcgtac tgctgcaata ttgttaacgt gagtcttgta
26401  aaaccttctt tttacgttta ctctcgtgtt aaaaatctga attcttctag agttcctgat
26461  cttctggtct aaacgaacta aatattatat tagtttttct gtttggaact ttaattttag
26521  ccatggcaga ttccaacggt actattaccg ttgaagagct aaaaagctc cttgaacaat
26581  ggaacctagt aataggtttc ctattcctta catggatttg tcttctacaa tttgcctatg
26641  ccaacaggaa taggttttg tatataatta agttaatttt cctctggctg ttatggccag
26701  taactttagc ttgttttgtg cttgctgctg tttacagaat aaattggatc accggtggaa
26761  ttgctatcgc aatggcttgt cttgtaggct tgatgtggct cagctacttc attgcttctt
26821  tcagactgtt tgcgcgtacg cgttccatgt ggtcattcaa tccagaaact aacattcttc
26881  tcaacgtgcc actccatggc actattctga ccagaccgct tctagaaagt gaactcgtaa
26941  tcggagctgt gatccttcgt ggacatcttc gtattgctgg acaccatcta ggacgctgtg
27001  acatcaagga cctgcctaaa gaaatcactg ttgctacatc acgaacgctt tcttattaca
27061  aattgggagc ttcgcagcgt gtagcaggtg actcaggttt tgctgcatac agtcgctaca
27121  ggattggcaa ctataaatta aacacagacc attccagtag cagtgacaat attgctttgc
27181  ttgtacagta agtgacaaca gatgtttcat ctcgttgact ttcaggttac tatagcagag
27241  atattactaa ttattatgag gactttttaaa gtttccattt ggaatcttga ttacatcata
27301  aacctcataa ttaaaaattt atctaagtca ctaactgaga ataaatattc tcaattagat
27361  gaagagcaac caatggagat tgattaaacg aacatgaaaa ttattctttt cttggcactg
27421  ataacactcg ctacttgtga gctttatcac taccaagagt gtgttagagg tacaacagta
27481  cttttaaaag aaccttgctc ttctggaaca tacgagggca attccaccatt tcatcctcta
27541  gctgataaca aatttgcact gacttgcttt agcactcaat tgcttttgc ttgtcctgac
```

-continued

```
27601  ggcgtaaaac acgtctatca gttacgtgcc agatcagttt cacctaaact gttcatcaga
27661  caagaggaag ttcaagaact ttactctcca atttttctta ttgttgcggc aatagtgttt
27721  ataacacttt gcttcacact caaaagaaag acagaatgat tgaactttca ttaattgact
27781  tctatttgtg cttttttagcc tttctgctat tccttgtttt aattatgctt attatctttt
27841  ggttctcact tgaactgcaa gatcataatg aaacttgtca cgcctaaacg aacatgaaat
27901  ttcttgtttt cttaggaatc atcacaactg tagctgcatt tcaccaagaa tgtagtttac
27961  agtcatgtac tcaacatcaa ccatatgtag ttgatgaccc gtgtcctatt cacttctatt
28021  ctaaatggta tattagagta ggagctagaa aatcagcacc tttaattgaa ttgtgcgtgg
28081  atgaggctgg ttctaaatca cccattcagt acatcgatat cggtaattat acagtttcct
28141  gttcaccttt tacaattaat tgccaggaac ctaaattggg tagtcttgta gtgcgttgtt
28201  cgttctatga agacttttta gagtatcatg acgttcgtgt tgtttagat ttcatctaaa
28261  cgaacaaact aaaatgtctg ataatggacc ccaaaatcag cgaaatgcac cccgcattac
28321  gtttggtgga ccctcagatt caactggcag taaccagaat ggagaacgca gtggggcgcg
28381  atcaaaacaa cgtcggcccc aaggtttacc caataatact gcgtcttggt tcaccgctct
28441  cactcaacat ggcaaggaag accttaaatt ccctcgagga caaggcgttc caattaacac
28501  caatagcagt ccagatgacc aaattggcta ctaccgaaga gctaccagac gaattcgtgg
28561  tggtgacggt aaaatgaaag atctcagtcc aagatggtat ttctactacc taggaactgg
28621  gccagaagct ggacttccct atggtgctaa caaagacggc atcatatggg ttgcaactga
28681  gggagccttg aatacaccaa aagatcacat tggcacccgc aatcctgcta caatgctgc
28741  aatcgtgcta caacttcctc aaggaacaac attgccaaaa ggcttctacg cagaagggag
28801  cagaggcggc agtcaagcct cttctcgttc ctcatcacgt agtcgcaaca gttcaagaaa
28861  ttcaactcca ggcagcagta ggggaacttc tcctgctaga atggctggca atggcggtga
28921  tgctgctctt gctttgctgc tgcttgacag attgaaccag cttgagagca aaatgtctgg
28981  taaaggccaa caacaacaag gccaaactgt cactaagaaa tctgctgctg aggcttctaa
29041  gaagcctcgg caaaaacgta ctgccactaa agcatacaat gtaacacaag ctttcggcag
29101  acgtggtcca gaacaaaccc aaggaaattt tggggaccag gaactaatca gacaaggaac
29161  tgattacaaa cattggccgc aaattgcaca atttgccccc agcgcttcag cgttcttcgg
29221  aatgtcgcgc attggcatgg aagtcacacc ttcgggaacg tggttgacct acacaggtgc
29281  catcaaattg gatgacaaag atccaaattt caaagatcaa gtcattttgc tgaataagca
29341  tattgacgca tacaaaacat tcccaccaac agagcctaaa aaggacaaaa agaagaaggc
29401  tgatgaaact caagccttac cgcagagaca gaagaaacag caaactgtga ctcttcttcc
29461  tgctgcagat ttggatgatt tctccaaaca attgcaacaa tccatgagca gtgctgactc
29521  aactcaggcc taaactcatg cagaccacac aaggcagatg ggctatataa acgttttcgc
29581  ttttccgttt acgatatata gtctactctt gtgcagaatg aattctcgta actacatagc
29641  acaagtagat gtagttaact ttaatctcac atagcaatct ttaatcagtg tgtaacatta
29701  gggaggactt gaaagagcca ccacattttc accgaggcca cgcggagtac gatcgagtgt
29761  acagtgaaca atgctaggga gagctgccta tatggaagag ccctaatgtg taaaattaat
29821  tttagtagtg ctatccccat gtgatttta tagcttctta ggagaatgac aaaaaaaaaa
29881  aa.
```

GenBank Accession No. GenBank: AY274119.3, which is specifically incorporated by reference herein in its entirety, provides the following (DNA) genomic sequence for SARS-CoV (Severe acute respiratory syndrome-related coronavirus isolate Tor2, complete genome):

(SEQ ID NO: 3)

```
   1 atattaggtt tttacctacc caggaaaagc caaccaacct cgatctcttg tagatctgtt
  61 ctctaaacga actttaaaat ctgtgtagct gtcgctcggc tgcatgccta gtgcacctac
 121 gcagtataaa caataataaa ttttactgtc gttgacaaga acgagtaac tcgtccctct
 181 tctgcagact gcttacggtt tcgtccgtgt tgcagtcgat catcagcata cctaggtttc
 241 gtccgggtgt gaccgaaagg taagatggag agccttgttc ttggtgtcaa cgagaaaaca
 301 cacgtccaac tcagtttgcc tgtccttcag gttagagacg tgctagtgcg tggcttcggg
 361 gactctgtgg aagaggccct atcggaggca cgtgaacacc tcaaaaatgg cacttgtggt
 421 ctagtagagc tggaaaaagg cgtactgccc cagcttgaac agccctatgt gttcattaaa
 481 cgttctgatg ccttaagcac caatcacggc cacaaggtcg ttgagctggt tgcagaaatg
 541 gacggcattc agtacggtcg tagcggtata acactgggag tactcgtgcc acatgtgggc
 601 gaaaccccaa ttgcataccg caatgttctt cttcgtaaga acggtaataa gggagccggt
 661 ggtcatagct atggcatcga tctaaagtct tatgacttag gtgacgagct tggcactgat
 721 cccattgaag attatgaaca aaactggaac actaagcatg gcagtggtgc actccgtgaa
 781 ctcactcgtg agctcaatgg aggtgcagtc actcgctatg tcgacaacaa tttctgtggc
 841 ccagatgggt accctcttga ttgcatcaaa gattttctcg cacgcgcggg caagtcaatg
 901 tgcactcttt ccgaacaact tgattacatc gagtcgaaga gaggtgtcta ctgctgccgt
 961 gaccatgagc atgaaattgc ctggttcact gagcgctctg ataagagcta cgagcaccag
1021 acaccctctcg aaattaagag tgccaagaaa tttgacactt caaagggga atgcccaaag
1081 tttgtgtttc ctcttaactc aaaagtcaaa gtcattcaac cacgtgttga aagaaaaag
1141 actgagggtt tcatggggcg tatacgctct gtgtaccctg ttgcatctcc acaggagtgt
1201 aacaatatgc acttgtctac cttgatgaaa tgtaatcatt gcgatgaagt ttcatggcag
1261 acgtgcgact ttctgaaagc cacttgtgaa cattgtggca ctgaaaattt agttattgaa
1321 ggacctacta catgtgggta cctacctact aatgctgtag tgaaaatgcc atgtcctgcc
1381 tgtcaagacc cagagattgg acctgagcat agtgttgcag attatcacaa ccactcaaac
1441 attgaaactc gactccgcaa gggaggtagg actagatgtt tggaggctg tgtgtttgcc
1501 tatgttggct gctataataa gcgtgcctac tgggttcctc gtgctagtgc tgatattggc
1561 tcaggccata ctggcattac tggtgacaat gtggagacct gaatgagga tctccttgag
1621 atactgagtc gtgaacgtgt taacattaac attgttggcg attttcattt gaatgaagag
1681 gttgccatca ttttggcatc tttctctgct tctacaagtg cctttattga cactataaag
1741 agtcttgatt acaagtcttt caaaaccatt gttgagtcct gcggtaacta taagttacc
1801 aagggaaagc ccgtaaaagg tgcttggaac attggacaac agagatcagt tttaacacca
1861 ctgtgtggtt ttccctcaca ggctgctggt gttatcagat caatttttgc gcgcacactt
1921 gatgcagcaa accactcaat tcctgatttg caaagagcag ctgtcaccat acttgatggt
1981 atttctgaac agtcattacg tcttgtcgac gccatggttt atacttcaga cctgctcacc
2041 aacagtgtca ttattatggc atatgtaact ggtggtcttg tacaacagac ttctcagtgg
2101 ttgtctaatc ttttgggcac tactgttgaa aaactcaggc ctatctttga atggattgag
2161 gcgaaactta gtgcaggagt tgaatttctc aaggatgctt gggagattct caaatttctc
```

-continued

```
2221  attacaggtg ttttttgacat cgtcaagggt caaatacagg ttgcttcaga taacatcaag 2281  gattgtgtaa aatgcttcat tgatgttgtt aacaaggcac tcgaaatgtg cattgatcaa 2341  gtcactatcg ctggcgcaaa gttgcgatca ctcaacttag gtgaagtctt catcgctcaa 2401  agcaagggac tttaccgtca gtgtatacgt ggcaaggagc agctgcaact actcatgcct 2461  cttaaggcac caaaagaagt aacctttctt gaaggtgatt cacatgacac agtacttacc 2521  tctgaggagg ttgttctcaa gaacggtgaa ctcgaagcac tcgagacgcc cgttgatagc 2581  ttcacaaatg gagctatcgt tggcacacca gtctgtgtaa atggcctcat gctcttagag 2641  attaaggaca aagaacaata ctgcgcattg tctcctggtt tactggctac aaacaatgtc 2701  tttcgcttaa aaggggggtgc accaattaaa ggtgtaacct ttggagaaga tactgtttgg 2761  gaagttcaag gttacaagaa tgtgagaatc acatttgagc ttgatgaacg tgttgacaaa 2821  gtgcttaatg aaaagtgctc tgtctacact gttgaatccg gtaccgaagt tactgagttt 2881  gcatgtgttg tagcagaggc tgttgtgaag actttacaac cagtttctga tctccttacc 2941  aacatgggta ttgatcttga tgagtggagt gtagctacat tctacttatt tgatgatgct 3001  ggtgaagaaa acttttcatc acgtatgtat tgttccttttt accctccaga tgaggaagaa 3061  gaggacgatg cagagtgtga ggaagaagaa attgatgaaa cctgtgaaca tgagtacggt 3121  acagaggatg attatcaagg tctccctctg gaatttggtg cctcagctga aacagttcga 3181  gttgaggaag aagaagagga agactggctg gatgatacta ctgagcaatc agagattgag 3241  ccagaaccag aacctcacacc tgaagaacca gttaatcagt ttactggtta tttaaaactt 3301  actgacaatg ttgccattaa atgtgttgac atcgttaagg aggcacaaag tgctaatcct 3361  atggtgattg taaatgctgc taacatacac ctgaaacatg gtggtggtgt agcaggtgca 3421  ctcaacaagg caaccaatgg tgccatgcaa aaggagagtg atgattacat taagctaaat 3481  ggccctctta cagtaggagg gtcttgtttg ctttctggac ataatcttgc taagaagtgt 3541  ctgcatgttg ttggacctaa cctaaatgca ggtgaggaca tccagcttct taaggcagca 3601  tatgaaaatt tcaattcaca ggacatctta cttgcaccat tgttgtcagc aggcatattt 3661  ggtgctaaac cacttcagtc tttacaagtg tgcgtgcaga cggttcgtac acaggtttat 3721  attgcagtca atgacaaagc tctttatgag caggttgtca tggattatct tgataacctg 3781  aagcctagag tggaagcacc taaacaagag gagccaccaa acacagaaga ttccaaaact 3841  gaggagaaat ctgtcgtaca gaagcctgtc gatgtgaagc aaaaattaa ggcctgcatt 3901  gatgaggtta ccacaacact ggaagaaact aagtttctta ccaataagtt actcttgttt 3961  gctgatatca atggtaagct ttaccatgat ctcagaaca tgcttagagg tgaagatatg 4021  tctttccttg agaaggatgc accttacatg gtaggtgatg ttatcactag tggtgatatc 4081  acttgtgttg taatacccctc caaaaaggct ggtggcacta ctgagatgct ctcaagagct 4141  ttgaagaaag tgccagttga tgagtatata accacgtacc ctggacaagg atgtgctggt 4201  tatacacttg aggaagctaa gactgctctt aagaaatgca atctgcatt ttatgtacta 4261  ccttcagaag cacctaatgc taaggaagag attctaggaa ctgtatcctg gaatttgaga 4321  gaaatgcttg ctcatgctga agagacaaga aaattaatgc ctatatgcat ggatgttaga 4381  gccataatgg caaccatcca acgtaagtat aaaggaatta aaattcaaga gggcatcgtt 4441  gactatggtg tccgattctt cttttatact agtaaagagc ctgtagcttc tattattacg 4501  aagctgaact ctctaaatga gccgcttgtc acaatgccaa ttggttatgt gacacatggt 4561  tttaatcttg aagaggctgc gcgctgtatg cgttctctta agctcctgc cgtagtgtca
```

-continued

```
4621 gtatcatcac cagatgctgt tactacatat aatggatacc tcacttcgtc atcaaagaca
4681 tctgaggagc actttgtaga aacagtttct ttggctggct cttacagaga ttggtcctat
4741 tcaggacagc gtacagagtt aggtgttgaa tttcttaagc gtggtgacaa aattgtgtac
4801 cacactctgg agagcccgt cgagtttcat cttgacggtg aggttctttc acttgacaaa
4861 ctaaagagtc tcttatccct gcgggaggtt aagactataa aagtgttcac aactgtggac
4921 aacactaatc tccacacaca gcttgtggat atgtctatga catatggaca gcagtttggt
4981 ccaacatact tggatggtgc tgatgttaca aaaattaaac ctcatgtaaa tcatgagggt
5041 aagactttct ttgtactacc tagtgatgac acactacgta gtgaagcttt cgagtactac
5101 catactcttg atgagagttt tcttggtagg tacatgtctg ctttaaacca cacaaagaaa
5161 tggaaatttc ctcaagttgg tggtttaact tcaattaaat gggctgataa caattgttat
5221 ttgtctagtg ttttattagc acttcaacag cttgaagtca aattcaatgc accagcactt
5281 caagaggctt attatagagc ccgtgctggt gatgctgcta acttttgtgc actcatactc
5341 gcttacagta ataaaactgt tggcgagctt ggtgatgtca gagaaactat gacccatctt
5401 ctacagcatg ctaatttgga atctgcaaag cgagttctta atgtggtgtg taaacattgt
5461 ggtcagaaaa ctactacctt aacgggtgta gaagctgtga tgtatatggg tactctatct
5521 tatgataatc ttaagacagg tgtttccatt ccatgtgtgt gtggtcgtga tgctacacaa
5581 tatctagtac aacaagagtc ttcttttgtt atgatgtctg caccacctgc tgagtataaa
5641 ttacagcaag gtacattctt atgtgcgaat gagtacactg gtaactatca gtgtggtcat
5701 tacactcata taactgctaa ggagaccctc tatcgtattg acggagctca ccttacaaag
5761 atgtcagagt acaaaggacc agtgactgat gttttctaca aggaaacatc ttacactaca
5821 accatcaagc ctgtgtcgta taaactcgat ggagttactt acacagagat tgaaccaaaa
5881 ttggatgggt attataaaaa ggataatgct tactatacag agcagcctat agaccttgta
5941 ccaactcaac cattaccaaa tgcgagtttt gataatttca aactcacatg ttctaacaca
6001 aaatttgctg atgatttaaa tcaaatgaca ggcttcacaa agccagcttc acgagagcta
6061 tctgtcacat tcttcccaga cttgaatggc gatgtagtgg ctattgacta tagacactat
6121 tcagcgagtt tcaagaaagg tgctaaatta ctgcataagc caattgtttg gcacattaac
6181 caggctacaa ccaagacaac gttcaaacca aacacttggt gtttacgttg tctttggagt
6241 acaaagccag tagatacttc aaaattcattt gaagttctgg cagtagaaga cacacaagga
6301 atggacaatc ttgcttgtga aagtcaacaa cccacctctg aagaagtagt ggaaaatcct
6361 accatacaga aggaagtcat agagtgtgac gtgaaaacta ccgaagttgt aggcaatgtc
6421 atacttaaac catcagatga aggtgttaaa gtaacacaag agttaggtca tgaggatctt
6481 atggctgctt atgtggaaaa cacaagcatt accattaaga acctaatga gctttcacta
6541 gccttaggtt aaaaacaat tgccactcat ggtattgctg caattaatag tgttccttgg
6601 agtaaaattt tggcttatgt caaaccattc ttaggacaag cagcaattac aacatcaaat
6661 tgcgctaaga gattagcaca acgtgtgttt aacaattata tgccttatgt gtttacatta
6721 ttgttccaat tgtgtacttt tactaaaagt accaattcta gaattagagc ttcactacct
6781 acaactattg ctaaaaatag tgttaagagt gttgctaaat tatgtttgga tgccggcatt
6841 aattatgtga agtcacccaa attttctaaa ttgttcacaa tcgctatgtg ctattgttg
6901 ttaagtattt gcttaggttc tctaatctgt gtaactgctg cttttggtgt actcttatct
6961 aattttgtg ctccttctta ttgtaatggc gttagagaat tgtatcttaa ttcgtctaac
7021 gttactacta tggatttctg tgaaggttct tttcccttgca gcatttgttt aagtggatta
```

-continued

```
7081  gactcccttg attcttatcc agctcttgaa accattcagg tgacgatttc atcgtacaag
7141  ctagacttga caattttagg tctggccgct gagtgggttt tggcatatat gttgttcaca
7201  aaattctttt atttattagg tctttcagct ataatgcagg tgttctttgg ctattttgct
7261  agtcatttca tcagcaattc ttggctcatg tggtttatca ttagtattgt acaaatggca
7321  cccgtttctg caatggttag gatgtacatc ttctttgctt ctttctacta catatggaag
7381  agctatgttc atatcatgga tggttgcacc tcttcgactt gcatgatgtg ctataagcgc
7441  aatcgtgcca cacgcgttga gtgtacaact attgttaatg gcatgaagag atctttctat
7501  gtctatgcaa atggaggccg tggcttctgc aagactcaca attggaattg tctcaattgt
7561  gacacatttt gcactggtag tacattcatt agtgatgaag ttgctcgtga tttgtcactc
7621  cagtttaaaa gaccaatcaa ccctactgac cagtcatcgt atattgttga tagtgttgct
7681  gtgaaaaatg gcgcgcttca cctctacttt gacaaggctg tcaaaagac ctatgagaga
7741  catccgctct cccattttgt caatttagac aatttgagag ctaacaacac taaaggttca
7801  ctgcctatta atgtcatagt ttttgatggc aagtccaaat gcgacgagtc tgcttctaag
7861  tctgcttctg tgtactacag tcagctgatg tgccaaccta ttctgttgct tgaccaagct
7921  cttgtatcag acgttggaga tagtactgaa gtttccgtta agatgtttga tgcttatgtc
7981  gacaccttt cagcaacttt tagtgttcct atggaaaaac ttaaggcact tgttgctaca
8041  gctcacagcg agttagcaaa gggtgtagct ttagatggtg tcctttctac attcgtgtca
8101  gctgcccgac aaggtgttgt tgataccgat gttgacacaa aggatgttat tgaatgtctc
8161  aaactttcac atcactctga cttagaagtg acaggtgaca gttgtaacaa tttcatgctc
8221  acctataata aggttgaaaa catgacgccc agagatcttg gcgcatgtat tgactgtaat
8281  gcaaggcata tcaatgccca agtagcaaaa agtcacaatg tttcactcat ctggaatgta
8341  aaagactaca tgtctttatc tgaacagctg cgtaaacaaa ttcgtagtgc tgccaagaag
8401  aacaacatac cttttagact aacttgtgct acaactagac aggttgtcaa tgtcataact
8461  actaaaatct cactcaaggg tggtaagatt gttagtactt gttttaaact tatgcttaag
8521  gccacattat tgtgcgttct tgctgcattg gtttgttata tcgttatgcc agtacataca
8581  ttgtcaatcc atgatggtta cacaaatgaa atcattggtt acaaagccat tcaggatggt
8641  gtcactcgtg acatcatttc tactgatgat tgttttgcaa ataaacatgc tggttttgac
8701  gcatggttta gccagcgtgg tggttcatac aaaaatgaca aaagctgccc tgtagtagct
8761  gctatcatta caagagagat tggtttcata gtgcctggct taccgggtac tgtgctgaga
8821  gcaatcaatg gtgacttctt gcattttcta cctcgtgttt ttagtgctgt tggcaacatt
8881  tgctacacac cttccaaact cattgagtat agtgattttg ctacctctgc ttgcgttctt
8941  gctgctgagt gtacaatttt taaggatgct atgggcaaac ctgtgccata ttgttatgac
9001  actaatttgc tagagggttc tatttcttat agtgagcttc gtccagacac tcgttatgtg
9061  cttatggatg gttccatcat acagtttcct aacacttacc tggagggttc tgttagagta
9121  gtaacaactt ttgatgctga gtactgtaga catggtacat gcgaaaggtc agaagtaggt
9181  atttgcctat ctaccagtgg tagatgggtt cttaataatg agcattacag agctctatca
9241  ggagttttct gtggtgttga tgcgatgaat ctcatagcta acatctttac tcctcttgtg
9301  caacctgtgg gtgctttaga tgtgtctgct tcagtagtgg ctggtggtat tattgccata
9361  ttggtgactt gtgctgccta ctactttatg aaattcgac gtgttttttgg tgagtacaac
9421  catgttgttg ctgctaatgc acttttgttt ttgatgtctt tcactatact ctgtctggta
```

-continued

```
 9481 ccagcttaca gctttctgcc gggagtctac tcagtctttt acttgtactt gacattctat
 9541 ttcaccaatg atgtttcatt cttggctcac cttcaatggt ttgccatgtt ttctcctatt
 9601 gtgccttttt ggataacagc aatctatgta ttctgtattt ctctgaagca ctgccattgg
 9661 ttctttaaca actatcttag gaaaagagtc atgtttaatg gagttacatt tagtaccttc
 9721 gaggaggctg ctttgtgtac cttttgtgctc aacaaggaaa tgtacctaaa attgcgtagc
 9781 gagacactgt tgccacttac acagtataac aggtatcttg ctctatataa caagtacaag
 9841 tatttcagtg gagccttaga tactaccagc tatcgtgaag cagcttgctg ccacttagca
 9901 aaggctctaa atgactttag caactcaggt gctgatgttc tctaccaacc accacagaca
 9961 tcaatcactt ctgctgttct gcagagtggt tttaggaaaa tggcattccc gtcaggcaaa
10021 gttgaagggt gcatggtaca agtaacctgt ggaactacaa ctcttaatgg attgtggttg
10081 gatgacacag tatactgtcc aagacatgtc atttgcacag cagaagacat gcttaatcct
10141 aactatgaag atctgctcat tcgcaaatcc aaccatagct ttcttgttca ggctggcaat
10201 gttcaacttc gtgttattgg ccattctatg caaaattgtc tgcttaggct taaagttgat
10261 acttctaacc ctaagacacc caagtataaa tttgtccgta tccaacctgg tcaaacattt
10321 tcagttctag catgctacaa tggttcacca tctggtgttt atcagtgtgc catgagacct
10381 aatcatacca ttaaaggttc tttccttaat ggatcatgtg gtagtgttgg ttttaacatt
10441 gattatgatt gcgtgtcttt ctgctatatg catcatatgg agcttccaac aggagtacac
10501 gctggtactg acttagaagg taaattctat ggtccatttg ttgacagaca aactgcacag
10561 gctgcaggta cagacacaac cataacatta aatgttttgg catggctgta tgctgctgtt
10621 atcaatggtg ataggtggtt tcttaataga ttcaccacta ctttgaatga ctttaacctt
10681 gtggcaatga agtacaacta tgaacctttg acacaagatc atgttgacat attgggacct
10741 ctttctgctc aaacaggaat tgccgtctta gatatgtgtg ctgctttgaa agagctgctg
10801 cagaatggta tgaatggtcg tactatcctt ggtagcacta ttttagaaga tgagtttaca
10861 ccatttgatg ttgttagaca atgctctggt gttaccttcc aaggtaagtt caagaaaatt
10921 gttaagggca ctcatcattg gatgctttta actttcttga catcactatt gattcttgtt
10981 caaagtacac agtggtcact gtttttcttt gtttacgaga atgctttctt gccatttact
11041 cttggtatta tggcaattgc tgcatgtgct atgctgcttg ttaagcataa gcacgcattc
11101 ttgtgcttgt ttctgttacc tttctcttgca acagttgctt acttaaatat ggtctacatg
11161 cctgctagct gggtgatgcg tatcatgaca tggcttgaat tggctgacac tagcttgtct
11221 ggttataggc ttaaggattg tgttatgtat gcttcagctt tagttttgct tattctcatg
11281 acagctcgca ctgtttatga tgatgctgct agacgtgttt ggacactgat gaatgtcatt
11341 acacttgttt acaaagtcta ctatggtaat gctttagatc aagctatttc catgtgggcc
11401 ttagttattt ctgtaacctc taactattct ggtgtcgtta cgactatcat gttttttagct
11461 agagctatag tgtttgtgtg tgttgagtat tacccattgt tatttattac tggcaacacc
11521 ttacagtgta tcatgcttgt ttattgtttc ttaggctatt gttgctgctg ctactttggc
11581 cttttctgtt tactcaaccg ttacttcagg cttactcttg gtgtttatga ctacttggtc
11641 tctacacaag aatttaggta tatgaactcc aggggctttt gcctcctaa gagtagtatt
11701 gatgctttca gcttaacat taagttgttg ggtattggag gtaaaccatg tatcaaggtt
11761 gctactgtac agtctaaaat gtctgacgta aagtgcacat ctgtggtact gctctcggtt
11821 cttcaacaac ttagagtaga gtcatcttct aaattgtggg cacaatgtgt acaactccac
11881 aatgatattc ttcttgcaaa agacacaact gaagctttcg agaagatggt ttctctttg
```

```
11941  tctgttttgc tatccatgca gggtgctgta gacattaata ggttgtgcga ggaaatgctc
12001  gataaccgtg ctactcttca ggctattgct tcagaattta gttctttacc atcatatgcc
12061  gcttatgcca ctgcccagga ggcctatgag caggctgtag ctaatggtga ttctgaagtc
12121  gttctcaaaa agttaaagaa atctttgaat gtggctaaat ctgagtttga ccgtgatgct
12181  gccatgcaac gcaagttgga aaagatggca gatcaggcta tgacccaaat gtacaaacag
12241  gcaagatctg aggacaagag ggcaaaagta actagtgcta tgcaaacaat gctcttcact
12301  atgcttagga agcttgataa tgatgcactt aacaacatta tcaacaatgc gcgtgatggt
12361  tgtgttccac tcaacatcat accattgact acagcagcca aactcatggt tgttgtccct
12421  gattatggta cctacaagaa cacttgtgat ggtaacacct ttacatatgc atctgcactc
12481  tgggaaatcc agcaagttgt tgatgcggat agcaagattg ttcaacttag tgaaattaac
12541  atggacaatt caccaaattt ggcttggcct cttattgtta cagctctaag agccaactca
12601  gctgttaaac tacagaataa tgaactgagt ccagtagcac tacgacagat gtcctgtgcg
12661  gctggtacca cacaaacagc ttgtactgat gacaatgcac ttgcctacta taacaattcg
12721  aagggaggta ggtttgtgct ggcattacta tcagaccacc aagatctcaa atgggctaga
12781  ttccctaaga gtgatggtac aggtacaatt tacacagaac tggaaccacc ttgtaggttt
12841  gttacagaca caccaaaagg gcctaaagtg aaatacttgt acttcatcaa aggcttaaac
12901  aacctaaata gaggtatggt gctgggcagt ttagctgcta cagtacgtct tcaggctgga
12961  aatgctacag aagtacctgc caattcaact gtgctttcct tctgtgcttt tgcagtagac
13021  cctgctaaag catataagga ttacctagca agtggaggac aaccaatcac caactgtgtg
13081  aagatgttgt gtacacacac tggtacagga caggcaatta ctgtaacacc agaagctaac
13141  atggaccaag agtcctttgg tggtgcttca tgttgtctgt attgtagatg ccacattgac
13201  catccaaatc ctaaaggatt ctgtgacttg aaaggtaagt acgtccaaat acctaccact
13261  tgtgctaatg acccagtggg ttttacactt agaaacacag tctgtaccgt ctgcggaatg
13321  tggaaaggtt atggctgtag ttgtgaccaa ctccgcgaac ccttgatgca gtctgcggat
13381  gcatcaacgt ttttaaacgg gtttgcggtg taagtgcagc ccgtcttaca ccgtgcggca
13441  caggcactag tactgatgtc gtctacaggg cttttgatat ttacaacgaa aaagttgctg
13501  gttttgcaaa gttcctaaaa actaattgct gtcgcttcca ggagaaggat gaggaaggca
13561  atttattaga ctcttacttt gtagttaaga ggcatactat gtctaactac caacatgaag
13621  agactattta aacttggtt aaagattgtc cagcggttgc tgtccatgac tttttcaagt
13681  ttagagtaga tggtgacatg gtaccacata tatcacgtca gcgtctaact aaatacacaa
13741  tggctgattt agtctatgct ctacgtcatt ttgatgaggg taattgtgat acattaaaag
13801  aaatactcgt cacatacaat tgctgtgatg atgattattt caataagaag gattggtatg
13861  acttcgtaga gaatcctgac atcttacgcg tatatgctaa cttaggtgag cgtgtacgcc
13921  aatcattatt aaagactgta caattctgcg atgctatgcg tgatgcaggc attgtaggcg
13981  tactgacatt agataatcag gatcttaatg gaactggta cgatttcggt gatttcgtac
14041  aagtagcacc aggctgcgga gttcctattg tggattcata ttactcattg ctgatgccca
14101  tcctcacttt gactagggca ttggctgctg agtcccatat ggatgctgat ctcgcaaaac
14161  cacttattaa gtgggattg ctgaaatatg attttacgga agagagactt tgtctcttcg
14221  accgttattt taaatattgg gaccagacat accatcccaa ttgtattaac tgtttggatg
14281  ataggtgtat ccttcattgt gcaaacttta atgtgttatt ttctactgtg tttccaccta
```

-continued

```
14341 caagttttgg accactagta agaaaaatat ttgtagatgg tgttccttt gttgtttcaa
14401 ctggatacca ttttcgtgag ttaggagtcg tacataatca ggatgtaaac ttacatagct
14461 cgcgtctcag tttcaaggaa cttttagtgt atgctgctga tccagctatg catgcagctt
14521 ctggcaattt attgctagat aaacgcacta catgcttttc agtagctgca ctaacaaaca
14581 atgttgcttt tcaaactgtc aaacccggta attttaataa agacttttat gactttgctg
14641 tgtctaaagg tttctttaag gaaggaagtt ctgttgaact aaaacacttc ttctttgctc
14701 aggatggcaa cgctgctatc agtgattatg actattatcg ttataatctg ccaacaatgt
14761 gtgatatcag acaactccta ttcgtagttg aagttgttga taaatacttt gattgttacg
14821 atggtggctg tattaatgcc aaccaagtaa tcgttaacaa tctggataaa tcagctggtt
14881 tcccatttaa taaatggggt aaggctagac tttattatga ctcaatgagt tatgaggatc
14941 aagatgcact tttcgcgtat actaagcgta atgtcatccc tactataact caaatgaatc
15001 ttaagtatgc cattagtgca aagaatagag ctcgcaccgt agctggtgtc tctatctgta
15061 gtactatgac aaatagacag tttcatcaga aattattgaa gtcaatagcc gccactagag
15121 gagctactgt ggtaattgga acaagcaagt tttacggtgg ctggcataat atgttaaaaa
15181 ctgtttacag tgatgtgaaa actccacacc ttatgggttg ggattatcca aaatgtgaca
15241 gagccatgcc taacatgctt aggataatgg cctctcttgt tcttgctcgc aaacataaca
15301 cttgctgtaa cttatcacac cgtttctaca ggttagctaa cgagtgtgcg caagtattaa
15361 gtgagatggt catgtgtggc ggctcactat atgttaaacc aggtggaaca tcatccggtg
15421 atgctacaac tgcttatgct aatagtgtct ttaacatttg tcaagctgtt acagccaatg
15481 taaatgcact tctttcaact gatggtaata agatagctga caagtatgtc cgcaatctac
15541 aacacaggct ctatgagtgt ctctatagaa atagggatgt tgatcatgaa ttcgtggatg
15601 agttttacgc ttacctgcgt aaacatttct ccatgatgat tctttctgat gatgccgttg
15661 tgtgctataa cagtaactat gcggctcaag gtttagtagc tagcattaag aactttaagg
15721 cagttctttta ttatcaaaat aatgtgttca tgtctgaggc aaaatgttgg actgagactg
15781 accttactaa aggacctcac gaattttgct cacagcatac aatgctagtt aaacaaggag
15841 atgattacgt gtacctgcct tacccagatc catcaagaat attaggcgca ggctgttttg
15901 tcgatgatat tgtcaaaaca gatggtacac ttatgattga aaggttcgtg tcactggcta
15961 ttgatgctta cccacttaca aaacatccta atcaggagta tgctgatgtc tttcacttgt
16021 atttacaata cattagaaag ttacatgatg agcttactgg ccacatgttg gacatgtatt
16081 ccgtaatgct aactaatgat aacacctcac ggtactggga acctgagttt tatgaggcta
16141 tgtacacacc acatacagtc ttgcaggctg taggtgcttg tgtattgtgc aattcacaga
16201 cttcacttcg ttgcggtgcc tgtattagga gaccattcct atgttgcaag tgctgctatg
16261 accatgtcat ttcaacatca cacaaattag tgttgtctgt taatcctat gtttgcaatg
16321 ccccaggttg tgatgtcact gatgtgacac aactgtatct aggaggtatg agctattatt
16381 gcaagtcaca taagcctccc attagttttc cattatgtgc taatggtcag ttttttggtt
16441 tatacaaaaa cacatgtgta ggcagtgaca atgtcactga cttcaatgcg atagcaacat
16501 gtgattggac taatgctggc gattacatac ttgccaacac ttgtactgag agactcaagc
16561 ttttcgcagc agaaacgctc aaagccactg aggaaacatt taagctgtca tatggtattg
16621 ccactgtacg cgaagtactc tctgacagag aattgcatct ttcatgggag gttggaaaac
16681 ctagaccacc attgaacaga aactatgtct ttactggtta ccgtgtaact aaaaatagta
16741 aagtacagat tggagagtac acctttgaaa aggtgactaa tggtgatgct gttgtgtaca
```

-continued

```
16801 gaggtactac gacatacaag ttgaatgttg gtgattactt tgtgttgaca tctcacactg
16861 taatgccact tagtgcacct actctagtgc cacaagagca ctatgtgaga attactggct
16921 tgtacccaac actcaacatc tcagatgagt tttctagcaa tgttgcaaat tatcaaaagg
16981 tcggcatgca aaagtactct acactccaag gaccacctgg tactggtaag agtcattttg
17041 ccatcggact tgctctctat tacccatctg ctcgcatagt gtatacggca tgctctcatg
17101 cagctgttga tgccctatgt gaaaaggcat taaaatattt gcccatagat aaatgtagta
17161 gaatcatacc tgcgcgtgcg cgcgtagagt gttttgataa attcaaagtg aattcaacac
17221 tagaacagta tgttttctgc actgtaaatg cattgccaga acaactgct gacattgtag
17281 tctttgatga aatctctatg gctactaatt atgacttgag tgttgtcaat gctagacttc
17341 gtgcaaaaca ctacgtctat attggcgatc ctgctcaatt accagccccc cgcacattgc
17401 tgactaaagg cacactagaa ccagaatatt ttaattcagt gtgcagactt atgaaaacaa
17461 taggtccaga catgttcctt ggaacttgtc gccgttgtcc tgctgaaatt gttgacactg
17521 tgagtgcttt agtttatgac aataagctaa aagcacacaa ggataagtca gctcaatgct
17581 tcaaaatgtt ctacaaaggt gttattacac atgatgtttc atctgcaatc aacagacctc
17641 aaataggcgt tgtaagagaa tttcttacac gcaatcctgc ttggagaaaa gctgttttta
17701 tctcacctta taattcacag aacgctgtag cttcaaaaat cttaggattg cctacgcaga
17761 ctgttgattc atcacagggt tctgaatatg actatgtcat attcacacaa actactgaaa
17821 cagcacactc ttgtaatgtc aaccgcttca atgtggctat cacaagggca aaaattggca
17881 ttttgtgcat aatgtctgat agagatcttt atgacaaact gcaatttaca agtctagaaa
17941 taccacgtcg caatgtggct acattacaag cagaaaatgt aactggactt tttaaggact
18001 gtagtaagat cattactggt cttcatccta cacaggcacc tacacacctc agcgttgata
18061 taaagttcaa gactgaagga ttatgtgttg acataccagg cataccaaag gacatgacct
18121 accgtagact catctctatg atgggtttca aaatgaatta ccaagtcaat ggttacccta
18181 atatgtttat cacccgcgaa gaagctattc gtcacgttcg tgcgtggatt ggctttgatg
18241 tagagggctg tcatgcaact agagatgctg tgggtactaa cctacctctc cagctaggat
18301 tttctacagg tgttaactta gtagctgtac cgactggtta tgttgacact gaaaataaca
18361 cagaattcac cagagttaat gcaaaacctc caccaggtga ccagtttaaa catcttatac
18421 cactcatgta taaaggcttg ccctggaatg tagtgcgtat taagatagta caaatgctca
18481 gtgatacact gaaaggattg tcagacagag tcgtgttcgt cctttgggcg catggctttg
18541 agcttacatc aatgaagtac tttgtcaaga ttggacctga agaacgtgt tgtctgtgtg
18601 acaaacgtgc aacttgcttt tctacttcat cagatactta tgcctgctgg aatcattctg
18661 tgggttttga ctatgtctat aacccattta tgattgatgt tcagcagtgg ggctttacgg
18721 gtaaccttca gagtaaccat gaccaacatt gccaggtaca tggaaatgca catgtggcta
18781 gttgtgatgc tatcatgact agatgtttag cagtccatga gtgctttgtt aagcgcgttg
18841 attggtctgt tgaataccct attataggag atgaactgag gttaattct gcttgcagaa
18901 aagtacaaca catggttgtg aagtctgcat tgcttgctga taagtttcca gttcttcatg
18961 acattggaaa tccaaaggct atcaagtgtg tgcctcaggc tgaagtagaa tggaagttct
19021 acgatgctca gccatgtagt gacaaagctt acaaaataga ggaactcttc tattcttatg
19081 ctacacatca cgataaattc actgatggtg tttgtttgtt ttggaattgt aacgttgatc
19141 gttacccagc caatgcaatt gtgtgtaggt ttgacacaag agtcttgtca aacttgaact
```

-continued

```
19201 taccaggctg tgatggtggt agtttgtatg tgaataagca tgcattccac actccagctt
19261 tcgataaaag tgcatttact aatttaaagc aattgccttt cttttactat tctgatagtc
19321 cttgtgagtc tcatggcaaa caagtagtgt cggatattga ttatgttcca ctcaaatctg
19381 ctacgtgtat tacacgatgc aatttaggtg gtgctgtttg cagacaccat gcaaatgagt
19441 accgacagta cttggatgca tataatatga tgatttctgc tggatttagc ctatggattt
19501 acaaacaatt tgatacttat aacctgtgga atacatttac caggttacag agtttagaaa
19561 atgtggctta taatgttgtt aataaaggac actttgatgg acacgccggc gaagcacctg
19621 tttccatcat taataatgct gtttacacaa aggtagatgg tattgatgtg gagatctttg
19681 aaaataagac aacacttcct gttaatgttg catttgagct ttgggctaag cgtaacatta
19741 aaccagtgcc agagattaag atactcaata atttgggtgt tgatatcgct gctaatactg
19801 taatctggga ctacaaaaga gaagccccag cacatgtatc tacaataggt gtctgcacaa
19861 tgactgacat tgccaagaaa cctactgaga gtgcttgttc ttcacttact gtcttgtttg
19921 atggtagagt ggaaggacag gtagaccttt ttagaaacgc ccgtaatggt gttttaataa
19981 cagaaggttc agtcaaaggt ctaacacctt caaagggacc agcacaagct agcgtcaatg
20041 gagtcacatt aattggagaa tcagtaaaaa cacagtttaa ctactttaag aaagtagacg
20101 gcattattca acagttgcct gaaacctact ttactcagag cagagactta gaggatttta
20161 agcccagatc acaaatggaa actgactttc tcgagctcgc tatggatgaa ttcatacagc
20221 gatataagct cgagggctat gccttcgaac acatcgttta tggagatttc agtcatggac
20281 aacttggcgg tcttcattta atgataggct tagccaagcg ctcacaagat tcaccactta
20341 aattagagga ttttatccct atggacagca cagtgaaaaa ttacttcata acagatgcgc
20401 aaacaggttc atcaaaatgt gtgtgttctg tgattgatct tttacttgat gactttgtcg
20461 agataataaa gtcacaagat ttgtcagtga tttcaaaagt ggtcaaggtt acaattgact
20521 atgctgaaat ttcattcatg ctttggtgta aggatggaca tgttgaaacc ttctacccaa
20581 aactacaagc aagtcaagcg tggcaaccag gtgttgcgat gcctaacttg tacaagatgc
20641 aaagaatgct tcttgaaaag tgtgaccttc agaattatgg tgaaaatgct gttataccaa
20701 aaggaataat gatgaatgtc gcaaagtata tcaactgtgt caatacttta aatacactta
20761 cttttagctgt accctacaac atgagagtta ttcactttgg tgctggctct gataaaggag
20821 ttgcaccagg tacagctgtg ctcagacaat ggttgccaac tggcacacta cttgtcgatt
20881 cagatcttaa tgacttcgtc tccgacgcag attctacttt aattggagac tgtgcaacag
20941 tacatacggc taataaatgg gaccttatta ttagcgatat gtatgaccct aggaccaaac
21001 atgtgacaaa agagaatgac tctaaagaag gttttttcac ttatctgtgt ggatttataa
21061 agcaaaaact agccctgggt ggttctatag ctgtaaagat aacagagcat tcttggaatg
21121 ctgaccttta caagcttatg ggccatttct catggtggac agcttttgtt acaaatgtaa
21181 atgcatcatc atcggaagca ttttttaattg gggctaacta tcttggcaag ccgaaggaac
21241 aaattgatgg ctataccatg catgctaact acattttctg gaggaacaca aatcctatcc
21301 agttgtcttc ctattcactc tttgacatga gcaaatttcc tcttaaatta gaggaactg
21361 ctgtaatgtc tcttaaggag aatcaaatca atgatatgat ttattctctt ctggaaaaag
21421 gtaggcttat cattagaaa acaacagag ttgtggtttc aagtgatatt cttgttaaca
21481 actaaacgaa catgtttatt ttcttattat ttcttactct cactagtggt agtgaccttg
21541 accggtgcac cacttttgat gatgttcaag ctcctaatta cactcaacat acttcatcta
21601 tgaggggggt ttactatcct gatgaaattt ttagatcaga cactctttat ttaactcagg
```

-continued

```
21661 atttatttct tccattttat tctaatgtta cagggtttca tactattaat catacgtttg
21721 gcaaccctgt catacctttt aaggatggta tttattttgc tgccacagag aaatcaaatg
21781 ttgtccgtgg ttgggttttt ggttctacca tgaacaacaa gtcacagtcg gtgattatta
21841 ttaacaattc tactaatgtt gttatacgag catgtaactt tgaattgtgt gacaaccctt
21901 tctttgctgt ttctaaaccc atgggtacac agacacatac tatgatattc gataatgcat
21961 ttaattgcac tttcgagtac atatctgatg ccttttcgct tgatgtttca gaaagtcag
22021 gtaattttaa acacttacga gagtttgtgt ttaaaaataa agatgggttt ctctatgttt
22081 ataagggcta tcaacctata gatgtagttc gtgatctacc ttctggtttt aacactttga
22141 aacctatttt taagttgcct cttggtatta acattacaaa ttttagagcc attcttacag
22201 ccttttcacc tgctcaagac atttggggca cgtcagctgc agcctatttt gttggctatt
22261 taaagccaac tacatttatg ctcaagtatg atgaaaatgg tacaatcaca gatgctgttg
22321 attgttctca aaatccactt gctgaactca atgctctgt taagagcttt gagattgaca
22381 aaggaattta ccagacctct aatttcaggg ttgttccctc aggagatgtt gtgagattcc
22441 ctaatattac aaacttgtgt ccttttggag aggttttaa tgctactaaa tcccttctg
22501 tctatgcatg ggagagaaaa aaaatttcta attgtgttgc tgattactct gtgctctaca
22561 actcaacatt ttttcaacc tttaagtgct atggcgtttc tgccactaag ttgaatgatc
22621 tttgcttctc caatgtctat gcagattctt ttgtagtcaa gggagatgat gtaagacaaa
22681 tagcgccagg acaaactggt gttattgctg attataatta taaattgcca gatgatttca
22741 tgggttgtgt ccttgcttgg aatactagga acattgatgc tacttcaact ggtaattata
22801 attataaata taggtatctt agacatggca agcttaggcc ctttgagaga gacatatcta
22861 atgtgccttt ctcccctgat ggcaaacctt gcaccccacc tgctcttaat tgttattggc
22921 cattaaatga ttatggtttt tacaccacta ctggcattgg ctaccaacct tacagagttg
22981 tagtactttc ttttgaactt ttaaatgcac cggccacggt ttgtggacca aaattatcca
23041 ctgaccttat taagaaccag tgtgtcaatt ttaattttaa tggactcact ggtactggtg
23101 tgttaactcc ttcttcaaag agatttcaac catttcaaca atttggccgt gatgtttctg
23161 atttcactga ttccgttcga gatcctaaaa catctgaaat attagacatt tcaccttgcg
23221 cttttgggg tgtaagtgta attacacctg aacaaatgc ttcatctgaa gttgctgttc
23281 tatatcaaga tgttaactgc actgatgttt ctacagcaat tcatgcagat caactcacac
23341 cagcttggcg catatattct actggaaaca atgtattcca gactcaagca ggctgtctta
23401 taggagctga gcatgtcgac acttcttatg agtgcgacat tcctattgga gctggcattt
23461 gtgctagtta ccatacagtt tctttattac gtagtactag ccaaaaatct attgtggctt
23521 atactatgtc tttaggtgct gatagttcaa ttgcttactc taataacacc attgctatac
23581 ctactaactt ttcaattagc attactacag aagtaatgcc tgtttctatg gctaaaacct
23641 ccgtagattg taatatgtac atctgcggag attctactga atgtgctaat ttgcttctcc
23701 aatatggtag cttttgcaca caactaaatc gtgcactctc aggtattgct gctgaacagg
23761 atcgcaacac acgtgaagtg ttcgctcaag tcaaacaaat gtacaaaacc caactttga
23821 aatattttgg tggttttaat ttttcacaaa tattacctga ccctctaaag ccaactaaga
23881 ggtctttat tgaggacttg ctctttaata aggtgacact cgctgatgct ggcttcatga
23941 agcaatatgg cgaatgccta ggtgatatta atgctagaga tctcatttgt gcgcagaagt
24001 tcaatggact tacagtgttg ccacctctgc tcactgatga tatgattgct gcctacactg
```

-continued

```
24061 ctgctctagt tagtggtact gccactgctg gatggacatt tggtgctggc gctgctcttc 24121 aaataccttt tgctatgcaa atggcatata ggttcaatgg cattggagtt acccaaaatg 24181 ttctctatga gaaccaaaaa caaatcgcca accaatttaa caaggcgatt agtcaaattc 24241 aagaatcact tacaacaaca tcaactgcat tgggcaagct gcaagacgtt gttaaccaga 24301 atgctcaagc attaaacaca cttgttaaac aacttagctc taattttggt gcaatttcaa 24361 gtgtgctaaa tgatatcctt tcgcgacttg ataaagtcga ggcggaggta caaattgaca 24421 ggttaattac aggcagactt caaagccttc aaacctatgt aacacaacaa ctaatcaggg 24481 ctgctgaaat cagggcttct gctaatcttg ctgctactaa aatgtctgag tgtgttcttg 24541 gacaatcaaa aagagttgac ttttgtggaa agggctacca ccttatgtcc ttcccacaag 24601 cagccccgca tggtgttgtc ttcctacatg tcacgtatgt gccatcccag gagaggaact 24661 tcaccacagc gccagcaatt tgtcatgaag gcaaagcata cttccctcgt gaaggtgttt 24721 ttgtgtttaa tggcacttct tggtttatta cacagaggaa cttcttttct ccacaaataa 24781 ttactacaga caatacattt gtctcaggaa attgtgatgt cgttattggc atcattaaca 24841 acacagttta tgatcctctg caacctgagc ttgactcatt caaagaagag ctggacaagt 24901 acttcaaaaa tcatacatca ccagatgttg atcttggcga catttcaggc attaacgctt 24961 ctgtcgtcaa cattcaaaaa gaaattgacc gcctcaatga ggtcgctaaa aatttaaatg 25021 aatcactcat tgaccttcaa gaattgggaa aatatgagca atatattaaa tggccttggt 25081 atgtttggct cggcttcatt gctggactaa ttgccatcgt catggttaca atcttgcttt 25141 gttgcatgac tagttgttgc agttgcctca agggtgcatg ctcttgtggt tcttgctgca 25201 agtttgatga ggatgactct gagccagttc tcaagggtgt caaattacat tacacataaa 25261 cgaacttatg gatttgttta tgagattttt tactcttaga tcaattactg cacagccagt 25321 aaaaattgac aatgcttctc ctgcaagtac tgttcatgct acagcaacga taccgctaca 25381 agcctcactc cctttcggat ggcttgttat tggcgttgca tttcttgctg tttttcagag 25441 cgctaccaaa ataattgcgc tcaataaaag atggcagcta gccctttata agggcttcca 25501 gttcatttgc aatttactgc tgctatttgt taccatctat tcacatcttt tgcttgtcgc 25561 tgcaggtatg gaggcgcaat ttttgtacct ctatgccttg atatattttc tacaatgcat 25621 caacgcatgt agaattatta tgagatgttg gctttgttgg aagtgcaaat ccaagaaccc 25681 attactttat gatgccaact actttgtttg ctggcacaca cataactatg actactgtat 25741 accatataac agtgtcacag atacaattgt cgttactgaa ggtgacggca tttcaacacc 25801 aaaactcaaa gaagactacc aaattggtgg ttattctgag gataggcact caggtgttaa 25861 agactatgtc gttgtacatg gctatttcac cgaagtttac taccagcttg agtctacaca 25921 aattactaca gacactggta ttgaaaatgc tacattcttc atctttaaca gcttgttaa 25981 agacccaccg aatgtgcaaa tacacacaat cgacggctct tcaggagttg ctaatccagc 26041 aatggatcca atttatgatg agccgacgac gactactagc gtgcctttgt aagcacaaga 26101 aagtgagtac gaacttatgt actcattcgt ttcggaagaa acaggtacgt taatagttaa 26161 tagcgtactt ctttttcttg ctttcgtggt attcttgcta gtcacactag ccatccttac 26221 tgcgcttcga ttgtgtgcgt actgctgcaa tattgttaac gtgagtttag taaaaccaac 26281 ggtttacgtc tactcgcgtg ttaaaaatct gaactcttct gaaggagttc ctgatcttct 26341 ggtctaaacg aactaactat tattattatt ctgtttggaa ctttaacatt gcttatcatg 26401 gcagacaacg gtactattac cgttgaggag cttaaacaac tcctggaaca atggaaccta 26461 gtaataggtt tcctattcct agcctggatt atgttactac aatttgccta ttctaatcgg
```

```
-continued
26521  aacaggtttt tgtacataat aaagcttgtt ttcctctggc tcttgtggcc agtaacactt
26581  gcttgttttg tgcttgctgc tgtctacaga attaattggg tgactggcgg gattgcgatt
26641  gcaatggctt gtattgtagg cttgatgtgg cttagctact tcgttgcttc cttcaggctg
26701  tttgctcgta cccgctcaat gtggtcattc aacccagaaa caaacattct tctcaatgtg
26761  cctctccggg ggacaattgt gaccagaccg ctcatggaaa gtgaacttgt cattggtgct
26821  gtgatcattc gtggtcactt gcgaatggcc ggacactccc tagggcgctg tgacattaag
26881  gacctgccaa aagagatcac tgtggctaca tcacgaacgc tttcttatta caaattagga
26941  gcgtcgcagc gtgtaggcac tgattcaggt tttgctgcat acaaccgcta ccgtattgga
27001  aactataaat taaatacaga ccacgccggt agcaacgaca atattgcttt gctagtacag
27061  taagtgacaa cagatgtttc atcttgttga cttccaggtt acaatagcag agatattgat
27121  tatcattatg aggactttca ggattgctat ttggaatctt gacgttataa taagttcaat
27181  agtgagacaa ttatttaagc ctctaactaa gaagaattat tcggagttag atgatgaaga
27241  acctatggag ttagattatc cataaaacga acatgaaaat tattctcttc ctgacattga
27301  ttgtatttac atcttgcgag ctatatcact atcaggagtg tgttagaggt acgactgtac
27361  tactaaaaga accttgccca tcaggaacat acgagggcaa ttcaccattt caccctcttg
27421  ctgacaataa atttgcacta acttgcacta gcacacactt tgcttttgct tgtgctgacg
27481  gtactcgaca tacctatcag ctgcgtgcaa gatcagtttc accaaaactt ttcatcagac
27541  aagaggaggt tcaacaagag ctctactcgc cacttttttct cattgttgct gctctagtat
27601  ttttaatact ttgcttcacc attaagagaa agacagaatg aatgagctca ctttaattga
27661  cttctatttg tgcttttag cctttctgct attccttgtt ttaataatgc ttattatatt
27721  ttggttttca ctcgaaatcc aggatctaga agaaccttgt accaaagtct aaacgaacat
27781  gaaacttctc attgtttga cttgtatttc tctatgcagt tgcatatgca ctgtagtaca
27841  gcgctgtgca tctaataaac ctcatgtgct tgaagatcct tgtaaggtac aacactaggg
27901  gtaatactta tagcactgct tggctttgtg ctctaggaaa ggttttacct tttcatagat
27961  ggcacactat ggttcaaaca tgcacaccta atgttactat caactgtcaa gatccagctg
28021  gtggtgcgct tatagctagg tgttggtacc ttcatgaagg tcaccaaact gctgcattta
28081  gagacgtact tgttgtttta aataaacgaa caaattaaaa tgtctgataa tggaccccaa
28141  tcaaaccaac gtagtgcccc ccgcattaca tttggtggac ccacagattc aactgacaat
28201  aaccagaatg gaggacgcaa tggggcaagg ccaaaacagc gccgacccca aggtttaccc
28261  aataatactg cgtcttggtt cacagctctc actcagcatg gcaaggagga acttagattc
28321  cctcgaggcc agggcgttcc aatcaacacc aatagtggtc cagatgacca aattggctac
28381  taccgaagag ctacccgacg agttcgtggt ggtgacggca aaatgaaaga gctcagcccc
28441  agatggtact tctattacct aggaactggc ccagaagctt cacttcccta cggcgctaac
28501  aaagaaggca tcgtatgggt tgcaactgag ggagccttga atacacccaa agaccacatt
28561  ggcacccgca atcctaataa caatgctgcc accgtgctac aacttcctca aggaacaaca
28621  ttgccaaaag gcttctacgc agagggaagc agaggcggca gtcaagcctc ttctcgctcc
28681  tcatcacgta gtcgcggtaa ttcaagaaat tcaactcctg gcagcagtag gggaaattct
28741  cctgctcgaa tggctagcgg aggtggtgaa actgccctcg cgctattgct gctagacaga
28801  ttgaaccagc ttgagagcaa agtttctggt aaaggccaac aacaacaagg ccaaactgtc
28861  actaagaaat ctgctgctga ggcatctaaa aagcctcgcc aaaaacgtac tgccacaaaa
```

-continued

```
28921 cagtacaacg tcactcaagc atttgggaga cgtggtccag aacaaaccca aggaaatttc 28981 ggggaccaag acctaatcag acaaggaact gattacaaac attggccgca aattgcacaa 29041 tttgctccaa gtgcctctgc attctttgga atgtcacgca ttggcatgga agtcacacct 29101 tcgggaacat ggctgactta tcatggagcc attaaattgg atgacaaaga tccacaattc 29161 aaagacaacg tcatactgct gaacaagcac attgacgcat acaaaacatt cccaccaaca 29221 gagcctaaaa aggacaaaaa gaaaaagact gatgaagctc agcctttgcc gcagagacaa 29281 aagaagcagc ccactgtgac tcttcttcct gcggctgaca tggatgattt ctccagacaa 29341 cttcaaaatt ccatgagtgg agcttctgct gattcaactc aggcataaac actcatgatg 29401 accacacaag gcagatgggc tatgtaaacg ttttcgcaat tccgtttacg atacatagtc 29461 tactcttgtg cagaatgaat tctcgtaact aaacagcaca agtaggttta gttaacttta 29521 atctcacata gcaatcttta atcaatgtgt aacattaggg aggacttgaa agagccacca 29581 cattttcatc gaggccacgc ggagtacgat cgagggtaca gtgaataatg ctagggagag 29641 ctgcctatat ggaagagccc taatgtgtaa aattaatttt agtagtgcta tccccatgtg 29701 attttaatag cttcttagga gaatgacaaa aaaaaaaaaa aaaaaaaaa a.
```

GenBank Accession No. GenBank: JX869059.2, which is specifically incorporated by reference herein in its entirety, provides the following (DNA) genomic sequence for MERS-CoV (Human betacoronavirus 2c EMC/2012, complete genome):

(SEQ ID NO: 4)
```
   1 gatttaagtg aatagcttgg ctatctcact tcccctcgtt ctcttgcaga actttgattt 61 taacgaactt aaataaaagc cctgttgttt agcgtatcgt tgcacttgtc tggtgggatt 121 gtggcattaa tttgcctgct catctaggca gtggacatat gctcaacact gggtataatt 181 ctaattgaat actatttttc agttagagcg tcgtgtctct tgtacgtctc ggtcacaata 241 cacggtttcg tccggtgcgt ggcaattcgg ggcacatcat gtctttcgtg gctggtgtga 301 ccgcgcaagg tgcgcgcggt acgtatcgag cagcgctcaa ctctgaaaaa catcaagacc 361 atgtgtctct aactgtgcca ctctgtggtt caggaaacct ggttgaaaaa cttttcaccat 421 ggttcatgga tggcgaaaat gcctatgaag tggtgaaggc catgttactt aaaaaggagc 481 cacttctcta tgtgcccatc cggctggctg acacactag acacctccca ggtcctcgtg 541 tgtacctggt tgagaggctc attgcttgtg aaaatccatt catggttaac caattggctt 601 atagctctag tgcaaatggc agcctggttg gcacaacttt gcagggcaag cctattggta 661 tgttcttccc ttatgacatc gaacttgtca caggaaagca aaatattctc ctgcgcaagt 721 atggccgtgg tggttatcac tacaccccat tccactatga gcgagacaac acctcttgcc 781 ctgagtggat ggacgatttt gaggcggatc ctaaaggcaa atatgcccag aatctgctta 841 agaagttgat tggcggtgat gtcactccag ttgaccaata catgtgtggc gttgatgaa 901 aacccattag tgcctacgca ttttaatgg ccaaggatgg aataaccaaa ctggctgatg 961 ttgaagcgga cgtcgcagca cgtgctgatg acgaaggctt catcacatta aagaacaatc 1021 tatatagatt ggtttggcat gttgagcgta agacgttcc atatcctaag caatctattt 1081 ttactattaa tagtgtggtc caaaggatg tgttgaaaa cactcctcct cactattta 1141 ctcttggatg caaaatttta acgctcaccc cacgcaacaa gtggagtggc gtttctgact 1201 tgtccctcaa acaaaactc ctttacacct tctatggtaa ggagtcactt gagaacccaa 1261 cctacattta ccactccgca ttcattgagt gtggaagttg tggtaatgat tcctggctta
```

-continued

```
1321 cagggaatgc tatccaaggg tttgcctgtg gatgtggggc atcatataca gctaatgatg
1381 tcgaagtcca atcatctggc atgattaagc caaatgctct tctttgtgct acttgcccct
1441 ttgctaaggg tgatagctgt tcttctaatt gcaaacattc agttgctcag ttggttagtt
1501 acctttctga acgctgtaat gttattgctg attctaagtc cttcacactt atctttggtg
1561 gcgtagctta cgcctacttt ggatgtgagg aaggtactat gtactttgtg cctagagcta
1621 agtctgttgt ctcaaggatt ggagactcca tctttacagg ctgtactggc tcttggaaca
1681 aggtcactca aattgctaac atgttcttgg aacagactca gcattccctt aactttgtgg
1741 gagagttcgt tgtcaacgat gttgtcctcg caattctctc tggaaccaca actaatgttg
1801 acaaaatacg ccagcttctc aaaggtgtca cccttgacaa gttgcgtgat tatttagctg
1861 actatgacgt agcagtcact gccggcccat tcatggataa tgctattaat gttggtggta
1921 caggattaca gtatgccgcc attactgcac cttatgtagt tctcactggc ttaggtgagt
1981 cctttaagaa agttgcaacc ataccgtata aggtttgcaa ctctgttaag gatactctgg
2041 cttattatgc tcacagcgtg ttgtacagag ttttttcctta tgacatggat tctggtgtgt
2101 catcctttag tgaactactt tttgattgcg ttgatctttc agtagcttct acctattttt
2161 tagtccgcat cttgcaagat aagactggcg actttatgtc tacaattatt acttcctgcc
2221 aaactgctgt tagtaagctt ctagatacat gttttgaagc tacagaagca acatttaact
2281 tcttgttaga tttggcagga ttgttcagaa tctttctccg caatgcctat gtgtacactt
2341 cacaagggtt tgtggtggtc aatggcaaag tttctacact tgtcaaacaa gtgttagact
2401 tgcttaataa gggtatgcaa cttttgcata caaaggtctc ctgggctggt tctaaaatca
2461 ttgctgttat ctacagcggc agggagtctc taatattccc atcgggaacc tattactgtg
2521 tcaccactaa ggctaagtcc gttcaacaag atcttgacgt tattttgcct ggtgagtttt
2581 ccaagaagca gttaggactg ctccaaccta ctgacaattc tacaactgtt agtgttactg
2641 tatccagtaa catggttgaa actgttgtgg gtcaacttga gcaaactaat atgcatagtc
2701 ctgatgttat agtaggtgac tatgtcatta ttagtgaaaa attgtttgtg cgtagtaagg
2761 aagaagacgg atttgccttc taccctgctt gcactaatgg tcatgctgta ccgactctct
2821 ttagacttaa gggaggtgca cctgtaaaaa agtagccttt ggcggtgat caagtacatg
2881 aggttgctgc tgtaagaagt gttactgtcg agtacaacat tcatgctgta ttagacacac
2941 tacttgcttc ttctagtctt agaacctttg ttgtagataa gtctttgtca attgaggagt
3001 ttgctgacgt agtaaaggaa caagtctcag acttgcttgt taaattactg cgtggaatgc
3061 cgattccaga ttttgattta gacgatttta ttgacgcacc atgctattgc tttaacgctg
3121 agggtgatgc atcctggtct tctactatga tcttctctct tcaccccgtc gagtgtgacg
3181 aggagtgttc tgaagtagag gcttcagatt tagaagaagg tgaatcagag tgcatttctg
3241 agacttcaac tgaacaagtt gacgtttctc atgagacttc tgacgacgag tgggctgctg
3301 cagttgatga agcgttccct ctcgatgaag cagaagatgt tactgaatct gtgcaagaag
3361 aagcacaacc agtagaagta cctgttgaag atattgcgca ggttgtcata gctgacacct
3421 tacaggaaac tcctgttgtg cctgatactg ttgaagtccc accgcaagtg gtgaaacttc
3481 cgtctgcacc tcagactatc cagcccgagg taaagaagt tgcacctgtc tatgaggctg
3541 ataccgaaca gacacagaat gttactgtta aacctaagag gttacgcaaa aagcgtaatg
3601 ttgaccctt gtccaatttt gaacataagg ttattacaga gtgcgttacc atagttttag
3661 gtgacgcaat tcaagtagcc aagtgctatg gggagtctgt gttagttaat gctgctaaca
```

-continued

```
3721 cacatcttaa gcatggcggt ggtatcgctg gtgctattaa tgcggcttca aaaggggctg 3781 tccaaaaaga gtcagatgag tatattctgg ctaaagggcc gttacaagta ggagattcag 3841 ttctcttgca aggccattct ctagctaaga atatcctgca tgtcgtaggc ccagatgccc 3901 gcgctaaaca ggatgtttct ctccttagta agtgctaaa ggctatgaat gcatatcctc 3961 ttgtagtcac tcctcttgtt tcagcaggca tatttggtgt aaaaccagct gtgtcttttg 4021 attatcttat tagggaggct aagactagag ttttagtcgt cgttaattcc caagatgtct 4081 ataagagtct taccatagtt gacattccac agagtttgac ttttcatat gatgggttac 4141 gtggcgcaat acgtaaagct aaagattatg gttttactgt ttttgtgtgc acagacaact 4201 ctgctaacac taaagttctt aggaacaagg gtgttgatta tactaagaag tttcttacag 4261 ttgacggtgt gcaatattat tgctacacgt ctaaggacac tttagatgat atcttacaac 4321 aggctaataa gtctgttggt attatatcta tgcctttggg atatgtgtct catggtttag 4381 acttaatgca agcagggagt gtcgtgcgta gagttaacgt gccctacgtg tgtctcctag 4441 ctaataaaga gcaagaagct attttgatgt ctgaagacgt aagttaaac ccttcagaag 4501 attttataaa gcacgtccgc actaatggtg gttacaattc ttggcattta gtcgagggtg 4561 aactattggt gcaagactta cgcttaaata agctcctgca ttggtctgat caaaccatat 4621 gctacaagga tagtgtgttt tatgttgtaa agaatagtac agcttttcca tttgaaacac 4681 tttcagcatg tcgtgcgtat ttggattcac gcacgacaca gcagttaaca atcgaagtct 4741 tagtgactgt cgatggtgta aattttagaa cagtcgttct aaataataag aacacttata 4801 gatcacagct tggatgcgtt ttctttaatg gtgctgatat ttctgacacc attcctgatg 4861 agaaacagaa tggtcacagt ttatatctag cagacaattt gactgctgat gaaacaaagg 4921 cgcttaaaga gttatatggc cccgttgatc ctacttttct acacagattc tattcactta 4981 aggctgcagt ccatgggtgg aagatggttg tgtgtgataa ggtacgttct ctcaaattga 5041 gtgataataa ttgttatctt aatgcagtta ttatgacact gatttattg aaggacatta 5101 aatttgttat acctgctcta cagcatgcat ttatgaaaca taagggcggt gattcaactg 5161 acttcatagc cctcattatg gcttatggca attgcacatt tggtgctcca gatgatgcct 5221 ctcggttact tcataccgtg cttgcaaagg ctgagttatg ctgttctgca cgcatggttt 5281 ggagagagtg gtgcaatgtc tgtggcataa agatgttgt tctacaaggc ttaaaagctt 5341 gttgttacgt gggtgtgcaa actgttgaag atctgcgtgc tcgcatgaca tatgtatgcc 5401 agtgtggtgg tgaacgtcat cggcaattag tcgaacacac caccccctgg ttgctgctct 5461 caggcacacc aaatgaaaaa ttggtgacaa cctccacggc gcctgatttt gtagcattta 5521 atgtctttca gggcattgaa acggctgttg ccattatgt tcatgctcgc ctgaagggtg 5581 gtcttatttt aaagtttgac tctggcaccg ttagcaagac ttcagactgg aagtgcaagg 5641 tgacagatgt acttttcccc ggccaaaaat acagtagcga ttgtaatgtc gtacggtatt 5701 ctttggacgg taatttcaga acagaggttg atcccgacct atctgctttc tatgttaagg 5761 atggtaaata ctttacaagt gaaccacccg taacatattc accagctaca attttagctg 5821 gtagtgtcta cactaatagc tgccttgtat cgtctgatgg acaacctggc ggtgatgcta 5881 ttagtttgag ttttaataac cttttagggg ttgattctag taaaccagtc actaagaaat 5941 acacttactc cttccttgcc aaagaagacg gcgatgtgtt gttggctgag tttgacactt 6001 atgaccctat ttataagaat ggtgccatgt ataaaggcaa accaattctt gggtcaata 6061 aagcatctta tgatactaat cttaataagt tcaatagagc tagtttgcgt caaattttg 6121 acgtagcccc cattgaactc gaaaataaat tcacaccttt gagtgtggag tctacaccag
```

-continued

```
6181  ttgaacctcc aactgtagat gtggtagcac ttcaacagga aatgacaatt gtcaaatgta
6241  agggtttaaa taaacctttc gtgaaggaca atgtcagttt cgttgctgat gattcaggta
6301  ctcccgttgt tgagtatctg tctaaagaag acctacatac attgtatgta gaccctaagt
6361  atcaagtcat tgtcttaaaa gacaatgtac tttcttctat gcttagattg cacaccgttg
6421  agtcaggtga tattaacgtt gttgcagctt ccggatcttt gacacgtaaa gtgaagttac
6481  tatttagggc ttcatttat ttcaaagaat ttgctacccg cactttcact gctaccactg
6541  ctgtaggtag ttgtataaag agtgtagtgc ggcatctagg tgttactaaa ggcatattga
6601  caggctgttt tagttttgcc aagatgttat ttatgcttcc actagcttac tttagtgatt
6661  caaaactcgg caccacagag gttaaagtga gtgctttgaa acagccggc gttgtgacag
6721  gtaatgttgt aaaacagtgt tgcactgctg ctgttgattt aagtatggaa aagttgcgcc
6781  gtgtggattg gaaatcaacc ctacggttgt tacttatgtt atgcacaact atggtattgt
6841  tgtcttctgt gtatcacttg tatgtcttca atcaggtctt atcaagtgat gttatgtttg
6901  aagatgccca aggtttgaaa aagttctaca agaagttag agcttaccta ggaatctctt
6961  ctgcttgtga cggtcttgct tcagcttata gggcgaattc ctttgatgta cctacattct
7021  gcgcaaaccg ttctgcaatg tgtaattggt gcttgattag ccaagattcc ataactcact
7081  acccagctct taagatggtt caaacacatc ttagccacta tgttcttaac atagattggt
7141  tgtggtttgc atttgagact ggtttggcat acatgctcta tacctcggcc ttcaactggt
7201  tgttgttggc aggtacattg cattatttct ttgcacagac ttccatattt gtagactggc
7261  ggtcatacaa ttatgctgtg tctagtgcct tctggttatt cacccacatt ccaatggcgg
7321  gtttggtacg aatgtataat ttgttagcat gcctttggct tttacgcaag ttttatcagc
7381  atgtaatcaa tggttgcaaa gatacggcat gcttgctctg ctataagagg aaccgactta
7441  ctagagttga agcttctacc gttgtctgtg gtggaaaacg tacgttttat atcacagcaa
7501  atggcggtat ttcattctgt cgtaggcata attggaattg tgtggattgt gacactgcag
7561  gtgtggggaa taccttcatc tgtgaagaag tcgcaaatga cctcactacc gccctacgca
7621  ggcctattaa cgctacggat agatcacatt attatgtgga ttccgttaca gttaaagaga
7681  ctgttgttca gtttaattat cgtagagacg gtcaaccatt ctacgagcgg tttccctct
7741  gcgctttac aaatctagat aagttgaagt tcaaagaggt ctgtaaaact actactggta
7801  tacctgaata caactttatc atctacgact catcagatcg tggccaggaa agtttagcta
7861  ggtctgcatg tgtttattat tctcaagtct tgtgtaaatc aattcttttg gttgactcaa
7921  gtttggttac ttctgttggt gattctagtg aaatcgccac taaaatgttt gattcctttg
7981  ttaatagttt cgtctcgctg tataatgtca cacgcgataa gttggaaaaa cttatctcta
8041  ctgctcgtga tggcgtaagg cgaggcgata acttccatag tgtcttaaca acattcattg
8101  acgcagcacg aggccccgca ggtgtggagt ctgatgttga gaccaatgaa attgttgact
8161  ctgtgcagta tgctcataaa catgacatac aaattactaa tgagagctac aataattatg
8221  taccctcata tgttaaacct gatagtgtgt ctaccagcga tttaggtagt ctcattgatt
8281  gtaatgcggc ttcagttaac caaattgtct tgcgtaattc taatggtgct tgcatttgga
8341  acgctgctgc atatatgaaa ctctcggatg cacttaaacg acagattcgc attgcatgcc
8401  gtaagtgtaa tttagctttc cggttaacca cctcaaagct acgcgctaat gataatatct
8461  tatcagttag attcactgct aacaaaattg ttggtggtgc tcctacatgg tttaatgcgt
8521  tgcgtgactt tacgttaaag ggttatgttc ttgctaccat tattgtgttt ctgtgtgctg
```

-continued

```
8581  tactgatgta tttgtgttta cctacatttt ctatggcacc tgttgaattt tatgaagacc
8641  gcatcttgga ctttaaagtt cttgataatg gtatcattag ggatgtaaat cctgatgata
8701  agtgctttgc taataagcac cggtccttca cacaatggta tcatgagcat gttggtggtg
8761  tctatgacaa ctctatcaca tgcccattga cagttgcagt aattgctgga gttgctggtg
8821  ctcgcattcc agacgtacct actacattgg cttgggtgaa caatcagata attttctttg
8881  tttctcgagt cttttgctaat acaggcagtg tttgctacac tcctatagat gagatacact
8941  ataagagttt ctctgatagt ggttgcattc ttccatctga gtgcactatg tttagggatg
9001  cagagggccg tatgacacca tactgccatg atcctactgt tttgcctggg gcttttgcgt
9061  acagtcagat gaggcctcat gttcgttacg acttgtatga tggtaacatg tttattaaat
9121  ttcctgaagt agtatttgaa agtacactta ggattactag aactctgtca actcagtact
9181  gccggttcgg tagttgtgag tatgcacaag agggtgtttg tattaccaca aatggctcgt
9241  gggccatttt taatgaccac catcttaata gacctggtgt ctattgtggc tctgatttta
9301  ttgacattgt caggcggtta gcagtatcac tgttccagcc tattacttat ttccaattga
9361  ctacctcatt ggtcttgggt ataggtttgt gtgcgttcct gactttgctc ttctattata
9421  ttaataaagt aaaacgtgct tttgcagatt acacccagtg tgctgtaatt gctgttgttg
9481  ctgctgttct taatagcttg tgcatctgct ttgttacctc tataccattg tgtatagtac
9541  cttacactgc attgtactat tatgctacat tctattttac taatgagcct gcatttatta
9601  tgcatgtttc ttggtacatt atgttcgggc ctatcgttcc catatggatg acctgcgtct
9661  atacagttgc aatgtgcttt agacacttct tctgggtttt agcttatttt agtaagaaac
9721  atgtagaagt ttttactgat ggtaagctta attgtagttt ccaggacgct gcctctaata
9781  tctttgttat taacaaggac acttatgcag ctcttagaaa ctctttaact aatgatgcct
9841  attcacgatt tttggggttg tttaacaagt ataagtactt ctctggtgct atggaaacag
9901  ccgcttatcg tgaagctgca gcatgtcatc ttgctaaagc cttacaaaca tacagcgaga
9961  ctggtagtga tcttcttttac caaccaccca actgtagcat aacctctggc gtgttgcaaa
10021 gcggtttggt gaaaatgtca catcccagtg gagatgttga ggcttgtatg gttcaggtta
10081 cctgcggtag catgactctt aatggtcttt ggcttgacaa cacagtctgg tgcccacgac
10141 acgtaatgtg cccggctgac cagttgtctg atcctaatta tgatgccttg ttgatttcta
10201 tgactaatca tagtttcagt gtgcaaaaac acattggcgc tccagcaaac ttgcgtgttg
10261 ttggtcatgc catgcaaggc actcttttga gttgactgt cgatgttgct aaccctagca
10321 ctccagccta cacttttaca acagtgaaac ctggcgcagc atttagtgtg ttagcatgct
10381 ataatggtcg tccgactggt acattcactg ttgtaatgcg ccctaactac acaattaagg
10441 gttcctttct gtgtggttct tgtggtagtg ttggttacac caaggagggt agtgtgatca
10501 atttctgtta catgcatcaa atggaacttg ctaatggtac acataccggt tcagcatttg
10561 atggtactat gtatggtgcc tttatggata acaagtgca ccaagttcag ttaacagaca
10621 aatactgcag tgttaatgta gtagcttggc tttacgcagc aatacttaat ggttgcgctt
10681 ggtttgtaaa acctaatcgc actagtgttg tttctttta tgaatgggct cttgccaacc
10741 aattcactga atttgttggc actcaatccg ttgacatgtt agctgtcaaa acaggcgttg
10801 ctattgaaca gctgctttat gcgatccaac aactgtatac tgggttccag ggaaagcaaa
10861 tccttggcag taccatgttg gaagatgaat tcacacctga ggatgttaat atgcagatta
10921 tgggtgtggt tatgcagagt ggtgtgagaa aagttacata tggtactgcg cattggttgt
10981 ttgcgaccct tgtctcaacc tatgtgataa tcttacaagc cactaaattt actttgtgga
```

```
11041 actacttgtt tgagactatt cccacacagt tgttcccact cttatttgtg actatggcct
11101 tcgttatgtt gttggttaaa cacaaacaca cctttttgac acttttcttg ttgcctgtgg
11161 ctatttgttt gacttatgca aacatagtct acgagcccac tactcccatt tcgtcagcgc
11221 tgattgcagt tgcaaattgg cttgccccca ctaatgctta tatgcgcact acacatactg
11281 atattggtgt ctacattagt atgtcacttg tattagtcat tgtagtgaag agattgtaca
11341 acccatcact ttctaacttt gcgttagcat tgtgcagtgg tgtaatgtgg ttgtacactt
11401 atagcattgg agaagcctca agccccattg cctatctggt ttttgtcact acactcacta
11461 gtgattatac gattacagtc tttgttactg tcaaccttgc aaaagtttgc acttatgcca
11521 tctttgctta ctcaccacag cttacacttg tgtttccgga agtgaagatg atactttat
11581 tatacacatg tttaggtttc atgtgtactt gctattttgg tgtcttctct cttttgaacc
11641 ttaagcttag agcacctatg ggtgtctatg actttaaggt ctcaacacaa gagttcagat
11701 tcatgactgc taacaatcta actgcaccta gaaattcttg ggaggctatg gctctgaact
11761 ttaagttaat aggtattggc ggtacacctt gtataaaggt tgctgctatg cagtctaaac
11821 ttacagatct taaatgcaca tctgtggttc tcctctctgt gctccaacag ttacacttag
11881 aggctaatag tagggcctgg gctttctgtg ttaaatgcca taatgatata ttggcagcaa
11941 cagacccag tgaggctttc gagaaattcg taagtctctt tgctactta atgactttt
12001 ctggtaatgt agatcttgat gcgttagcta gtgatatttt tgacactcct agcgtacttc
12061 aagctactct ttctgagttt tcacacttag ctacctttgc tgagttggaa gctgcgcaga
12121 aagcctatca ggaagctatg gactctggtg acacctcacc acaagttctt aaggctttgc
12181 agaaggctgt taatatagct aaaaacgcct atgagaagga taaggcagtg gcccgtaagt
12241 tagaacgtat ggctgatcag gctatgactt ctatgtataa gcaagcacgc gctgaagaca
12301 agaaagcaaa aattgtcagt gctatgcaaa ctatgttgtt tggtatgatt aagaagctcg
12361 acaacgatgt tcttaatggt atcatttcta acgctaggaa tggttgtata cctcttagtg
12421 tcatcccact gtgtgcttca aataaacttc gcgttgtaat tcctgacttc accgtctgga
12481 atcaggtagt cacatatccc tcgcttaact acgctggggc tttgtgggac attacagtta
12541 taaacaatgt ggacaatgaa attgttaagt cttcagatgt tgtagacagc aatgaaaatt
12601 taacatggcc acttgtttta gaatgcacta gggcatccac ttctgccgtt aagttgcaaa
12661 ataatgagat caaaccttca ggtctaaaaa ccatggttgt gtctgcgggt caagagcaaa
12721 ctaactgtaa tactagttcc ttagcttatt acgaacctgt gcagggtcgt aaaatgctga
12781 tggctcttct ttctgataat gcctatctca atgggcgcg tgttgaaggt aaggacggat
12841 ttgtcagtgt agagctacaa cctccttgca aattcttgat tgcgggacca aaaggacctg
12901 aaatccgata tctctatttt gttaaaaatc ttaacaacct tcatcgcggg caagtgttag
12961 ggcacattgc tgcgactgtt agattgcaag ctggttctaa caccgagttt gcctctaatt
13021 cctcggtgtt gtcacttgtt aacttcaccg ttgatcctca aaaagcttat ctcgatttcg
13081 tcaatgcggg aggtgcccca ttgacaaatt gtgttaagat gcttactcct aaaactggta
13141 caggtatagc tatatctgtt aaaccagaga gtacagctga tcaagagact tatggtggag
13201 cttcagtgtg tctctattgc cgtgcgcata tagaacatcc tgatgtctct ggtgtttgta
13261 aatataaggg taagtttgtc caaatccctg ctcagtgtgt ccgtgaccct gtgggatttt
13321 gtttgtcaaa taccccctgt aatgtctgtc aatattggat tggatatggg tgcaattgtg
13381 actcgcttag gcaagcagca ctgccccaat ctaaagattc caattttta aacgagtccg
```

-continued

```
13441 gggttctatt gtaaatgccc gaatagaacc ctgttcaagt ggtttgtcca ctgatgtcgt 13501 ctttagggca tttgacatct gcaactataa ggctaaggtt gctggtattg gaaaatacta 13561 caagactaat acttgtaggt ttgtagaatt agatgaccaa gggcatcatt tagactccta 13621 ttttgtcgtt aagaggcata ctatggagaa ttatgaacta gagaagcact gttacgactt 13681 gttacgtgac tgtgatgctg tagctcccca tgatttcttc atctttgatg tagacaaagt 13741 taaaacacct catattgtac gtcagcgttt aactgagtac actatgatgg atcttgtata 13801 tgccctgagg cactttgatc aaaatagcga agtgcttaag gctatcttag tgaagtatgg 13861 ttgctgtgat gttacctact ttgaaaataa actctggttt gattttgttg aaaatcccag 13921 tgttattggt gtttatcata aacttggaga acgtgtacgc caagctatct taaacactgt 13981 taaattttgt gaccacatgg tcaaggctgg tttagtcggt gtgctcacac tagacaacca 14041 ggaccttaat ggcaagtggt atgattttgg tgacttcgta atcactcaac ctggttcagg 14101 agtagctata gttgatagct actattctta tttgatgcct gtgctctcaa tgaccgattg 14161 tctggccgct gagacacata gggattgtga ttttaataaa ccactcattg agtggccact 14221 tactgagtat gattttactg attataaggt acaactcttt gagaagtact ttaaatattg 14281 ggatcagacg tatcacgcaa attgcgttaa ttgtactgat gaccgttgtg tgttacattg 14341 tgctaatttc aatgtattgt ttgctatgac catgcctaag acttgtttcg gacccatagt 14401 ccgaaagatc tttgttgatg gcgtgccatt tgtagtatct tgtggttatc actacaaaga 14461 attaggttta gtcatgaata tggatgttag tctccataga cataggctct ctcttaagga 14521 gttgatgatg tatgccgctg atccagccat gcacattgcc tcctctaacg ctttttcttga 14581 tttgaggaca tcatgtttta gtgtcgctgc acttacaact ggtttgactt tcaaactgt 14641 gcggcctggc aattttaacc aagacttcta tgatttcgtg tatctaaag gtttctttaa 14701 ggagggctct tcagtgacgc tcaaacattt tttctttgct caagatggta atgctgctat 14761 tacagattat aattactatt cttataatct gcctactatg tgtgacatca acaaatgtt 14821 gttctgcatg gaagttgtaa acaagtactt cgaaatctat gacggtggtt gtcttaatgc 14881 ttctgaagtg gttgttaata atttagacaa gagtgctggc catccttta ataagtttgg 14941 caaagctcgt gtctattatg agagcatgtc ttaccaggag caagatgaac ttttttgccat 15001 gacaaagcgt aacgtcattc ctaccatgac tcaaatgaat ctaaaatatg ctattagtgc 15061 taagaataga gctcgcactg ttgcaggcgt gtccatactt agcacaatga ctaatcgcca 15121 gtaccatcag aaaatgctta agtccatggc tgcaactcgt ggagcgactt gcgtcattgg 15181 tactacaaag ttctacggtg gctgggattt catgcttaaa acattgtaca aagatgttga 15241 taatccgcat cttatgggtt gggattaccc taagtgtgat agagctatgc ctaatatgtg 15301 tagaatcttc gcttcactca tattagctcg taaacatggc acttgttgta ctacaaggga 15361 cagattttat cgcttggcaa atgagtgtgc tcaggtgcta agcgaatatg ttctatgtgg 15421 tggtggttac tacgtcaaac ctggaggtac cagtagcgga gatgccacca ctgcatatgc 15481 caatagtgtc tttaacattt tgcaggcgac aactgctaat gtcagtgcac ttatgggtgc 15541 taatggcaac aagattgttg acaaagaagt taaagacatg cagtttgatt gtatgtcaa 15601 tgtttacagg agcactagcc cagaccccaa atttgttgat aaatactatg cttttcttaa 15661 taagcacttt tctatgatga tactgtctga tgacggtgtc gtttgctata atagtgatta 15721 tgcagctaag ggttacattg ctggaataca gaattttaag gaaacgctgt attatcagaa 15781 caatgtcttt atgtctgaag ctaaatgctg ggtggaaacc gatctgaaga agggccaca 15841 tgaattctgt tcacagcata cgctttatat taaggatggc gacgatggtt acttccttcc
```

```
15901 ttatccagac ccttcaagaa ttttgtctgc cggttgcttt gtagatgata tcgttaagac
15961 tgacggtaca ctcatggtag agcggtttgt gtctttggct atagatgctt accctctcac
16021 aaagcatgaa gatatagaat accagaatgt attctgggtc tacttacagt atatagaaaa
16081 actgtataaa gaccttacag gacacatgct tgacagttat tctgtcatgc tatgtggtga
16141 taattctgct aagttttggg aagaggcatt ctatagagat ctctatagtt cgcctaccac
16201 tttgcaggct gtcggttcat gcgttgtatg ccattcacag acttccctac gctgtgggac
16261 atgcatccgt agaccatttc tctgctgtaa atgctgctat gatcatgtta tagcaactcc
16321 acataagatg gttttgtctg tttctcctta cgtttgtaat gccctggtt gtggcgtttc
16381 agacgttact aagctatatt taggtggtat gagctacttt tgtgtagatc atagacctgt
16441 gtgtagtttt ccactttgcg ctaatggtct tgtattcggc ttatacaaga atatgtgcac
16501 aggtagtcct tctatagttg aatttaatag gttggctacc tgtgactgga ctgaaagtgg
16561 tgattacacc cttgccaata ctacaacaga accactcaaa cttttttgctg ctgagacttt
16621 acgtgccact gaagaggcgt ctaagcagtc ttatgctatt gccaccatca agaaaattgt
16681 tggtgagcgc caactattac ttgtgtggga ggctggcaag tccaaaccac cactcaatcg
16741 taattatgtt tttactggtt atcatataac caaaaatagt aaagtgcagc tcggtgagta
16801 catttttcgag cgcattgatt atagtgatgc tgtatcctac aagtctagta caacgtataa
16861 actgactgta ggtgacatct tcgtacttac ctctcactct gtggctacct tgacggcgcc
16921 cacaattgtg aatcaagaga ggtatgttaa aattactggg ttgtacccaa ccattacggt
16981 acctgaagag ttcgcaagtc atgttgccaa cttccaaaaa tcaggttata gtaaatatgt
17041 cactgttcag ggaccacctg gcactggcaa aagtcatttt gctatagggt tagcgattta
17101 ctaccctaca gcacgtgttg tttatacagc atgttcacac gcagctgttg atgctttgtg
17161 tgaaaaagct tttaaatatt tgaacattgc taaatgttcc cgtatcattc ctgcaaaggc
17221 acgtgttgag tgctatgaca ggtttaaagt taatgagaca aattctcaat atttgtttag
17281 tactattaat gctctaccag aaacttctgc cgatattctg tgggttgatg aggttagtat
17341 gtgcactaat tatgatcttt caattattaa tgcacgtatt aaagctaagc acattgtcta
17401 tgtaggagat ccagcacagt tgccagctcc taggactttg ttgactagag gcacattgga
17461 accagaaaat ttcaatagtc tcactagatt gatgtgtaac ttaggtcctg acatatttt
17521 aagtatgtgc tacaggtgtc ctaaggaaat agtaagcact gtgagcgctc ttgtctacaa
17581 taataaattg ttagccaaga aggagctttc aggccagtgc tttaaaatac tctataaggg
17641 caatgtgacg catgatgcta gctctgccat taatagacca caactcacat ttgtgaagaa
17701 ttttattact gccaatccgg catggagtaa ggcagtcttt atttcgcctt acaattcaca
17761 gaatgctgtg tctcgttcaa tgctgggtct taccactcag actgttgatt cctcacaggg
17821 ttcagaatac cagtacgtta tcttctgtca acagcagat acggcacatg ctaacaacat
17881 taacagattt aatgttgcaa tcactcgtgc ccaaaaaggt attctttgtg ttatgacatc
17941 tcaggcactc tttgagtcct tagagtttac tgaattgtct tttactaatt acaagctcca
18001 gtctcagatt gtaactggcc tttttaaaga ttgctctaga gaaacttctg gcctctcacc
18061 tgcttatgca ccaacatatg ttagtgttga tgacaagtat aagacgagtg atgagctttg
18121 cgtgaatctt aatttacccg caaatgtccc atactctcgt gttatttcca ggatgggctt
18181 taaactcgat gcaacagttc ctggatatcc taagcttttc attactcgtg aagaggctgt
18241 aaggcaagtt cgaagctgga taggcttcga tgttgagggt gctcatgctt cccgtaatgc
```

-continued

```
18301 atgtggcacc aatgtgcctc tacaattagg attttcaact ggtgtgaact ttgttgttca 18361 gccagttggt gttgtagaca ctgagtgggg taacatgtta acgggcattg ctgcacgtcc 18421 tccaccaggt gaacagttta agcacctcgt gcctcttatg cataagggg ctgcgtggcc 18481 tattgttaga cgacgtatag tgcaaatgtt gtcagacact ttagacaaat tgtctgatta 18541 ctgtacgttt gtttgttggg ctcatggctt tgaattaacg tctgcatcat acttttgcaa 18601 gataggtaag gaacagaagt gttgcatgtg caatagacgc gctgcagcgt actcttcacc 18661 tctgcaatct tatgcctgct ggactcattc ctgcggttat gattatgtct acaacccttt 18721 cttttgtcgat gttcaacagt ggggttatgt aggcaatctt gctactaatc acgatcgtta 18781 ttgctctgtc catcaaggag ctcatgtggc ttctaatgat gcaataatga ctcgttgttt 18841 agctattcat tcttgtttta tagaacgtgt ggattgggat atagagtatc cttatatctc 18901 acatgaaaag aaattgaatt cctgttgtag aatcgttgag cgcaacgtcg tacgtgctgc 18961 tcttcttgcc ggttcatttg acaaagtcta tgatattggc aatcctaaag gaattcctat 19021 tgttgatgac cctgtggttg attggcatta ttttgatgca cagcccttga ccaggaaggt 19081 acaacagctt ttctatacag aggacatggc ctcaagattt gctgatgggc tctgcttatt 19141 ttggaactgt aatgtaccaa aatatcctaa taatgcaatt gtatgcaggt ttgacacacg 19201 tgtgcattct gagttcaatt tgccaggttg tgatggcggt agtttgtatg ttaacaagca 19261 cgcttttcat acaccagcat atgatgtgag tgcattccgt gatctgaaac ctttaccatt 19321 cttttattat tctactacac catgtgaagt gcatggtaat ggtagtatga tagaggatat 19381 tgattatgta cccctaaaat ctgcagtctg tattacagct tgtaatttag ggggcgctgt 19441 ttgtaggaag catgctacag agtacagaga gtatatggaa gcatataatc ttgtctctgc 19501 atcaggtttc cgcctttggt gttataagac cttttgatatt tataatctct ggtctacttt 19561 tacaaaagtt caaggtttgg aaaacattgc ttttaatgtt gttaaacaag gccatttat 19621 tggtgttgag ggtgaactac ctgtagctgt agtcaatgat aagatcttca ccaagagtgg 19681 cgttaatgac atttgtatgt ttgagaataa aaccactttg cctactaata tagcttttga 19741 actctatgct aagcgtgctg tacgctcgca tcccgatttc aaattgctac acaatttaca 19801 agcagacatt tgctacaagt tcgtcctttg ggattatgaa cgtagcaata tttatggtac 19861 tgctactatt ggtgtatgta gtacactga tattgatgtt aattcagctt tgaatatatg 19921 ttttgacata cgcgataatt gttcattgga gaagttcatg tctactccca atgccatctt 19981 tatttctgat agaaaaatca agaaataccc ttgtatggta ggtcctgatt atgcttactt 20041 caatggtgct atcatccgtg atagtgatgt tgttaaacaa ccagtgaagt tctacttgta 20101 taagaaagtc aataatgagt ttattgatcc tactgagtgt atttacactc agtcgctc 20161 ttgtagtgac ttcctacccc tttctgacat ggagaaagac tttctatctt ttgatagtga 20221 tgtttttcatt aagaagtatg gcttggaaaa ctatgctttt gagcacgtag tctatggaga 20281 cttctctcat actacgttag gcggtcttca cttgcttatt ggtttataca agaagcaaca 20341 ggaaggtcat attattatgg aagaaatgct aaaaggtagc tcaactattc ataactattt 20401 tattactgag actaacacag cggcttttaa ggcggtgtgt tctgttatag atttaaagct 20461 tgacgacttt gttatgattt taaagagtca agaccttggc gtagtatcca aggttgtcaa 20521 ggttcctatt gacttaacaa tgattgagtt tatgttatgg tgtaaggatg acaggttca 20581 aaccttctac cctcgactcc aggcttctgc agattggaaa cctggtcatg caatgccatc 20641 cctctttaaa gttcaaaatg taaaccttga acgttgtgag cttgctaatt acaagcaatc 20701 tattcctatg cctcgcggtg tgcacatgaa catcgctaaa tatatgcaat tgtgccagta
```

-continued

```
20761 tttaaatact tgcacattag ccgtgcctgc caatatgcgt gttatacatt ttggcgctgg
20821 ttctgataaa ggtatcgctc ctggtacctc agttttacga cagtggcttc ctacagatgc
20881 cattattata gataatgatt taaatgagtt cgtgtcagat gctgacataa ctttatttgg
20941 agattgtgta actgtacgtg tcggccaaca agtggatctt gttatttccg acatgtatga
21001 tcctactact aagaatgtaa caggtagtaa tgagtcaaag gctttattct ttacttacct
21061 gtgtaacctc attaataata atcttgctct tggtgggtct gttgctatta aaataacaga
21121 acactcttgg agcgttgaac tttatgaact tatgggaaaa tttgcttggt ggactgtttt
21181 ctgcaccaat gcaaatgcat cctcatctga aggattcctc ttaggtatta attacttggg
21241 tactattaaa gaaaatatag atggtggtgc tatgcacgcc aactatatat tttggagaaa
21301 ttccactcct atgaatctga gtacttactc acttttgat ttatccaagt ttcaattaaa
21361 attaaaagga acaccagttc ttcaattaaa ggagagtcaa attaacgaac tcgtaatatc
21421 tctcctgtcg cagggtaagt tacttatccg tgacaatgat acactcagtg tttctactga
21481 tgttcttgtt aacacctaca gaaagttacg ttgatgtagg gccagattct gttaagtctg
21541 cttgtattga ggttgatata caacagactt tctttgataa aacttggcct aggccaattg
21601 atgtttctaa ggctgacggt attatatacc ctcaaggccg tacatattct aacataacta
21661 tcacttatca aggtcttttt ccctatcagg agaccatgg tgatatgtat gtttactctg
21721 caggacatgc tacaggcaca actccacaaa agttgtttgt agctaactat tctcaggacg
21781 tcaaacagtt tgctaatggg tttgtcgtcc gtataggagc agctgccaat tccactggca
21841 ctgttattat tagcccatct accagcgcta ctatacgaaa aatttaccct gcttttatgc
21901 tgggttcttc agttggtaat ttctcagatg gtaaaatggg ccgcttcttc aatcatactc
21961 tagttctttt gcccgatgga tgtggcactt tacttagagc tttttattgt attctagagc
22021 ctcgctctgg aaatcattgt cctgctggca attcctatac ttcttttgcc acttatcaca
22081 ctcctgcaac agattgttct gatggcaatt acaatcgtaa tgccagtctg aactcttta
22141 aggagtattt taatttacgt aactgcacct ttatgtacac ttataacatt accgaagatg
22201 agattttaga gtggtttggc attacacaaa ctgctcaagg tgttcacctc ttctcatctc
22261 ggtatgttga tttgtacggc ggcaatatgt ttcaatttgc caccttgcct gtttatgata
22321 ctattaagta ttattctatc attcctcaca gtattcgttc tatccaaagt gatagaaaag
22381 cttgggctgc cttctacgta tataaacttc aaccgttaac tttcctgttg gatttttctg
22441 ttgatggtta tacgcagca gctatagact gtggttttaa tgatttgtca caactccact
22501 gctcatatga atccttcgat gttgaatctg gagtttattc agtttcgtct ttcgaagcaa
22561 aaccttctgg ctcagttgtg aacaggctg aaggtgttga atgtgatttt tcacctcttc
22621 tgtctggcac acctcctcag gtttataatt tcaagcgttt ggttttacc aattgcaatt
22681 ataatcttac caaattgctt cactttttt ctgtgaatga ttttacttgt agtcaaatat
22741 ctccagcagc aattgctagc aactgttatt cttcactgat tttggattac ttttcatacc
22801 cacttagtat gaaatccgat ctcagtgtta gttctgctgg tccaatatcc cagtttaatt
22861 ataaacagtc ttttctaat cccacatgtt tgattttagc gactgttcct cataaccta
22921 ctactattac taagcctctt aagtacagct atattaacaa gtgctctcgt cttctttctg
22981 atgatcgtac tgaagtacct cagttagtga acgctaatca atactcaccc tgtgtatcca
23041 ttgtcccatc cactgtgtgg gaagacggtg attattatag gaaacaacta tctccacttg
23101 aaggtggtgg ctggcttgtt gctagtggct caactgttgc catgactgag caattacaga
```

-continued

```
23161 tgggctttgg tattacagtt caatatggta cagacaccaa tagtgtttgc cccaagcttg 23221 aatttgctaa tgacacaaaa attgcctctc aattaggcaa ttgcgtggaa tattccctct 23281 atggtgtttc gggccgtggt gttttcaga attgcacagc tgtaggtgtt cgacagcagc 23341 gctttgttta tgatgcgtac cagaatttag ttggctatta ttctgatgat ggcaactact 23401 actgtttgcg tgcttgtgtt agtgttcctg tttctgtcat ctatgataaa gaaactaaaa 23461 cccacgctac tctatttggt agtgttgcat gtgaacacat ttcttctacc atgtctcaat 23521 actcccgttc tacgcgatca atgcttaaac ggcgagattc tacatatggc cccttcaga 23581 cacctgttgg ttgtgtccta ggacttgtta attcctcttt gttcgtagag gactgcaagt 23641 tgcctcttgg tcaatctctc tgtgctcttc ctgacacacc tagtactctc acacctcgca 23701 gtgtgcgctc tgttccaggt gaaatgcgct tggcatccat tgcttttaat catcctattc 23761 aggttgatca acttaatagt agttatttta aattaagtat acccactaat ttttcctttg 23821 gtgtgactca ggagtacatt cagacaacca ttcagaaagt tactgttgat tgtaaacagt 23881 acgtttgcaa tggtttccag aagtgtgagc aattactgcg cgagtatggc cagttttgtt 23941 ccaaaataaa ccaggctctc catggtgcca atttacgcca ggatgattct gtacgtaatt 24001 tgtttgcgag cgtgaaaagc tctcaatcat ctcctatcat accaggtttt ggaggtgact 24061 ttaatttgac acttctagaa cctgtttcta tatctactgg cagtcgtagt gcacgtagtg 24121 ctattgagga tttgctattt gacaaagtca ctatagctga tcctggttat atgcaaggtt 24181 acgatgattg catgcagcaa ggtccagcat cagctcgtga tcttatttgt gctcaatatg 24241 tggctggtta caaagtatta cctcctctta tggatgttaa tatggaagcc gcgtatactt 24301 catctttgct tggcagcata gcaggtgttg gctggactgc tggcttatcc tcctttgctg 24361 ctattccatt tgcacagagt atcttttata ggttaaacgg tgttggcatt actcaacagg 24421 ttctttcaga gaaccaaaag cttattgcca ataagtttaa tcaggctctg ggagctatgc 24481 aaacaggctt cactacaact aatgaagctt ttcagaaggt tcaggatgct gtgaacaaca 24541 atgcacaggc tctatccaaa ttagctagcg agctatctaa tacttttggt gctatttccg 24601 cctctattgg agacatcata caacgtcttg atgttctcga acaggacgcc caaatagaca 24661 gacttattaa tggccgtttg acaacactaa atgcttttgt tgcacagcag cttgttcgtt 24721 ccgaatcagc tgctctttcc gctcaattgg ctaaagataa agtcaatgag tgtgtcaagg 24781 cacaatccaa gcgttctgga ttttgcggtc aaggcacaca tatagtgtcc tttgttgtaa 24841 atgcccctaa tggcctttac ttcatgcatg ttggttatta ccctagcaac cacattgagg 24901 ttgtttctgc ttatggtctt tgcgatgcag ctaaccctac taattgtata gcccctgtta 24961 atggctactt tattaaaact aataacacta ggattgttga tgagtggtca tatactggct 25021 cgtccttcta tgcacctgag cccattacct cccttaatac taagtatgtt gcaccacagg 25081 tgacatacca aaacatttct actaacctcc ctcctcctct tctcggcaat tccacgggga 25141 ttgacttcca agatgagttg gatgagtttt tcaaaaatgt tagcaccagt atacctaatt 25201 ttggttccct aacacagatt aatactacat tactcgatct tacctacgag atgttgtctc 25261 ttcaacaagt tgttaaagcc cttaatgagt cttacataga ccttaaagag cttggcaatt 25321 atacttatta caacaaatgg ccgtggtaca tttggcttgg tttcattgct gggcttgttg 25381 ccttagctct atgcgtcttc ttcatactgt gctgcactgg ttgtggcaca aactgtatgg 25441 gaaaacttaa gtgtaatcgt tgttgtgata gatacgagga atacgacctc gagccgcata 25501 aggttcatgt tcactaatta acgaactatt aatgagagtt caaagaccac ccactctctt 25561 gttagtgttt tcactctctc ttttggtcac tgcatcctca aaacctctct atgtacctga
```

```
25621 gcattgtcag aattattctg gttgcatgct tagggcttgt attaaaactg cccaagctga
25681 tacagctggt ctttatacaa attttcgaat tgacgtccca tctgcagaat caactggtac
25741 tcaatcagtt tctgtcgatc ttgagtcaac ttcaactcat gatggtccta ccgaacatgt
25801 tactagtgtg aatcttttg acgttggtta ctcagttaat taacgaactc tatggattac
25861 gtgtctctgc ttaatcaaat ttggcagaag taccttaact caccgtatac tacttgtttg
25921 tacatcccta aacccacagc taagtataca cctttagttg gcacttcatt gcaccctgtg
25981 ctgtggaact gtcagctatc ctttgctggt tatactgaat ctgctgttaa ttctacaaaa
26041 gctttggcca aacaggacgc agctcagcga atcgcttggt tgctacataa ggatggagga
26101 atccctgatg gatgttccct ctacctccgg cactcaagtt tattcgcgca aagcgaggaa
26161 gaggagccat tctccaacta agaaactgcg ctacgttaag cgtagatttt ctcttctgcg
26221 ccatgaagac cttagtgtta ttgtccaacc aacacactat gtcagggtta catttttcaga
26281 ccccaacatg tggtatctac gttcgggtca tcatttacac tcagttcaca attggcttaa
26341 accttatggc ggccaacctg tttctgagta ccatattact ctagctttgc taaatctcac
26401 tgatgaagat ttagctagag attttcacc cattgcgctc ttttgcgca atgtcagatt
26461 tgagctacat gagttcgcct tgctgcgcaa aactcttgtt cttaatgcat cagagatcta
26521 ctgtgctaac atacatagat ttaagcctgt gtatagagtt aacacggcaa tccctactat
26581 taaggattgg cttctcgttc agggattttc cctttaccat agtggcctcc ctttacatat
26641 gtcaatctct aaattgcatg cactggatga tgttactcgc aattacatca ttacaatgcc
26701 atgctttaga acttaccctc aacaaatgtt tgttactcct ttggccgtag atgttgtctc
26761 catacggtct tccaatcagg gtaataaaca aattgttcat tcttatccca ttttacatca
26821 tccaggattt taacgaacta tggctttctc ggcgtcttta tttaaacccg tccagctagt
26881 cccagtttct cctgcatttc atcgcattga gtctactgac tctattgttt tcacatacat
26941 tcctgctagc ggctatgtag ctgctttagc tgtcaatgtg tgtctcattc cctattatt
27001 actgctacgt caagatactt gtcgtcgcag cattatcaga actatggttc tctatttcct
27061 tgttctgtat aacttttat tagccattgt actagtcaat ggtgtacatt atccaactgg
27121 aagttgcctg atagccttct tagttatcct cataatactt tggtttgtag atagaattcg
27181 tttctgtctc atgctgaatt cctacattcc actgtttgac atgcgttccc actttattcg
27241 tgttagtaca gtttcttctc atggtatggt ccctgtaata cacaccaaac cattatttat
27301 tagaaacttc gatcagcgtt gcagctgttc tcgttgtttt tatttgcact cttccactta
27361 tatagagtgc acttatatta gccgttttag taagattagc ctagtttctg taactgactt
27421 ctccttaaac ggcaatgttt ccactgtttt cgtgcctgca acgcgcgatt cagttcctct
27481 tcacataatc gccccgagct cgcttatcgt ttaagcagct ctgcgctact atgggtcccg
27541 tgtagaggct aatccattag tctctctttg gacatatgga aaacgaacta tgttaccctt
27601 tgtccaagaa cgaatagggt tgttcatagt aaactttttc attttaccg tagtatgtgc
27661 tataacactc ttggtgtgta tggctttcct tacggctact agattatgtg tgcaatgtat
27721 gacaggcttc aatacctgt tagttcagcc cgcattatac ttgtataata ctggacgttc
27781 agtctatgta aaattccagg atagtaaacc ccctctacca cctgacgagt gggtttaacg
27841 aactccttca taatgtctaa tatgacgcaa ctcactgagg cgcagattat tgccattatt
27901 aaagactgga actttgcatg gtccctgatc tttctcttaa ttactatcgt actacagtat
27961 ggatacccat cccgtagtat gactgtctat gtctttaaaa tgtttgtttt atggctccta
```

-continued

```
28021 tggccatctt ccatggcgct atcaatattt agcgccgttt atccaattga tctagcttcc
28081 cagataatct ctggcattgt agcagctgtt tcagctatga tgtggatttc ctactttgtg
28141 cagagtatcc ggctgtttat gagaactgga tcatggtggt cattcaatcc tgagactaat
28201 tgccttttga acgttccatt tggtggtaca actgtcgtac gtccactcgt agaggactct
28261 accagtgtaa ctgctgttgt aaccaatggc cacctcaaaa tggctggcat gcatttcggt
28321 gcttgtgact acgacagact tcctaatgaa gtcaccgtgg ccaaacccaa tgtgctgatt
28381 gctttaaaaa tggtgaagcg gcaaagctac ggaactaatt ccggcgttgc catttaccat
28441 agatataagg caggtaatta caggagtccg cctattacgg cggatattga acttgcattg
28501 cttcgagctt aggctcttta gtaagagtat cttaattgat tttaacgaat ctcaatttca
28561 ttgttatggc atcccctgct gcacctcgtg ctgtttcctt tgccgataac aatgatataa
28621 caaatacaaa cctatctcga ggtagaggac gtaatccaaa accacgagct gcaccaaata
28681 acactgtctc ttggtacact gggcttaccc aacacgggaa agtccctctt acctttccac
28741 ctgggcaggg tgtacctctt aatgccaatt ctacccctgc gcaaaatgct gggtattggc
28801 ggagacagga cagaaaaatt aataccggga atggaattaa gcaactggct cccaggtggt
28861 acttctacta cactggaact ggacccgaag cagcactccc attccgggct gttaaggatg
28921 gcatcgtttg ggtccatgaa gatggcgcca ctgatgctcc ttcaactttt gggacgcgga
28981 accctaacaa tgattcagct attgttacac aattcgcgcc cggtactaag cttcctaaaa
29041 acttccacat tgaggggact ggaggcaata gtcaatcatc ttcaagagcc tctagcttaa
29101 gcagaaactc ttccagatct agttcacaag gttcaagatc aggaaactct acccgcggca
29161 cttctccagg tccatctgga atcggagcag taggaggtga tctactttac cttgatcttc
29221 tgaacagact acaagccctt gagtctggca aagtaaagca atcgcagcca aaagtaatca
29281 ctaagaaaga tgctgctgct gctaaaaata agatgcgcca caagcgcact tccaccaaaa
29341 gtttcaacat ggtgcaagct tttggtcttc gcggaccagg agacctccag ggaaactttg
29401 gtgatcttca attgaataaa ctcggcactg aggacccacg ttggccccaa attgctgagc
29461 ttgctcctac agccagtgct tttatgggta tgtcgcaatt taaacttacc catcagaaca
29521 atgatgatca tggcaaccct gtgtacttcc ttcggtacag tggagccatt aaacttgacc
29581 caaagaatcc caactacaat aagtggttgg agcttcttga gcaaaatatt gatgcctaca
29641 aaaccttccc taagaaggaa aagaaacaaa aggcaccaaa agaagaatca acagaccaaa
29701 tgtctgaacc tccaaaggag cagcgtgtgc aaggtagcat cactcagcgc actcgcaccc
29761 gtccaagtgt tcagcctggt ccaatgattg atgttaacac tgattagtgt cactcaaagt
29821 aacaagatcg cggcaatcgt ttgtgtttgg caaccccatc tcaccatcgc ttgtccactc
29881 ttgcacagaa tggaatcatg ttgtaattac agtgcaataa ggtaattata acccatttaa
29941 ttgatagcta tgctttatta aagtgtgtag ctgtagagag aatgttaaag actgtcacct
30001 ctgcttgatt gcaagtgaac agtgcccccc gggaagagct ctacagtgtg aaatgtaaat
30061 aaaaaatagc tattattcaa ttagattagg ctaattagat gatttgcaaa aaaaaaaaa.
```

The disclosed compositions and methods can be further understood through the following numbered paragraphs.

1. A method of treating a subject for a coronavirus infection comprising administering the subject an effective amount of probenecid, a metabolite or analog thereof, or a pharmaceutically acceptable salt thereof.

2. The method of paragraph 1, wherein the method comprises administering the subject probenecid.

3. The method of paragraphs 1 or 2, wherein the probenecid, metabolite or analog thereof, or pharmaceutically acceptable salt thereof is in a pharmaceutical composition further comprising a pharmaceutically acceptable carrier and/or excipient.

4. The method of any one of paragraphs 1-3, wherein the probenecid, metabolite or analog thereof, or pharmaceutically acceptable salt thereof is administered systemically.

5. The method of any one of paragraphs 1-4, wherein the probenecid, metabolite or analog thereof, or pharmaceutically acceptable salt thereof is administered orally, parenterally, topically or mucosally.

6. The method of any one of paragraphs 1-4, wherein the probenecid, metabolite or analog thereof, or pharmaceutically acceptable salt thereof is administered orally.

7. The method of any one of paragraphs 1-4, wherein the probenecid, metabolite or analog thereof, or pharmaceutically acceptable salt thereof is administered to the lungs (e.g., pulmonary administration).

8. The method of any one of paragraphs 1-4, wherein the probenecid, metabolite or analog thereof, or pharmaceutically acceptable salt thereof is administered intranasally.

9. The method of any one of paragraph 1-8, wherein the probenecid, metabolite or analog thereof, or pharmaceutically acceptable salt thereof is administered in an effective amount to reduce viral replication.

10. The method of any one of paragraph 1-9, wherein the probenecid, metabolite or analog thereof, or pharmaceutically acceptable salt thereof is administered in an effective amount to reduce one or more symptoms of disease, disorder, or illness associated with virus.

11. The method of any one of paragraphs 1-10, wherein the symptoms include fever, congestion in the nasal sinuses and/or lungs, runny or stuffy nose, cough, sneezing, sore throat, body aches, fatigue, shortness of breath, chest tightness, wheezing when exhaling, chills, muscle aches, headache, diarrhea, tiredness, nausea, vomiting, and combinations thereof.

12. The method of any one of paragraphs 1-11, wherein the virus is a Severe acute respiratory syndrome-related coronavirus, a Bat Hp-betacoronavirus Zhejiang2013, a *Rousettus* bat coronavirus GCCDC1, a *Rousettus* bat coronavirus HKU9, a *Eidolon* bat coronavirus C704, a *Pipistrellus* bat coronavirus HKU5, a *Tylonycteris* bar coronovirus HKU4, a Middle East respiratory syndrome-related coronavirus, a Hedgehog coronavirus, a murine coronavirus, a Human coronavirus HKU1, a China *Rattus* coronavirus HKU24, a Betacoronavirus 1, a Myodes coronavirus 2JL14, a Human coronavirus NL63, a Human coronavirus 229E, or a Human coronavirus OC43.

13. The method of paragraph 12, wherein the virus is a Severe acute respiratory syndrome-related coronavirus.

14. The method of paragraph 13, wherein the Severe acute respiratory syndrome-related coronavirus is SARS-CoV-2, SARS-CoV, SARSr-CoV RaTG13, SARS-CoV PC4-227, or SARSr-CoV BtKY72.

15. The method of paragraph 14, wherein the Severe acute respiratory syndrome-related coronavirus is SARS-CoV-2.

16. The method of paragraph 15, wherein the SARS-CoV-2 comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:1 or 2.

17. The method of paragraph 14, wherein the Severe acute respiratory syndrome-related coronavirus is SARS-CoV.

18. The method of paragraph 17, wherein the SAR-CoV comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:3.

19. The method of paragraph 12, wherein the virus is a Middle East respiratory syndrome-related coronavirus.

20. The method of paragraph 19, wherein the Middle East respiratory syndrome-related coronavirus is MERS-CoV.

21. The method of 20, wherein the MERS-CoV comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:4.

22. The method of any one of paragraphs 1-21, wherein the subject has been exposed to the coronavirus.

23. The method of paragraph 22, wherein the subject is presently suffering from an infection of the coronavirus.

24. The method of paragraph 23, wherein the subject has COVID-19.

25. The method of any one of paragraphs 1-20, wherein the subject has been exposed to the coronavirus, but is asymptomatic.

26. A method of treating a subject for SAR-CoV-2 infection comprising administering the subject an effective amount of probenecid or a pharmaceutically acceptable salt thereof.

27. The method of paragraph 26, wherein the subject has COVID-19.

28. A prophylactic method comprising administering to a subject that has not be exposed to a coronavirus, an effective amount of probenecid, metabolite or analog thereof, or a pharmaceutically acceptable salt thereof, to reduce viral infection in the subject upon exposure to the virus relative to viral infection in the absence of treatment.

29. The method of paragraph 28, wherein the coronavirus is SAR-CoV-2.

30. The method of any one of paragraphs 1-29, wherein the subject is administered 10 mg-1,000 mg or 50 mg-500 mg of probenecid, a metabolite or analog thereof, or a pharmaceutically acceptable salt thereof 1 to 5 times per day until symptoms are reduced, the infection clears, or a combination thereof.

31. The method of any one of paragraphs 1-30, wherein the subject is treated by pulse dosing.

32. The method of paragraph 31, wherein the pulse dosing comprises a 1-5 bolus doses of 1,000 mg to 5,000 mg probenecid, a metabolite or analog thereof, or a pharmaceutically acceptable salt thereof.

33. The method of paragraph 32, wherein the bolus dose(s) is followed by a drug holiday until the serum levels of the probenecid, metabolite or analog thereof, or a pharmaceutically acceptable salt thereof are about 0.

34. The method of any one of paragraphs 31-33, wherein the probenecid, metabolite or analog thereof, or a pharmaceutically acceptable salt thereof is administered orally or by infusion.

35. A pharmaceutical composition comprising an effective amount of probenecid, metabolite or analog thereof, or a pharmaceutically acceptable salt thereof for use in the method of any one of paragraphs 1-34.

EXAMPLE

Example 1: Probenecid Reduces SARS-CoV-2 Plaque Formation In Vitro

Materials and Methods
Plaque Reduction Assay
Prophylactic Treatment
Vero E6 cells were plated in a 12 well plates at $5 \times 10^5$ cells/well and incubated overnight.

Cells were washed 1× with PBS and probenecid at 0.1 µM, 1 µM, 2.5 µM, or 5 µM was added to the wells in culture media and incubated for 24 hours (FIG. 1). All wells were normalized to 0.05% DMSO. Each concentration was completed in duplicate.

Following pre-treatment, media was discarded and cells were replenished with media containing probenecid (as above) and SARS-CoV-2 (stock grown from Isolate USA-WA1/2020, BEI Resources Catalogue Ref. Number NR-52281). The complete genome of SARS-CoV-2, USA-WA1/2020 has been sequenced (the isolate—GenBank Accession Number: MN985325 and after one passage in Vero cells—GenBank Accession Number: MT020880 and after four passages in Vero cells—GenBank Accession Number: MT246667).

Cells were infected at a MOI of 0.01 for 4 days. Post-infection cells were fixed and stained to visualize plaques. Plaques were quantified manually (FIG. 1).

Figure 2:
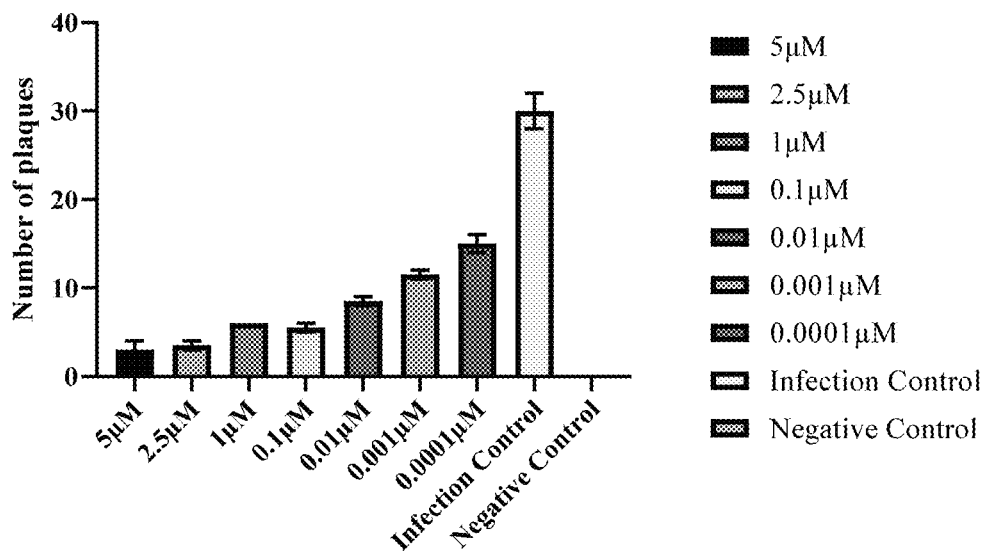
FIG. 2 is a bar graph showing (left-to-right) the effect of probenecid pre-treatment (5 µM, 2.5 µM, 1 µM, 0.1 µM 0.01 µM, 0.001 µM, or 0.0001 µM) compared to controls (DMSO (infected), DMSO (only)) on viral replication using a plaque reduction assay.

In another experiment, probenecid at 0.0001 µM, 0.001 µM, 0.01 µM, 0.1 µM, 1 µM, 2.5 µM, or 5 µM (FIG. 2) was added. Vero E6 cells were plated in a 6 well plate at 8E5 cells/well and incubated overnight. Cells were washed once with PBS and the compound was added to the wells in culture media and incubated for 24 hours. All wells were normalized to 0.05% DMSO. Each concentration was completed in duplicate. Following pre-treatment, media was discarded and cells were replenished with media containing drug (as above) and SARS-CoV-2. Cells were infected at a MOI of 0.01 for 4 days. Post-infection the cells were fixed and stained to visualize plaques. Plaques were quantified (FIG. 2).

Therapeutic Treatment

Figure 3:
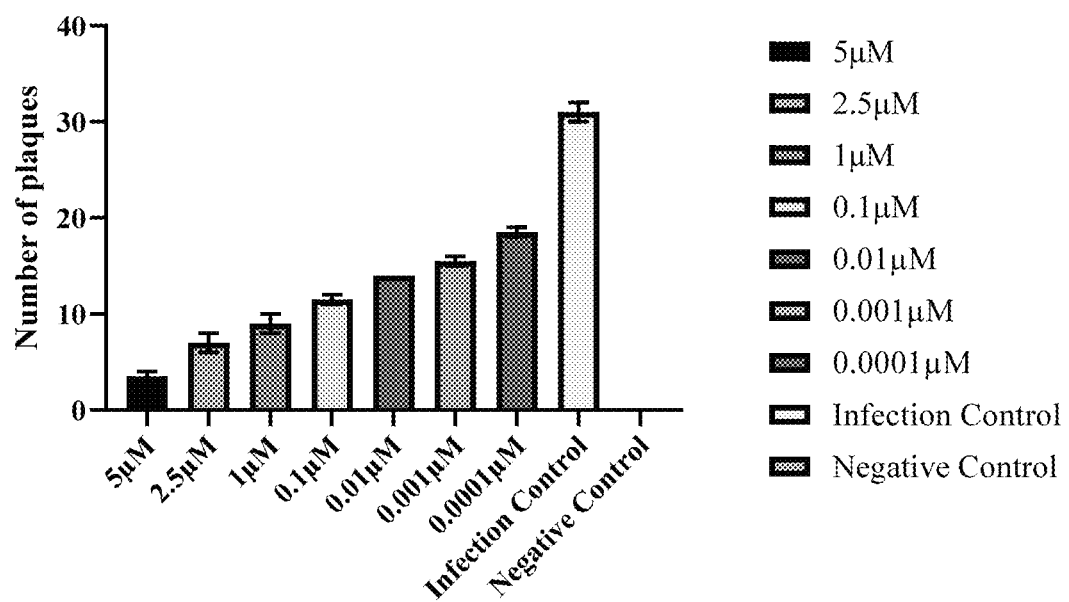
FIG. 3 is a bar graph showing (left-to-right) the effect of probenecid post-treatment (5 µM, 2.5 µM, 1 µM, 0.1 µM 0.01 µM, 0.001 µM, or 0.0001 µM) compared to controls (DMSO (infected), DMSO (only)) on viral replication using a plaque reduction assay.

Vero E6 cells were plated in a 6 well plate at 8E5 cells/well and incubated overnight. Cells were washed once with PBS and infected with virus at a MOI of 0.01 for 1 hour. Following 1 hour infection probenecid at 0.0001 µM, 0.001 µM, 0.01 µM, 0.1 µM, 1 µM, 2.5 µM, or 5 µM was added to the wells in overlay media and incubated 4 days. Post-infection the cells were fixed and stained to visualize plaques. Plaques were quantified (FIG. 3).

Results

The effect of probenecid on viral replication was investigated using an in vitro plaque formation assay.

Probenecid pre-treatment resulted in a dose dependent reduction in plaque formation for concentrations tested (5 µM-0.1 µM) in two independent experiments. 5 µM-0.1 µM reduced plaque formation from ~89% to 72% (FIG. 1), respectively, compared to DMSO treated infected control.

In another experiment, probenecid pre-treatment resulted in a dose dependent reduction in plaque formation for concentrations tested (5 µM-0.0001 µM) in two independent experiments. 5 µM-0.0001 µM reduced plaque formation from ~93% to 50%, respectively, (FIG. 2), compared to DMSO treated infected control.

In another experiment, probenecid post-treatment resulted in a dose dependent reduction in plaque formation for concentrations tested (5 µM-0.0001 µM). 5 µM-0.0001 µM reduced plaque ~90% to 40% (FIG. 3), respectively, compared to DMSO treated infected control.

These results show that probenecid significantly reduces viral titer/plaque formation with 24 hour pretreatment at the concentrations tested. These results also show that probenecid significantly reduces viral titer/plaque formation with post-treatment at the concentrations tested.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of preventing a Severe acute respiratory syndrome coronavirus 2 (SARS-CoV-2) infection comprising administering to a subject that has been exposed to SARS-CoV-2 an effective amount of probenecid or a pharmaceutically acceptable salt thereof.

2. The method of claim 1, wherein the probenecid or pharmaceutically acceptable salt thereof is in a pharmaceutical composition further comprising a pharmaceutically acceptable carrier and/or excipient.

3. The method of claim 1, wherein the probenecid or pharmaceutically acceptable salt thereof is administered systemically.

4. The method of claim 1, wherein the probenecid or pharmaceutically acceptable salt thereof is administered orally, parenterally, topically, or mucosally.

5. The method of claim 4, wherein the probenecid or pharmaceutically acceptable salt thereof is administered mucosally to the lungs, nasal mucosa, or combination thereof.

6. The method of claim 1, wherein the probenecid or pharmaceutically acceptable salt thereof is administered in an effective amount to reduce viral replication.

7. The method of claim 1, wherein the probenecid or pharmaceutically acceptable salt thereof is administered in an effective amount to reduce one or more symptoms of a disease, disorder, or illness associated with the SARS-CoV 2.

8. The method of claim 7, wherein the symptoms include fever, congestion in the nasal sinuses and/or lungs, runny or stuffy nose, cough, sneezing, sore throat, body aches, fatigue, shortness of breath, chest tightness, wheezing when exhaling, chills, muscle aches, headache, diarrhea, tiredness, nausea, vomiting, and combinations thereof.

9. The method of claim 1, wherein the SARS-CoV-2 comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:1 or 2.

10. The method of claim 1, wherein the subject does not have COVID-19.

11. The method of claim 1, wherein the subject is asymptomatic.

12. The method of claim 1, wherein the subject is administered 10 mg-1,000 mg or 50 mg-500 mg of probenecid or a pharmaceutically acceptable salt thereof.

13. The method of claim 1, wherein the subject is treated by pulse dosing.

14. The method of claim 13, wherein the pulse dosing comprises 1-5 bolus doses of 1,000 mg to 5,000 mg probenecid or a pharmaceutically acceptable salt thereof.

15. The method of claim 14, wherein the bolus dose(s) is followed by a drug holiday.

16. The method of claim 13, wherein the probenecid or pharmaceutically acceptable salt thereof is administered orally or by infusion.

17. A method of preventing coronavirus disease 2019 (COVID-19) comprising administering to a subject that has been exposed to SARS-CoV-2 an effective amount of probenecid or a pharmaceutically acceptable salt thereof to reduce coronaviral infection in the subject.

18. The method of claim 17, wherein the subject is administered 10 mg-1,000 mg or 50 mg-500 mg of probenecid or a pharmaceutically acceptable salt thereof.

19. The method of claim 17, wherein the probenecid or pharmaceutically acceptable salt thereof is administered in an effective amount to reduce viral replication.

20. The method of claim 17, wherein the subject is asymptomatic.

21. The method of claim 1, comprising administering the subject 500 mg or 1,000 mg probenecid or a pharmaceutically acceptable salt thereof twice daily.

22. The method of claim 17, comprising administering the subject 500 mg or 1,000 mg probenecid or a pharmaceutically acceptable salt thereof twice daily.

23. A method of preventing a SARS-CoV-2 infection comprising administering to a subject an effective amount of probenecid or a pharmaceutically acceptable salt thereof and subsequently exposing the subject to the SARS-CoV-2.

24. The method of claim 23 comprising administering the subject the probenecid or a pharmaceutically acceptable salt thereof one day prior to exposure to the SARS-CoV-2.

25. The method of claim 23, comprising administering the subject 500 mg or 1,000 mg probenecid or a pharmaceutically acceptable salt thereof twice daily.

* * * * *